(12) United States Patent
Ochiai et al.

(10) Patent No.: US 8,680,092 B2
(45) Date of Patent: Mar. 25, 2014

(54) NITROGENOUS HETEROCYCLIC COMPOUND AND MEDICINAL USE THEREOF

(75) Inventors: Hiroshi Ochiai, Mishima-gun (JP); Akira Ohhata, Mishima-gun (JP); Yoshikazu Takaoka, Mishima-gun (JP); Shiro Shibayama, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 1403 days.

(21) Appl. No.: 11/816,940

(22) PCT Filed: Feb. 24, 2006

(86) PCT No.: PCT/JP2006/303477
§ 371 (c)(1),
(2), (4) Date: Aug. 23, 2007

(87) PCT Pub. No.: WO2006/090853
PCT Pub. Date: Aug. 31, 2006

(65) Prior Publication Data
US 2009/0233908 A1    Sep. 17, 2009

(30) Foreign Application Priority Data
Feb. 25, 2005    (JP) .................................. 2005-050098

(51) Int. Cl.
| | |
|---|---|
| *A61P 11/00* | (2006.01) |
| *A61P 19/02* | (2006.01) |
| *A61P 29/00* | (2006.01) |
| *A61P 31/18* | (2006.01) |
| *A61P 35/00* | (2006.01) |
| *A61P 37/06* | (2006.01) |
| *A61P 43/00* | (2006.01) |
| *C07D 401/14* | (2006.01) |
| *C07D 403/14* | (2006.01) |
| *C07D 405/14* | (2006.01) |
| *C07D 409/14* | (2006.01) |
| *C07D 413/14* | (2006.01) |
| *A61K 31/506* | (2006.01) |
| *A61K 31/5377* | (2006.01) |
| *A61K 39/21* | (2006.01) |
| *A61K 39/395* | (2006.01) |
| *A61K 45/00* | (2006.01) |

(52) U.S. Cl.
USPC ...................................... 514/217.06; 540/601

(58) Field of Classification Search
USPC ...................................... 514/217.06; 540/601
See application file for complete search history.

(56) References Cited

FOREIGN PATENT DOCUMENTS

| | | |
|---|---|---|
| EP | 1 378 510 A1 | 1/2004 |
| EP | 1 571 146 A1 | 9/2005 |
| EP | 1 604 981 A1 | 12/2005 |
| JP | 2001-55378 A | 2/2001 |
| WO | 02/22599 A2 | 3/2002 |
| WO | 02/45652 A2 | 6/2002 |
| WO | 03/062236 A1 | 7/2003 |
| WO | 2004/052862 A1 | 6/2004 |
| WO | 2004/080966 A1 | 9/2004 |
| WO | 2008/029276 A2 | 3/2008 |

OTHER PUBLICATIONS

Extended European Search Report issued in European Application No. 06714616.7 dated Mar. 17, 2010.

*Primary Examiner* — Brenda Coleman
(74) *Attorney, Agent, or Firm* — Sughrue Mion, PLLC

(57) ABSTRACT

A compound represented by formula (I):

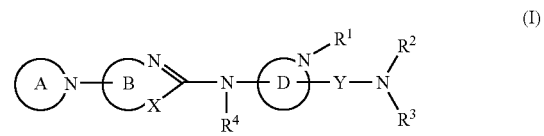

(wherein the symbols are the same as defined in the description), a salt thereof, an N-oxide thereof, a solvate thereof or a prodrug thereof, and medicinal use thereof.

The compound represented by formula (I) has CXCR4 antagonistic activity. It is hence useful as, e.g., a preventive and/or therapeutic agent for CXCR4-mediated diseases such as inflammatory/immunologic diseases (e.g., rheumatoid arthritis, arthritis, retinopathy, pulmonary fibrosis, and rejection reactions of transplanted organs), allergic diseases, infections diseases (e.g., human immunodeficiency virus infection and acquired immunologic deficiency syndrome), psychoneurotic diseases, cerebral diseases, cardiac/vascular disease, metabolic diseases, cancer diseases (e.g., cancer, cancer metastasis) or as an agent for regeneration therapy.

10 Claims, No Drawings

NITROGENOUS HETEROCYCLIC COMPOUND AND MEDICINAL USE THEREOF

TECHNICAL FIELD

The present invention relates to a nitrogen-containing heterocyclic compound which is useful as medicaments, and use thereof.

More specifically, the present invention relates to (1) compounds represented by formula (I):

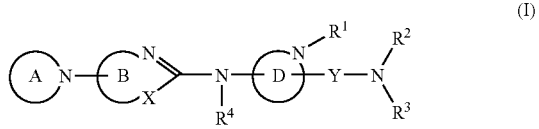

(I)

wherein all symbols have the same meanings as described hereinafter, and salts thereof, N-oxides thereof or solvates thereof or prodrugs thereof, (2) use thereof, and (3) a method for producing the same.

BACKGROUND ART

Chemokine is known as a basic protein which has chemotaxis and an activating activity against endogenous leucocytes and also has strong heparin-binding abilities. It is now considered that chemokine is associated with not only control of infiltration of specific leucocytes upon inflammatory and immune responses, but also development, homing of lymphocytes under physiological conditions and migration of hemocyte precursor cells and somatic cells.

Differentiation, proliferation and cell death of blood cells are controlled by various cytokines. Inflammation occurs at a local region in a living body. Differentiation and maturation of lymphocytes, and the like are carried out at a specific site. More particularly, required various cells migrate and accumulate in the specific site and a sequence of inflammatory and immune responses arise. Thus, in addition to differentiation, proliferation and death of cells, cell migration is also an essential phenomenon to an immune system.

In the living body, migration of blood cells start with sifting hemopoiesis that started at AGM (Aorta Gonad Mesonephros) region via fetal liver to permanent hematopoiesis at bone marrow in a development course. Moreover, precursors of T cells and thymus dendritic cells migrate from fetal liver into bone marrow and then into the thymus gland. They differentiate under thymus environment. The T cells are subjected to clonal selection migrates into secondary lymphoid tissues, where they contribute to immune responses in periphery. Skin Langerhans cells that caught antigen, thereby undergone activation and differentiation migrate to T cell region in a topical lymph node, where they activate naive T cells therein as dendritic cells. The memory T cells again perform its homing into the lymph node via lymphatic and blood vessels. In addition, B cells, T cells in intestinal epithelia, γδT cells, NKT cells, and dendritic cells migrate from bone marrow not via thymus, differentiate and contribute to immune responses.

Chemokine is closely associated with such a migration of the various cells. For example, SDF-1 (Stromal cell derived factor-1) and its receptor, CXCR4 also act on various immune- and inflammatory reactions. For example, they have been reported to be associated with accumulation and activation of CD4+T cells in a synovial membrane from a human patient suffering from rheumatoid arthritis (*J. Immunol.*, 165, 6590-6598 (2000)). In addition, in a CIA model mouse, CXCR4 inhibitor inhibited accumulation of leucocytes in a joint and dramatically reduced arthritis score (*J. Immunol.*, 167, 4648-4692 (2001)). In a mouse OVA-induced airway hypersensitive model, an anti-CXCR4 antibody reduced the number of eosinophiles accumulating in pulmonary interstitial tissues and prevented airway hypersensitivity (*J. Immunol.*, 165, 499-508 (2000)). In a murine model of bleomycin-induced pulmonary damage, an anti-SDF-1 antibody prevented fibrocellular infiltration to lung and fibrosis of lung tissue (*J. Cli. I*, 114, 438-446 (2004)). In a murine model of retinopathy, an anti-SDF-1 antibody prevented infiltration of vascular endothelial precursor cell to retina and retinal neovascularization (*J. Cli. I*, 115, 86-93 (2005)).

There has been reported that SDF-1 and its receptor, CXCR4 play an important role in maintaining hemopoietic stem cells in bone marrow (*J. Exp. Med.*, 185, 111-120 (1997), *Blood*, 97, 3354-3360 (2001)). Accordingly, control of SDF-1 and CXCR4 is expected to modulate recruitment of hemopoietic stem cells to peripheral blood and are useful for peripheral blood stem cell transplantation and reproduction transplantation treatment.

SDF-1 and CXCR4 are associated with proliferation and infiltration of various cancer cells such as breast cancer, prostate cancer, ovarian cancer and brain cancer (*Nature*, 410, 50-56 (2001), *Cancer Res.*, 62, 1832-1837 (2002), *Cancer Res.*, 62, 5930-5938 (2002)). In a model of transplanting a human breast cancer cell strain into a SCID mouse, an anti-CXCR4 antibody prevented metastasis of breast cancer cells to lung (*Nature*, 410, 50-56 (2001)). And also, an anti-SDF-1 antibody prevented neoangiogenesis of tumor periphery and tumor cell proliferation (*Cell*, 121, 335-348 (2005)). Inhuman ovarian epithelial tumor, highly expression of SDF-1 brings in plasmacytoid precursor dendritic cells which decrease T cell's function and suppresses tumor immune (*Nat. Med.*, 12, 1339 (2001)). Moreover, SDF-1 is associated with proliferation and migration of non-Hodgkin's lymphoma cells, and in a model of transferring a human non-Hodgkin's lymphoma cells into a NOD/SCID mouse, an anti-CXCR4 antibody inhibited proliferation of the tumor cells and improved mouse mortality (*Cancer Res.*, 62, 3106-3112 (2002)). Also, a small-molecule antagonist of CXCR4 increased murine intracranial medulloblastoma xenografts apoptosis and inhibits the proliferation of tumor (*Proc. Nat. Acad. Sci. USA*, 100, 13513-13518 (2003)).

SDF-1 and CXCR4 play an important role for formation of hippocampus dentate gyrus granulocyte, that is essential for memory and learning and are associated with development of a disease associated with adult plasticity and pathology of hippocampus, for example Alzheimer's disease, stroke and epilepsy (*Development*, 129, 4249-4260 (2002), *Trends in Neuroscience*, 25, 548-549 (2002)).

SDF-1 and CXCR4 are essential for a function of self-reactive B cells associated with development of diabetes. In NOD mouse, an anti-SDF-1 antibody reduced blood glucose level and the number of mature IgM+B cells in a periphery tissue (*Immunology*, 107, 222-232 (2002)). In a human arteriosclerotic plaque, SDF-1 was highly expressed and activated blood platelets (*Circ. Res.*, 86, 131-138 (2000)).

In addition, the results of SDF-1/CXCR4 knock-out mice showed that SDF-1 is essential for functions of central nervous system, heart and vessels of gastrointestinal tract in addition to lymphocytes (*Nature*, 382, 635-639 (1996), *Nature*, 393, 591-594 (1998), *Nature*, 393, 595-599 (1998)). Accordingly, it may be associated with a disease of these tissues.

Thus, chemokine receptors are expressed at various specific cells and at a specific time. They are largely associated with the control of inflammatory- and immune-responses through a mechanism by which their effector cells accumulate in a site where chemokine is produced.

Acquired immunodeficiency syndrome (also called AIDS) that caused by infection of human immunodeficiency virus (hereinafter abbreviated to HIV) is one of diseases for which therapies are the most eagerly desired lately. Once HIV infection has been established in a main target cell, CD4+ cell, HIV repetitively proliferates in a patient's body and in the event deathly destroys T cells responsible for immunological functions by necrosis. In this process, immunological functions are gradually deteriorated, various immunocompromised states become to develop such as fever, diarrhea and swelling of a lymph node, and various opportunistic infections such as carinii pneumonia are easily complicated. It is well known that such a state is the onset of AIDS and induces malignant tumors such as Kaposi's sarcoma and becomes severe.

Currently, there are tried various preventive and therapeutic treatments for AIDS as follows: for example, (1) inhibition of HIV proliferation by administration of reverse transcriptase inhibitors and protease inhibitors, and (2) prevention or alleviation of opportunistic infections by administration of an immunostimulant, etc.

HIV mainly infects helper T cells which play a key role in the immune system. Since 1985, it has been known that in this process HIV utilizes a membrane protein CD4 that is expressed on the membrane of T cells (*Cell,* 52, 631 (1985)). CD4 molecule consists of 433 amino acid residues and is expressed in macrophages, some B cells, vascular endothelial cells, Langerhans cells in skin tissues, dendritic cells located in lymphatic tissues, glia cells of central nervous system and the like in addition to mature helper T cells. However, as it becomes obvious that HIV infection cannot be established with only CD4 molecule, the possible presence of some factor that is responsible for infection of cell with HIV, other than CD4 molecule, has been suggested.

In 1996, a cell membrane protein called Fusin has been identified as a factor responsible for HIV infection other than a CD4 molecule (*Science,* 272, 872 (1996)). This Fusin molecule has been demonstrated to be a receptor for SDF-1, namely, CXCR4. In addition, it has been shown that SDF-1 specifically inhibits infection of T cell-directed (X4) HIV in vitro (*Nature,* 382, 829 (1996), *Nature,* 382, 833 (1996)). This may be considered that SDF-1 binds to CXCR4 prior to HIV, thereby taking away a scaffold for infecting a cell from HIV resulting in inhibition of HIV infection.

Also, at the same period, there has been found that another chemokine receptor CCR5, that is a receptor for RANTES, MIP-1α, and MIP-1β, is utilized at infection of macrophage-directed (R5) HIV (*Science,* 272, 1955 (1996)).

Accordingly, those which can compete with HIV for CXCR4 and CCR5 or those which bind to a HIV virus and prevent for said virus from binding to CXCR4 and CCR5 may be a HIV infection inhibitor. In addition, there is a case where a low molecular weight compound discovered as a HIV infection inhibitor was showed to be indeed an antagonist of CXCR4 (*Nature Medicine,* 4, 72 (1998)).

As described above, compounds having an antagonistic activity against CXCR4 is effective, such as, for prevention and/or treatment of inflammatory and immune diseases, allergic diseases, infections, particularly HIV infection, and diseases associated with the infection, psychoneurotic diseases, cerebral diseases, cardiovascular diseases, metabolic diseases, cancerous diseases and the like. Also, the compounds are useful for cell medical treatment and regeneration therapy.

In patent literature 1, it is disclosed that a compound represented by formula (a):

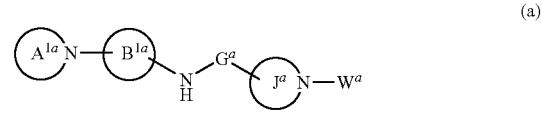

(a)

wherein ring $A^{1a}$ represents a 5- to 10-membered nitrogen-containing saturated heterocyclic ring which may have a substituent(s) or a 5- to 10-membered nitrogen-containing heterocyclic ring which may have a substituent(s), and have a double bond;

ring $B^{1a}$ represents a 6- to 11-membered nitrogen-containing mono- or bicyclic heterocyclic ring which may have a substituent(s);

$G^a$ represents a bond or a spacer having a main chain of 1 to 3 atom(s);

ring $J^a$ represents a 4- to 7-membered nitrogen-containing heterocyclic ring which may have a substituent(s); and $W^a$ represents a hydrogen atom, a hydrocarbon group which may have a substituent(s) or a heterocyclic ring group which may have a substituent(s) (only required portions were extracted.), or a salt thereof, an N-oxide thereof or a solvate thereof, or a prodrug thereof is useful as CXCR4 regulator.

[Patent literature 1] WO2004/052862

DISCLOSURE OF THE INVENTION

It is useful that a preventive and/or therapeutic agent for inflammatory and immune diseases (for example, rheumatoid arthritis, arthritis, retinopathy, pulmonary fibrosis, transplanted organ rejection, etc.), allergic diseases, infections (for example, human immunodeficiency virus infection, acquired immunodeficiency syndrome, etc.), and cancerous diseases (for example, cancer, cancer metastasis, etc.), or an agent for regeneration therapy is a medicinal drug. However, it is earnestly desired to develop a CXCR4 antagonist which has a high activity and also causes fewer side effects and is safe, because of administration of multiple drugs for the common medicament therapy of HIV infection or acquired immunodeficiency syndrome, etc.

In order to find a compound binding CXCR4 as a useful medicinal drug, the present inventors have intensively studied and found that a compound of the present invention which has at least three basic nitrogen atoms has a very strong antagonistic activity against CXCR4, and thus the present invention has been completed.

Namely, the present invention relates to:

[1] A compound represented by formula (I):

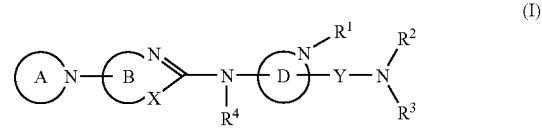

(I)

wherein ring A represents a 5- to 10-membered nitrogen-containing heterocyclic ring which may have a substituent(s);

ring B represents a 5- to 15-membered nitrogen-containing unsaturated heterocyclic ring which may have a further substituent(s);

ring D represents a 4- to 15-membered nitrogen-containing heterocyclic ring which may have a further substituent(s);

X represents a nitrogen atom or a carbon atom;

Y represents a spacer having a main chain of 1 to 8 atom(s);

$R^1$ represents a hydrogen atom, a hydrocarbon group which may have a substituent(s) or a cyclic group which may have a substituent(s);

$R^2$ and $R^3$ each independently represents a hydrogen atom, a hydrocarbon group which may have a substituent(s) or a cyclic group which may have a substituent(s), or may be taken together with the nitrogen atom to which they are attached to form a nitrogen-containing heterocyclic ring which may have a substituent(s); and $R^4$ represents a hydrogen atom or a hydrocarbon group which may have a substituent(s), or a salt thereof, an N-oxide thereof or a solvate thereof, or a prodrug thereof,

[2] The compound according to the above [1], wherein ring A represents a 5- to 8-membered nitrogen-containing saturated monocyclic heterocyclic ring which may have a substituent(s), or a salt thereof, an N-oxide thereof or a solvate thereof, or a prodrug thereof;

[3] The compound according to the above [1], wherein ring B represents a 5- to 8-membered nitrogen-containing unsaturated monocyclic heterocyclic ring which may have a further substituent(s), or a salt thereof, an N-oxide thereof or a solvate thereof, or a prodrug thereof;

[4] The compound according to the above [1], wherein ring D represents a 4- to 8-membered nitrogen-containing monocyclic heterocyclic ring which may have a further substituent(s), or a salt thereof, an N-oxide thereof or a solvate thereof, or a prodrug thereof;

[5] The compound according to the above [1], wherein Y represents a spacer having a main chain of 2 to 5 atoms, or a salt thereof, an N-oxide thereof or a solvate thereof, or a prodrug thereof;

[6] The compound according to the above [1], wherein $R^4$ represents a hydrogen atom, or a salt thereof, an N-oxide thereof or a solvate thereof, or a prodrug thereof;

[7] The compound according to the above [1], wherein the compound represented by formula (I) represents a compound represented by formula (I-1):

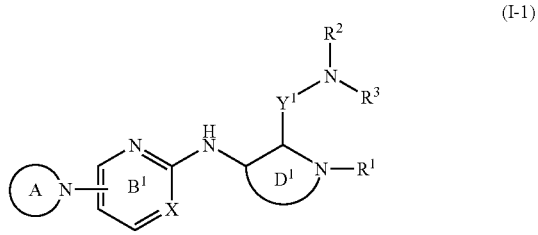

(I-1)

wherein ring $B^1$ represents pyridine or pyrimidine which may have a further substituent(s);

ring $D^1$ represents a 4- to 8-membered nitrogen-containing saturated monocyclic heterocyclic ring which may have a further substituent(s);

$Y^1$ represents a spacer having a main chain of 1 to 5 atom(s); and other symbols have the same meanings as described in the above [1], or a salt thereof, an N-oxide thereof or a solvate thereof, or a prodrug thereof;

[8] The compound according to the above [7], wherein X represents a nitrogen atom, or a salt thereof, an N-oxide thereof or a solvate thereof, or a prodrug thereof;

[9] The compound according to the above [7], wherein $R^1$ represents a monocyclic cyclic group which may have a substituent(s), or a salt thereof, an N-oxide thereof or a solvate thereof, or a prodrug thereof;

[10] The compound according to the above [9], wherein the monocyclic cyclic group which may have a substituent(s) represented by $R^1$ represents a monocyclic cyclic group which is unsubstituted or substituted by a C1-4 aliphatic hydrocarbon group or a hydroxyl group, or a salt thereof, an N-oxide thereof or a solvate thereof, or a prodrug thereof;

[11] The compound according to the above [7], wherein $Y^1$ represents —$(CR^5R^6)_n$—;

$R^5$ and $R^6$ each represents a hydrogen atom, or $R^5$ and $R^6$ taken together represents an oxo group; and n represents an integer of 1 to 4;

wherein when n represents an integer of 2 to 4, $CR^5R^6$s are the same or different, or a salt thereof, an N-oxide thereof or a solvate thereof, or a prodrug thereof;

[12] The compound according to the above [7], wherein $R^2$ represents —(CO)—$R^{2A}$;

$R^{2A}$ represents (i) a hydrocarbon group which is substituted by a basic group, and may have a further substituent(s); (ii) a cyclic group which is substituted by a basic group, and may have a further substituent(s); or (iii) a 5- to 8-membered nitrogen-containing monocyclic heterocyclic ring; and $R^3$ represents a hydrocarbon group which may have a substituent(s) or a cyclic group which may have a substituent(s), or a salt thereof, an N-oxide thereof or a solvate thereof, or a prodrug thereof;

[13] The compound according to the above [12], wherein $R^{2A}$ represents a 5- to 8-membered nitrogen-containing monocyclic heterocyclic ring, or a salt thereof, an N-oxide thereof or a solvate thereof, or a prodrug thereof;

[14] The compound according to the above [13], wherein the 5- to 8-membered nitrogen-containing monocyclic heterocyclic ring represented by $R^{2A}$ represents pyrrolidine, piperidine or morpholine, or a salt thereof, an N-oxide thereof or a solvate thereof, or a prodrug thereof;

[15] The compound according to the above [7], wherein the ring which is formed by taking $R^2$ and $R^3$ together with the nitrogen atom to which they are attached represents a 5- to 8-membered nitrogen-containing heterocyclic ring which may have a substituent(s), or a salt thereof, an N-oxide thereof or a solvate thereof, or a prodrug thereof;

[16] The compound according to the above [7], wherein ring $D^1$ represents pyrrolidine or piperidine, or a salt thereof, an N-oxide thereof or a solvate thereof, or a prodrug thereof;

[17] The compound according to the above [1], wherein the compound represented by formula (I) represents:
a compound represented by formula (I-2):

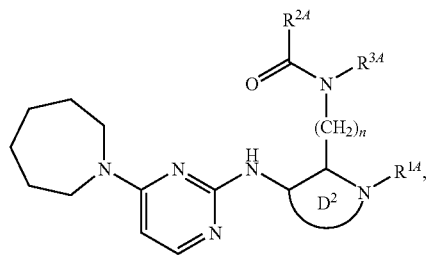

(I-2)

a compound represented by formula (I-3):

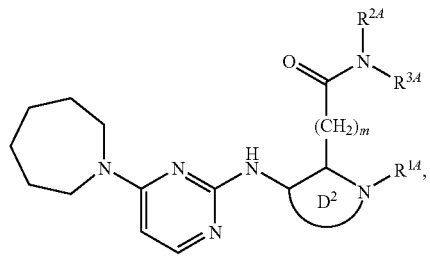

(I-3)

a compound represented by formula (I-4):

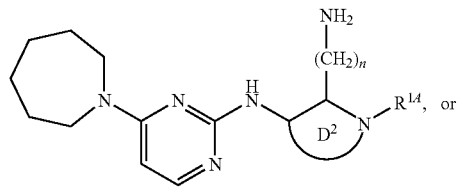

(I-4)

a compound represented by formula (I-5):

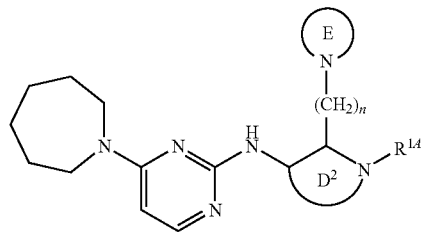

(I-5)

wherein ring $D^2$ represents pyrrolidine or piperidine;
m represents an integer of 1 to 3;
$R^{1A}$ represents a hydrocarbon group which may have a substituent(s) or a monocyclic cyclic group which may have a substituent(s);
$R^{3A}$ represents a hydrocarbon group which may have a substituent(s) or a cyclic group which may have a substituent(s);

ring E represents a 5- to 8-membered nitrogen-containing monocyclic heterocyclic ring which may have a further substituent(s); and
other symbols have the same meanings as described in the above [1], the above [11] or the above [12], or
a salt thereof, an N-oxide thereof or a solvate thereof, or a prodrug thereof;

[18] The compound according to the above [1], wherein the compound represented by formula (I) represents
N-[(2R,3S)-2-(aminomethyl)-1-cyclohexyl-3-pyrrolidinyl]-4-(1-azepanyl)-2-pyrimidinamine;
N-[(2R,3S)-2-(2-aminoethyl)-1-cyclohexyl-3-pyrrolidinyl]-4-(1-azepanyl)-2-pyrimidinamine;
N-[(2R,3S)-2-(3-aminopropyl)-1-cyclohexyl-3-pyrrolidinyl]-4-(1-azepanyl)-2-pyrimidinamine;
N-[(2R,3S)-2-(5-aminopentyl)-1-cyclohexyl-3-pyrrolidinyl]-4-(1-azepanyl)-2-pyrimidinamine;
N-[(2R,3S)-2-(aminomethyl)-1-cyclohexyl-3-pyrrolidinyl]-4-(1-azepanyl)-2-pyrimidinamine;
4-(1-azepanyl)-N-{(2R,3S)-1-cyclohexyl-2-[2-(dimethylamino)ethyl]-3-pyrrolidinyl}-2-pyrimidinamine;
4-(1-azepanyl)-N-{(2R,3S)-1-cyclohexyl-2-[3-(dimethylamino)propyl]-3-pyrrolidinyl}-2-pyrimidinamine;
4-(1-azepanyl)-N-{(2R,3S)-1-cyclohexyl-2-[5-(dimethylamino)pentyl]-3-pyrrolidinyl}-2-pyrimidinamine;
4-(1-azepanyl)-N-{(2RS,3SR)-1-cyclohexyl-2-[3-(dipropylamino)propyl]-3-pyrrolidinyl}-2-pyrimidinamine;
cis-4-((2RS,3SR)-2-(3-aminopropyl)-3-{[4-(1-azepanyl)-2-pyrimidinyl]amino}-1-pyrrolidinyl)cyclohexanol;
4-(1-azepanyl)-N-{(2RS,3SR)-1-cyclohexyl-2-[3-(diethylamino)propyl]-3-pyrrolidinyl}-2-pyrimidinamine;
4-(1-azepanyl)-N-{(2RS,3SR)-1-cyclohexyl-2-[3-(1-pyrrolidinyl)propyl]-3-pyrrolidinyl}-2-pyrimidinamine;
4-(1-azepanyl)-N-{(2RS,3SR)-1-cyclohexyl-2-[3-(1-piperidinyl)propyl]-3-pyrrolidinyl}-2-pyrimidinamine;
4-(1-azepanyl)-N-{(2RS,3SR)-2-[3-(1-azepanyl)propyl]-1-cyclohexyl-3-pyrrolidinyl}-2-pyrimidinamine;
N-[(2RS,3SR)-2-(2-aminoethyl)-1-cyclohexyl-3-piperidinyl]-4-(1-azepanyl)-2-pyrimidinamine;
N-{(2RS,3SR)-2-(3-aminopropyl)-1-[1-(cyclohexylcarbonyl)-4-piperidinyl]-3-pyrrolidinyl}-4-(1-azepanyl)-2-pyrimidinamine;
N-{(2RS,3SR)-2-(3-aminopropyl)-1-[1-(cyclopentylcarbonyl)-4-piperidinyl]-3-pyrrolidinyl}-4-(1-azepanyl)-2-pyrimidinamine;
N-{(2RS,3SR)-2-(3-aminopropyl)-1-[1-(3-fluorobenzoyl)-4-piperidinyl]-3-pyrrolidinyl}-4-(1-azepanyl)-2-pyrimidinamine;
N-(3-aminopropyl)-2-((2RS,3SR)-3-{[4-(1-azepanyl)-2-pyrimidinyl]amino}-1-cyclohexyl-2-piperidinyl)acetamide;
2-((2RS,3SR)-3-{[4-(1-azepanyl)-2-pyrimidinyl]amino}-1-cyclohexyl-2-piperidinyl)-N-[3-(dimethylamino)propyl]acetamide;
N-[2-((2RS,3SR)-3-{[4-(1-azepanyl)-2-pyrimidinyl]amino}-1-cyclohexyl-2-piperidinyl)ethyl]-4-piperidinecarboxamide;
cis-4-{(2RS,3SR)-3-{[4-(1-azepanyl)-2-pyrimidinyl]amino}-2-[3-(diethylamino)propyl]-1-pyrrolidinyl}cyclohexanol;
N-{2-[(2RS,3SR)-3-{[4-(1-azepanyl)-2-pyrimidinyl]amino}-1'-(3-fluorobenzoyl)-1,4'-bipiperidin-2-yl]ethyl}-4-piperidinecarboxamide;
N-{2-[(2RS,3SR)-3-{[4-(1-azepanyl)-2-pyrimidinyl]amino}-1'-(cyclohexylcarbonyl)-1,4'-bipiperidin-2-yl]ethyl}-4-piperidinecarboxamide;

N-[2-((2RS,3SR)-3-{[4-(1-azepanyl)-2-pyrimidinyl]
  amino}-1-cyclohexyl-2-piperidinyl)ethyl]-2-morpholin-
  ecarboxamide;
(3S)- N-[2-((2RS,3SR)-3-{[4-(1-azepanyl)-2-pyrimidinyl]
  amino}-1-cyclohexyl-2-piperidinyl)ethyl]-3-piperidin-
  ecarboxamide;
(3R)- N-[2-((2RS,3SR)-3-{[4-(1-azepanyl)-2-pyrimidinyl]
  amino}-1-cyclohexyl-2-piperidinyl)ethyl]-3-piperidin-
  ecarboxamide;
(3R)- N-[2-((2RS,3SR)-3-{[4-(1-azepanyl)-2-pyrimidinyl]
  amino}-1-cyclohexyl-2-piperidinyl)ethyl]-3-pyrrolidin-
  ecarboxamide;
2-amino-N-[2-((2RS,3SR)-3-{[4-(1-azepanyl)-2-pyrimidi-
  nyl]amino}-1-cyclohexyl-2-piperidinyl)ethyl]-2-methyl-
  propanamide;
N-(4-aminobutyl)-2-((2RS,3SR)-3-{[4-(1-azepanyl)-2-pyri-
  midinyl]amino}-1-cyclohexyl-2-piperidinyl)acetamide;
N-(2-aminoethyl)-2-((2RS,3SR)-3-{[4-(1-azepanyl)-2-pyri-
  midinyl]amino}-1-cyclohexyl-2-piperidinyl)acetamide;
(3S)- N-[2-((2RS,3SR)-3-{[4-(1-azepanyl)-2-pyrimidinyl]
  amino}-1-cyclohexyl-2-pyrrolidinyl)ethyl]-3-piperidin-
  ecarboxamide;
N-[2-((2RS,3SR)-3-{[4-(1-azepanyl)-2-pyrimidinyl]
  amino}-1-cyclohexyl-2-pyrrolidinyl)ethyl]-2-morpholin-
  ecarboxamide;
N-[2-((2RS,3SR)-3-{[4-(1-azepanyl)-2-pyrimidinyl]
  amino}-1-cyclohexyl-2-piperidinyl)ethyl]-1-isopropyl-4-
  piperidinecarboxamide;
N-[2-((2RS,3SR)-3-{[4-(1-azepanyl)-2-pyrimidinyl]
  amino}-1-cyclohexyl-2-piperidinyl)ethyl]-N-(tetrahydro-
  2H-pyran-4-yl)-4-piperidinecarboxamide;
N-[2-((2RS,3SR)-3-{[4-(1-azepanyl)-2-pyrimidinyl]
  amino}-1-cyclohexyl-2-piperidinyl)ethyl]-N-(2-meth-
  oxyethyl)-4-piperidinecarboxamide;
N-[2-((2RS,3SR)-3-{[4-(1-azepanyl)-2-pyrimidinyl]
  amino}-1-cyclohexyl-2-piperidinyl)ethyl]-N-(2-hydroxy-
  ethyl)-4-piperidinecarboxamide;
(2S)- N-[2-((2RS,3SR)-3-{[4-(1-azepanyl)-2-pyrimidinyl]
  amino}-1-cyclohexyl-2-piperidinyl)ethyl]-2-piperidin-
  ecarboxamide;
N-[2-((2RS,3SR)-3-{[4-(1-azepanyl)-2-pyrimidinyl]
  amino}-1-cyclohexyl-2-piperidinyl)ethyl]-1-ethyl-4-pip-
  eridinecarboxamide;
N-[2-((2RS,3SR)-3-{[4-(1-azepanyl)-2-pyrimidinyl]
  amino}-1-cyclohexyl-2-piperidinyl)ethyl]-4-hydroxy-4-
  piperidinecarboxamide;
(2R)-2-amino-N-[2-((2RS,3SR)-3-{[4-(1-azepanyl)-2-pyri-
  midinyl]amino}-1-cyclohexyl-2-piperidinyl)ethyl]-3-(4-
  hydroxyphenyl)propanamide;
(2S)-2-amino-N-[2-((2RS,3SR)-3-{[4-(1-azepanyl)-2-pyri-
  midinyl]amino}-1-cyclohexyl-2-piperidinyl)ethyl]-4-hy-
  droxybutanamide;
N-(2-aminoethyl)-N-[2-((2RS,3SR)-3-{[4-(1-azepanyl)-2-
  pyrimidinyl]amino}-1-cyclohexyl-2-piperidinyl)ethyl]-4-
  piperidinecarboxamide;
N-[2-((2RS,3SR)-3-{[4-(1-azepanyl)-2-pyrimidinyl]
  amino}-1-ethyl-2-piperidinyl)ethyl]-4-piperidinecar-
  boxamide;
N-{2-[(2RS,3SR)-3-{[4-(1-azepanyl)-2-pyrimidinyl]
  amino}-1-(tetrahydro-2H-thiopyran-4-yl)-2-piperidinyl]
  ethyl}-4-piperidinecarboxamide;
N-[2-((2RS,3SR)-3-{[4-(1-azepanyl)-2-pyrimidinyl]
  amino}-1-isopropyl-2-piperidinyl)ethyl]-4-piperidinecar-
  boxamide;
N-(2-{(2RS,3SR)-3-{[4-(1-azepanyl)-2-pyrimidinyl]
  amino}-1-[2-hydroxy-1-(hydroxymethyl)ethyl]-2-
  piperidinyl}ethyl)-4-piperidinecarboxamide;
(2R)-2-amino-N-[2-((2RS,3SR)-3-{[4-(1-azepanyl)-2-pyri-
  midinyl]amino}-1-cyclohexyl-2-piperidinyl)ethyl]-3-
  (1H-imidazol-4-yl)propanamide;
(2S)-2-amino-N-[2-((2RS,3SR)-3-{[4-(1-azepanyl)-2-pyri-
  midinyl]amino}-1-cyclohexyl-2-piperidinyl)ethyl]-3-
  (1H-imidazol-4-yl)propanamide;
N-{2-[(2RS,3SR)-3-{[4-(1-azepanyl)-2-pyrimidinyl]
  amino}-1-(tetrahydro-2H-pyran-4-yl)-2-piperidinyl]
  ethyl}-4-piperidinecarboxamide;
N-[2-((2RS,3SR)-3-{[4-(1-azepanyl)-2-pyrimidinyl]
  amino}-1-cyclohexyl-2-piperidinyl)ethyl]-2-pyridinecar-
  boxamide;
N-[2-((2RS,3SR)-3-{[4-(1-azepanyl)-2-pyrimidinyl]
  amino}-1-cyclohexyl-2-piperidinyl)ethyl]nicotinamide;
N-[2-((2RS,3SR)-3-{[4-(1-azepanyl)-2-pyrimidinyl]
  amino}-1-cyclohexyl-2-piperidinyl)ethyl]isonicotina-
  mide;
N-{2-[(2RS,3SR)-3-{[4-(1-azepanyl)-2-pyrimidinyl]
  amino}-1-(1-oxidotetrahydro-2H-thiopyran-4-yl)-2-pip-
  eridinyl]ethyl}-4-piperidinecarboxamide;
N-{2-[(2RS,3SR)-3-{[4-(1-azepanyl)-2-pyrimidinyl]
  amino}-1-(1,1-dioxidotetrahydro-2H-thiopyran-4-yl)-2-
  piperidinyl]ethyl}-4-piperidinecarboxamide;
N-[2-((2RS,3SR)-1-cyclohexyl-3-{[4-(1-pyrrolidinyl)-2-py-
  rimidinyl]amino}-2-piperidinyl)ethyl]-4-piperidinecar-
  boxamide;
N-[2-((2RS,3SR)-3-{[4-(1-azepanyl)-2-pyrimidinyl]
  amino}-1-isopropyl-2-piperidinyl)ethyl]-1-ethyl-4-pip-
  eridinecarboxamide;
N-[2-((2RS,3SR)-1-ethyl-3-{[4-(1-piperidinyl)-2-pyrimidi-
  nyl]amino}-2-piperidinyl)ethyl]-4-piperidinecarboxam-
  ide;
N-[2-((2RS,3SR)-3-{[4-(1-azepanyl)-2-pyrimidinyl]
  amino}-1-cyclohexyl-2-piperidinyl)ethyl]-N-(tetrahydro-
  2H-pyran-4-yl)-2-morpholinecarboxamide; or
N-{2-[(2RS,3SR)-3-{[4-(1-azepanyl)-2-pyrimidinyl]
  amino}-1-(3-hydroxypropyl)-2-piperidinyl]ethyl}-4-pip-
  eridinecarboxamide, or
a salt thereof, an N-oxide thereof or a solvate thereof, or a
  prodrug thereof;
[19] A compound having molecular weight of 300 to 1000,
  which has:
  at least three basic nitrogen atoms;
  a partial structure represented by formula (C):

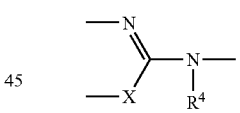

(C)

wherein X represents a nitrogen atom or a carbon atom;
R⁴ represents a hydrogen atom or a hydrocarbon group
  which may have a substituent(s); and
50% or more inhibitory activity of binding human SDF-1
  to CEM Cells in a concentration of 10 μM, or
a salt thereof, an N-oxide thereof or a solvate thereof, or a
  prodrug thereof;
[20] A pharmaceutical composition comprising the com-
  pound represented by formula (I) described in the above
  [1], a salt thereof, an N-oxide thereof or a solvate thereof,
  or a prodrug thereof;
[21] The pharmaceutical composition according to the above
  [20], which is a CXCR4 antagonist;
[22] The pharmaceutical composition according to the above
  [20], which is an agent for preventing and/or treating a
  CXCR4-mediated disease, or an agent for regeneration
  therapy;
[23] The pharmaceutical composition according to the above
  [22], wherein the CXCR4-mediated disease is human
  immunodeficiency virus infection, acquired immunodefi-
  ciency syndrome, cancer, cancer metastasis, rheumatoid arthritis, arthritis, pulmonary fibrosis or transplanted organ rejection, or the agent for regeneration therapy is an agent for transplantation medical treatment;

[24] The pharmaceutical composition according to the above [23], wherein the CXCR4-mediated disease is human immunodeficiency virus infection;

[25] A pharmaceutical composition comprising the compound represented by formula (I) described in the above [1], a salt thereof, an N-oxide thereof or a solvate thereof, or a prodrug thereof, and one or more kinds selected from reverse transcriptase inhibitor, protease inhibitor, CCR2 antagonist, CCR3 antagonist, CCR4 antagonist, CCR5 antagonist, HIV integrase inhibitor, fusion inhibitor, CD4 antagonist, antibody against surface antigen of HIV, and vaccine of HIV;

[26] A method for antagonizing CXCR4 in a mammal, which comprises administering an effective amount of the compound represented by formula (I) described in the above [1], a salt thereof, an N-oxide thereof or a solvate thereof, or a prodrug thereof to the mammal;

[27] A method of preventing and/or treating a CXCR4-mediated disease in a mammal, which comprises administering an effective amount of the compound represented by formula (I) described in the above [1], a salt thereof, an N-oxide thereof or a solvate thereof, or a prodrug thereof to the mammal;

[28] Use of the compound represented by formula (I) described in the above [1], a salt thereof, an N-oxide thereof or a solvate thereof or a prodrug thereof for producing a CXCR4 antagonist;

[29] Use of the compound represented by formula (I) described in the above [1], a salt thereof, an N-oxide thereof or a solvate thereof or a prodrug thereof for producing an agent for preventing and/or treating a CXCR4-mediated disease; and

[30] A process for the preparation of the compound represented by formula (I) described in the above [1], a salt thereof, an N-oxide thereof or a solvate thereof or a prodrug thereof.

BEST MODE FOR CARRYING OUT THE INVENTION

In the present specification, a "basic nitrogen atom" in the "at least three basic nitrogen atoms" represents a basic nitrogen atom which pKa value calculated with ACD/pKaDB of Advanced Chemistry Development Company (version 6) showed the value of 6 or more over.

For example,

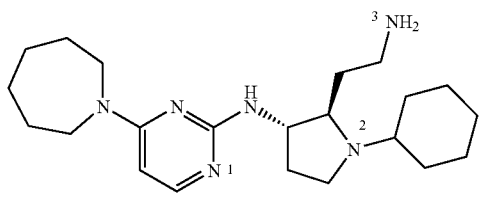 [SMILES: NCC[C@@H]1[C@@H](Nc2nccc(N3CCCCCC3)n2)CCN1C1CCCCC1]

The pKa value of nitrogen atom 1, nitrogen atom 2 and nitrogen atom 3 in the formula represents respectively 8.48, 9.23 and 10.48.

In the present specification, the "hydrocarbon group" in the "hydrocarbon group which may have a substituent(s)" includes, for example, linear or branched aliphatic hydrocarbon group, etc.

The "linear or branched aliphatic hydrocarbon group" includes, for example, "C1-8 aliphatic hydrocarbon group" etc. and the "C1-8 aliphatic hydrocarbon group" includes, for example, C1-8 alkyl such as methyl, ethyl, propyl, isopropyl, butyl, sec-butyl, tert-butyl, pentyl, hexyl, heptyl, octyl etc.; C2-8 alkenyl such as vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl, etc.; C2-8 alkynyl such as ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl etc.

In the present specification, the "cyclic group" in the "cyclic group which may have a substituent(s)" includes, for example, carbocyclic ring or heterocyclic ring.

The "carbocyclic ring" includes "unsaturated carbocyclic ring" or "saturated carbocyclic ring". The "saturated carbocyclic ring" includes, for example, cycloalkane such as cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane ring etc.; "3- to 15-membered saturated carbocyclic ring" such as perhydropentalene, perhydroazulene, perhydroindene, perhydronaphthalene, perhydroheptalene, spiro[4.4]nonane, spiro[4.5]decane, spiro[5.5]undecane, spiro[3.4]octane, spiro[3.5]nonane, bicyclo[2.2.1]heptane, bicyclo[3.1.1]heptane, bicyclo[2.2.2]octane, adamantane, noradamantane, bicyclo[2.2.1]hepta-2-ene, bicyclo[3.1.1]hepta-2-ene, bicyclo[3.2.1]octane, bicyclo[2.2.2]octa-2-ene, bicyclo[2.1.1]hexane, bicyclo[3.3.1]nonane, bicyclo[3.2.1]octane, bicyclo[3.3.2]decane ring etc. The "unsaturated carbocyclic ring" includes, for example, cycloalkene such as cyclopentene, cyclohexene, cycloheptene, cyclooctene, cyclopentadiene, cyclohexadiene, cycloheptadiene or cyclooctadiene ring etc; aromatic carbocyclic ring such as benzene, azulene, naphthalene, phenanthrene, anthracene ring etc; "3- to 15-membered unsaturated carbocyclic ring" such as pentalene, indene, indan, dihydronaphthalene, tetrahydronaphthalene, heptalene, biphenylene, as-indacene, s-indacene, acenaphthene, acenaphthylene, fluorene, phenalene, bicyclo[2.2.1]hept-2-ene, bicyclo[3.1.1]hept-2-ene, bicyclo[2.2.2]oct-2-ene ring etc.

The "heterocyclic ring" includes, for example, 3- to 15-membered monocyclic or polycyclic heterocyclic ring having, as a hetero atom, 1 to 4 nitrogen atom(s), 1 to 2 oxygen atom(s) and/or 1 to 2 sulfur atom(s). The "3- to 15-membered monocyclic or polycyclic heterocyclic ring" as used herein, includes, for example, "3- to 15-membered monocyclic or polycyclic unsaturated heterocyclic ring" or "3- to 15-membered monocyclic or polycyclic saturated heterocyclic ring" etc.

The "3- to 15-membered monocyclic or polycyclic unsaturated heterocyclic ring having, as a hetero atom, 1 to 4 nitrogen atom(s), 1 to 2 oxygen atom(s) and/or 1 to 2 sulfur atom(s)" includes, for example, monocyclic aromatic heterocyclic ring such as pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole, thiadiazole ring etc; polycyclic aromatic heterocyclic ring such as indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, beta-carboline, acridine, phenazine, dibenzofuran, dibenzothiophene, phenanthridine, phenanthroline, perimidine ring etc; unsaturated nonaromatic heterocyclic ring such as azepine, diazepine, pyran, oxepine, thiopyran, thiepine, oxazine, oxadiazine, oxazepine, oxadiazepine, thiazine, thiadiazine, thiazepine, thiadiazepine, indolizine, dithianaphthalene, quinolizine, chromene, benzoxepine, benzoxazepine, benzoxadiazepine, benzothiepine, benzothiazepine, benzothiadiazepine, benzoazepine, benzodiazepine, xanthene, phenothiazine, phenoxazine, phenoxathiin, thianthrene, pyrroline, imidazoline, 2,3-dihydro-1H-pyrazole, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydro isoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzoazepin, dihydrobenzodiazepine, tetrahydrobenzodiazepine, benzodioxepane, dihydrobenzoxazepine, tetrahydrobenzoxazepine, dihydrocarbazole, tetrahydrocarbazole, dihydro-beta-carboline, tetrahydro-beta-carboline, dihydroacridine, tetrahydroacridine, dihydrodibenzofuran, dihydrodibenzothiophene, tetrahydrodibenzofuran, tetrahydrodibenzothiophene, dioxaindane, benzodioxane, chroman, benzodithiolane, benzodithiane ring etc. Additionally, the "3- to 15-membered monocyclic or polycyclic saturated heterocyclic ring having, as a hetero atom, 1 to 4 nitrogen atom(s), 1 to 2 oxygen atom(s) and/or 1 to 2 sulfur atom(s)" includes, for example, aziridine, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, oxirane, oxetane, tetrahydrofuran, tetrahydropyran, perhydrooxepine, thiirane, thietane, tetrahydrothiophene, tetrahydrothiopyran, perhydrothiepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydro carbazole, perhydro-beta-carboline, perhydroacridine, perhydrodibenzofuran, perhydrodibenzothiophene, dioxolane, dioxane, dithiolane, dithiane ring etc; spiro-bound polycyclic heterocyclic ring such as azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane ring etc; bridged polycyclic heterocyclic ring such as azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, 3,7-diazabicyclo[3.3.1]nonane ring etc.

The "substituent" in the "hydrocarbon group which may have a substituent(s)" and "cyclic group which may have a substituent(s)" described above includes 1 to 5 of substituents selected from primary group (1) to (39) described below, if the number of substituents is two or more, each substituent may be same or different;

The primary group:
(1) hydrocarbon group which may have a substituent(s) (the "hydrocarbon group" has the same meaning as the "hydrocarbon group" in the "hydrocarbon group which may have a substituent(s)" described above), (2) carbocyclic ring group which may have a substituent(s) (the "carbocyclic ring" has the same meaning as the "carbocyclic ring" in the "cyclic ring" in the "cyclic ring which may have a substituent(s)" described above), (3) heterocyclic ring which may have a substituent(s) (the "heterocyclic ring" has the same meaning as the "heterocyclic ring" in the "cyclic ring" in the "cyclic ring which may have a substituent(s)" described above), (4) amino group, (5) C1-10 acylamino which may have a substituent(s), (6) secondary or tertiary amine substituted by substituent(s) (e.g. methylamino, ethylamino, n-propylamino, isopropylamino, n-butylamino, dimethylamino, diethylamino, cyclohexylamino, 1-carbamoyl-2-cyclohexylethylamino, N-butyl-N-cyclohexylmethylamino or phenylamino etc.), (7) C1-8 alkylsulfonylamino group which may have a substituent(s), C2-8 alkynylsulfonylamino group which may have a substituent(s) or C2-8 alkenylsulfonylamino group which may have a substituent(s), (8) phenylsulfonylamino group which may have a substituent(s), (9) C1-8 alkylsulfonyl group which may have a substituent(s), C2-8 alkynylsulfonyl group which may have a substituent(s) or C2-8 alkenylsulfonyl group which may have a substituent(s), (10) phenylsulfonyl group which may have a substituent(s), (11) halogen atom (fluorine, chlorine, bromine or iodine), (12) carboxyl group, (13) cyano group, (14) nitro group, (15) oxo group, (16) thioxo group, (17) hydroxy group, (18) C1-8 alkoxy group which may have a substituent(s), C2-8 alkynyloxy group which may have a substituent(s) or C2-8 alkenyloxy group which may have a substituent(s), (19) C3-8 cycloalkoxy group which may have a substituent(s), (20) phenoxy group which may have a substituent(s), (21) mercapto group, (22) C1-8 alkylthio group which may have a substituent(s), C2-8 alkynylthio group which may have a substituent(s) or C2-8 alkenylthio group which may have a substituent(s) (e.g. methylthio, ethylthio, propylthio, isopropylthio, butylthio, isobutylthio, tert-butylthio, pentylthio, hexylthio, heptylthio, octylthio, propenylthio, butenylthio, pentenylthio, hexenylthio, propynylthio, butynylthio, pentynylthio, hexynylthio etc.), (23) phenylthio group which may have a substituent(s) (e.g. 4-chlorophenylthio, phenylthio etc.), (24) carbamoyl group, (25) aminocarbonyl group substituted by substituent(s) (e.g. N-butylaminocarbonyl, N-cyclohexylmethylaminocarbonyl, N-butyl-N-cyclohexylmethylaminocarbonyl, N-cyclohexylaminocarbonyl, phenylaminocarbonyl etc.), (26) sulfamoyl group, (27) aminosulfonyl group substituted by substituent(s) (e.g. methylaminosulfonyl etc.), (28) C1-8 alkoxycarbonyl group which may have a substituent(s), C2-8 alkynyloxycarbonyl group which may have a substituent(s) or C2-8 alkenyloxycarbonyl group which may have a substituent(s) (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, heptyloxycarbonyl, octyloxycarbonyl etc.), (29) sulfo group (—SO₃H), (30) sulfino group, (31) phosphono group, (32) amidino group, (33) imino group, (34) —B(OH)₂ group, (35) C1-8 alkylsulfinyl group which may have a substituent(s), (36) C1-10 acyl group which may have a substituent(s), (37) hydroxyimino group, (38) C1-8 alkyloxyimino group (e.g. methyloxyimino, ethyloxyimino etc.), (39) basic group.

The "substituent" represented by (1) to (3), (5), (7) to (10), (18) to (20), (22), (23), (28), (35) and (36) in the primary group described above includes, for example, the C1-8 aliphatic hydrocarbon group (the "C1-8 aliphatic hydrocarbon group" has the same meaning as the "C1-8 aliphatic hydrocarbon group" in the "hydrocarbon group which may have a substituent(s)" described above.) which may have a substituent(s) (e.g. amino group, halogen atom, hydroxy group, methoxy group, trifluoromethyl group, trifluoromethoxy group, acetyloxy group, carbamoyl group etc.), the cyclic group (the "cyclic group" has the same meaning as the "cyclic group" in the "cyclic group which may have a substituent(s)" described above.) which may have a substituent(s) (e.g. amino group, halogen atom, hydroxy group, methoxy group, trifluoromethyl group, trifluoromethoxy group, acetyloxy group, carbamoyl group etc.), amino group, dimethylamino group, sulfo group, halogen atom, carboxyl group, cyano group, nitro group, oxo group, thioxo group, hydroxy group, methoxy group, acetyl group, methoxycarbonyl group, trifluoromethyl group, trifluoromethoxy etc. and these substituent(s) may be substituted on the substitutable position and the number of substituents may be from 1 to 5, if the number of substituents is two or more, each substituent may be same or different. The "halogen atom" as used herein, has the same meaning as (11) in the primary group described above.

The "C1-10 acylamino group" represented by (5) in the primary group described above includes, for example, acethylamino, propionylamino, propanoylamino, isopropanoylamino, butanoylamino, isobutanoylamino, tert-butanoylamino, pentanoylamino, hexanoylamino, heptanoylamino, octanoylamino, propenoylamino, butenoylamino, pentenoylamino, hexenoylamino, propinoylamino, butynoylamino, pentynoylamino, hexynoylamino etc.

The "C1-8 alkylsulfonylamino group", "C2-8 alkynylsulfonylamino group" and "C2-8 alkenylsulfonylamino group" represented by (7) in the primary group described above includes, for example, methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, heptylsulfonyl, octylsulfonyl, propenylsulfonyl, butenylsulfonyl, pentenylsulfonyl, hexenylsulfonyl, propynylsulfonyl, butynylsulfonyl, pentynylsulfonyl, hexynylsulfonyl etc.

The "C1-8 alkylsulfonyl group", "C2-8 alkynylsulfonyl group" and "C2-8 alkenylsulfonyl group" represented by (9) in the primary group described above includes, for example, methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, heptylsulfonyl, octylsulfonyl, propenylsulfonyl, butenylsulfonyl, pentenylsulfonyl, hexenylsulfonyl, propynylsulfonyl, butynylsulfonyl, pentynylsulfonyl, hexynylsulfonyl etc.

The "C1-8 alkoxy", "C2-8 alkynyloxy" and "C2-8 alkenyloxy" represented by (18) and (28) in the primary group described above includes, for example, methoxy, ethoxy, propoxy, isopropoxy, butoxy, isobutoxy, tert-butoxy, pentyloxy, hexyloxy, heptyloxy, octyloxy, propenyloxy, butenyloxy, pentenyloxy, hexenyloxy, propynyloxy, butynyloxy, pentynyloxy, hexynyloxy, sec-butoxy, cyclohexylmethyloxy, 2-propenyloxy etc.

The "C3-8 cycloalkoxy group" represented by (19) in the primary group described above includes, for example, cyclopropyloxy, cyclobutyloxy, cyclopentyloxy, cyclohexyloxy, cycloheptyloxy, cyclooctyloxy etc.

The "substituent" represented by (6), (25) and (27) in the primary group described above includes, for example, the substituent represented by (1), (2), (3) and (24) in the primary group described above, these substituent(s) may be substituted by one or two hydrogen atom(s) of amino group. If the number of substituents is two, each substituent may be same or different.

The "C1-10 acyl" represented by (5) and (36) in the primary group described above includes, for example, C1-8 alkanoyl such as formyl, acetyl, propanoyl, butanoyl, pentanoyl, hexanoyl, heptanoyl, octanoyl, pivaloyl etc; C6-10 aromatic carbocyclic ring carbonyl such as benzoyl, phenylmethylcarbonyl, 2-phenylethylcarbonyl etc.

The "C1-8 alkyl" represented by (35) and (38) in the primary group described above have the same meaning as the "C1-8 alkyl group" in the "C1-8 aliphatic hydrocarbon group" in the "hydrocarbon group which may have a substituent(s)" described above.

The "C1-8 alkyl", "C2-8 alkynyl" and "C2-8 alkenyl" represented by (7), (9) and (22) in the primary group described have the same meaning as the "C1-8 alkyl group", "C2-8 alkynyl group" and "C2-8 alkenyl group" in the "C1-8 aliphatic hydrocarbon group" in the "hydrocarbon group which may have a substituent(s)" described above.

The "basic group" represented by (39) in the primary group described above includes, for example, (a) amino group, (b)

amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing heterocyclic ring which may have a substituent(s).

The "substituent" in the "mono- or di-substituted amino group" represented by (e) described above includes, for example, the substituent represented by (1) to (38) in the primary group described above etc. These arbitrary substituent(s) may be substituted on the substitutable position and the number of substituents may be from 1 to 2, if the number of substituents is two or more, each substituent may be same or different. The "mono- or di-substituted amino group" includes, for example, methylamino, ethylamino, propylamino, isopropylamino, butylamino, isobutylamino, tert-butylamino, pentylamino, hexylamino, heptylamino, octylamino, dimethylamino, diethylamino, dipropylamino, dibutylamino, dipentylamino, dihexylamino, diheptylamino, dioctylamino, N-methyl-N-ethylamino, cyclopropylamino, cyclopentylamino, cyclohexylamino, phenylamino, diphenylamino, dibenzylamino, N-phenyl-N-methylamino, N-phenyl-N-ethylamino, N-benzyl-N-methylamino, N-benzyl-N-ethylamino, N-benzyl-N-cyclohexylamino, N-cyclohexyl-N-propylamino, N-cyclohexyl-N-(3-hydroxypropyl)amino, N-(4-hydroxycyclohexyl)-N-propylamino, N-(4-hydroxycyclohexyl)-N-(3-hydroxypropyl)amino, N-(4-hydroxycyclohexyl)methyl-N-propylamino, N-cyclohexyl-N-acetylamino, N-(3-methoxypropyl)-N-propylamino, N-(2-carboxyethyl)-N-propylamino, N-(2-ethylpropyl)-N-propylamino, N-cyclohexyl-N-(methylsulfonyl)amino, N-(tetrahydropyran-4-yl)-N-propylamino, and N-(indan-2-yl)-N-propylamino etc.

The "substituent" in the "mono-, di- or tri-substituted amidino group" represented by (f) described above includes, for example, the substituent represented by (1) to (38) in the primary group described above etc. These arbitrary substituent(s) may be substituted on the substitutable position and the number of substituents may be from 1 to 3, if the number of substituents is two or more, each substituent may be same or different. The "mono-, di- or tri-substituted amidino group" includes, for example, methylamidino, ethylamidino, propylamidino, isopropylamidino, butylamidino, isobutylamidino, tert-butylamidino, pentylamidino, hexylamidino, heptylamidino, octylamidino, N,N-dimethylamidino, N,N'-dimethylamidino, N,N,N'-trimethylamidino, N,N-diethylamidino, N,N'-diethylamidino, N,N,N'-triethylamidino, N,N-dipropylamidino, N,N'-dipropylamidino, N,N,N'-tripropylamidino, N,N-dibutylamidino, N,N'-dibutylamidino, N,N,N'-tributylamidino, N,N-dipentylamidino, N,N'-dipentylamidino, N,N,N'-tripentylamidino, N,N-dihexylamidino, N,N'-dihexylamidino, N,N,N'-trihexylamidino, N,N-diheptylamidino, N,N'-diheptylamidino, N,N,N'-triheptylamidino, N,N-dioctylamidino, N,N'-dioctylamidino, N,N,N'-trioctylamidino, N-methyl-N-ethylamidino, N-methyl-N'-ethylamidino, cyclopropylamidino, cyclopentylamidino, cyclohexylamidino, phenylamidino, N,N-diphenylamidino, N,N'-diphenylamidino, N,N,N'-triphenylamidino, N,N-dibenzylamidino, N,N'-dibenzylamidino, N,N,N'-tribenzylamidino, N-phenyl-N'-methylamidino, N-phenyl-N'-ethylamidino, N-benzyl-N-methylamidino, N-benzyl-N-ethylamidino etc.

The "substituent" in the "mono-, di-, tri- or tetra-substituted guanidino group" represented by (g) described above includes, for example, the substituent represented by (1) to (38) in the primary group described above etc. These arbitrary substituent(s) may be substituted on the substitutable position and the number of substituents may be from 1 to 3, if the number of substituents is two or more, each substituent may be same or different. The "mono-, di-, tri- or tetra-substituted guanidino group" includes, for example, methylguanidino, ethylguanidino, propylguanidino, isopropylguanidino, butylguanidino, isobutylguanidino, tert-butylguanidino, pentylguanidino, hexylguanidino, heptylguanidino, octylguanidino, N,N-dimethylguanidino, N,N'-dimethylguanidino, N,N,N'-trimethylguanidino, N,N,N',N''-tetramethylguanidino, N,N-diethylguanidino, N,N'-diethylguanidino, N,N,N'-triethylguanidino, N,N,N',N''-tetraethylguanidino, N,N-dipropylguanidino, N,N'-dipropylguanidino, N,N,N'-tripropylguanidino, N,N,N',N''-tetrapropylguanidino, N,N-dibutylguanidino, N,N'-dibutylguanidino, N,N,N'-tributylguanidino, N,N,N',N''-tetrabutylguanidino, N,N-dipentylguanidino, N,N'-dipentylguanidino, N,N,N'-tripentylguanidino, N,N,N',N''-tetrapentylguanidino, N,N-dihexylguanidino, N,N'-dihexylguanidino, N,N,N'-trihexylguanidino, N,N,N',N''-tetrahexylguanidino, N,N-diheptylguanidino, N,N'-diheptylguanidino, N,N,N'-triheptylguanidino, N,N,N',N''-tetraheptylguanidino, N,N-dioctylguanidino, N,N'-dioctylguanidino, N,N,N'-trioctylguanidino, N,N,N',N''-tetraoctylguanidino, N-methyl-N-ethylguanidino, N-methyl-N'-ethylguanidino, cyclopropylguanidino, cyclopentylguanidino, cyclohexylguanidino, phenylguanidino, N,N-diphenylguanidino, N,N'-diphenylguanidino, N,N,N'-triphenylguanidino, N,N,N',N''-tetraphenylguanidino, N,N-dibenzylguanidino, N,N'-dibenzylguanidino, N,N,N'-tribenzylguanidino, N,N,N',N''-tetrabenzylguanidino, N-phenyl-N'-methylguanidino, N-phenyl-N'-ethylguanidino, N-benzyl-N-methylguanidino, N-benzyl-N-ethylguanidino etc.

The "substituent" in the "mono-, di- or tri-substituted hydrazino group" represented by (h) described above includes, for example, the substituent represented by (1) to (38) in the primary group described above etc. These arbitrary substituent(s) may be substituted on the substitutable position and the number of substituents may be from 1 to 3, if the number of substituents is two or more, each substituent may be same or different. The "mono-, di- or tri-substituted hydrazino group" includes, for example, methylhydrazino, ethylhydrazino, propylhydrazino, isopropylhydrazino, butylhydrazino, isobutylhydrazino, tert-butylhydrazino, pentylhydrazino, hexylhydrazino, heptylhydrazino, octylhydrazino, N,N-dimethylhydrazino, N,N'-dimethylhydrazino, N,N,N'-trimethylhydrazino, N,N-diethylhydrazino, N,N'-diethylhydrazino, N,N,N'-triethylhydrazino, N,N-dipropylhydrazino, N,N'-dipropylhydrazino, N,N,N'-tripropylhydrazino, N,N-dibutylhydrazino, N,N'-dibutylhydrazino, N,N,N'-tributylhydrazino, N,N-dipentylhydrazino, N,N'-dipentylhydrazino, N,N,N'-tripentylhydrazino, N,N-dihexylhydrazino, N,N'-dihexylhydrazino, N,N,N'-trihexylhydrazino, N,N-diheptylhydrazino, N,N'-diheptylhydrazino, N,N,N'-triheptylhydrazino, N,N-dioctylhydrazino, N,N'-dioctylhydrazino, N,N,N'-trioctylhydrazino, N-methyl-N-ethylhydrazino, N-methyl-N'-ethylhydrazino, cyclopropylhydrazino, cyclopentylhydrazino, cyclohexylhydrazino, phenylhydrazino, N,N-diphenylhydrazino, N,N'-diphenylhydrazino, N,N,N'-triphenylhydrazino, N,N-dibenzylhydrazino, N,N'-dibenzylhydrazino, N,N,N'-tribenzylhydrazino, N-phenyl-N'-methylhydrazino, N-phenyl-N'-ethylhydrazino, N-benzyl-N-methylhydrazino, N-benzyl-N-ethylhydrazino etc.

The "nitrogen-containing heterocyclic ring" in the "nitrogen-containing heterocyclic ring which may have a substituent(s)" represented by (i) described above includes, for example, "3- to 15-membered monocyclic or condensed heterocyclic ring which has at least one nitrogen atom", "bridged heterocyclic ring" and "spiro-bound heterocyclic ring", pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydro quinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane ring etc.

The "substituent" in the "nitrogen-containing heterocyclic ring which may have a substituent(s)" represented by (i) described above includes, for example, the substituent represented by (1) to (38) in the primary group described above etc. These arbitrary substituent(s) may be substituted on the arbitrary substitutable position in arbitrary substitutable number. The number of substituents is preferably from 1 to 8, and more preferably from 1 to 5. If the number of substituents is two or more, each substituent may be same or different.

The "5- to 10-membered nitrogen-containing heterocyclic ring" represented by ring A represents monocyclic or polycyclic heterocyclic ring which may have one to five hetero atom(s) selected from nitrogen atom, oxygen atom and sulfur atom, except the described nitrogen atom. The "5- to 10-membered nitrogen-containing heterocyclic ring" includes, for example, "5- to 10-membered nitrogen-containing unsaturated heterocyclic ring" or "5- to 10-membered nitrogen-containing saturated heterocyclic ring".

The "5- to 10-membered nitrogen-containing unsaturated heterocyclic ring" includes, for example, 5- to 8-membered nitrogen-containing unsaturated monocyclic heterocyclic ring such as pyrrole, imidazole, triazole, tetrazole, pyrazole, azepin, diazepin, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydro furazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine ring etc; 5- to 10-membered nitrogen-containing unsaturated polycyclic heterocyclic ring such as indole, isoindole, indazole, purine, benzimidazole, benzoxazepine, benzodiazepine, benzotriazole, indoline, isoindoline, dihydro indazole, dihydro quinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole ring etc. Additionally, the "5- to 10-membered nitrogen-containing saturated heterocyclic ring" includes, for example, 5- to 8-membered nitrogen-containing saturated monocyclic heterocyclic ring such as pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine ring etc; 5- to 10-membered nitrogen-containing saturated polycyclic heterocyclic ring such as perhydroindazole, perhydroquinoline, perhydroisoquinoline, perhydrophthalazine, perhydronaphthyridine, perhydroquinoxaline, perhydroquinazoline, perhydro cinnoline, perhydrobenzoxazole, perhydrobenzothiazole, perhydrobenzimidazole ring etc.

The ring A is preferably, for example, the 5- to 8-membered nitrogen-containing monocyclic heterocyclic ring, and more preferably the 5- to 8-membered nitrogen-containing saturated monocyclic heterocyclic ring, and particularly preferably, for example, perhydroazepine ring and the like.

The ring A may have one to five substituent(s) on the substitutable position, if the number of substituents is two or more, each substituent may be same or different. The substituent(s) includes the substituent(s) of the primary group described above.

The "5- to 15-membered nitrogen-containing unsaturated heterocyclic ring" represented by ring B represents monocyclic or polycyclic heterocyclic ring which may have one to five hetero atom(s) selected from nitrogen atom, oxygen atom and sulfur atom, except the described nitrogen atom. The "5- to 15-membered nitrogen-containing unsaturated heterocyclic ring" includes, for example, 5- to 8-membered nitrogen-containing unsaturated monocyclic heterocyclic ring such as pyrrole, imidazole, triazole, tetrazole, pyrazole, pyridine, pyrazine, pyrimidine, pyridazine, triazine, azepin, diazepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine ring etc; or 5- to 15-membered nitrogen-containing unsaturated polycyclic heterocyclic ring such as indole, isoindole, indazole, quinoline, isoquinoline, purine, phthalazine, pteridine, naphthyridine, quinoxaline, quinazoline, cinnoline, benzoxazole, benzothiazole, benzimidazole, benzoxazepine, benzoxadiazepine, benzothiazepine, benzothiadiazepine, benzoazepine, benzodiazepine, beta-carboline, phenanthridine, phenanthroline, perimidine, dihydroindazole, dihydroquinoline, tetrahydro quinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, dihydrobenzoazepine, tetrahydrobenzoazepine, dihydrobenzodiazepine, tetrahydrobenzodiazepine, dihydrobenzoxazepine, tetrahydrobenzoxazepine, dihydro-beta-carboline, tetrahydro-beta-carboline ring etc.

The ring B is preferably, for example, the 5- to 8-membered nitrogen-containing unsaturated monocyclic heterocyclic ring, and more preferably the 5- or 6-membered nitrogen-containing unsaturated monocyclic heterocyclic ring, and particularly preferably, for example, pyridine, pyrimidine ring and the like.

The ring B may have one to five substituent(s) on the substitutable position, if the number of substituents is two or more, each substituent may be same or different. The substituent(s) includes the substituent(s) of the primary group described above.

The "substituent" in the "pyridine or pyrimidine which may have a further substituent(s)" represented by ring $B^1$ is not specifically limited. It includes, for example, the substituent represented by the primary group described above; the ring $B^1$ may be substituted by one to five of this "substituent", and preferably one to two on the substitutable position. If the number of substituents is two or more, each substituent may be same or different.

The "4- to 15-membered nitrogen-containing heterocyclic ring" represented by ring D represents monocyclic or polycyclic heterocyclic ring which may have one to five hetero atom(s) selected from nitrogen atom, oxygen atom and sulfur atom, except the described nitrogen atom. The "4- to 15-membered nitrogen-containing heterocyclic ring" includes, for example, "4- to 15-membered nitrogen-containing unsaturated heterocyclic ring" or "4- to 15-membered nitrogen-containing saturated heterocyclic ring".

The "4- to 15-membered nitrogen-containing unsaturated heterocyclic ring" includes, for example, 4- to 8-membered nitrogen-containing unsaturated monocyclic heterocyclic ring such as pyrrole, imidazole, triazole, tetrazole, pyrazole, azepin, diazepin, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine ring etc; 4- to 15-membered nitrogen-containing unsaturated polycyclic heterocyclic ring such as indole, isoindole, indazole, purine, benzimidazole, benzoxazepine, benzoxadiazepine, benzotriazole, carbazole, beta-carboline, phenothiazine, phenoxazine, perimidine, indoline, isoindoline, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzoazepin, dihydrobenzodiazepine, tetrahydrobenzodiazepine, dihydrobenzoxazepine, tetrahydrobenzoxazepine, dihydrocarbazole, tetrahydrocarbazole, dihydroacridine, tetrahydroacridine ring etc. Additionally, the "4- to 15-membered nitrogen-containing saturated heterocyclic ring" includes, for example, 4- to 8-membered nitrogen-containing saturated monocyclic heterocyclic ring such as azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine ring etc; or 4- to 15-membered nitrogen-containing saturated polycyclic heterocyclic ring such as perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydro acridine, perhydroindole, perhydroisoindole, perhydro-beta-carboline, perhydrophenazine, perhydrophenothiazine, perhydrophenoxazine, perhydrophenanthridine, perhydrophenanthroline, perhydroperimidine, azabicyclo[3.2.2]nonane, azabicyclo[3.3.2]decane, azabicyclo[2.2.2]octane, azabicyclo[3.3.3]undecane, azabicyclo[4.3.3]dodecane, azabicyclo[4.4.3]tridecane, azabicyclo[4.4.4]tetradecane ring etc.

The ring D is preferably, for example, the 4- to 8-membered nitrogen-containing monocyclic heterocyclic ring, and more preferably the 4- or 8-membered nitrogen-containing saturated monocyclic heterocyclic ring, and particularly preferably, for example, azetidine, pyrrolidine, piperidine, perhydroazepine or perhydroazocine ring and the like.

The ring D may have one to five substituent(s) on the substitutable position, if the number of substituents is two or more, each substituent may be same or different. The substituent(s) includes the substituent(s) of the primary group described above.

Additionally, $R^2$ and the substituent of the ring D may be taken together to form nitrogen-containing heterocyclic ring. The "nitrogen-containing heterocyclic ring" includes, for example, 5- to 8-membered nitrogen-containing monocyclic heterocyclic ring etc. The "5- to 8-membered nitrogen-containing monocyclic heterocyclic ring" includes, for example, the "5- to 8-membered nitrogen-containing unsaturated monocyclic heterocyclic ring" and the "5- to 8-membered nitrogen-containing saturated monocyclic heterocyclic ring" represented by ring A described above.

The "4- to 8-membered nitrogen-containing saturated monocyclic heterocyclic ring" in the "4- to 8-membered nitrogen-containing saturated monocyclic heterocyclic ring which may have a further substituent(s)" represented by ring $D^1$ have the same meaning as the "4- to 8-membered nitrogen-containing saturated monocyclic heterocyclic ring" in the "4- to 15-membered nitrogen-containing saturated heterocyclic ring" represented by ring D described above.

The "substituent" in the "4- to 8-membered nitrogen-containing saturated monocyclic heterocyclic ring which may have a further substituent(s)" represented by ring $D^1$ is not specifically limited. It includes, for example, the substituent represented by the primary group described above; the ring $D^1$ may be substituted by one to five of this "substituent", and preferably one to two on the substitutable position. If the number of substituents is two or more, each substituent may be same or different.

The "5- to 8-membered nitrogen-containing monocyclic heterocyclic ring" in the "5- to 8-membered nitrogen-containing monocyclic heterocyclic ring which may have a further substituent(s)" represented by ring E includes the "5- to 8-membered nitrogen-containing unsaturated monocyclic heterocyclic ring" and the "5- to 8-membered nitrogen-containing saturated monocyclic heterocyclic ring" represented by ring A described above.

The "substiutent" in the "5- to 8-membered nitrogen-containing monocyclic heterocyclic ring which may have a further substituent(s)" represented by ring E is not specifically limited. It includes, for example, the substituent represented by the primary group described above; the ring E may be substituted by one to five of this "substituent", and preferably one to two on the substitutable position. If the number of substituents is two or more, each substituent may be same or different.

A "spacer having a main chain of 1 to 8 atom(s)" represented by Y represents the space wherein 1 to 8 atom(s) of the main chain are arranged in a line. "Number of atoms of main chain" as used herein, is counted so that the number of atoms of the main chain is minimized. For example, it is counted that the number of atoms of 1,2-cyclopentylene is 2 and the number of atoms of 1,3-cyclopentylene is 3. The "spacer having a main chain of 1 to 8 atom(s)" include, for example, a bivalent group comprising 1 to 8 selected from a bivalent hydrocarbon group which may have a substituent(s), nitrogen atom (—NH—) which may have a substituent(s), —CO—, —O—, —S—, —SO—, —$SO_2$—, -(carbocyclic ring which may have a substituent(s))- and -(heterocyclic ring which may have a substituent(s))-. The "bivalent hydrocarbon group" as used herein, includes, for example, C1-8 alkylene group (e.g. methylene, ethylene, propylene, butylene, pentylene, hexylene, heptylene, octylene etc.), C2-8 alkenylene group (e.g. ethenylene, propenylene, butenylene, butadienylene, pentenylene, pentadienylene, hexenylene, hexadienylene, heptenylene, heptadienylene, octenylene, octadienylene etc.) and C2-8 alkynylene group (e.g. ethynylene, propynylene, butynylene, butadienylene, pentynylene, pentadienylene, hexynylene, hexadienylene, heptynylene, heptadienylene, octynylene, octadienylene etc.). The "carbocyclic ring" and the "heterocyclic ring" have the same meaning as the "carbocyclic ring" and the "heterocyclic ring" described above, respectively. The "substituent" in the "bivalent hydrocarbon group which may have a substituent(s)", the "carbocyclic ring which may have a substituent(s)" and the "heterocyclic ring which may have a substituent(s)" includes, for example, the substituent represented by the primary group described above. The "substituent" in the nitrogen atom which may have a substituent(s) includes (1) the hydrocarbon group which may have a substituent(s), (2) the carbocyclic ring which may have a substituent(s) or (3) the heterocyclic ring which may have a substituent(s) described above etc.

The "substituent" in the "spacer having a main chain of 1 to 8 atom(s)" represented by Y may be taken together with the nitrogen atom to which $R^2$ and $R^3$ are attached to form a nitrogen-containing heterocyclic ring. The "nitrogen-containing heterocyclic ring" includes, for example, 5- to 8-membered nitrogen-containing monocyclic heterocyclic ring etc. The "5- to 8-membered nitrogen-containing monocyclic heterocyclic ring" includes the "5- to 8-membered nitrogen-containing unsaturated monocyclic heterocyclic ring" or the "5- to 8-membered nitrogen-containing saturated monocyclic heterocyclic ring" represented by ring A described above.

Y is preferably, for example, a spacer having a main chain of 2 to 5 atoms, and more preferably C2-5 alkylene group which may have a substituent(s) (e.g. ethylene, propylene, butylene or pentylene).

The "spacer having a main chain of 1 to 5 atom(s)" represented by $Y^1$ includes a number of 1 to 5 atom(s) in the "spacer having a main chain of 1 to 8 atom(s)" represented by Y described above.

The "hydrocarbon group which may have a substituent(s)" and the "cyclic ring which may have a substituent(s)" represented by $R^1$, $R^2$ and $R^3$ have the same meaning as the "hydrocarbon group which may have a substituent(s)" and the "cyclic ring which may have a substituent(s)" described above, respectively.

$R^2$ and $R^3$ and each may be taken together with the nitrogen atom to which they are attached to form a nitrogen-containing heterocyclic ring which may have a substituent(s). The "nitrogen-containing heterocyclic ring" in the "nitrogen-containing heterocyclic ring which may have a substituent(s)" includes, for example, 5- to 8-membered nitrogen-containing monocyclic heterocyclic ring etc. The "5- to 8-membered nitrogen-containing monocyclic heterocyclic ring" includes, for example, the "5- to 8-membered nitrogen-containing unsaturated monocyclic heterocyclic ring" and the "5- to 8-membered nitrogen-containing saturated monocyclic heterocyclic ring" represented by ring A described above. The "substituent" in the "nitrogen-containing heterocyclic ring which may have a substituent(s)" is not specifically limited. It includes, for example, the substituent represented by the primary group described above; the ring may be substituted by one to five of this "substituent", and preferably one to two on the substitutable position. If the number of substituents is two or more, each substituent may be same or different.

The "monocyclic cyclic group" in the "monocyclic cyclic group which may have a substituent(s)" represented by $R^1$ and $R^{1.4}$ includes, for example, 3- to 8-membered monocyclic cyclic group etc. The "3- to 8-membered monocyclic cyclic group" as used herein, includes, for example, 3- to 8-membered monocyclic carbocyclic ring and 3- to 8-membered monocyclic heterocyclic ring etc. The "3- to 8-membered monocyclic carbocyclic ring" includes 3- to 8-membered unsaturated monocyclic carbocyclic ring and 3- to 8-membered monocyclic saturated carbocyclic ring etc. The "3- to 8-membered unsaturated monocyclic carbocyclic ring" includes, for example, cyclopentene, cyclohexene, cycloheptene, cyclooctene, cyclopentadiene, cyclohexadiene, cycloheptadiene, cyclooctadiene, benzene ring etc. Additionally, the "3- to 8-membered monocyclic saturated carbocyclic ring" includes, for example, cyclopropane, cyclobutane, cyclopentane, cyclohexane, cycloheptane, cyclooctane ring etc. Among these, the "3- to 8-membered monocyclic aromatic carbocyclic ring" includes, for example, benzene ring etc.

The "3- to 8-membered monocyclic heterocyclic ring" includes, for example, 3- to 8-membered monocyclic heterocyclic ring having, as a hetero atom, 1 to 4 nitrogen atom(s), 1 to 2 oxygen atom(s) and/or 1 to 2 sulfur atom(s) etc. The "3- to 8-membered monocyclic heterocyclic ring having, as a hetero atom, 1 to 4 nitrogen atom(s), 1 to 2 oxygen atom(s) and/or 1 to 2 sulfur atom(s)" as used herein, includes 3- to 8-membered unsaturated monocyclic heterocyclic ring or 3- to 8-membered saturated monocyclic heterocyclic ring having, as a hetero atom, 1 to 4 nitrogen atom(s), 1 to 2 oxygen atom(s) and/or 1 to 2 sulfur atom(s). The "3- to 8-membered unsaturated monocyclic heterocyclic ring having, as a hetero atom, 1 to 4 nitrogen atom(s), 1 to 2 oxygen atom(s) and/or 1 to 2 sulfur atom(s)" includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine ring etc. The "3- to 8-membered saturated monocyclic heterocyclic ring having, as a hetero atom, 1 to 4 nitrogen atom(s), 1 to 2 oxygen atom(s) and/or 1 to 2 sulfur atom(s)" includes, for example, aziridine, azetidine, pyrroline, pyrrolidine, imidazoline, imidazolidine, triazoline, triazolysine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, perhydrobenzofuran, dioxolane, dioxane, dithiolane, dithiane ring etc. Among these, the "3- to 8-membered monocyclic aromatic heterocyclic ring having, as a hetero atom, 1 to 4 nitrogen atom(s), 1 to 2 oxygen atom(s) and/or 1 to 2 sulfur atom(s)" includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole ring etc. As used herein, the "3- to 8-membered saturated monocyclic heterocyclic ring having, as a hetero atom, a nitrogen atom(s), an oxygen atom(s) or a sulfur atom(s)" includes, for example, aziridine, azetidine, pyrrolidine, piperidine, azepane, oxirane, oxetane, tetrahydrofuran, tetrahydropyran, oxepane, thiirane, thierane, tetrahydrothiophene, tetrahydrothiopyrane, thiepane ring etc. The "substituent" in the "monocyclic cyclic group which may have a substituent(s)" is not specifically limited. It includes, for example, the substituent represented by the primary group described above; the ring represented by $R^1$ and $R^{1A}$ may be substituted by one to five of this "substituent", and preferably one to two on the substitutable position. If the number of substituents is two or more, each substituent may be same or different.

The "C1-4 aliphatic hydrocarbon group" as the "substituent" in the "monocyclic cyclic group which may have a substituent(s)" represented by $R^1$ includes the C1-4 aliphatic hydrocarbon group in the "C1-8 aliphatic hydrocarbon group" in the "hydrocarbon group which may have a substituent(s)" described above.

The "hydrocarbon group which may have a substituent(s)" represented by $R^{1A}$ have the same meaning as the "hydrocarbon group which may have a substituent(s)" described above.

The "basic group" in the "hydrocarbon group which is substituted by a basic group, and may have a further substituent(s)" and the "cyclic group which is substituted by a basic group, and may have a further substituent(s)" represented by $R^{2A}$ have the same meaning as (39) in the primary group described above.

The "substituent" in the "hydrocarbon group which is substituted by a basic group, and may have a further substituent(s)" and the "cyclic group which is substituted by a basic group, and may have a further substituent(s)" represented by $R^{2A}$ includes the substituent represented by the primary group described above, the compound represented by $R^{2A}$ may be substituted by one to five of this "substituent", and preferably one to two on the substitutable position. If the number of substituents is two or more, each substituent may be same or different.

The "hydrocarbon group which may have a substituent(s)" in the "hydrocarbon group which is substituted by a basic group, and may have a further substituent(s)" represented by $R^{2A}$ have the same meaning as the "hydrocarbon group which may have a substituent(s)" described above.

The "cyclic group which may have a substituent(s)" in the "cyclic group which is substituted by a basic group, and may have a further substituent(s)" represented by $R^{2A}$ have the same meaning as the "cyclic group which may have a substituent(s)" described above.

The "5- to 8-membered nitrogen-containing monocyclic heterocyclic ring" represented by $R^{2A}$ includes the "5- to 8-membered nitrogen-containing unsaturated monocyclic heterocyclic ring" and the "5- to 8-membered nitrogen-containing saturated monocyclic heterocyclic ring" represented by ring A.

The "hydrocarbon group which may have a substituent(s)" and the "cyclic group which may have a substituent(s)" represented by $R^{3A}$ have the same meaning as the "hydrocarbon group which may have a substituent(s)" and the "cyclic group which may have a substituent(s)" described above, respectively.

The "hydrocarbon group which may have a substituent(s)" represented by $R^4$ have the same meaning as the "hydrocarbon group which may have a substituent(s)" described above. The "substituent" in the "nitrogen-containing heterocyclic ring which may have a substituent(s)" is not specifically limited. It includes, for example, the substituent represented by the primary group described above; the hydrocarbon group represented by $R^4$ may be substituted by one to five of this "substituent", and preferably one to two on the substitutable position. If the number of substituents is two or more, each substituent may be same or different.

$R^1$ is preferably, for example, a carbocyclic ring which may have a substituent(s) and the like, more preferably, for example, a 3- to 15-membered saturated carbocyclic ring and the like, and especially preferably, for example, cyclohexane, adamantane ring and the like.

The "monocyclic cyclic group" in the "monocyclic cyclic group which may have a substituent(s)" represented by $R^{1A}$ is preferably a 3- to 8-membered saturated monocyclic carbocyclic ring and a 3- to 8-membered saturated monocyclic heterocyclic ring. The saturated monocyclic heterocyclic ring is preferably a 3- to 8-membered saturated monocyclic heterocyclic ring having, as a hetero atom, a nitrogen atom(s), a sulfur atom(s) or an oxygen atom(s).

The "substituent" in the "monocyclic cyclic group which may have a substituent(s)" represented by $R^{1A}$ is preferably, a C1-4 aliphatic hydrocarbon group, amino group, a C1-10 acylamino group, a carboxyl group, an oxo group, a thioxo group, a hydroxy group, a C1-8 alkoxy group, a C3-8 cycloalkoxy group, a carbamoyl group or an aminocarbonyl group, and more preferably a C1-4 aliphatic hydrocarbon group or a hydroxy group. Additionally, the "monocyclic cyclic group which may have a substituent(s)" represented by $R^{1A}$ is also preferably non-substituted one.

The "substitutent" in the "hydrocarbon group which may have a substituent(s)" represented by $R^{1A}$ is preferably, an amino group, a C1-10 acylamino group, a carboxyl group, an oxo group, a thioxo group, a hydroxy group, a C1-8 alkoxy group, a C3-8 cycloalkoxy group, a carbamoyl group or an aminocarbonyl group, and more preferably a hydroxy group. Additionally, the "hydrocarbon group which may have a substituent(s)" represented by $R^{1A}$ is also preferably non-substituted one.

$R^2$ is preferably, for example, a hydrogen atom or a hydrocarbon group which may have a substituent(s), more preferably, a hydrogen atom or a C1-8 alkyl group and the like, and especially preferably, for example, a hydrogen atom or a methyl and the like.

$R^{2A}$ is preferably, a 5- to 7-membered nitrogen-containing monocyclic heterocyclic ring, a hydrocarbon group which is substituted by a basic group, and may have a further substituent(s) or a 3- to 8-membered monocyclic carbocyclic ring which is substituted by a basic group, and may have a further substituent(s). The "basic group" as used herein, is preferably, an amino group, an amidino group, a guanidino group, a hydrazino group, a mono- or di-substituted amino group or a nitrogen-containing heterocyclic ring. The "hydrocarbon group" as used herein, is preferably, a C1-4 aliphatic hydrocarbon group, and the "monocyclic carbocyclic ring" is preferably, a 5- to 7-membered monocyclic carbocyclic ring. Additionally, the "substituent" in the "hydrocarbon group which may have a further substituent(s)" is preferably, a hydroxy group.

$R^3$ is preferably, for example, a hydrogen atom or a hydrocarbon group which may have a substituent(s), and more preferably, a hydrogen atom or a C1-8 alkyl group and the like, and especially preferably, for example, a hydrogen atom or a methyl group and the like.

$R^{3A}$ is preferably, a 5- to 7-membered monocyclic heterocyclic ring or a C1-4 aliphatic hydrocarbon which have a substituent(s). The "substituent" in the "C1-4 aliphatic hydrocarbon which have a substituent(s)" as used herein is preferably, an amino group, a C1-10 acylamino group, a carboxyl group, an oxo group, a thioxo group, a hydroxy group, a C1-8 alkoxy group, a C3-8 cycloalkoxy group, a carbamoyl group or an amino carbonyl group.

$R^4$ is preferably, for example, a hydrogen atom.

The compound represented by formula (I) is preferably, for example, a compound represented by formula (I-1):

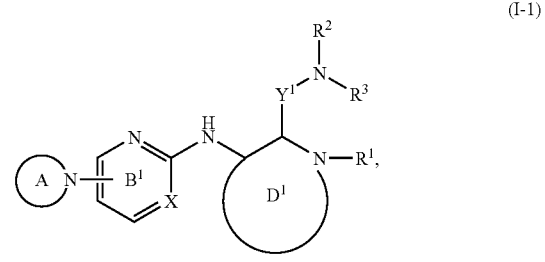

formula (I-2):

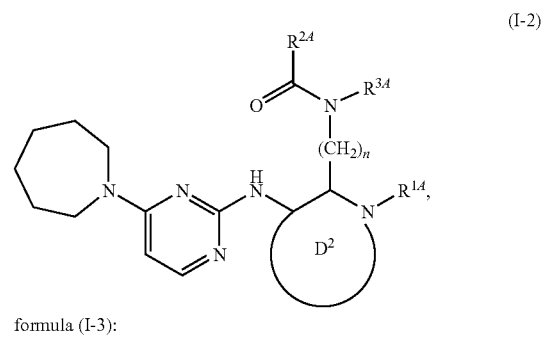

formula (I-3):

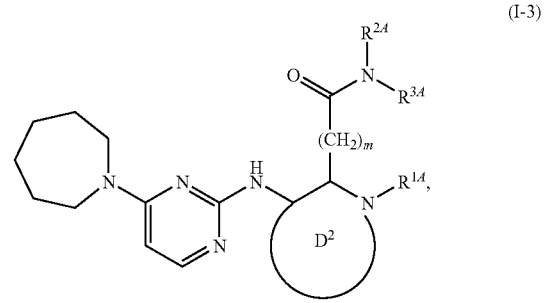

formula (I-4):

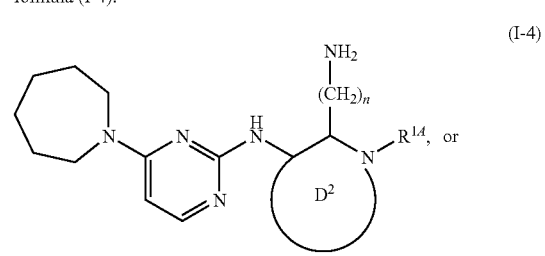

formula (I-5):

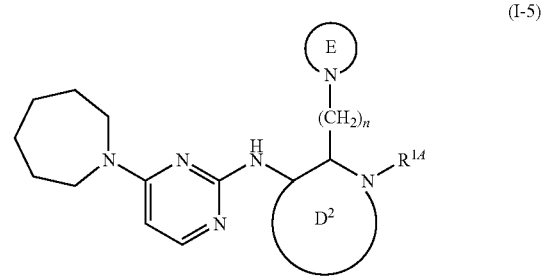

wherein all symbols have the same meanings as described above.

Additionally, the compound described in the example, an N-oxide thereof or a solvate thereof or a prodrug thereof is all preferable. And it is more preferably, for example, N-[(2R, 3S)-2-(aminomethyl)-1-cyclohexyl-3-pyrrolidinyl]-4-(1- azepanyl)-2-pyrimidinamine, N-[(2R,3S)-2-(2-aminoethyl)-1-cyclohexyl-3-pyrrolidinyl]-4-(1-azepanyl)-2-pyrimidinamine, N-[(2R,3S)-2-(3-aminopropyl)-1-cyclohexyl-3-pyrrolidinyl]-4-(1-azepanyl)-2-pyrimidinamine, N-[(2R,3S)-2-(5-aminopentyl)-1-cyclohexyl-3-pyrrolidinyl]-4-(1-azepanyl)-2-pyrimidinamine, N-[(2R,3S)-2-(aminomethyl)-1-cyclohexyl-3-pyrrolidinyl]-4-(1-azepanyl)-2-pyrimidinamine, 4-(1-azepanyl)-N-{(2R,3S)-1-cyclohexyl-2-[2-(dimethylamino)ethyl]-3-pyrrolidinyl}-2-pyrimidinamine, 4-(1-azepanyl)-N-{(2R,3S)-1-cyclohexyl-2-[3-(dimethylamino)propyl]-3-pyrrolidinyl}-2-pyrimidinamine, 4-(1-azepanyl)-N-{(2R,3S)-1-cyclohexyl-2-[5-(dimethylamino)pentyl]-3-pyrrolidinyl}-2-pyrimidinamine, 4-(1-azepanyl)-N-{(2RS,3SR)-1-cyclohexyl-2-[3-(dipropylamino)propyl]-3-pyrrolidinyl}-2-pyrimidinamine, cis-4-((2RS,3SR)-2-(3-aminopropyl)-3-{[4-(1-azepanyl)-2-pyrimidinyl]amino}-1-pyrrolidinyl)cyclohexanol, 4-(1-azepanyl)-N-{(2RS,3SR)-1-cyclohexyl-2-[3-(diethylamino)propyl]-3-pyrrolidinyl}-2-pyrimidinamine, 4-(1-azepanyl)-N-{(2RS,3SR)-1-cyclohexyl-2-[3-(1-pyrrolidinyl)propyl]-3-pyrrolidinyl}-2-pyrimidinamine, 4-(1-azepanyl)-N-{(2RS,3SR)-1-cyclohexyl-2-[3-(1-piperidinyl)propyl]-3-pyrrolidinyl}-2-pyrimidinamine, 4-(1-azepanyl)-N-{(2RS,3SR)-2-[3-(1-azepanyl)propyl]-1-cyclohexyl-3-pyrrolidinyl}-2-pyrimidinamine, N-[(2RS,3SR)-2-(2-aminoethyl)-1-cyclohexyl-3-piperidinyl]-4-(1-azepanyl)-2-pyrimidinamine, N-{(2RS,3SR)-2-(3-aminopropyl)-1-[1-(cyclohexylcarbonyl)-4-piperidinyl]-3-pyrrolidinyl}-4-(1-azepanyl)-2-pyrimidinamine, N-{(2RS,3SR)-2-(3-aminopropyl)-1-[1-(cyclopentylcarbonyl)-4-piperidinyl]-3-pyrrolidinyl}-4-(1-azepanyl)-2-pyrimidinamine, N-{(2RS,3SR)-2-(3-aminopropyl)-1-[1-(3-fluorobenzoyl)-4-piperidinyl]-3-pyrrolidinyl}-4-(1-azepanyl)-2-pyrimidinamine, N-(3-aminopropyl)-2-((2RS,3SR)-3-{[4-(1-azepanyl)-2-pyrimidinyl]amino}-1-cyclohexyl-2-piperidinyl)acetamide, 2-((2RS,3SR)-3-{[4-(1-azepanyl)-2-pyrimidinyl]amino}-1-cyclohexyl-2-piperidinyl)-N-[3-(dimethylamino)propyl]acetamide, N-[2-((2RS,3SR)-3-{[4-(1-azepanyl)-2-pyrimidinyl]amino}-1-cyclohexyl-2-piperidinyl)ethyl]-4-piperidinecarboxamide, cis-4-{(2RS,3SR)-3-{[4-(1-azepanyl)-2-pyrimidinyl]amino}-2-[3-(diethylamino)propyl]-1-pyrrolidinyl}cyclohexanol, N-{2-[(2RS,3SR)-3-{[4-(1-azepanyl)-2-pyrimidinyl]amino}-1'-(3-fluorobenzoyl)-1,4'-bipiperidin-2-yl]ethyl}-4-piperidinecarboxamide, N-{2-[(2RS,3SR)-3-{[4-(1-azepanyl)-2-pyrimidinyl]amino}-1'-(cyclohexylcarbonyl)-1,4'-bipiperidin-2-yl]ethyl}-4-piperidinecarboxamide, N-[2-((2RS,3SR)-3-{[4-(1-azepanyl)-2-pyrimidinyl]amino}-1-cyclohexyl-2-piperidinyl)ethyl]-2-morpholinecarboxamide, (3S)-N-[2-((2RS,3SR)-3-{[4-(1-azepanyl)-2-pyrimidinyl]amino}-1-cyclohexyl-2-piperidinyl)ethyl]-3-piperidinecarboxamide, (3R)-N-[2-((2RS,3SR)-3-{[4-(1-azepanyl)-2-pyrimidinyl]amino}-1-cyclohexyl-2-piperidinyl)ethyl]-3-piperidinecarboxamide, (3R)-N-[2-((2RS,3SR)-3-{[4-(1-azepanyl)-2-pyrimidinyl]amino}-1-cyclohexyl-2-piperidinyl)ethyl]-3-pyrrolidinecarboxamide, 2-amino-N-[2-((2RS,3SR)-3-{[4-(1-azepanyl)-2-pyrimidinyl]amino}-1-cyclohexyl-2-piperidinyl)ethyl]-2-methylpropanamide, N-(4-aminobutyl)-2-((2RS,3SR)-3-{[4-(1-azepanyl)-2-pyrimidinyl]amino}-1-cyclohexyl-2-piperidinyl)acetamide, N-(2-aminoethyl)-2-((2RS,3SR)-3-{[4-(1-azepanyl)-2-pyrimidinyl]amino}-1-cyclohexyl-2-piperidinyl)acetamide, (3S)-N-[2-((2RS,3SR)-3-{[4-(1-azepanyl)-2-pyrimidinyl]amino}-1-cyclohexyl-2-pyrrolidinyl)ethyl]-3-piperidinecarboxamide, N-[2-((2RS,3SR)-3-{[4-(1-azepanyl)-2-pyrimidinyl]amino}-1-cyclohexyl-2-pyrrolidinyl)ethyl]-2-morpholinecarboxamide, N-[2-((2RS,3SR)-3-{[4-(1-azepanyl)-2-pyrimidinyl]amino}-1-cyclohexyl-2-piperidinyl)ethyl]-1-isopropyl-4-piperidinecarboxamide, N-[2-((2RS,3SR)-3-{[4-(1-azepanyl)-2-pyrimidinyl]amino}-1-cyclohexyl-2-piperidinyl)ethyl]-N-(tetrahydro-2H-pyran-4-yl)-4-piperidinecarboxamide, N-[2-((2RS,3SR)-3-{[4-(1-azepanyl)-2-pyrimidinyl]amino}-1-cyclohexyl-2-piperidinyl)ethyl]-N-(2-methoxyethyl)-4-piperidinecarboxamide, N-[2-((2RS,3SR)-3-{[4-(1-azepanyl)-2-pyrimidinyl]amino}-1-cyclohexyl-2-piperidinyl)ethyl]-N-(2-hydroxyethyl)-4-piperidinecarboxamide, (2S)-N-[2-((2RS,3SR)-3-{[4-(1-azepanyl)-2-pyrimidinyl]amino}-1-cyclohexyl-2-piperidinyl)ethyl]-2-piperidinecarboxamide, N-[2-((2RS,3SR)-3-{[4-(1-azepanyl)-2-pyrimidinyl]amino}-1-cyclohexyl-2-piperidinyl)ethyl]-1-ethyl-4-piperidinecarboxamide, N-[2-((2RS,3SR)-3-{[4-(1-azepanyl)-2-pyrimidinyl]amino}-1-cyclohexyl-2-piperidinyl)ethyl]-4-hydroxy-4-piperidinecarboxamide, (2R)-2-amino-N-[2-((2RS,3SR)-3-{[4-(1-azepanyl)-2-pyrimidinyl]amino}-1-cyclohexyl-2-piperidinyl)ethyl]-3-(4-hydroxyphenyl)propanamide, (2S)-2-amino-N-[2-((2RS,3SR)-3-{[4-(1-azepanyl)-2-pyrimidinyl]amino}-1-cyclohexyl-2-piperidinyl)ethyl]-4-hydroxybutanamide, N-(2-aminoethyl)-N-[2-((2RS,3SR)-3-{[4-(1-azepanyl)-2-pyrimidinyl]amino}-1-cyclohexyl-2-piperidinyl)ethyl]-4-piperidinecarboxamide, N-[2-((2RS,3SR)-3-{[4-(1-azepanyl)-2-pyrimidinyl]amino}-1-ethyl-2-piperidinyl)ethyl]-4-piperidinecarboxamide, N-{2-[(2RS,3SR)-3-{[4-(1-azepanyl)-2-pyrimidinyl]amino}-1-(tetrahydro-2H-thiopyran-4-yl)-2-piperidinyl]ethyl}-4-piperidinecarboxamide, N-[2-((2RS,3SR)-3-{[4-(1-azepanyl)-2-pyrimidinyl]amino}-1-isopropyl-2-piperidinyl)ethyl]-4-piperidinecarboxamide, N-(2-{(2RS,3SR)-3-{[4-(1-azepanyl)-2-pyrimidinyl]amino}-1-[2-hydroxy-1-(hydroxymethyl)ethyl]-2-piperidinyl}ethyl)-4-piperidinecarboxamide, (2R)-2-amino-N-[2-((2RS,3SR)-3-{[4-(1-azepanyl)-2-pyrimidinyl]amino}-1-cyclohexyl-2-piperidinyl)ethyl]-3-(1H-imidazol-4-yl)propanamide, (2S)-2-amino-N-[2-((2RS,3SR)-3-{[4-(1-azepanyl)-2-pyrimidinyl]amino}-1-cyclohexyl-2-piperidinyl)ethyl]-3-(1H-imidazol-4-yl)propanamide, N-{2-[(2RS,3SR)-3-{[4-(1-azepanyl)-2-pyrimidinyl]amino}-1-(tetrahydro-2H-pyran-4-yl)-2-piperidinyl]ethyl}-4-piperidinecarboxamide, N-[2-((2RS,3SR)-3-{[4-(1-azepanyl)-2-pyrimidinyl]amino}-1-cyclohexyl-2-piperidinyl)ethyl]-2-pyridinecarboxamide, N-[2-((2RS,3SR)-3-{[4-(1-azepanyl)-2-pyrimidinyl]amino}-1-cyclohexyl-2-piperidinyl)ethyl] nicotinamide, N-[2-((2RS,3SR)-3-{[4-(1-azepanyl)-2-pyrimidinyl]amino}-1-cyclohexyl-2-piperidinyl)ethyl] isonicotinamide, N-{2-[(2RS,3SR)-3-{[4-(1-azepanyl)-2-pyrimidinyl]amino}-1-(1-oxidotetrahydro-2H-thiopyran-4-yl)-2-piperidinyl]ethyl}-4-piperidinecarboxamide, N-{2-[(2RS,3SR)-3-{[4-(1-azepanyl)-2-pyrimidinyl]amino}-1-(1,1-dioxidotetrahydro-2H-thiopyran-4-yl)-2-piperidinyl]ethyl}-4-piperidinecarboxamide, N-[2-((2RS,3SR)-1-cyclohexyl-3-{[4-(1-pyrrolidinyl)-2-pyrimidinyl]amino}-2-piperidinyl)ethyl]-4-piperidinecarboxamide, N-[2-((2RS,3SR)-3-{[4-(1-azepanyl)-2-pyrimidinyl]amino}-1-isopropyl-2-piperidinyl)ethyl]-1-ethyl-4-piperidinecarboxamide, N-[2-((2RS,3SR)-1-ethyl-3-{[4-(1-piperidinyl)-2-pyrimidinyl]amino}-2-piperidinyl)ethyl]-4-piperidinecarboxamide, N-[2-((2RS,3SR)-3-{[4-(1-azepanyl)-2-pyrimidinyl]amino}-1-cyclohexyl-2-piperidinyl)ethyl]-N-(tetrahydro-2H-pyran-4-yl)-2-morpholinecarboxamide or N-{2-[(2RS,3SR)-3-{[4-(1- azepanyl)-2-pyrimidinyl]amino}-1-(3-hydroxypropyl)-2-piperidinyl]ethyl}-4-piperidinecarboxamide, or a salt thereof, an N-oxide thereof or a solvate thereof, or a prodrug thereof and the like.

The compound of the present invention is more preferably, cis-4-((2RS,3SR)-2-(3-aminopropyl)-3-{[4-(1-azepanyl)-2-pyrimidinyl]amino}-1-pyrrolidinyl)cyclohexanol, 4-(1-azepanyl)-N-{(2RS,3SR)-1-cyclohexyl-2-[3-(diethylamino)propyl]-3-pyrrolidinyl}-2-pyrimidinamine, 4-(1-azepanyl)-N-{(2RS,3SR)-1-cyclohexyl-2-[3-(1-pyrrolidinyl)propyl]-3-pyrrolidinyl}-2-pyrimidinamine, N-[(2RS,3SR)-2-(2-aminoethyl)-1cyclohexyl-3-piperidinyl]-4-(1-azepanyl)-2-pyrimidinamine, N-{(2RS,3SR)-2-(3-aminopropyl)-1-[1-(cyclohexylcarbonyl)-4-piperidinyl]-3-pyrrolidinyl}-4-(1-azepanyl)-2-pyrimidinamine, N-(3-aminopropyl)-2-((2RS,3SR)-3-{[4-(1-azepanyl)-2-pyrimidinyl]amino}-1-cyclohexyl-2-piperidinyl)acetamide, 2-((2RS,3SR)-3-{[4-(1-azepanyl)-2-pyrimidinyl]amino}-1-cyclohexyl-2-piperidinyl)-N-[3-(dimethylamino)propyl]acetamide, N-[2-((2RS,3SR)-3-{[4-(1-azepanyl)-2-pyrimidinyl]amino}-1-cyclohexyl-2-piperidinyl)ethyl]-4-piperidinecarboxamide, cis-4-{(2RS,3SR)-3-{[4-(1-azepanyl)-2-pyrimidinyl]amino}-2-[3-(diethylamino)propyl]-1-pyrrolidinyl}cyclohexanol, N-[2-((2RS,3SR)-3-{[4-(1-azepanyl)-2-pyrimidinyl]amino}-1-cyclohexyl-2-piperidinyl)ethyl]-2-morpholinecarboxamide, 2-amino-N-[2-((2RS,3SR)-3-{[4-(1-azepanyl)-2-pyrimidinyl]amino}-1-cyclohexyl-2-piperidinyl)ethyl]-2-methylpropanamide, N-[2-((2RS,3SR)-3-{[4-(1-azepanyl)-2-pyrimidinyl]amino}-1-cyclohexyl-2-pyrrolidinyl)ethyl]-2-morpholinecarboxamide, N-[2-((2RS,3SR)-3-{[4-(1-azepanyl)-2-pyrimidinyl]amino}-1-cyclohexyl-2-piperidinyl)ethyl]-N-(tetrahydro-2H-pyran-4-yl)-4-piperidinecarboxamide, N-[2-((2RS,3SR)-3-{[4-(1-azepanyl)-2-pyrimidinyl]amino}-1-cyclohexyl-2-piperidinyl)ethyl]-N-(2-methoxyethyl)-4-piperidinecarboxamide, N-[2-((2RS,3SR)-3-{[4-(1-azepanyl)-2-pyrimidinyl]amino}-1-cyclohexyl-2-piperidinyl)ethyl]-N-(2-hydroxyethyl)-4-piperidinecarboxamide, N-[2-((2RS,3SR)-3-{[4-(1-azepanyl)-2-pyrimidinyl]amino}-1-cyclohexyl-2-piperidinyl)ethyl]-1-ethyl-4-piperidinecarboxamide, N-[2-((2RS,3SR)-3-{[4-(1-azepanyl)-2-pyrimidinyl]amino}-1-cyclohexyl-2-piperidinyl)ethyl]-4-hydroxy-4-piperidinecarboxamide, (2R)-2-amino-N-[2-((2RS,3SR)-3-{[4-(1-azepanyl)-2-pyrimidinyl]amino}-1-cyclohexyl-2-piperidinyl)ethyl]-3-(4-hydroxyphenyl)propanamide, (2S)-2-amino-N-[2-((2RS,3SR)-3-{[4-(1-azepanyl)-2-pyrimidinyl]amino}-1-cyclohexyl-2-piperidinyl)ethyl]-4-hydroxybutanamide, N-(2-aminoethyl)-N-[2-((2RS,3SR)-3-{[4-(1-azepanyl)-2-pyrimidinyl]amino}-1-cyclohexyl-2-piperidinyl)ethyl]-4-piperidinecarboxamide, N-[2-((2RS,3SR)-3-{[4-(1-azepanyl)-2-pyrimidinyl]amino}-1-isopropyl-2-piperidinyl)ethyl]-4-piperidinecarboxamide, (2R)-2-amino-N-[2-((2RS,3SR)-3-{[4-(1-azepanyl)-2-pyrimidinyl]amino}-1-cyclohexyl-2-piperidinyl)ethyl]-3-(1H-imidazol-4-yl)propanamide, N-{2-[(2RS,3SR)-3-{[4-(1-azepanyl)-2-pyrimidinyl]amino}-1-(tetrahydro-2H-pyran-4-yl)-2-piperidinyl]ethyl}-4-piperidinecarboxamide, N-[2-((2RS,3SR)-3-{[4-(1-azepanyl)-2-pyrimidinyl]amino}-1-isopropyl-2-piperidinyl)ethyl]-1-ethyl-4-piperidinecarboxamide, N-[2-((2RS,3SR)-3-{[4-(1-azepanyl)-2-pyrimidinyl]amino}-1-cyclohexyl-2-piperidinyl)ethyl]-N-(tetrahydro-2H-pyran-4-yl)-2-morpholinecarboxamide or N-{2-[(2RS,3SR)-3-{[4-(1-azepanyl)-2-pyrimidinyl]amino}-1-(3-hydroxypropyl)-2-piperidinyl]ethyl}-4-piperidinecarboxamide, or a salt thereof, an N-oxide thereof or a solvate thereof, or a prodrug thereof.

Additionally, a compound having an antagonistic activity against CXCR4 is preferably, a compound having molecular weight of 300 to 1000, which has at least three basic nitrogen atoms; a partial structure represented by formula (C):

wherein X represents a nitrogen atom or a carbon atom;
R$^4$ represents a hydrogen atom or a hydrocarbon group which may have a substituent(s); and
50% or more inhibitory activity of binding human SDF-1 to CEM Cells in a concentration of 10 μM, or
a salt thereof, an N-oxide thereof or a solvate thereof, or a prodrug thereof

[Isomers]

All isomers are included in the present invention, unless otherwise specified. For example, an alkyl group, an alkenyl group, an alkynyl group, an alkyloxy group, an alkoxy group, an alkenyloxy group, an alkynyloxy group, an alkylthio group, an alkylsulfinyl group, an alkylsulfonyl group, an alkylene group, an alkenylene group, an alkynylene group, an acyl group, and an acyloxy group includes a straight or branched one. In addition, isomers on double bond, ring, fused ring (E-, Z-, cis-, trans-isomers), isomers generated due to asymmetric carbon atom(s) (R-form, S-form, α-configuration, β-configuration, enantiomer, diastereomer), optically active isomers with optical rotation (D-, L-, d-, l-isomers), polar compounds generated by chromatographic separation (more polar compound, less polar compound), equilibrium compounds, rotational isomer, mixtures thereof with arbitrary ratio and racemic mixtures are also included in the present invention. Further, isomers due to the tautomerism are all included in the present invention.

In addition, the optically active compound in the present invention may include other optical isomer of less than 50% as well as 100% pure.

In the present invention, as is apparent to those skilled in the art, the symbol ⁓ represents that it is bonded to a configuration, the symbol ◢ represents that it is bonded to β configuration, and the symbol ╱ represents that it is bonded to α configuration or β configuration, and it is an arbitary ration of a mixture of the α configuration and the β configuration.

[Salts and Solvates]

Salts of the compound represented by formula (I) include all of pharmaceutically acceptable salts. The pharmaceutically acceptable salt is preferably a water soluble salt which shows less toxicity. Examples of the suitable salt include salts of alkali metal (potassium, sodium, lithium, etc.), salts of alkali earth metal (calcium, magnesium, etc.), ammonium salts (tetramethylammonium salt, tetrabutylammonium salt, etc.), salts of organic amine (triethylamine, methylamine, dimethylamine, cyclopentylamine, benzylamine, phenethylamine, piperidine, monoethanolamine, diethanolamine, tris (hydroxymethyl)methylamine, lysine, arginine, N-methyl-D-glucamine, etc.), acid addition salts (inorganic acid salts (hydrochloride, hydrobromide, hydroiodide, sulfate, phosphate, nitrate, etc.), and organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.)) and the like.

Furthermore, salts include quaternary ammonium salts. The quaternary ammonium salt is obtained by quaternizing a nitrogen atom of the compound represented by formula (I) with a R⁰ group (R⁰ group represents a C1-8 alkyl group or a C1-8 alkyl group substituted by a phenyl group).

Also, salts include N-oxide. The compound of the present invention can be converted into N-oxide by an optional method. N-oxide is obtained by oxidizing a nitrogen atom of the compound represented by formula (I).

Examples of suitable solvate of the compound represented by formula (I) include solvates such as water, alcoholic solvent (for example, methanol, ethanol, etc.) and the like. The solvate is preferably nontoxic and water soluble. The solvate of the compound of the present invention also includes solvates of alkali (earth) metal salts, ammonium salts, salts of organic amine, and acid addition salts of the compound of the present invention.

The compound of the present invention can be converted into the above salts and solvates by a known method.

[Prodrugs]

A prodrug of the compound represented by formula (I) means a compound which is converted into the compound represented by formula (I) in the living body by the reaction with an enzyme, gastric acid or the like. Examples of the prodrug of the compound represented by formula (I) include compound wherein an amino group is acylated, alkylated, or phosphorylated (for example, compound wherein an amino group of the compound represented by formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.) when the compound represented by formula (I) has an amino group; compound wherein a hydroxyl group is acylated, alkylated, phosphorylated, boricated or the like (for example, compound wherein a hydroxyl group of the compound represented by formula (I) is acetylated, palmitoylated, propanoylated, pivaloylated, succinylated, fumarylated, alanylated, dimethylaminomethylcarbonylated, etc.) when the compound represented by formula (I) has a hydroxyl group; and compound wherein a carboxy group is esterificated, amidated or the like (for example, compound wherein a carboxy group of the compound represented by formula (I) is ethylesterificated, phenylesterificated, carboxymethylesterificated, dimethylaminomethylesterificated, pivaloyloxymethylesterificated, ethoxycarbonyloxyethylesterificated, phthalidylesterificated, (5-methyl-2-oxo-1,3-dioxolen-4-yl) methylesterificated, cyclohexyloxycarbonylethylesterificated, methylamidated, etc.) when the compound represented by formula (I) has a carboxy group. These compounds can be prepared by a per se known method. The prodrug of the compound represented by formula (I) may be either of a hydrate and a non-hydrate. Also, the prodrug of the compound represented by formula (I) may be converted into the compound represented by formula (I) under physiological conditions described in "Development of Drug" published in 1990 by Hirokawa Shoten, Vol. 7, "Molecular Design", pp. 163-198. Furthermore, the compound represented by formula (I) may be labelled with isotope (for example, ³H, ¹⁴C, ³⁵S, ¹²⁵I, etc.) and the like.

The nomenclature of the compound of the present invention is performed using a computer program conducting designation generally according to IUPAC regulations, ACD/Name™ manufactured by Advanced Chemistry Development Inc. For example, the compound described below:

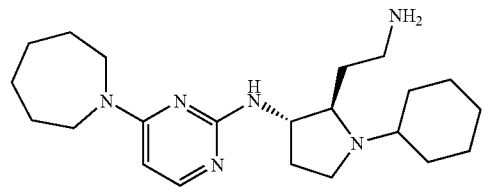 [SMILES: NCC[C@@H]1[C@@H](Nc2nccc(N3CCCCCC3)n2)CCN1C1CCCCC1]

is named as N-[(2R,3S)-2-(2-aminoethyl)-1-cyclohexyl-3-pyrrolidinyl]-4-(1-azepanyl)-2-pyrimidinamine.

[Method for Producing Compound of the Present Invention]

The compound represented by formula (I), or a salt thereof, an N-oxide thereof or a solvate thereof, or a prodrug thereof (hereinafter abbreviated to a compound of the present invention, sometimes) can be prepared by appropriately improving a known method, for example, methods shown below, methods described in Examples, and a method described in Comprehensive Organic Transformations: A Guide to Functional Group Preparations, Second edition (written by Richard C. Larock, John Wiley & Sons Inc, 1999) and using improved methods in combination. In the following production methods, starting compounds may be used in the form of a salt. As the salt, those described as a salt of the above described formula (I) are used.

[1] The compound represented by formula (I) can be prepared by subjecting a compound represented by formula (II):

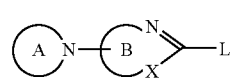

(II)

wherein L represents leaving group such as a halogen atom, a methansulfonyloxy group (OMs group), a p-toluenesulfonyloxy group (OTs group), a trifluoromethansulfonyloxy group (OTf group), an alkylthio group, an alkylsulfinyl group, an alkylsulfonyl group, a hydroxysulfonyl group, etc; and other symbols have the same meanings as described above, and a compound represented by formula (III):

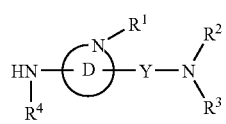

(III)

wherein all symbols have the same meanings as described above, to the reaction and if necessary to the deprotection reaction of a protective group.

This reaction is known and is carried out, for example, in an organic solvent (toluene, benzene, xylene, acetonitrile, dioxane, tetrahydrofuran, pyridine, diethyl ether, diisopropyl ether, tert-butylmethyl ether, chloroform, dichloromethane, 1,2-dichloromethane, N,N-dimethylformamide, N,N-dimethylacetamide, dimethylsulfoxide, alcoholic solvent (methanol, ethanol, propanol, 2-propanol, 1-hexanol, 3-hexanol, cyclopropanol, cyclohexanol, benzylalcol etc.) etc.), alkaline aqueous solution (lithium hydroxide aqueous solution, sodium hydroxide aqueous solution, potassium hydroxide aqueous solution etc.) and the mixed solvent thereof or absence of solvent at −78 to 200° C.

As apparent for those skilled in the art, when a starting material represented by formula (II) or formula (III) has a hydroxy group, a carboxyl group, an amino group or a mercapto group, these functional group can be appropriately protected in advance, the desired compound represented by formula (I) can be prepared by the reaction and then by a deprotection of protective groups.

The protective group of amino includes such as benzyloxycarbonyl group, tert-butoxycarbonyl group, allyloxycarbonyl (Alloc) group, 1-methyl-1-(4-biphenyl)ethoxycarbonyl (Bpoc) group, trifluoroacetyl group, 9-fluorenylmethoxycarbonyl group, benzyl (Bn) group, p-methoxybenzyl group, benzyloxymethyl (BOM) group, 2-(trimethylsilyl)ethoxymethyl (SEM) group and phthalimide group and the like.

The protective group of hydroxy includes, for example, methyl group, trityl group, methoxymethyl (MOM) group, 1-ethoxyethyl (EE) group, methoxyethoxymethyl (MEM) group, 2-tetrahydropyranyl (THP) group, trimethylsilyl (TMS) group, triethylsilyl (TES) group, tert-butyldimethylsilyl (TBDMS) group, tert-butyldiphenylsilyl (TBDPS) group, acetyl (Ac) group, pivaloyl group, benzoyl group, benzyl (Bn) group, p-methoxybenzyl group, allyloxycarbonyl (Alloc) group, and 2,2,2-trichloroethoxycarbonyl (Troc) group etc.

The protective group of mercapto includes, for example, benzyl group, methoxybenzyl group, methoxymethyl (MOM) group, 2-tetrahydropyranyl (THP) group, diphenylmethyl and acetyl (Ac) group etc.

The protective group of carboxy includes, for example, methyl group, ethyl group, tert-butyl group, allyl group, phenacyl group and benzyl group etc.

With regard to the protective group for carboxyl group, hydroxyl group, amino group and mercapto group, there is no particular limitation to the above ones so far as it is a group which is able to be easily and selectively removed. For example, a deprotection reaction may be carried out by a method mentioned in "T. W. Greene, *Protective Groups in Organic Synthesis*, John Wiley & Sons Inc, 1999".

Deprotection reaction of a protective group for carboxyl group, hydroxyl group, amino group or mercapto group is known and its examples are as follows.

(1) a deprotection reaction by hydrolysis with an alkali;
(2) a deprotection reaction under an acidic condition;
(3) a deprotection reaction by hydrogenolysis;
(4) a deprotection reaction using metal complex;
(5) a deprotection reaction using an organic metal;
(6) a deprotection reaction of silyl group; and
(7) a deprotection reaction of phthalimide group and the like.

Those methods will be specifically illustrated as follows;

(1) A deprotection reaction by hydrolysis with an alkali (for example, a deprotection of trifluoroacetyl group etc.) is carried out, for example, at the temperature of 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and 1,4-dioxane etc. alone, or a mixed solvent containing two or more solvents thereof at an optional ratio).

(2) A deprotection reaction under an acidic condition (e.g. a deprotection of tert-butoxycarbonyl group or trityl group etc.) is carried out, for example, at the temperature of 0 to 100° C. in an organic acid (e.g. acetic acid, trifluoroacetic acid, methanesulfonic acid), an inorganic acid (e.g. hydrochloric acid and sulfuric acid) or a mixture thereof (such as hydrogen bromide/acetic acid) in water or an organic solvent (such as dichloromethane, chloroform, 1,4-dioxane, ethyl acetate and anisole etc.).

(3) A deprotection reaction by hydrogenolysis (for example, a deprotection reaction of benzyl group, benzhydril group, benzyloxycarbonyl group, allyloxycarbonyl group etc.) is carried out, for example, at the temperature of 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent [such as an ether type (such as tetrahydrofuran, 1,4-dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as N,N-dimethylformamide), water, ethyl acetate, acetic acid or a mixed solvent comprising two or more thereof].

(4) A deprotection reaction using a metal complex (e.g. a deprotection of allyloxycarbonyl etc.) is carried out, for example, at the temperature of 0 to 40° C. using a metal complex [such as tetrakistriphenylphosphine palladium (0), bis(triphenylphosphine) palladium (II) dichloride, palladium (II) acetate and tris(triphenylphosphine) rhodium (I) chloride] in the presence or absence of a phosphine agent (such as triphenylphosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, N,N-dimethylformamide, tetrahydrofuran, ethyl acetate, acetonitrile, dioxane and ethanol), water or a mixed solvent thereof (5) A deprotection reaction using metal is carried out, for example, at the temperature of 0 to 40° C. with or without ultrasonic wave in the presence of powdery zinc in an acidic solvent (such as acetic acid, a buffer of pH 4.2 to 7.2 and a mixed solution of a solution thereof with an organic solvent such as tetrahydrofuran).

(6) A deprotection reaction of silyl group is carried out, for example, at the temperature of 0 to 40° C. using tetrabutylammonium fluoride in an organic solvent miscible with water (such as tetrahydrofuran and acetonitrile etc.).

(7) A deprotection reaction of phthalimide group is carried out, for example, at the temperature of 0 to 100° C. using hydrazine or amine in an organic solvent (methanol, ethanol etc.), water or a mixed solution of a solution thereof.

As persons skilled in the art can easily understand that the aimed compound of the present invention is able to be easily produced by using appropriate ones among those deprotection reactions.

[2] The compound represented by formula (I) can be prepared by subjecting a compound represented by formula (IV):

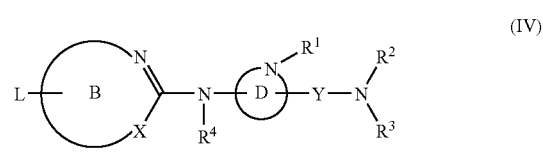

wherein all symbols have the same meanings as described above, and a compound represented by formula (V):

wherein all symbols have the same meanings as described above, to the reaction and if necessary to the deprotection reaction of a protective group.

This reaction is known and is carried out, for example, at the temperature of −78 to 200° C. in an organic solvent (toluene, benzene etc.), in the presense of metal salt (palladium acetate etc.) and ligand (tri(tert-butyl)phosphine, dicyclohexyl(2-biphenyl)phosphine, 2,2'-bis(diphenylphosphino)-1,1'-binaphthyl(BINAP) etc.), by addition of base (potassium phosphate, potassium carbonate, sodium tert-butoxide, sodium hydride, sodium amyloxide etc.). The deprotection of the protecting group can be carried out according to the method described above.

[3] Among the compound represented by formula (I), a compound wherein $R^2$ represents —(CO)—$R^{2A}$, that is, a compound represented by formula (I-A):

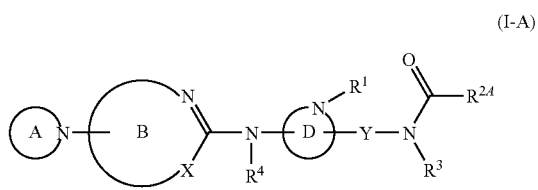

wherein all symbols have the same meanings as described above, can be prepared by subjecting a compound represented by formula (I-A-1):

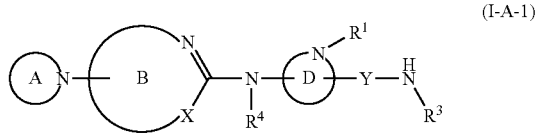

wherein all symbols have the same meanings as described above, and a compound represented by formula (I-A-2):

wherein W represents a hydroxy group or a chlorine atom, other symbols have the same meanings described above, to the amidation reaction and if necessary to the deprotection reaction of a protective group and/or the cleavage reaction from a resin.

This amidation reaction is known and examples thereof include:
(1) a method using an acyl halide,
(2) a method using a mixed acid anhydride, and
(3) a method using a condensing agent.

These methods are described in detail below.

(1) The method using an acyl halide is carried out, for example, by reacting carboxylic acid with an acid halogenating agent (oxalyl chloride, thionyl chloride, etc.) in an organic solvent (chloroform, dichloromethane, diethyl ether, tetrahydrofuran, etc.) or in the absence of the solvent at −20° C. to reflux temperature. Then the obtained acyl halide derivative may be with amine in the presence of a base (pyridine, triethylamine, N,N-dimethylaniline, 4-dimethylaminopyridine, diisopropylethylamine, etc.) in an organic solvent (chloroform, dichloromethane, diethyl ether, tetrahydrofuran, etc.) at 0 to 40° C. Alternatively, the obtained acyl halide can be reacted with amine in an organic solvent (dioxane, tetrahydrofuran, etc.) at 0 to 40° C. using an aqueous alkali solution (sodium bicarbonate solution or sodium hydroxide solution, etc.).

(2) The method using a mixed acid anhydride is carried out, for example, by reacting carboxylic acid with an acyl halide (pivaloyl chloride, tosyl chloride, mesyl chloride, etc.) or an acid derivative (ethyl chloroformate, butyl chloroformate, etc.) in the presence of a base (pyridine, triethylamine, N,N-dimethylaniline, 4-dimethylaminopyridine, diisopropylethylamine, etc.) in an organic solvent (chloroform, dichloromethane, diethyl ether, tetrahydrofuran, etc.) or in the absence of the solvent at 0 to 40° C., and reacting the resulting mixed acid anhydride with amine in an organic solvent (chloroform, dichloromethane, diethyl ether, tetrahydrofuran, etc.) at 0 to 40° C.

(3) The method using a condensing agent is carried out, for example, by reacting carboxylic acid with amine in an organic solvent (chloroform, dichloromethane, dimethyl formamide, diethyl ether, tetrahydrofuran, etc.) or in the absence of the solvent at 0 to 40° C. in the presence or absence of a base (pyridine, triethylamine, diisopropylethylamine, N,N-dimethylaniline, N-methylmorpholine, 4-dimethylaminopyridine, etc.), using a condensing agent (1,3-dicyclohexylcarbodiimide (DCC), 1-ethyl-3-[3-(dimethylamino)propyl]carbodiimide (EDC), 1,1'-carbonyldiimidazole (CDI), O-(7-azabenzotriazol-1-yl)N,N,N',N'-tetramethyluronium hexafluorophosphate (HATU), 2-chloro-1-methylpyridiniumiodine, 1-propylphosphonic acid cyclic anhydride (1-propanephosphonic acid cyclic anhydride, PPA), etc.) and using, or not using, 1-hydroxybenztriazole (HOBt) or 1-hydroxy-7-azabenzotriazole (HOAt).

The reactions described in (1), (2) and (3) are preferably carried out under an inert gas (argon, nitrogen, etc.) atmosphere on anhydrous condition.

Also, if the compound has a moiety to bind to a resin in the molecule and the resin is a polystyrene resin, the compound of the present invention can be cleaved from the resin by the following method. The reaction for cleavage from the resin is known and can be carried out, for example, by reacting in an organic solvent (dichloromethane, 1,2-dichloroethane, toluene, etc.) at 0 to 100° C. using an acid (acetic acid, trifluoroacetic acid, hydrochloric acid, etc.).

[4] Among the compound represented by formula (I), a compound wherein Y represents a spacer having a main chain of 1 to 7 atom(s) which have a carbonyl group at end, that is, a compound represented by formula (I-B):

(I-B)

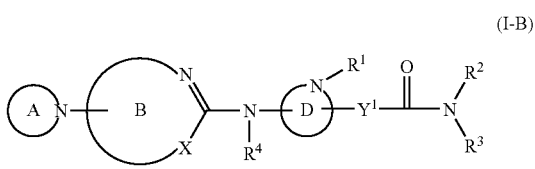

wherein $Y^1$ represents a spacer having a main chain of 1 to 7 atom(s) and other symbols have the same meanings as described above, can be prepared by subjecting a compound represented by formula (I-B-1):

(I-B-1)

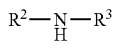

wherein all symbols have the same meanings as described above, and a compound represented by formula (I-B-2):

(I-B-2)

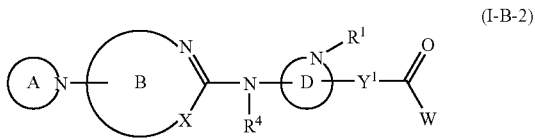

wherein all symbols have the same meanings as described above, to the amidation reaction and if necessary to the deprotection reaction of a protective group and/or the cleavage reaction from a resin.

The amidation reaction, the deprotection reaction of a protective group or the cleavage reaction from a resin can be carried out by the same method as described above.

The compound prepared by the method [1] to [4] described above, if necessary, can be carried out the procedure of converting into the objective salt by a known method after this reaction.

The compounds represented by formulae (II) to (V), (I-A-1), (I-A-2), (I-B-1) and (I-B-2) used as a starting materials or reagents can be easily prepared by using per se known methods or known methods, for example, methods described in Comprehensive Organic Transformations: A Guide to Functional Group Preparations, Second edition (written by Richard C. Larock, John Wiley & Sons Inc, 1999) in combination.

In the respective reactions in the present specification, a solid phase supported reagent obtained by supporting on a polymer (for example, polystyrene, polyacrylamide, polypropylene, polyethylene glycol, etc.) may be used.

In the respective reactions in the present specification, the reaction product can be purified by conventional purification means, for example, distillation under normal pressure or reduced pressure, high performance liquid chromatography using a silica gel or magnesium silicate, thin layer chromatography or chromatography or washing, or recrystallization. The purification may be carried out for every reaction, or may be carried out after the completion of some reactions.

In the respective reactions in the present specification, as is apparent to those skilled in the art, the reaction with heating can be carried out using a water bath, an oil bath, a sand bath, or microwave.

[Toxicity]

The compound of the present invention has very low toxicity and is considered to be safe enough for pharmaceutical use.

[Application to Pharmaceuticals]

The compound of the present invention has CXCR4 antagonistic activity in an animal including human, particularly human, and is therefore effective, for example, for a preventive and/or therapeutic agent for inflammatory and immune diseases, allergic diseases, infections, particularly HIV infection, and diseases associated with the infection, psychoneurotic diseases, cerebral diseases, cardiovascular diseases, metabolic diseases, and cancerous diseases. Also, the compound is useful as an agent for regeneration therapy for the purpose of in vitro or in vivo amplification of stem cells for gene therapy as well as peripheral blood stem cells mobilization and tissue repair. The compound is particularly useful as an agent for transplantation medical treatment used in organ transplantation including bone marrow transplantation, peripheral blood stem cell transplantation and tissue repair among in the regeneration therapy. Furthermore, the compound is useful as an antiangiogenic agent which is effective for prevention and/or treatment of diseases associated with neoangiogenesis, such as retinopathy (diabetic retinopathy, aged macular degeneration, glaucoma, etc.) and cancer proliferation.

Examples of the inflammatory and immune disease include rheumatoid arthritis, arthritis, retinopathy, gout, transplanted organ rejection, graft-versus-host disease (GVHD), nephritis, psoriasis, rhinitis, conjunctivitis, multiple sclerosis, ulcerative colitis, Crohn's disease, shock associated with bacterial infection, pulmonary fibrosis, systemic inflammatory response syndrome (SIRS), acute lung injury, and diabetes.

Examples of the allergic disease include asthma, atopic dermatitis, rhinitis, and conjunctivitis Examples of the disease associated with infection, particularly HIV infection, include acquired immunodeficiency syndrome (AIDS), candidiasis, *Pneumocystis carinii* pneumonia, Cytomegalovirus retinitis, Kaposi's sarcoma, malignant lymphoma, AIDS encephalopathy, and bacterial sepsis.

Examples of the psychoneurotic disease and cerebral disease include dementia including Alzheimer's disease, Parkinson's disease, stroke, cerebral infarction, cerebral hemorrhage, epilepsia, schizophrenia, and peripheral nerve disorder.

Examples of the cardiovascular disease include arteriosclerosis, ischemia reperfusion, hypertension, myocardial infarction, stenocardia, and heart failure.

Examples of the metabolic diseases include diabetes, osteoporosis, enlarged prostate, and frequent micturition.

Examples of the cancerous disease include malignant tumor such as breast cancer or malignant lymphoma, cancer metastasis, and myelosuppression or thrombocytopenia after radiation therapy/chemotherapy.

The compound of the present invention may be administered as a concomitant drug by using in combination with other drugs for the purpose of:

1) complementation and/or enhancement of the preventive and/or therapeutic effects of the compound of the present invention,
2) improvement of pharmacokinetics and absorption of the compound of the present invention and reduction of the dosage, and/or
3) reduction of side effects of the compound of the present invention.

Also, the compound of the present invention may be administered as a concomitant drug by using in combination with other drugs the purpose of (1) complementation and/or enhancement of preventive and/or therapeutic effects, (2)

improvement of pharmacokinetics and absorption of the compound and reduction of the dosage, and/or (3) reduction of side effects.

The concomitant drug of the compound of the present invention and other drugs may be administered in the form of a compounding agent(s) comprising both these components, or may be in the form of separately. In case of separately administering a preparation, simultaneous administration and administration with time-lag are included. In case of administration with time-lag, other drugs may be administered after the compound of the present invention is administered, or the compound of the present invention may be administered after other drugs may be administered. The administration method may be the same or different.

The disease, on which the preventive and/or therapeutic effects are exerted by the concomitant drug, is not specifically limited, and may be any disease which complements and/or enhances the preventive and/or therapeutic effects of the compound of the present invention.

A mass ratio of the compound of the present invention drug to other drugs is not specifically limited.

A combination of any two or more kinds other drugs may be administered.

The other drugs, which complements and/or enhances the preventive and/or therapeutic effects of the compound of the present invention, includes not only those which have ever been found based on the above described mechanism, but also those which may be found in future.

Examples of the preventive and/or therapeutic agents for HIV infection and acquired immunodeficiency syndrome, which is used in combination of the compound of the present invention, include reverse transcriptase inhibitors, protease inhibitors, chemokine (for example, CCR2, CCR3, CCR4, CCR5, CXCR4, etc.) antagonists, fusion inhibitor, CD4 antagonists, antibody against surface antigen of HIV (for example, HIV-1, HIV-2, etc.) and vaccine of HIV (for example, HIV-1, HIV-2, etc.).

Examples of the reverse transcriptase inhibitors include (1) nucleoside reverse transcriptase inhibitors such as zidovudine (trade name: Retrovir), didanosine (trade name: Videx), zalcitabine (trade name: Hivid), stavudine (trade name: Zerit), lamivudine (trade name: Epivir), abacavir (trade name: Ziagen), adefovir, dipivoxil, emtricitabine (trade name: coviracil), or tenofovir (trade name: viread), (2) non-nucleoside reverse transcriptase inhibitors such as nevirapine (trade name: viramune), delavirdine (trade name: Rescriptor), efavirenz (trade name: Sustiva, Stocrin), or capravirine (AG1549).

Examples of the protease inhibitors include indinavir (trade name: Kurikisiban), ritonavir (trade name: norvir), nelfinavir (trade name: Viracept), saquinavir (trade name: Invirase, Fortovase), amprenavir (trade name: agenerase), lopinavir (trade name: Kaletra), tipranavir and the like.

Examples of the chemokine antagonists include endogenous ligands of a chemokine receptor, or derivatives and nonpeptidic low molecular compounds thereof, or an antibody against a chemokine receptor.

Examples of the endogenous ligands of the chemokine receptor include MIP-1α, MIP-1β, RANTES, SDF-1α, SDF-1β, MCP-1, MCP-2, MCP-4, eotaxin, MDC and the like.

Examples of the derivative of the endogenous ligands include AOP-RANTES, Met-SDF-1α, Met-SDF-1β and the like.

Examples of the antibody of the chemokine receptor include Pro-140 and the like.

Examples of the CCR2 antagonists include compounds described in WO99/07351, WO99/40913, WO00/46195, WO00/46196, WO00/46197, WO00/46198, WO00/46199, WO00/69432, WO00/69815, and Bioorg. Med. Chem. Lett., 10, 1803 (2000), and the like.

Examples of the CCR3 antagonists include compounds described in DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327, and WO01/09088, and the like.

Examples of the CCR4 antagonists include compounds described in WO02/030357 and WO02/030358, and the like.

Examples of the CCR5 antagonists include compounds described in WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000-309598, WO00/51607, WO00/51608, WO00/51609, WO00/51610, WO00/56729, WO00/59497, WO00/59498, WO00/59502, WO00/59503, WO00/76933, WO98/25605, WO99/04794, WO99/38514 and Bioorg. Med. Chem. Lett., 10, 1803 (2000), TAK-779, SCH-351125 (SCH-C), SCH-417690 (SCH-D), UK-427857, GW 873140A, TAK-220, TAK-652, and the like.

Examples of the CXCR4 antagonists include AMD-3100, T-22, KRH-1120, KRH-1636, and compounds described in WO00/66112 and WO2004/052862, and the like.

Examples of the fusion inhibitors include T-20 (pentafuside), T-1249, and the like.

Examples of the HIV integrase inhibitors include Equisetin, Temacrazine, PL-2500, V-165, NSC-618929, L-870810, L-708906 analog, S-1360, 1838 and the like.

The conventional clinical dosage of typical reverse transcriptase inhibitors and protease inhibitors is, for example, as described below, but is not limited thereto in the present invention.

Zidovudine: 100 mg capsule, three times per day in a dosage of 200 mg; 300 mg tablet, twice per day in a dosage of 300 mg;
Didanosine: 25 to 200 mg tablet, twice per day in a dosage of 125 to 200 mg;
Zalcitabine: 0.375 mg to 0.75 mg tablet, three times per day in a dosage of 0.75 mg;
Stavudine: 15 to 40 mg capsule, twice per day in a dosage of 30 to 40 mg;
Lamivudine: 150 mg tablet, twice per day in a dosage of 150 mg;
Abacavir: 300 mg tablet, twice per day in a dosage of 300 mg;
Nevirapine: 200 mg tablet, once per day for 14 days in a dosage of 200 mg, followed by twice per day;
Delavirdine: 100 mg tablet, three times per day in a dosage of 400 mg;
Efavirenz: 50 to 200 mg capsule, once per day in a dosage of 600 mg;
Indinavir: 200 to 400 mg capsule, three times per day in a dosage of 800 mg;
Ritonavir: 100 mg capsule, twice per day in a dosage of 600 mg;
Nelfinavir: 250 mg tablet, three times per day in a dosage of 750 mg;
Saquinavir: 200 mg capsule, three times per day in a dosage of 1,200 mg;

Amprenavir: 50 to 150 mg tablet, twice per day in a dosage of 1,200 mg.

Examples of the other drugs for complementation and/or enhancement of the preventive and/or therapeutic effects of the compound of the present invention against asthma include antihistaminic agents, antiallergic agents (chemical mediator release inhibitors, histamine antagonists, thromboxane synthetase inhibitors, thromboxane antagonists, Th2 cytokine inhibitors), steroids, bronchodilator agents (xanthine derivatives, sympathomimetic agents, parasympathomimetic agents), vaccinotherapeutic agents, gold preparations, Chinese medicines, basic nonsteroidal anti-inflammatory drugs, 5-lipoxygenase inhibitors, 5-lipoxygenase activation protein antagonists, leukotriene synthesis inhibitors, prostaglandins, cannabinoid-2 receptor stimulants, antitussive drugs, expectorants, and the like.

Examples of the antihistaminic agents include diphenhydramine, diphenylpyraline hydrochloride, diphenylpyraline chlorotheophyllinate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andolast, auranofin, acrivastine and the like.

Examples of the chemical mediator release inhibitors include disodium cromoglycate, tranilast, amlexanox, repirinast, ibudilast, pemirolast potassium, tazanolast, nedocromil, cromoglicate, israpafant and the like.

Examples of the histamine antagonists include ketotifen fumarate, azelastine hydrochloride, oxatomide, mequitazine, terfenadine, emedastine fumarate, epinastine hydrochloride, ebastine, cetirizine hydrochloride, olopatadine hydrochloride, loratadine, fexofenadine and the like.

Examples of the thromboxane synthetase inhibitors include ozagrel hydrochloride imitrodast sodium and the like.

Examples of the thromboxane antagonists include seratrodast, ramatroban, domitroban calcium hydrate, KT-2-962 and the like.

Examples of the Th2 cytokine inhibitors include suplatast tosilate and the like.

Examples of the steroids include, for example, external medicine such as clobetasol propionate, diflorasone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone dipropionate, triamcinolone acetonide, flumetasone pivalate, alclometasone propionate, clobetasone butyrate, prednisolone, beclomethasone propionate, fludroxycortide, and the like.

Examples of drugs for internal use and injections include cortisone acetate, hydrocortisone, hydrocortisone sodium phosphate, hydrocortisone sodium succinate, fludrocortisone acetate, prednisolone, prednisolone acetate, prednisolone sodium succinate, predniso lone butylacetate, prednisolone sodium phosphate, halopredone acetate, methyl prednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone and the like.

Examples of the inhalations include beclometasone dipropionate, fluticasone propionate, budesonide, flunisolide, triamcinolone, ST-126P, ciclesonide, dexamethasone palmitate, mometasone furoate, prasterone sulfonate, deflazacort, methylprednisolone suleptanate, methylprednisolone sodium succinate and the like.

Examples of the xanthine derivative include aminophylline, theophylline, doxophylline, cipamfylline, diprophylline, proxyphylline, choline theophylline and the like.

Examples of the sympathomimetic agents include epinephrine, ephedrine hydrochloride, dl-methylephedrine hydrochloride, methoxyphenamine hydrochloride, isoproterenol sulfate, isoproterenol hydrochloride, orciprenaline sulfate, chloroprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromate, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KUR-1246, KUL-7211, AR-C89855, S-1319 and the like.

Examples of the parasympathomimetic agents include ipratropium bromide, flutropium bromide, oxitropium bromide, cimetropium bromide, temiverine, tiotropium bromide, revatropate (UK-112166) and the like.

Examples of the vaccinotherapeutic agents include paspat, asthremedin, Broncasma Berna, CS-560 and the like.

Examples of the gold preparations include gold sodium thiomalate and the like.

Examples of the basic nonsteroidal anti-inflammatory drugs include tiaramide hydrochloride, tinoridine hydrochloride, epirizole, emorfazone and the like.

Examples of the 5-lipoxygenase inhibitors include zyleuton, docebenone, piriprost, SCH-40120, WY-50295, E-6700, ML-3000, TMK-688, ZD-2138, dalbufelone mesilate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175, ETH-615 and the like.

Examples of the 5-lipoxygenase activation protein antagonists include MK-591, MK-886 and the like.

Examples of the leukotriene synthesis inhibitors include auranofin, proglumetacin maleate, L-674636, A-81834, UPA-780, A-93178, MK-886, REV-5901A, SCH-40120, MK-591, Bay-x-1005, Bay-y-1015, DTI-0026, Amlexanox, E-6700 and the like.

Examples of the prostaglandins (hereinafter abbreviated to as PG) include PG receptor agonists, PG receptor antagonists and the like.

Examples of the PG receptor include PGE receptor (EP1, EP2, EP3, and EP4), PGD receptor (DP, CRTH2), PGF receptor (FP), PGI receptor (IP), TX receptor (TP) and the like.

Examples of the antitussive drugs include codeine phosphate, dihydrocodeine phosphate, oxymetebanol, dextromethorphan hydrobromate, pentoxyverine citrate, dimemorfan phosphate, oxeladin citrate, cloperastine, benproperine phosphate, clofedanol hydrochloride, fominoben hydrochloride, noscapine, tipepidine hibenzate, eprazinone hydrochloride, plantago herb extract and the like.

Examples of the expectorants include foeniculated ammonia spirit, sodium hydrogencarbonate, potassium iodide, bromhexine hydrochloride, cherry bark extract, carbocysteine, fudosteine, ambroxol hydrochloride, ambroxol hydrochloride sustained-release tablet, methylcysteine hydrochloride, acetylcysteine, L-ethylcysteine hydrochloride, tyloxapol and the like.

Examples of the other drugs for complementation and/or enhancement of the preventive and/or therapeutic effects against atopic dermatitis (urticaria, etc.) of the compound of the present invention include steroids, non-steroid anti-inflammatory drug (NSAID), immune inhibitor, prostaglandins, antiallergic agent, mediator release inhibitor, antihistaminic agent, forskolin preparation, phosphodiesterase inhibitor, and cannabinoid-2 receptor stimulant.

Examples of the other drugs for complementation and/or enhancement of the preventive and/or therapeutic effects against allergic diseases (allergic bronchopulmonary aspergillosis, allergic eoisinophilic gastroenteritis, etc.) of the compound of the present invention include antiasthmatic drug, inhaled steriod drug, inhaled β2 stimulant, methylxanthine-based stimulant, antiallergic agent, anti-inflammatory agent, anticholinergic agent, thromboxane antagonist, leukotriene antagonist, LTD4 antagonist, PAF antagonist, phosphodiesterase inhibitor, β2 agonist, steroid drug, mediator release inhibitor, eosinophile leukocytechemotaxis inhibitor, macrolide-based antibiotic, immune inhibitor, hyposensitization (allergen) injection and the like.

Examples of the antiasthmatic drug include theophylline, procaterol, ketotifen, azelastine and the like.

Examples of the inhaled steriod drug include beclomethasone, fluticasone, budesonide and the like.

Examples of the inhaled β2 stimulant include fenoterol, salbutamol, formoterol, salmeterol and the like.

Examples of the methylxanthine-based stimulant include theophylline and the like.

Examples of the antiallergic agent include ketotifen, terfenadine, azelastine, epinastine, suplatast, disodium cromoglycate and the like.

Examples of the anti-inflammatory agent include dichlofenac sodium, ibuprofen, indomethacin and the like.

Examples of the anticholinergic agent include ipratropium bromide, flutropium bromide, oxitropium bromide, tiotropium bromide and the like.

Examples of the thromboxane antagonist include ozagrel, seratrodast and the like.

Examples of the leukotriene antagonist include pranlukast, montelukast, zafirlukast, zyleuton and the like.

Examples of the macrolide-based antibiotic include erythromycin, roxithromycin and the like.

Examples of the immune inhibitor include cyclosporine, tacrolimus, FTY720, and the like.

Examples of the other drug for complementation and/or enhancement of the preventive and/or therapeutic effects against hepatitis of the compound of the present invention include liver hydrolysate preparation, polyenephosphatidylcholine, glycyrrhizin preparation, protoporphyrin sodium, ursodeoxycholic acid, steroids, anticholinergic agent, gastric antiacid, propagermanium, lipid peroxidase inhibitor, and mitochondrial benzodiazepine receptor antagonist.

Examples of the other drug for complementation and/or enhancement of the preventive and/or therapeutic effects against arthritis and rheumatoid arthritis of the compound of the present invention include metalloproteinase inhibitor, immune inhibitor, non-steroid anti-inflammatory drug (NSAID), steroid drug, prostaglandins, phosphodiesterase inhibitor, cannabinoid-2 receptor stimulant, disease modifying anti-rheumatic drug (slow-acting anti-rheumatic drug), anti-inflammatory enzyme preparation, cartilage protective agent, T cell inhibitor, TNFα inhibitor, prostaglandin synthetase inhibitor, IL-6 inhibitor, interferon γ agonist, IL-1 inhibitor and the like.

Examples of the other drug for complementation and/or enhancement of the preventive and/or therapeutic effects against psoriasis of the compound of the present invention include steroid drug, vitamin D derivative and the like.

Examples of the other drug for complementation and/or enhancement of the preventive and/or therapeutic effects against rhinitis of the compound of the present invention include antihistaminic agent, mediator release inhibitor, thromboxane synthetase inhibitor, thromboxane $A_2$ receptor antagonist, leukotriene receptor antagonist, steroids, a adrenalin receptor stimulant, xanthine derivative, anticholinergic agent, prostaglandins, nitrogen monoxide synthetase inhibitor, $β_2$ adrenalin receptor stimulant, phosphodiesterase inhibitor, cannabinoid-2 receptor stimulant and the like.

Examples of the other drug for complementation and/or enhancement of the preventive and/or therapeutic effects against conjunctivitis of the compound of the present invention include leukotriene receptor antagonist, antihistaminic agent, mediator release inhibitor, non-steroid anti-inflammatory drug, prostaglandins, steroid drug, nitrogen monoxide synthetase inhibitor, cannabinoid-2 receptor stimulant and the like.

Examples of the other drug for complementation and/or enhancement of the preventive and/or therapeutic effects against multiple sclerosis of the compound of the present invention include immune inhibitor, cannabinoid-2 receptor stimulant and the like.

Examples of the other drug for complementation and/or enhancement of the preventive and/or therapeutic effects against ulcerative colitis of the compound of the present invention include mesalazine, salazosulfapyridine, digestive tract ulcer therapeutic substance, anticholinergic agent, steroid drug, 5-lipoxygenase inhibitor, antioxidant, LTB4 antagonist, local anesthetic, immune inhibitor, protection factor enhancer, MMP inhibitor, and mitochondrial benzodiazepine receptor antagonist.

Examples of the other drug for complementation and/or enhancement of the preventive and/or therapeutic effects against diabetic complication of the compound of the present invention include sulfonyl urea-based hypoglycemic agent, biguanide-based drug formulation, α-glucosidase inhibitor, ultrashort-acting insulinotropic agent, insulin drug formulation, PPAR agonist, insulin sensitive enhancer having no PPAR antagonism, β3 adrenalin receptor agonist, aldose reductase inhibitor, dipeptidyl peptidase IV inhibitor and the like.

Examples of the sulfonyl urea-based hypoglycemic agent include acetohexamide, glibenclamide, gliclazide, glyclopyramide, chlorpropamide, tolazamide, tolbutamide, Glimepiride and the like.

Examples of the biguanide-based drug include buformin hydrochloride, metformin hydrochloride and the like.

Examples of the α-glucosidase inhibitor include acarbose, voglibose and the like.

Examples of the ultrashort-acting insulinotropic agent include nateglinide, repaglinide and the like.

Examples of the PPAR agonist include pioglitazone, troglitazone, rosiglitazone, JTT-501, and the like.

Examples of the insulin sensitive enhancer having no PPAR antagonism include ONO-5816, YM-440 and the like.

Examples of the β3 adrenalin receptor agonist include AJ9677, L750355, and CP331648.

Examples of the aldose reductase inhibitor include epalrestat, fidarestat, zenarestat and the like.

Examples of the other drug for complementation and/or enhancement of the preventive and/or therapeutic effects against cancer (malignant tumor) and cancer metastasis of the compound of the present invention include anticancer agent (for example, MMP inhibitor, alkylation agent (for example, cyclophosphamide, melphalan, thiotepa, mytomycin C, busulfan, procarbazine hydrochloride, etc.), antimetabolite (for example, methotrexate, mercaptpurine, azathiopurine, fluorouracil, tegafur, cytarabine, azaserine, etc.), antibiotic (for example, mytomycin C, bleomycin, Peplomycin, doxorubicin hydrochloride, aclarubicin, daunorubicin, actinomycin D, etc.), mitosis inhibitor, platinum complex (for example, Cisplatin), plant-derived antineoplastic agent (for example, vincristine sulfate, vinblastine sulfate, etc.), anticancerous hormone (for example, methyltestosterone, testosterone propionate, testosterone enanthate, mepitiostane, fosfestrol, chlormadinone acetate, etc.), immunopotentiator (for example, picibanil, krestin, etc.), and interferon (for example, IFNα, IFNα-2a, IFNα-2b, IFNβ, IFNγ-1a, etc.). Examples thereof include biologics capable of conducting T cell activation (for example, anti-CTLA-4 antibody, anti-PD-1 antibody, etc.), antiangiogenic agent (for example, bevacizumab, pegaptanib, SU-6668, vatalanib, ranibizumab, sorafenib, SU-11248, neovastat), etc.), and the like.

Examples of the other drug for complementation and/or enhancement of the preventive and/or therapeutic effects against immune disease (for example, autoimmune disease, transplanted organ rejection, etc.) of the compound of the present invention include immune inhibitor (for example, cyclosporine, tacrolimus, FTY720, etc.).

Examples of the other drug for complementation and/or enhancement of the preventive and/or therapeutic effects against dementia such as Senile dementia with Alzheimer's type of the compound of the present invention include acetylcholine esterase inhibitor, nicotinic receptor modifier, cerebral ameliorator, monoamineoxidase inhibitor, vitamin E, aldose reductase inhibitor and the like.

Examples of the other drug for complementation and/or enhancement of the preventive and/or therapeutic effects against epilepsia of the compound of the present invention include phenyloin, trimethadione, ethosuximide, carbamazepine, phenobarbitone, primidone, acetazolamide, sultiame, sodium valproate, clonazepam, diazepam, nitrazepam and the like.

Examples of the other drug for complementation and/or enhancement of the preventive and/or therapeutic effects against arteriosclerosis of the compound of the present invention include HMG-CoA reductase inhibitor, fibrates, probucol preparation, anion-exchange resin, EPA preparation, nicotinic acid preparation, MTP inhibitor, other anti-high cholesterol agent, EDG-2 antagonist and the like.

Examples of the other drug for complementation and/or enhancement of the effects when the compound of the present invention is used in a regeneration therapy include cytokines and various growth factors, for example, various CSFs (for example, G-CSF, GM-CSF, etc.), various interleukins (for example, IL-3, 6, 7, 11, 12, etc.), EPO, TPO, SCF, FLT3 ligand, MIP-1α and the like.

Examples of the other drug for complementation and/or enhancement of the preventive and/or therapeutic effects against retinopathy of the compound of the present invention include antiangiogenic agent (for example, bevacizumab, pegaptanib, SU-6668, vatalanib, ranibizumab, sorafenib, SU-11248, neovastat, etc.) and the like.

The compound of the present invention is safe and has low toxicity and therefore can be administered to human and mammal other than human (for example, rat, mouse, rabbit, sheep, pig, cow, cat, dog, monkey, etc.).

In order to use a pharmaceutical composition comprising the compound of the present invention or a concomitant drug of the compound of the present invention and other drugs, it is commonly administered, systematically or locally, in an oral or parenteral dosage form.

The dosage of the pharmaceutical preparation varies depending on the age, body weight, symptom, and the desired therapeutic effect, the route of administration and duration of treatment. For the human adult, the dosage per person is between 1 ng and 1000 mg, by oral administration, up to several times per day, between 0.1 ng and 100 mg, by parenteral administration, or continuous administration 1 hour to 24 hours per day from vein.

As a matter of course, since the dosage varies under various conditions as is described above, the dosage may be sometimes sufficient which is smaller than the above range, or sometimes the dosage must be more than the above range.

In case of administering a pharmaceutical composition comprising the compound of the present invention, or a concomitant drug of the compound of the present invention and other drugs, it is used as solid preparations for internal use and solutions for internal use for oral administration, and injections, external preparations, suppositories, ophthalmic solutions, nasal drops, inhalants and the like for parenteral administration.

Examples of the solid preparation for internal use for oral administration include tablets, pills, capsules, powders, and granules. Capsules include hard capsules and soft capsules.

In such a solid preparation for internal use, one or more active substances are used as they are, or used after mixing with excipients (lactose, mannitol, glucose, microcrystalline cellulose, starch, etc.), binders (hydroxypropyl cellulose, polyvinyl pyrrolidone, magnesium aluminometasilicate, etc.), disintegrants (calcium carboxymethyl cellulose, etc.), lubricants (magnesium stearate, etc.), stabilizers and solubilizing agents (glutamic acid, aspartic acid, etc.) and forming into a preparation according to a conventional method. If necessary, the preparation may be coated with a coating agent (saccharose, gelatin, hydroxypropyl cellulose, hydroxypropylmethyl cellulosephthalate, etc.) or may be coated with two or more layers. Furthermore, capsules made of an absorbable substance such as gelatin is included.

The solutions for internal use for oral administration include pharmaceutically acceptable water, suspensions, emulsions, syrups, and elixirs. In such a solution, one or more active substances are dissolved, suspended or emulsified in a diluent used commonly (purified water, ethanol, mixed solution thereof, etc.). Furthermore, this solution may contain humectants, suspending agents, emulsifiers, sweeteners, flavors, aromatics, preservatives, buffers, and the like.

The dosage form of the external preparation for parenteral administration includes, for example, ointment, gel, cream, fomentation, patch, liniment, propellant, inhalant, spray, aerosol, ophthalmic solution, and nasal drop. These products contain one or more active substances and are prepared according to the formulation which is known or commonly used.

An ointment is prepared in accordance with a well known formulation or a commonly employed formulation. For example, it is prepared by triturating or dissolving one or more active substances in a base. An ointment base is selected from well known ones or those commonly employed. For example, those selected from higher fatty acids or higher fatty acid esters (adipic acid, myristic acid, palmitic acid, stearic acid, oleic acid, adipate ester, myristate ester, palmitate ester, stearate ester, oleate ester, etc.), waxes (beeswax, whale wax, ceresin, etc.), surfactants (polyoxyethylene alkyl ether phosphate ester, etc.), higher alcohols (cetanol, stearyl alcohol, cetostearyl alcohol, etc.), silicone oils (dimethylpolysiloxane, etc.), hydrocarbons (hydrophilic petrolatum, white petrolatum, purified lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, egg yolk oil, squalane, squalene, etc.), water, absorption accelerators, agents for preventing contact dermatitis are used alone or in combination. Furthermore, it may contain humectants, preservatives, stabilizers, antioxidizing agents, flavors, and the like.

A gel is prepared according to the formulation which is known or commonly used. For example, it is prepared by dissolving one or more active substances in a base. A gel base is selected from a base which is known or commonly used. For example, those selected from lower alcohols (ethanol, isopropyl alcohol, etc.), gelling agents (carboxymethyl cellulose, hydroxyethyl cellulose, hydroxypropyl cellulose, ethyl cellulose, etc.), neutralizers (triethanolamine, diisopropanolamine, etc.), surfactants (monostearic acid polyethylene glycol, etc.), gums, water, absorption accelerator, and agent for preventing contact dermatitis are used alone or in combination. Furthermore, it may contain preservatives, antioxidizing agents, and flavoring agent.

A cream is prepared according to the formulation which is known or commonly used. For example, it is prepared by dissolving or emulsifying one or more active substances in a base. A cream base is selected from a base which is known or commonly used. For example, those selected from higher fatty acid esters, lower alcohols, hydrocarbons, polyhydric alcohols (propylene glycol, 1,3-butylene glycol, etc.), higher alcohols (2-hexyl decanol, cetanol, etc.), emulsifiers (polyoxyethylene alkyl ethers, fatty acid esters, etc.), water, absorption accelerators, and agents for preventing contact dermatitis are used alone or in combination. Furthermore, it may contain preservatives, antioxidizing agents, and flavoring agents.

A fomentation is prepared according to the formulation which is known or commonly used. For example, it is prepared by dissolving one or more active substances in a base to obtain a kneaded mixture and spreading the kneaded mixture over a substrate. A fomentation base is selected from a base which is known or commonly used. For example, those selected from thickeners (polyacrylic acid, polyvinyl pyrrolidone, gum arabic, starch, gelatin, methyl cellulose, etc.), humectants (urea, glycerin, propylene glycol, etc.), fillers (kaolin, zinc oxide, talc, calcium, magnesium, etc.), water, solubilizing agents, tackifiers, and agents for preventing contact dermatitis are used alone or in combination. Furthermore, it may contain preservatives, antioxidizing agents, and flavoring agent.

A patch is prepared according to the formulation which is known or commonly used. For example, it is prepared by dissolving one or more active substances in a base, and spreading the solution over a substrate. A patch base is selected from a base which is known or commonly used. For example, those selected from polymer bases, fats and oils, higher fatty acids, tackifiers, and agents for preventing contact dermatitis are used alone or in combination. Furthermore, it may contain preservatives, antioxidizing agents, and flavoring agent.

A liniment is prepared according to the formulation which is known or commonly used. For example, it is prepared by dissolving, suspending or emulsifying one or more active substances in one or more kinds selected from water, alcohol (ethanol, polyethylene glycol, etc.), higher fatty acid, glycerin, soap, emulsifier, and suspending agent. Furthermore, it may contain preservatives, antioxidizing agents, and flavoring agent.

A propellant, an inhalant, and a spray may contain, in addition to a diluent used commonly, a stabilizer such as sodium hydrogensulfite and a buffer capable of imparting isotonicity, for example, an isotonicity such as sodium chloride, sodium citrate or citric acid. The method for producing a spray is described in detail in U.S. Pat. Nos. 2,868,691 and 3,095,355.

An injection for parenteral administration includes all injections and also includes a drop. For example, it includes intramuscular injection, subcutaneous injection, endodermic injection, intraarterial injection, intravenous injection, intraperitoneal injection, intraspinal injection, and intravenous drop.

The injection for parenteral administration includes solutions, suspensions, emulsions, and solid injections used by dissolving or suspending in a solvent before use. The injection is used after dissolving, suspending, or emulsifying one or more active substances in a solvent. As the solvent, for example, distilled water for injection, physiological saline, vegetable oil, and alcohols such as propylene glycol, polyethylene glycol or ethanol are used alone or in combination. Furthermore, the injection may contain stabilizers, solubilizing agents (glutamic acid, aspartic acid, polysolvate 80®, etc.), suspending agents, emulsifiers, soothing agents, buffers, and preservatives. These injections are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An ophthalmic solution for parenteral administration includes ophthalmic solution, suspension type ophthalmic solution, emulsion type ophthalmic solution, ophthalmic solution soluble when used, and eye ointment.

These ophthalmic solutions are prepared according to a known method. For example, one or more active substances are dissolved, suspended or emulsified in a solvent before use. As the solvent for ophthalmic solution, for example, sterilized purified water, physiological saline, and other aqueous solvent or non-aqueous agent for injection (for example, vegetable oil, etc.) are used alone or in combination. If necessary, the ophthalmic solution may contain appropriately selected isotonizing agents (sodium chloride, concentrated glycerin, etc.), buffering agents (sodium phosphoate, sodium acetate, etc.), surfactants (polysolvate 80 (trade name), polyoxyl 40 stearate, polyoxyethylene hardened castor oil, etc.), stabilizers (sodium citrate, sodium edetate, etc.), and antiseptics (benzalkonium chloride, paraben, etc.) These ophthalmic solutions are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An inhalants for parenteral administration includes aerozol, inhalation powder, and inhalation solution, and the inhalation solution may be such a configuration that it is used after dissolving in water or other suitable medium at the point of use.

These inhalants are prepared according to a known method.

For example, an inhalation solution is prepared by appropriately selecting antiseptics (benzalkonium chloride, paraben, etc.), colorants, buffering agents (sodium phosphate, sodium acetate, etc.), isotonizing agents (sodium chloride, concentrated glycerin, etc.), thickeners (carboxyvinyl polymer, etc.), and absorption accelerator, if necessary.

An inhalation powder is prepared by appropriately selecting lubricants (stearic acid and a salt thereof, etc.), binders (starch, dextrin, etc.), excipients (lactose, cellulose, etc.), colorants, antiseptics (benzalkonium chloride, paraben, etc.), and absorption accelerator if necessary.

In case of administering the inhalation solution, a spraying apparatus (atomizer, nebulizer) is commonly used. In case of administering the inhalation powder, an inhalation administration apparatus for powder is commonly used.

The other composition for parenteral administration includes suppositories for intrarectal injection and pessaries for vaginal administration, which contain one or more active substances and are formulate by a conventional method.

[Effect of the Invention]

The compound of the present invention has an antagonistic activity against CXCR4 and is therefore useful as a preventive and/or therapeutic agent for diseases associated with CXCR4, namely, CXCR4-mediated diseases.

The present invention is described in detail based on Examples, but the present invention is not limited thereto.

The point of separation by chromatography and the solvent in the parentheses shown in TLC indicate a dissolution medium or an eluent used, and the proportion indicates a volume ratio. NMR is a measured value of $^1$HNMR at 300 MHz and the solvent shown in the parentheses of NMR indicates a solvent used in the measurement. Crystallinity of the solid product was confirmed using a polarizing microscope.

The compounds used in the present invention were commonly designated using a computer program ACD/Name Batch® (manufactured by Advanced Chemistry Development Inc.) which designates according to the regulation of IUPAC, or commonly designated according to IUPAC Nomenclature.

Regarding MS, detection for only positive ions (pos.) was conducted using ESI (electron spray ion) method unless otherwise specified.

HPLC conditions are as follows.
Apparatus used: Waters LC/MS®
Column: Xterra® MS $C_{18}$ 5 µm, 3×50 mm I.D.
Flow rate: 1.5 mL/min
Solvent:
Solution A: aqueous 0.1% trifluoroacetic acid solution
Solution B: 0.1% trifluoroacetic acid-acetonitrile solution For one minute after starting the measurement, the mixing ratio of the solution A to the solution B was fixed to 95:5. The mixing ratio of the solution A to the solution B was linearly changed to 5:95 over 3 minutes after fixation. Then, the mixing ratio of the solution A to the solution B was fixed to 5:95 for 0.5 minute. The mixing ratio of the solution A to the solution B was linearly changed to 95:5 for 0.01 minute after fixation.

In the present specification, (RS,SR) described in the compounds represents a mixture of (R,S) and (S,R) with arbitrary ratio. For example, ethyl {(2RS,3SR)-3-[(tert-butoxycarbonyl)amino]piperidin-2-yl}acetate represents a mixture of ethyl {(2R,3S)-3-[(tert-butoxycarbonyl)amino]piperidin-2-yl}acetate and ethyl {(2S,3R)-3-[(tert-butoxycarbonyl)amino]piperidin-2-yl}acetate with arbitrary ratio.

The compounds described in the examples were judged by chemical shift of $^1$HNMR as to whether it's a salt or not. If the compounds are hydrochloride, the number of hydrochloric acid which formed salt is a number to neutralize the basic nitrogen atom wherein pKa value calculated with ACD/pKaDB of Advanced Chemistry Development Company showes the value of 6 or more over, that is to say, regarded as an equal number of the basic nitrogen atom.

EXAMPLE 1

1,1-dimethylethyl (2R,3S)-3-{[(1,1-dimethylethyl)(dimethyl)silyl]oxy}-2-{[(methylsulfonyl)oxy]methyl}-1-pyrrolidinecarboxylate (compound 1)

To a solution of 1,1-dimethylethyl (2R,3S)-3-{[(1,1-dimethylethyl)(dimethyl)silyl]oxy}-2-(hydroxymethyl)-1-pyrrolidinecarboxylate (Registry No. 156129-73-6, 4.0 g) in ethyl acetate (100 mL), methanesulfonyl chloride (1.12 mL) and triethylamine (2.19 mL) was added at 0° C. The reaction mixture was stirred at 0° C. for 15 minutes. The reaction mixture was added by water and then extracted with ethyl acetate. The extract was washed with saturated brine, dried over anhydrous magnesium sulfate and then concentrated, obtained the title compound (4.87 g) having the following physical properties.

TLC: Rf 0.29 (n-hexane:ethyl acetate=3:1);
NMR (CDCl$_3$): δ 0.08 (s, 3 H), 0.09 (s, 3 H), 0.87 (s, 9 H), 1.46 (m, 9 H), 1.70-2.10 (m, 2 H), 3.00 (s, 3 H), 3.30-4.40 (m, 6 H).

EXAMPLE 2

1,1-dimethylethyl (2R,3S)-2-(azidemethyl)-3-{[(1,1-dimethylethyl)(dimethyl)silyl]oxy}-1-pyrrolidinecarboxylate (compound 2)

To a solution of the compound 1 (2.43 g) in N,N-dimethylformamide (15 mL), sodium azide (0.80 g) was added. The reaction mixture was stirred at 60° C. for 2 days. After cooling to room temperature, the reaction mixture was added water and extracted with a mixture solution of hexane:ethyl acetate=1:5. The extract was washed with saturated brine, dried over anhydrous magnesium sulfate and then concentrated. The obtained residue was purified by silica gel column chromatography (hexane:ethyl acetate=10:0→9:1→4:1) to obtain the title compound (2.01 g) having the following physical properties.

TLC: Rf 0.64 (n-hexane:ethyl acetate=4:1);
NMR (CDCl$_3$): δ 0.08 (s, 3 H), 0.08 (s, 3 H), 0.87 (s, 9 H), 1.47 (s, 9 H), 1.70-2.10 (m, 2 H), 3.10-3.80 (m, 5 H), 4.22 (m, 1 H).

EXAMPLE 3

1,1-dimethylethyl (2R,3S)-2-(azidomethyl)-3-hydroxy-1-pyrrolidinecarboxylate (compound 3)

To a solution of the compound 2 (1.96 g) in tetrahydrofuran (20 mL), 1 mol/L of a solution (6 mL) of tetrabutylammonium fluoride in tetrahydrofuran was added. The reaction mixture was stirred for overnight. The reaction mixture was added water and extracted with tert-butyl methyl ether. The extract was washed with water and saturated brine, dried over anhydrous magnesium sulfate and then concentrated. The obtained residue was purified by silica gel column chromatography (hexane:ethyl acetate=10:0→4:1) to obtain the title compound (1.30 g) having the following physical properties.

TLC: Rf 0.30 (n-hexane:ethyl acetate=1:1);
NMR (CDCl$_3$): δ 1.48 (s, 9 H), 1.81 (d, J=3.8 Hz, 1 H), 1.83-1.96 (m, 1 H), 2.05-2.22 (m, 1 H), 3.18-3.66 (m, 4 H), 3.68-3.87 (m, 1 H), 4.25-4.38 (m, 1 H).

EXAMPLE 4

1,1-dimethylethyl (2R,3S)-2-(azidomethyl)-3-{[(4-nitrophenyl)carbonyl]oxy}-1-pyrrolidinecarboxylate (compound 4)

To a solution of the compound 3 (1.30 g) in tetrahydrofuran (25 mL), triphenylphosphine (3.10 g), 4-nitrobenzoic acid (2.24 g) and 2.2 mol/L of a solution (5.4 mL) of diethyl azodicarboxylate in toluene were added at 0° C. The reaction mixture was stirred at room temperature for overnight. The reaction mixture was added water and extracted with ethyl acetate. The extract was washed with aqueous saturated sodium hydrogen carbonate solution and saturated brine, dried over anhydrous magnesium sulfate and then concentrated. The obtained residue was purified by silica gel column chromatography (hexane:ethyl acetate=10:0→4:1) to obtain the title compound (1.22 g) having the following physical properties.
TLC: Rf 0.81 (n-hexane:ethyl acetate=1:1);
NMR (CDCl$_3$): δ 1.50 (s, 9 H), 2.18-2.43 (m, 2 H), 3.44-3.66 (m, 3 H), 3.81 (s, 1 H), 4.19-4.33 (m, 1 H), 5.59 (q, J=6.8 Hz, 1 H), 8.23 (d, J=6.0 Hz, 2 H), 8.32 (d, J=6.0 Hz, 2 H).

EXAMPLE 5

1,1-dimethylethyl (2R,3R)-2-(azidomethyl)-3-hydroxy-1-pyrrolidinecarboxylate (compound 5)

To a solution of the compound 4 (1.22 g) in methanol (20 mL), potassium carbonate (0.91 g) was added. The reaction mixture was stirred at room temperature for overnight. The reaction mixture was added water and extracted with ethyl acetate. The extract was washed with saturated brine, dried over anhydrous magnesium sulfate and then concentrated. The obtained residue was purified by silica gel column chromatography (hexane:ethyl acetate=10:0→4:1→3:1) to obtain the title compound (0.66 g) having the following physical properties.
TLC: Rf 0.45 (n-hexane:ethyl acetate=1:1);
NMR (CDCl$_3$): δ 1.47 (s, 9 H), 1.87-2.03 (m, 1 H), 2.06-2.21 (m, 2 H), 3.36-3.55 (m, 2 H), 3.56-3.81 (m, 2 H), 3.89 (s, 1 H), 4.41-4.56 (m, 1 H).

EXAMPLE 6

1,1-dimethylethyl (2R,3S)-2-(azidomethyl)-3-(1,3-dioxo-1,3-dihydro-2H-isoindol-2-yl)-1-pyrrolidinecarboxylate (compound 6)

To a solution of the compound 5 (658 mg) in tetrahydrofuran (15 mL), phthalimide (600 mg), triphenylphosphine (1070 mg) and 2.2 mol/L of a solution (2.0 mL) of diethyl azodicarboxylate in toluene were added at 0° C. The reaction mixture was stirred at room temperature for overnight. The reaction mixture was added water and extracted with ethyl acetate. The extract was washed with aqueous saturated sodium hydrogen carbonate solution and saturated brine, dried over anhydrous magnesium sulfate and then concentrated. The obtained residue was purified by silica gel column chromatography (hexane:ethyl acetate=10:0→4:1) to obtain the title compound (508 mg) having the following physical properties.
TLC: Rf 0.43 (toluene:ethyl acetate=4:1);
NMR (CDCl$_3$): δ 1.51 (s, 9 H), 2.05-2.24 (m, 1 H), 2.41-2.63 (m, 1 H), 3.23-3.49 (m, 2 H), 3.62-4.07 (m, 2 H), 4.20-4.36 (m, 1 H), 4.78-4.94 (m, 1 H), 7.68-7.81 (m, 2 H), 7.83-7.93 (m, 2 H).

EXAMPLE 7

1,1-dimethylethyl (2R,3S)-3-amino-2-(azidomethyl)-1-pyrrolidinecarboxylate (compound 7)

To a solution of the compound 6 (493 mg) in methanol (13 mL), hydrazine monohydrate (339 mg) was added. The reaction mixture was stirred at room temperature for overnight. The reaction mixture was concentrated and then added dichloromethane. The appeared solid was collected by filtration and then the residue was concentrated and obtained the title compound (245 mg) having the following physical properties.
TLC: Rf 0.38 (dichloromethane:methanol=9:1);
NMR (CDCl$_3$): δ 1.40-1.52 (s, 9 H), 1.54-1.71 (m, 2 H), 2.05-2.20 (m, 1 H), 3.30-3.42 (m, 1 H), 3.43-3.72 (m, 4 H).

EXAMPLE 8

1,1-dimethylethyl (2R,3S)-3-{[4-(1-azepanyl)-2-pyrimidinyl]amino}-2-(azidomethyl)-1-pyrrolidinecarboxylate (compound 8)

To a solution of the compound 7 (240 mg) in cyclohexanol (0.4 mL), 1-(2-chloro-4-pyrimidinyl)azepane (210 mg) was added. The reaction mixture was stirred at 120° C. for 3.5 hours. After cooling to room temperature, the reaction mixture was added tert-butyl methyl ether, washed with aqueous 2N sodium hydroxide solution, dried over anhydrous magnesium sulfate and then concentrated. The obtained residue was purified by silica gel column chromatography (ethyl acetate:methanol:27% aqueous ammonia=100:0:0→90:10:0→90:10:1) to obtain the title compound (190 mg) having the following physical properties.
TLC: Rf 0.72 (chloroform:methanol:aqueous ammonia=8:1:0.1);
NMR (CDCl$_3$): δ 1.47 (s, 9 H), 1.51-1.62 (m, 4 H), 1.65-1.95 (m, 6 H), 2.20-2.39 (m, 1 H), 3.27-3.97 (m, 8 H), 4.32-4.54 (m, 1 H), 4.77-4.90 (m, 1 H), 5.81 (d, J=6.0 Hz, 1 H), 7.79 (d, J=6.0 Hz, 1 H).

EXAMPLE 9

4-(1-azepanyl)-N-[(2R,3S)-2-(azidomethyl)-1-cyclohexyl-3-pyrrolidinyl]-2-pyrimidinamine (compound 9)

To a solution of the compound 8 (185 mg) in methanol (3 mL) and dioxane (3 mL), a 2N hydrogen chloride-dioxane solution (5 mL) was added. The reaction mixture was stirred at room temperature for 1 hour. The reaction mixture was concentrated, added tert-butyl methyl ether, washed with aqueous 2N sodium hydroxide solution, dried over anhydrous magnesium sulfate and then concentrated. To a solution of the obtained 4-(1-azepanyl)-N-[(2R,3S)-2-(azidomethyl)-3-pyrrolidinyl]-2-pyrimidinamine and cyclohexanone (45 mg) in a 1% acetic acid-dichloromethane solution (5 mL), sodium triacetoxyborohydride (203 mg) was added. The reaction mixture was stirred at room temperature for 2 hours. The reaction mixture was added tert-butyl methyl ether, washed with aqueous 2N sodium hydroxide solution, dried over anhydrous sodium sulfate and then concentrated. The obtained residue was purified by silica gel column chromatography (ethyl acetate:methanol:27% aqueous ammonia=100:0:0→90:10:0→90:10:1) to obtain the title compound (133 mg) having the following physical properties.

TLC: Rf 0.13 (ethyl acetate:methanol=9:1);
NMR (CDCl$_3$): δ 1.01-1.37 (m, 4 H), 1.45-1.66 (m, 5 H), 1.68-1.95 (m, 10 H), 2.06-2.23 (m, 1 H), 2.45-2.60 (m, 1 H), 2.75-2.88 (m, 1 H), 2.91-3.07 (m, 2 H), 3.22-3.39 (m, 2 H), 3.39-3.94 (m, 4 H), 4.17-4.29 (m, 1 H), 4.77 (d, J=7.1 Hz, 1 H), 5.79 (d, J=6.2 Hz, 1 H), 7.78 (d, J=6.2 Hz, 1 H).

EXAMPLE 10

N-[(2R,3S)-2-(aminomethyl)-1-cyclohexyl-3-pyrrolidinyl]-4-(1-azepanyl)-2-pyrimidinamine (compound 10)

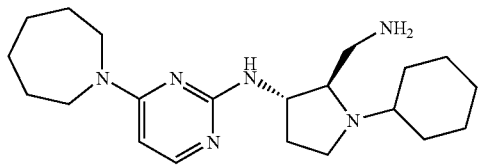 [SMILES: NC[C@@H]1[C@@H](Nc2nccc(N3CCCCCC3)n2)CCN1C1CCCCC1]

In a solution of the compound 9 (125 mg) in ethanol (4 mL), 10% palladium carbon (wet, 112 mg) was added under an argon atmosphere. The reaction mixture was stirred under a hydrogen atmosphere at room temperature for 30 minutes. The reaction mixture was filtered with Celite (trade name) and the filtrate was concentrated and obtained the title compound (116 mg) having the following physical properties.

TLC: Rf 0.33 (chloroform:methanol:aqueous ammonia=8:1:0.1);
NMR (DMSO-d$_6$): δ 1.02-1.40 (m, 6 H), 1.45-1.96 (m, 15 H), 2.05-2.21 (m, 1 H), 2.40-2.56 (m, 1 H), 2.60-2.85 (m, 4 H), 2.90-3.05 (m, 1 H), 3.25-3.90 (m, 4 H), 4.17-4.31 (m, 1 H), 4.72 (d, J=8.42 Hz, 1 H), 5.79 (d, J=6.04 Hz, 1 H), 7.80 (d, J=6.04 Hz, 1 H).

EXAMPLE 10(1) TO 10(6)

The same procedure as a series of reactions of Example 1→Example 2→Example 3→Example 4→Example 5→Example 6→Example 7→Example 8→Example 9→Example 10 was carried out and obtained the following compound of the present invention, except that a corresponding alcohol derivative was used in place of 1,1-dimethylethyl (2R,3S)-3-{[(1,1-dimethylethyl)(dimethyl)silyl]oxy}-2-(hydroxymethyl)-1-pyrrolidinecarboxylate in the corresponding procedure of Example 1.

EXAMPLE 10(1)

N-[(2R,3S)-2-(2-aminoethyl)-1-cyclohexyl-3-pyrrolidinyl]-4-(1-azepanyl)-2-pyrimidinamine (compound 10-1)

TLC: Rf 0.36 (ethyl acetate:methanol:ammonium hydroxide=20:5:1);
NMR (CDCl$_3$): δ 1.55 (m, 24H), 2.14 (m, 1 H), 2.49 (m, 1 H), 2.81 (m, 4 H), 3.56 (m, 4 H), 4.15 (m, 1 H), 5.04 (m, 1 H), 5.78 (d, J=6.00 Hz, 1 H), 7.78 (d, J=6.00 Hz, 1 H).

EXAMPLE 10(2)

N-[(2R,3S)-2-(3-aminopropyl)-1-cyclohexyl-3-pyrrolidinyl]-4-(1-azepanyl)-2-pyrimidinamine (compound 10-2)

TLC: Rf 0.36 (ethyl acetate:methanol:ammonium hydroxide=20:5:1);
NMR (CDCl$_3$): δ 1.55 (m, 24H), 2.10 (m, 1 H), 2.46 (m, 1 H), 2.70 (m, 3 H), 2.87 (m, 1 H), 3.55 (m, 4 H), 4.14 (m, 1 H), 4.78 (d, J=8.00 Hz, 1 H), 5.78 (d, J=6.00 Hz, 1 H), 7.80 (d, J=6.00 Hz, 1 H).

EXAMPLE 10(3)

N-[(2R,3S)-2-(5-aminopentyl)-1-cyclohexyl-3-pyrrolidinyl]-4-(1-azepanyl)-2-pyrimidinamine (compound 10-3)

TLC: Rf 0.16 (ethyl acetate:methanol:ammonium hydroxide=20:5:1);
NMR (CDCl$_3$): δ 1.50 (m, 27H), 2.09 (m, 1 H), 2.45 (m, 1 H), 2.70 (m, 4 H), 2.87 (m, 1 H), 3.55 (m, 4 H), 4.14 (m, 1 H), 4.77 (d, J=8.00 Hz, 1 H), 5.77 (d, J=6.00 Hz, 1 H), 7.79 (d, J=6.00 Hz, 1 H).

EXAMPLE 10(4)

N-[(3S,5R)-5-(aminomethyl)-1-cyclohexyl-3-pyrrolidinyl]-4-(1-azepanyl)-2-pyrimidinamine (compound 10-4)

TLC: Rf 0.55 (ethyl acetate:methanol:ammonium hydroxide=20:5:1);
NMR (CDCl$_3$): δ 1.74 (m, 23H), 2.46 (m, 2 H), 2.67 (d, J=5.00 Hz, 2 H), 3.38 (dd, J=9.00, 6.50 Hz, 1 H), 3.58 (m, 4 H), 4.39 (m, 1 H), 4.99 (m, 1 H), 5.79 (d, J=6.00 Hz, 1 H), 7.78 (d, J=6.00 Hz, 1 H).

EXAMPLE 10(5)

N-[(3S,5S)-5-(2-aminoethyl)-1-cyclohexyl-3-pyrrolidinyl]-4-(1-azepanyl)-2-pyrimidinamine (compound 10-5)

TLC: Rf 0.53 (ethyl acetate:methanol:ammonium hydroxide=20:5:1);
NMR (CDCl$_3$): δ 1.65 (dd, 24H) 2.40 (dd, J=9.00, 7.50 Hz, 1 H) 2.65 (m, 3 H) 3.00 (m, 1 H) 3.35 (dd, J=9.00, 7.00 Hz, 1 H) 3.56 (m, 4 H) 4.40 (m, 1 H) 5.29 (m, 1 H) 5.78 (d, J=6.00 Hz, 1 H) 7.74 (d, J=6.00 Hz, 1 H).

EXAMPLE 10(6)

N-[(3S,5S)-5-(3-aminopropyl)-1-cyclohexyl-3-pyrrolidinyl]-4-(1-azepanyl)-2-pyrimidinamine (compound 10-6)

TLC: Rf 0.19 (ethyl acetate:methanol:ammonium hydroxide=20:5:1);
NMR (CDCl$_3$): δ 1.48 (m, 26H), 1.96 (m, 1 H), 2.40 (dd, J=9.00, 7.50 Hz, 1 H), 2.54 (m, 1 H), 2.70 (t, J=7.00 Hz, 2 H), 2.90 (m, 1 H), 3.37 (m, J=9.00, 7.00 Hz, 1 H), 3.56 (m, 4 H), 4.41 (m, 1 H), 4.69 (d, J=7.50 Hz, 1 H), 7.79 (d, J=6.00 Hz, 1 H).

EXAMPLE 11

4-(1-azepanyl)-N-{(2R,3S)-1-cyclohexyl-2-[(dimethylamino)methyl]-3pyrrolidinyl}-2-pyrimidinamine (compound 11)

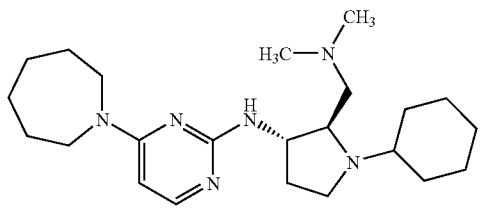 [SMILES: CN(C)C[C@@H]1[C@@H](Nc2nccc(N3CCCCCC3)n2)CCN1C1CCCCC1]

To a solution of the compound 10 (76 mg) in a 1% acetic acid-dichloromethane solution (2 mL), 37% formaldehyde-aqueous solution (0.07 mL) and sodium triacetoxyborohydride (159 mg) were added. The reaction mixture was stirred at room temperature for 6 hours. The reaction mixture was added tert-butyl methyl ether, washed with aqueous 2N sodium hydroxide solution, dried over anhydrous sodium sulfate and then concentrated. The obtained residue was purified by silica gel column chromatography (ethyl acetate:methanol: 27% aqueous ammonia=100:0:0→90:10:0→90:10:1) to obtain the title compound (64 mg) having the following physical properties.

TLC: Rf 0.45 (chloroform:methanol:ammonium hydroxide=8:1:0.1);
NMR (CDCl$_3$): δ 1.06-1.33 (m, 6 H), 1.46-1.68 (m, 5 H), 1.68-1.82 (m, 6 H), 1.82-1.95 (m, 3 H), 1.97-2.12 (m, 1 H), 2.19-2.30 (m, 7 H), 2.45-2.56 (m, 1 H), 2.67-2.80 (m, 2 H), 2.86-2.96 (m, 1 H), 3.40-3.65 (m, 4 H), 4.21 (t, J=6.22 Hz, 1 H), 4.86 (d, J=6.40 Hz, 1 H), 5.76 (d, J=6.04 Hz, 1 H), 7.79 (d, J=6.04 Hz, 1 H).

EXAMPLE 11(1) TO 11(6)

The same procedure as a series of reactions of Example 11 was carried out, except that the compounds 10-1 to 10-6 were used in place of the compound 10, to obtain the following compound of the present invention.

EXAMPLE 11(1)

4-(1-azepanyl)-N-{(2R,3S)-1-cyclohexyl-2-[2-(dimethylamino)ethyl]-3-pyrrolidinyl}-2-pyrimidinamine (compound 11-1)

TLC: Rf 0.58 (ethyl acetate:methanol:ammonium hydroxide=20:5:1);
NMR (CDCl$_3$): δ 1.46 (m, 22 H), 2.21 (m, 2 H), 2.21 (s, 6 H), 2.53 (m, 1 H), 2.73 (m, 2 H), 2.88 (m, 1 H), 3.56 (m, 4 H), 4.10 (m, 1 H), 5.18 (m, 1 H), 5.78 (d, J=6.00 Hz, 1 H), 7.80 (d, J=6.00 Hz, 1 H).

EXAMPLE 11(2)

4-(1-azepanyl)-N-{(2R,3S)-1-cyclohexyl-2-[3-(dimethylamino)propyl]-3-pyrrolidinyl}-2-pyrimidinamine (compound 11-2)

TLC: Rf 0.64 (ethyl acetate:methanol:ammonium hydroxide=20:5:1);
NMR (CDCl$_3$): δ 1.48 (m, 23 H), 2.08 (m, 1 H), 2.20 (s, 6 H), 2.26 (m, 2 H), 2.48 (m, 1 H), 2.66 (m, 1 H), 2.76 (m, 1 H), 2.88 (m, 1 H), 3.55 (m, 4 H), 4.14 (m, 1 H), 4.89 (d, J=6.00 Hz, 1 H), 5.77 (d, J=6.00 Hz, 1 H), 7.78 (d, J=6.00 Hz, 1 H).

EXAMPLE 11(3)

4-(1-azepanyl)-N-{(2R,3S)-1-cyclohexyl-2-[5-(dimethylamino)pentyl]-3-pyrrolidinyl}-2-pyrimidinamine (compound 11-3)

TLC: Rf 0.64 (ethyl acetate:methanol:ammonium hydroxide=20:5:1);
NMR (CDCl$_3$): δ 1.84 (m, 30 H), 2.20 (s, 6 H), 2.46 (m, 1 H), 2.61 (m, 1 H), 2.74 (m, 1 H), 2.88 (m, 1 H), 3.55 (m, 4 H), 4.14 (m, 1 H), 4.91 (m, 1 H), 5.77 (d, J=6.00 Hz, 1 H), 7.78 (d, J=6.00 Hz, 1 H).

EXAMPLE 11(4)

4-(1-azepanyl)-N-{(3S,5R)-1-cyclohexyl-5-[(dimethylamino)methyl]-3-pyrrolidinyl}-2-pyrimidinamine (compound 11-4)

TLC: Rf 0.22 (ethyl acetate:methanol:ammonium hydroxide=100:10:1);
NMR (CDCl$_3$): δ 1.41 (m, 19 H), 2.29 (m, 5 H), 2.23 (s, 6 H), 3.06 (m, 1 H), 3.39 (dd, J=9.00, 6.00 Hz, 1 H), 3.60 (m, 4 H), 4.41 (m, 1 H), 4.85 (m, 1 H), 5.77 (d, J=6.00 Hz, 1 H), 7.77 (d, J=6.00 Hz, 1 H).

EXAMPLE 11(5)

4-(1-azepanyl)-N-{(3S,5S)-1-cyclohexyl-5-[2-(dimethylamino)ethyl]-3-pyrrolidinyl}-2-pyrimidinamine (compound 11-5)

TLC: Rf 0.68 (ethyl acetate:methanol:ammonium hydroxide=20:5:1);
NMR (CDCl$_3$): δ 1.49 (m, 21 H), 1.98 (m, 1 H), 2.27 (m, 2 H), 2.22 (s, 6 H), 2.43 (dd, J=9.00, 7.50 Hz, 1 H), 2.57 (m, 1 H), 2.97 (m, 1 H), 3.38 (dd, J=9.00, 7.00 Hz, 1 H), 3.58 (m, 4 H), 4.41 (m, 2 H), 5.78 (d, J=6.00 Hz, 1 H), 7.72 (d, J=6.00 Hz, 1 H).

EXAMPLE 11(6)

4-(1-azepanyl)-N-{(3S,5S)-1-cyclohexyl-5-[3-(dimethylamino)propyl]-3-pyrrolidinyl}-2-pyrimidinamine (compound 11-6)

TLC: Rf 0.61 (ethyl acetate:methanol:ammonium hydroxide=20:5:1);
NMR (CDCl$_3$): δ 1.58 (m, 24 H), 2.21 (s, 6 H), 2.25 (t, J=7.50 Hz, 2 H), 2.40 (dd, J=9.00, 7.00 Hz, 1 H), 2.54 (m, 1 H), 2.90 (m, 1 H), 3.36 (dd, J=9.00, 6.50 Hz, 1 H), 3.58 (m, 4 H), 4.40 (m, 1 H), 4.73 (d, J=7.00 Hz, 1 H), 5.77 (d, J=6.00 Hz, 1 H), 7.78 (d, J=6.00 Hz, 1 H).

EXAMPLE 12 ethyl {(2RS,3SR)-3-[(tert-butoxycarbonyl)amino]piperidin-2-yl}acetate (compound 12)

According to the procedure described in Tetrahedron Letters, 34, 3593-3594 (1993), the title compound (4.39 g) was obtained.

TLC: Rf 0.32 (chloroform:methanol=9:1);
NMR (CDCl$_3$): δ 1.11-1.32 (m, 4 H), 1.44 (s, 9 H), 1.47-1.61 (m, 1 H), 1.62-1.76 (m, 1 H), 1.79-1.96 (m, 1 H), 1.99-2.12 (m, 1 H), 2.29-2.44 (m, 1 H), 2.50-2.64 (m, 1 H), 2.64-2.79 (m, 2 H), 2.94-3.07 (m, 1 H), 3.22-3.39 (m, 1 H), 4.06-4.22 (m, 2 H), 4.37 (d, J=8.5 Hz, 1 H).

EXAMPLE 13 benzyl (2RS,3SR)-3-[(tert-butoxycarbonyl)amino]-2-(2-ethoxy-2-oxoethyl)piperidine-1-carboxylate (compound 13)

Benzyloxycarbonyl chloride (2.55 mL) was added dropwise to the compound 12 (3.40 g), tetrahydrofuran (50 mL) and triethylamine (4.15 mL) with stirring at 0° C. The reaction solution was stirred at 0° C. for 20 minutes, added water and extracted with ethyl acetate. The extract was dried over anhydrous magnesium sulfate and then concentrated. The obtained residue was purified by silica gel column chromatography (hexane:ethyl acetate=1:1→0:1) to obtain the title compound (4.81 g) having the following physical properties.
TLC: Rf 0.89 (chloroform:methanol=9:1);
NMR (CDCl$_3$): δ 1.17 (t, J=7.1 Hz, 3 H), 1.41 (s, 9 H), 1.47-1.85 (m, 4 H), 2.53 (dd, J=14.3, 6.4 Hz, 1 H), 2.66 (dd, J=14.3, 8.7 Hz, 1 H), 2.85-3.02 (m, 1 H), 3.66-3.79 (m, 1 H), 3.99-4.09 (m, J=7.4 Hz, 3 H), 4.74 (t, J=7.6 Hz, 1 H), 4.82-4.96 (m, 1 H), 5.10 (d, J=12.9 Hz, 1 H), 5.15 (d, J=12.9 Hz, 1 H), 7.18-7.44 (m, 5 H).

EXAMPLE 14 benzyl (2RS,3SR)-3-[(tert-butoxycarbonyl)amino]-2-(2-hydroxyethyl)piperidine-1-carboxylate (compound 14)

1.0 M of a solution (3.15 mL) of Dibal-H in toluene was added dropwise to the compound 13 (440 mg) and toluene (8 mL) with stirring at −78° C. The reaction mixture was stirred at room temperature for 3 hours and then added water at 0° C. Generated salt was removed by filtration with Celite (trade name) and then the filtrate was extracted with ethyl acetate. The extract was dried over anhydrous magnesium sulfate and then concentrated. The obtained residue was dissolved in methanol (2 mL) and then sodium borohydride (40 mg) was added into the solution. The reaction solution was stirred at room temperature for 20 minuets, added water and extracted with ethyl acetate. The extract was dried over anhydrous magnesium sulfate, concentrated and obtained the title compound (267 mg) having the following physical properties.
TLC: Rf 0.41 (hexane:ethyl acetate=1:1);
NMR (CDCl$_3$): δ 1.44 (s, 9 H), 1.49-1.95 (m, 6 H), 2.71-2.92 (m, 1 H), 3.23-3.46 (m, 1 H), 3.49-3.81 (m, 2 H), 3.96-4.19 (m, 1 H), 4.25-4.50 (m, 1 H), 4.85-5.01 (m, 1 H), 5.05-5.30 (m, 2 H), 7.22-7.50 (m, 5 H).

EXAMPLE 15 benzyl (2RS,3SR)-2-(2-azidoethyl)-3-[(tert-butoxycarbonyl)amino]piperidine-1-carboxylate (compound 15)

Triphenylphosphine (202 mg) was added to the compound 14 (146 mg), tetrahydrofuran (1 mL), diphenylphosphoryl azide (0.17 mL) and 2.2 mol/L of a solution (0.35 mL) of diethyl azodicarboxylate in toluene with stirring at 0° C. The reaction solution was stirred at room temperature for 1 hour and then concentrated. The residue was purified by silica gel column chromatography (hexane:ethyl acetate=4:1→1:3) to obtain the title compound (136 mg) having the following physical properties.
TLC: Rf 0.43 (hexane:ethyl acetate=2:1);
NMR (CDCl$_3$): δ 1.42 (s, 9 H), 1.50-1.65 (m, 4 H), 1.67-1.82 (m, 1 H), 1.89-2.03 (m, 1 H), 2.74-2.98 (m, 1 H), 3.19-3.37 (m, 2 H), 3.58-3.77 (m, 1 H), 4.03-4.18 (m, 1 H), 4.33-4.43 (m, 1 H), 4.87 (d, J=7.7 Hz, 1 H), 5.15 (s, 2 H), 7.29-7.44 (m, 5 H).

EXAMPLE 16 benzyl (2RS,3SR)-3-amino-2-(2-azidoethyl)piperidine-1-carboxylate hydrochloride (compound 16)

The compound 15 (125 mg), methanol (0.5 mL) and 4N hydrogen chloride-dioxane solution (2 mL) were stirred at room temperature for 1 hour. The reaction solution was concentrated and obtained the title compound (118 mg) having the following physical properties.
TLC: Rf 0.31 (chloroform:methanol=9:1);
NMR (CDCl$_3$): δ 1.25-1.58 (m, 1 H), 1.62-2.42 (m, 5 H), 2.72-2.99 (m, 1 H), 3.18-3.40 (m, 2 H), 3.44-3.64 (m, 1 H), 4.06-4.29 (m, 1 H), 4.69-4.93 (m, 1 H), 4.96-5.43 (m, 2 H), 7.09-7.57 (m, 5 H), 8.31-8.96 (m, 3 H).

EXAMPLE 17 benzyl (2RS,3SR)-3-[(4-azepan-1-yl-6-chloropyrimidin-2-yl)amino]-2-(2-azidoethyl)piperidine-1-carboxylate (compound 17)

The compound 16 (118 mg), cyclohexanol (0.16 mL), aqueous 5N sodium hydroxide solution (0.25 mL) and 1-(2,6-dichloropyrimidin-4-yl)azepan (83.5 mg) were stirred at 120° C. for 6 hours. The reaction solution was purified by silica gel column chromatography (hexane:ethyl acetate=2:1→1:1) to obtain the title compound (71.2 mg) having the following physical properties.
TLC: Rf 0.38 (hexane:ethyl acetate=2:1);
NMR (CDCl$_3$): δ 1.39-1.63 (m, 4 H), 1.64-1.94 (m, 9 H), 1.94-2.12 (m, 1 H), 2.73-3.01 (m, 1 H), 3.12-3.79 (m, 7 H), 3.81-4.30 (m, 1 H), 4.42-4.73 (m, 1 H), 4.97-5.28 (m, 3 H), 5.79 (s, 1 H), 7.05-7.44 (m, 5 H).

EXAMPLE 18 benzyl (2RS,3SR)-2-(2-aminoethyl)-3-[(4-azepan-1-yl-6-chloropyrimidin-2-yl)amino]piperidine-1-carboxylate (compound 18)

The compound 17 (75.5 mg), tetrahydrofuran (2 mL) and triphenylphosphine (46.3 mg) were stirred at room temperature for 1 day and then added water (0.01 mL). The reaction solution was heated at reflux for 1 day and then concentrated. The residue was purified by silica gel column chromatography (dichloromethane:methanol:triethylamine=90:10:1) to obtain the title compound (55.5 mg) having the following physical properties.
TLC: Rf 0.50 (chloroform:methanol:28% aqueous ammonia=80:10:1);
NMR (CDCl$_3$): δ 1.33-1.62 (m, 5 H), 1.61-2.08 (m, 8 H), 2.16-2.49 (m, 3 H), 2.56-2.97 (m, 3 H), 3.20-3.81 (m, 4 H), 3.81-4.25 (m, 2 H), 4.43-4.64 (m, 1 H), 4.96-5.35 (m, 3 H), 5.79 (s, 1 H), 7.06-7.51 (m, 5 H).

EXAMPLE 19 benzyl (2RS,3SR)-3-[(4-azepan-1-yl-6-chloropyrimidin-2-yl)amino]-2-{2-[(tert-butoxycarbonyl)amino]ethyl}piperidine-1-carboxylate (compound 19)

tert-Butyl carbonate (165 mg) was added to the compound 18 (245 mg), tetrahydrofuran (2 mL), water (2 mL) and triethylamine (0.11 mL) with stirring at 0° C. The reaction solution was stirred at room temperature for 2 hours, added water and extracted with ethyl acetate. The extract was dried over anhydrous magnesium sulfate and then concentrated. The residue was filtered with hexane and obtained the title compound (225 mg) having the following physical properties.
TLC: Rf 0.53 (hexane:ethyl acetate=2:1);
NMR (CDCl$_3$): δ 1.29-2.03 (m, 23 H), 2.56-2.93 (m, 2 H), 3.07-4.29 (m, 7 H), 4.41-4.61 (m, 1 H), 4.91-5.55 (m, 4 H), 5.80 (s, 1 H), 7.12-7.48 (m, 5 H).

EXAMPLE 20 tert-butyl (2-{(2RS,3SR)-3-[(4-azepan-1-ylpyrimidin-2-yl)amino]piperidin-2-yl}ethyl)carbamate (compound 20)

The compound 19 (225 mg), acetic acid (4 mL) and 10% palladium carbon (20 mg) were stirred under hydrogen atmosphere at room temperature for 6 hours. The reaction solution was filtered and then the filtrate was concentrated. The residue was added aqueous 2N sodium hydroxide solution and extracted with dichloromethane. The extract was dried over anhydrous magnesium sulfate, concentrated and obtained the title compound (155 mg) having the following physical properties.
TLC: Rf 0.35 (chloroform:methanol=9:1);
NMR (CDCl$_3$): δ 1.19-1.34 (m, 1 H), 1.40-1.47 (m, 9 H), 1.49-1.63 (m, 5 H), 1.64-2.02 (m, 8 H), 2.07-2.19 (m, 1 H), 2.38-2.49 (m, 1 H), 2.49-2.61 (m, 1 H), 2.99-3.09 (m, 1 H), 3.10-3.21 (m, 1 H), 3.23-3.85 (m, 6 H), 4.54-4.86 (m, 1 H), 5.07-5.41 (m, 1 H), 5.78 (d, J=6.0 Hz, 1 H), 7.77 (d, J=6.0 Hz, 1 H).

EXAMPLE 21 tert-butyl (2-{(2RS,3SR)-3-[(4-azepan-1-ylpyrimidin-2-yl)amino]-1-cyclohexylpiperidin-2-yl}ethyl)carbamate (compound 21)

The compound 20 (151 mg), dimethylformamide (3 mL), acetic acid (0.03 mL), cyclohexanone (0.37 mL), anhydrous sodium sulfate (800 mg) and sodium triacetoxyborohydride (765 mg) were stirred at room temperature for 1 day. The reaction solution was added aqueous 2N sodium hydroxide solution and extracted with dichloromethane. The extract was dried over anhydrous magnesium sulfate and then concentrated. The residue was purified by silica gel column chromatography (ethyl acetate:methanol:triethylamine=80:10:1) to obtain the title compound (118 mg) having the following physical properties.
TLC: Rf 0.43 (chloroform:methanol=9:1);
NMR (CDCl$_3$): δ 0.98-1.34 (m, 7 H), 1.43 (s, 9 H), 1.49-1.64 (m, 5 H), 1.63-1.86 (m, 10 H), 1.87-2.07 (m, 2 H), 2.38-2.70 (m, 3 H), 2.75-2.91 (m, 1 H), 3.03-3.20 (m, 1 H), 3.24-3.84 (m, 5 H), 3.89-4.08 (m, 1 H), 5.31-5.64 (m, 2 H), 5.77 (d, J=6.2 Hz, 1 H), 7.81 (d, J=6.2 Hz, 1 H).

EXAMPLE 22

N-[(2RS,3SR)-2-(2-aminoethyl)-1-cyclohexyl-3-piperidinyl]-4-(1-azepanyl)-2-pyrimidinamine (compound 22)

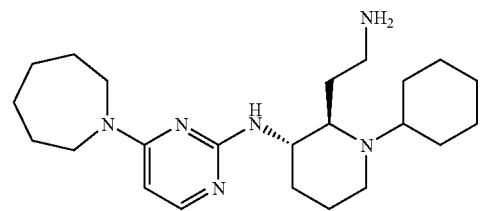 [SMILES: NCC[C@@H]1[C@@H](Nc2nccc(N3CCCCCC3)n2)CCCN1C1CCCCC1]

The compound 21 (102 mg) and 10% hydrogen chloride-methanol solution (2 mL) were stirred at room temperature for 5 hours. The reaction solution was concentrated, added aqueous 2N sodium hydroxide solution and then extracted with dichloromethane. The extract was dried over anhydrous magnesium sulfate, concentrated and obtained the title compound (71 mg) having the following physical properties.
Description: amorphous powder;
TLC: Rf 0.48 (chloroform:methanol:28% aqueous ammonia=80:10:1);
NMR (CDCl$_3$): δ 0.98-1.93 (m, 26 H), 2.32-2.47 (m, 1 H), 2.51-2.64 (m, 2 H), 2.69-2.91 (m, 3 H), 3.33-3.88 (m, 4 H), 3.90-4.05 (m, 1 H), 5.51-5.67 (m, 1 H), 5.74 (d, J=6.0 Hz, 1 H), 7.79 (d, J=6.0 Hz, 1 H).

EXAMPLE 22(1) TO EXAMPLE 22(11)

The same procedure as a series of reactions of Example 21→Example 22 was carried out, except that a corresponding carbonyl compound was used in place of cyclohexanone and a corresponding amine compound was used in place of the compound 20 in the process of Example 21, to obtain the following compound of the present invention.

EXAMPLE 22(1)

N-[(2RS,3SR)-2-(2-aminoethyl)-1-isopropyl-3-piperidinyl]-4-(1-azepanyl)-2-pyrimidinamine (compound 22-1)

TLC: Rf 0.46 (chloroform:methanol:28% aqueous ammonia=40:10:1);
NMR (CDCl$_3$): δ 0.98 (d, J=6.4 Hz, 3 H), 1.08 (d, J=6.4 Hz, 3 H), 1.60 (d, 16 H), 2.41-2.62 (m, 2 H), 2.68-2.82 (m, 3 H), 2.82-2.93 (m, 1 H), 3.28-3.84 (m, 4 H), 3.92-4.03 (m, 1 H), 5.43 (d, J=8.4 Hz, 1 H), 5.74 (d, J=6.2 Hz, 1 H), 7.80 (d, J=6.2 Hz, 1 H).

EXAMPLE 22(2)

(2RS,3SR)-2-(2-aminoethyl)-N-[4-(1-azepanyl)-2-pyrimidinyl]-1'-(3-fluorobenzoyl)-1,4'-bipiperidin-3-amine (compound 22-2)

TLC: Rf 0.32 (chloroform:methanol:28% aqueous ammonia=80:10:1);

NMR (CDCl₃): δ 1.10-2.05 (m, 20 H), 2.39-3.18 (m, 8 H), 3.23-3.87 (m, 5 H), 3.94-4.11 (m, 1 H), 4.42-4.71 (m, 1 H), 5.42-5.62 (m, 1 H), 5.76 (d, J=6.2 Hz, 1 H), 7.01-7.23 (m, 3 H), 7.32-7.46 (m, 1 H), 7.79 (d, J=6.2 Hz, 1 H).

EXAMPLE 22(3)

(2RS,3SR)-2-(2-aminoethyl)-N-[4-(1-azepanyl)-2-pyrimidinyl]-1'-(cyclohexylcarbonyl)-1,4'-bipiperidin-3-amine (compound 22-3)

TLC: Rf 0.32 (chloroform:methanol:28% aqueous ammonia=80:10:1);
NMR (CDCl₃): δ 1.13-1.35 (m, 4 H), 1.35-1.61 (m, 8 H), 1.63-1.96 (m, 16 H), 1.98-2.38 (m, 2 H), 2.39-2.71 (m, 5 H), 2.71-2.93 (m, 3 H), 2.93-3.17 (m, 1 H), 3.18-3.81 (m, 4 H), 3.82-4.16 (m, 2 H), 4.42-4.67 (m, 1 H), 5.42-5.65 (m, 1 H), 5.76 (d, J=6.0 Hz, 1 H), 7.79 (d, J=6.0 Hz, 1 H).

EXAMPLE 22(4)

N-{(2R,3S)-2-(3-aminopropyl)-1-[1-(cyclohexylcarbonyl)-4-piperidinyl]-3-pyrrolidinyl}-4-(1-azepanyl)-2-pyrimidinamine (compound 22-4)

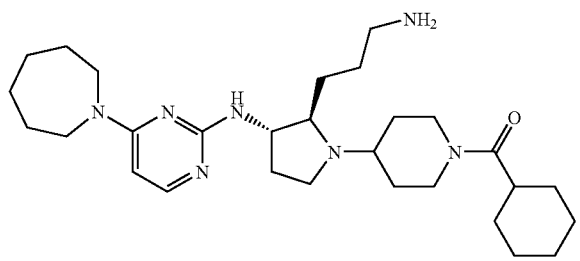 [SMILES: NCCC[C@@H]1[C@@H](Nc2nccc(N3CCCCCC3)n2)CCN1C1CCN(C(=O)C2CCCCC2)CC1]

TLC: Rf 0.50 (ethyl acetate:methanol:28% aqueous ammonia=20:5:1);
NMR (CDCl₃): δ 1.58 (m, 27 H), 2.11 (m, 1 H), 2.74 (m, 9 H), 3.56 (m, 4 H), 3.93 (m, 1 H), 4.15 (m, 1 H), 4.59 (m, J=11.50 Hz, 1 H), 5.14 (m, 1 H), 5.79 (d, J=6.00 Hz, 1 H), 7.77 (d, J=6.00 Hz, 1 H).

EXAMPLE 22(5)

N-{(2R,3S)-2-(3-aminopropyl)-1-[1-(cyclopentylcarbonyl)-4-piperidinyl]-3-pyrrolidinyl}-4-(1-azepanyl)-2-pyrimidinamine (compound 22-5)

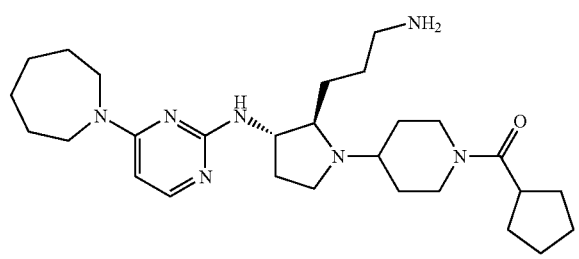 [SMILES: NCCC[C@@H]1[C@@H](Nc2nccc(N3CCCCCC3)n2)CCN1C1CCN(C(=O)C2CCCC2)CC1]

Description: amorphous powder;
TLC: Rf 0.50 (ethyl acetate:methanol:28% aqueous ammonia=20:5:1);
NMR (CDCl₃): δ 1.65 (m, 26 H), 2.11 (m, 1 H), 2.83 (m, 9 H), 3.57 (m, 4 H), 3.98 (d, J=13.50 Hz, 1 H), 4.15 (m, 1 H), 4.60 (d, J=13.00 Hz, 1 H), 5.79 (d, J=6.00 Hz, 1 H), 7.76 (d, J=6.00 Hz, 1 H).

EXAMPLE 22(6)

N-{(2R,3S)-2-(3-aminopropyl)-1-[1-(2-ethylbutanoyl)-4-piperidinyl]-3-pyrrolidinyl}-4-(1-azepanyl)-2-pyrimidinamine (compound 22-6)

TLC: Rf 0.50 (ethyl acetate:methanol:28% aqueous ammonia=20:5:1);
NMR (CDCl₃): δ 0.87 (m, 6 H), 1.62 (m, 21 H), 2.12 (m, 1 H), 2.69 (m, 8 H), 3.03 (m, 1 H), 3.57 (m, 4 H), 4.04 (d, J=13.00 Hz, 1 H), 4.15 (m, 1 H), 4.68 (d, J=13.50 Hz, 1 H), 5.21 (m, 1 H), 5.79 (d, J=6.00 Hz, 1 H), 7.76 (d, J=6.00 Hz, 1 H).

EXAMPLE 22(7)

N-{(2R,3S)-2-(3-aminopropyl)-1-[1-(cyclopentylacetyl)-4-piperidinyl]-3-pyrrolidinyl}-4-(1-azepanyl)-2-pyrimidinamine (compound 22-7)

TLC: Rf 0.50 (ethyl acetate:methanol:28% aqueous ammonia=20:5:1);
NMR (CDCl₃): δ 1.55 (m, 26 H), 2.18 (m, 1 H), 2.35 (m, 2 H), 2.70 (m, 7 H), 3.01 (m, 1 H), 3.55 (m, 4 H), 3.89 (d, J=13.00 Hz, 1 H), 4.15 (m, 1 H), 4.59 (d, J=13.50 Hz, 1 H), 5.05 (m, 1 H), 5.79 (d, J=6.00 Hz, 1 H), 7.77 (d, J=6.00 Hz, 1 H).

EXAMPLE 22(8)

N-{(2R,3S)-2-(3-aminopropyl)-1-[1-(3-fluorobenzoyl)-4-piperidinyl]-3-pyrrolidinyl}-4-(1-azepanyl)-2-pyrimidinamine (compound 22-8)

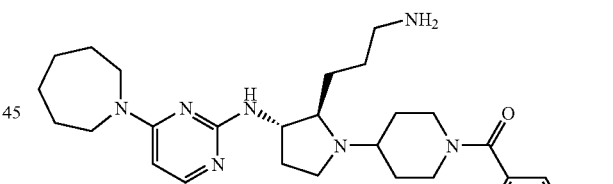

TLC: Rf 0.50 (ethyl acetate:methanol:28% aqueous ammonia=20:5:1);
NMR (CDCl₃): δ 1.64 (m, 17 H), 2.14 (m, 1 H), 2.88 (m, 8 H), 3.63 (m, 5 H), 4.16 (m, 1 H), 4.64 (m, 1 H), 5.21 (m, 1 H), 5.79 (d, J=6.00 Hz, 1 H), 7.10 (m, 2 H), 7.17 (dt, J=7.50, 1.00 Hz, 1 H), 7.38 (ddd, J=9.00, 7.50, 5.50 Hz, 1 H), 7.76 (d, J=6.00 Hz, 1 H).

EXAMPLE 22(9)

2-[4-((2R,3S)-2-(3-aminopropyl)-3-{[4-(1-azepanyl)-2-pyrimidinyl]amino}-1-pyrrolidinyl)-1-piperidinyl]-2-oxoethanol (compound 22-9)

TLC: Rf 0.06 (ethyl acetate:methanol:28% aqueous ammonia=20:5:1);

NMR (DMSO-D$_6$): δ 1.62 (m, 17 H), 1.89 (m, 1 H), 2.55 (m, 6 H), 2.91 (m, 1 H), 3.40 (m, 8 H), 4.06 (m, 3 H), 4.31 (d, J=12.99 Hz, 1 H), 4.43 (m, 1 H), 5.82 (d, J=6.00 Hz, 1 H), 6.25 (m, 1 H), 7.70 (d, J=6.00 Hz, 1 H).

EXAMPLE 22(10)

N-[(3R,4S)-4-(aminomethyl)-1-cyclohexyl-3-pyrrolidinyl]-4-(1-azepanyl)-2-pyrimidinamine (compound 22-10)

TLC: Rf 0.12 (ethyl acetate:methanol:28% aqueous ammonia=20:5:1);

NMR (CDCl$_3$): δ 1.71 (m, 20 H), 2.21 (m, 1 H), 2.64 (m, 1 H), 2.73 (dd, J=12.50, 6.50 Hz, 1 H), 2.89 (m, 2 H), 3.04 (t, J=8.50 Hz, 1 H), 3.57 (m, 4 H), 4.20 (m, 1 H), 4.98 (d, J=8.50 Hz, 1 H), 5.77 (d, J=6.00 Hz, 1 H), 7.79 (d, J=6.00 Hz, 1 H).

EXAMPLE 22(11)

N-[(3R,4S)-4-(2-aminoethyl)-1-cyclohexyl-3-pyrrolidinyl]-4-(1-azepanyl)-2-pyrimidinamine (compound 22-11)

TLC: Rf 0.12 (ethyl acetate:methanol:28% aqueous ammonia=20:5:1);

NMR (CDCl$_3$): δ 1.66 (m, 22 H), 2.84 (m, 5 H), 3.17 (m, 1 H), 3.55 (m, 4 H), 4.08 (m, 1 H), 5.36 (m, 1 H), 5.79 (d, J=6.00 Hz, 1 H), 7.80 (d, J=6.00 Hz, 1 H).

EXAMPLE 23 tert-butyl 4-{[(2-{(2RS,3SR)-3-[(4-azepan-1-ylpyrimidin-2-yl)amino]-1-cyclohexylpiperidin-2-yl}ethyl)amino]carbonyl}piperidine-1-carboxylate (compound 23)

N-[(2RS,3SR)-2-(2-aminoethyl)-1-cyclohexylpiperidin-3-yl]-4-azepan-1-ylpyrimidin-2-amine (63 mg) was dissolved in dichloromethane (3 mL), PS-carbodiimide (327 mg) was added and then 0.5 M of a solution (0.47 mL) of 1-(tert-butoxycarbonyl)piperidine-4-carboxylic acid in dimethylformamide:dichloromethane=1:1 and 0.5 M of a mixture solution (0.53 mL) of hydroxybenzotriazole in dimethylformamide:dichloromethane=1:1 were added and stirred at room temperature for overnight. MP-carbonate (271 mg) was added into the reaction solution, stirred for 1 hour and then filtered and concentrated. The residue was purified by silica gel column chromatography (ethyl acetate:methanol=90:10) to obtain the title compound (81 mg) having the following physical properties.

TLC: Rf 0.41 (chloroform:methanol:28% aqueous ammonia=80:10:1);

NMR (METHANOL-D$_4$): δ 1.04-1.98 (m, 37 H), 2.20-2.35 (m, 1 H), 2.49-2.64 (m, 1 H), 2.64-2.93 (m, 5 H), 3.12-3.28 (m, 2 H), 3.39-3.91 (m, 4 H), 3.91-4.17 (m, 3 H), 5.97 (d, J=6.6 Hz, 1 H), 7.68 (d, J=6.6 Hz, 1 H).

EXAMPLE 24

N-[2-((2RS,3SR)-3-{[4-(1-azepanyl)-2-pyrimidinyl]amino}-1-cyclohexyl-2-piperidinyl)ethyl]-4-piperidinecarboxamide trihydrochloride (compound 24)

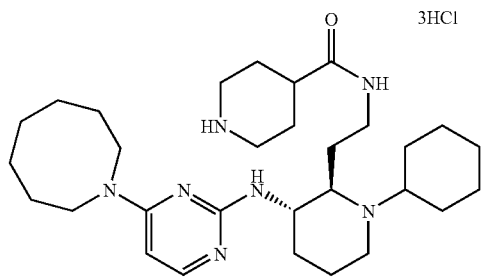 [SMILES: O=C(NCC[C@@H]1[C@@H](Nc2nccc(N3CCCCCCC3)n2)CCCN1C1CCCCC1)C1CCNCC1 ; "3HCl"]

The compound 23 (74 mg), ethyl acetate (0.6 mL) and 4N hydrogen chloride-ethyl acetate solution (0.6 mL) were stirred at room temperature for 2 hours. The reaction solution was concentrated and obtained the title compound (80 mg) having the following physical properties.

Description: amorphous powder;

TLC: Rf 0.57 (chloroform:methanol:28% aqueous ammonia=40:10:1);

NMR (METHANOL-D$_4$): δ 1.07-2.26 (m, 29 H), 2.46-2.64 (m, 1 H), 2.91-3.15 (m, 4 H), 3.32-3.50 (m, 4 H), 3.56-3.66 (m, 1 H), 3.70 (t, J=6.5 Hz, 2 H), 3.75-3.90 (m, 1 H), 3.90-3.99 (m, 2 H), 4.62-4.80 (m, 1 H), 6.44 (d, J=7.5 Hz, 1 H), 7.72 (d, J=7.7 Hz, 1 H).

EXAMPLE 24(1) TO EXAMPLE 24(18)

The same procedure as a series of reactions of Example 23 Example 24 was carried out, except that a corresponding carboxylic acid was used in place of 1-(tert-butoxycarbonyl)piperidine-4-carboxylic acid and a corresponding amine compound was used in place of N-[(2RS,3SR)-2-(2-aminoethyl)-1-cyclohexylpiperidin-3-yl]-4-azepan-1-ylpyrimidin-2-amine in the process of Example 23, to obtain the following compound of the present invention.

EXAMPLE 24(1)

(2R)-2-amino-N-[2-((2RS,3SR)-3-{[4-(1-azepanyl)-2-pyrimidinyl]amino}-1-cyclohexyl-2-piperidinyl)ethyl]-3-[4-(benzyloxy)phenyl]propanamide trihydrochloride (compound 24-1)

TLC: Rf 0.78 (ethyl acetate:methanol:28% aqueous ammonia=20:5:1).

EXAMPLE 24(2)

(2S)-2-amino-N-[2-((2RS,3SR)-3-{[4-(1-azepanyl)-2-pyrimidinyl]amino}-1-cyclohexyl-2-piperidinyl)ethyl]-3-[4-(benzyloxy)phenyl]propanamide trihydrochloride (compound 24-2)

TLC: Rf 0.78 (ethyl acetate:methanol:28% aqueous ammonia=20:5:1).

EXAMPLE 24(3)

(2R)-2-amino-N-[2-((2RS,3SR)-3-{[4-(1-azepanyl)-2-pyrimidinyl]amino}-1-cyclohexyl-2-piperidinyl)ethyl]-4-(benzyloxy)butanamide trihydrochloride (compound 24-3)

TLC: Rf 0.54 (ethyl acetate:methanol:28% aqueous ammonia=100:10:1).

EXAMPLE 24(4)

(2S)-2-amino-N-[2-((2RS,3SR)-3-{[4-(1-azepanyl)-2-pyrimidinyl]amino}-1-cyclohexyl-2-piperidinyl)ethyl]-4-(benzyloxy)butanamide trihydrochloride (compound 24-4)

TLC: Rf 0.54 (ethyl acetate:methanol:28% aqueous ammonia=100:10:1).

EXAMPLE 24(5)

(2R)-2-amino-N-[2-((2RS,3SR)-3-{[4-(1-azepanyl)-2-pyrimidinyl]amino}-1-cyclohexyl-2-piperidinyl)ethyl]-3-(benzyloxy)propanamide trihydrochloride (compound 24-5)

TLC: Rf 0.51 (ethyl acetate:methanol:28% aqueous ammonia=100:10:1).

EXAMPLE 24(6)

(2S)-2-amino-N-[2-((2RS,3SR)-3-{[4-(1-azepanyl)-2-pyrimidinyl]amino}-1-cyclohexyl-2-piperidinyl)ethyl]-3-(benzyloxy)propanamide trihydrochloride (compound 24-6)

TLC: Rf 0.51 (ethyl acetate:methanol:28% aqueous ammonia=100:10:1).

EXAMPLE 24(7)

N-[2-((2RS,3SR)-3-{[4-(1-azepanyl)-2-pyrimidinyl]amino}-1-cyclohexyl-2-piperidinyl)ethyl]-3-morpholinecarboxamide trihydrochloride (compound 24-7)

TLC: Rf 0.66 (chloroform:methanol:28% aqueous ammonia=40:10:1);
NMR (METHANOL-D$_4$): δ 1.18-1.39 (m, 1 H), 1.44-1.67 (m, 7 H), 1.68-1.78 (m, 3 H), 1.78-1.90 (m, 4 H), 1.90-1.99 (m, 2 H), 2.00-2.27 (m, 7 H), 2.91-3.09 (m, 1 H), 3.19-3.52 (m, 5 H), 3.56-3.79 (m, 5 H), 3.78-4.02 (m, 5 H), 4.03-4.21 (m, 2 H), 4.65-4.76 (m, 1 H), 6.35-6.50 (m, J=7.3 Hz, 1 H), 7.66-7.74 (m, 1 H), 8.53-8.65 (m, 1 H).

EXAMPLE 24(8)

(3S)-N-[2-((2RS,3SR)-3-{[4-(1-azepanyl)-2-pyrimidinyl]amino}-1-cyclohexyl-2-piperidinyl)ethyl]-3-pyrrolidinecarboxamide trihydrochloride (compound 24-8)

TLC: Rf 0.63 (chloroform:methanol:28% aqueous ammonia=40:10:1);
NMR (METHANOL-D$_4$): δ 1.18-1.36 (m, 1 H), 1.46-1.67 (m, 6 H), 1.68-1.79 (m, 3 H), 1.79-1.89 (m, 5 H), 1.90-2.00 (m, 2 H), 1.99-2.21 (m, 7 H), 2.20-2.40 (m, 3 H), 2.91-3.08 (m, 1 H), 3.10-3.22 (m, 1 H), 3.32-3.56 (m, 7 H), 3.56-3.66 (m, 1 H), 3.66-3.73 (m, 2 H), 3.79-3.90 (m, 1 H), 3.95 (t, J=6.1 Hz, 2 H), 4.62-4.76 (m, 1 H), 6.44 (d, J=7.5 Hz, 1 H), 7.72 (d, J=7.5 Hz, 1 H), 8.30-8.42 (m, 1 H).

EXAMPLE 24(9)

N-[2-((2RS,3SR)-3-{[4-(1-azepanyl)-2-pyrimidinyl]amino}-1-ethyl-2-piperidinyl)ethyl]-4-piperidinecarboxamide trihydrochloride (compound 24-9)

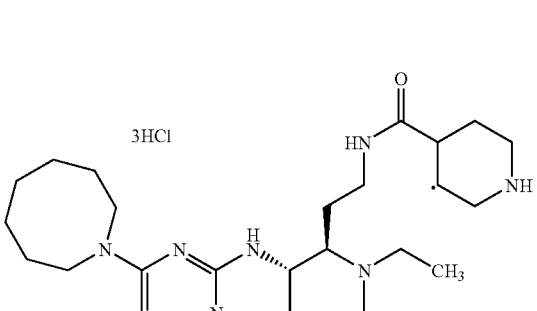

TLC: Rf 0.11 (chloroform:methanol:28% aqueous ammonia=80:10:1);
NMR (METHANOL-D$_4$): δ 1.33-1.48 (m, 3 H), 1.51-1.70 (m, 4 H), 1.71-2.26 (m, 13 H), 2.45-2.71 (m, 1 H), 2.95-3.16 (m, 2 H), 3.20-3.52 (m, 9 H), 3.54-3.78 (m, 3 H), 3.93 (q, J=5.87 Hz, 2 H), 4.38-4.68 (m, 1 H), 6.44 (dd, J=7.60, 2.93 Hz, 1 H), 7.71 (dd, J=7.60, 2.93 Hz, 1 H).

EXAMPLE 24(10)

N-{2-[(2RS,3SR)-3-{[4-(1-azepanyl)-2-pyrimidinyl]amino}-1-(tetrahydro-2H-thiopyran-4-yl)-2-piperidinyl]ethyl}-4-piperidinecarboxamide trihydrochloride (compound 24-10)

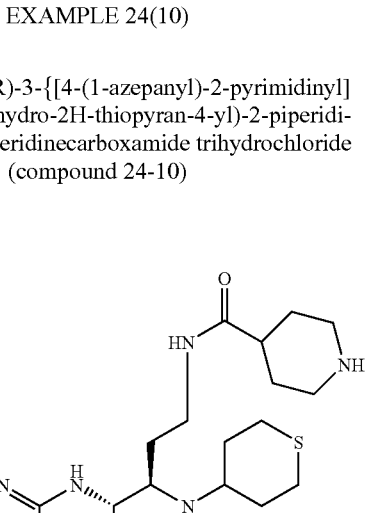

TLC: Rf 0.19 (chloroform:methanol:28% aqueous ammonia=80:10:1);
NMR (METHANOL-D$_4$): δ 1.53-1.67 (m, 4 H), 1.67-2.24 (m, 17 H), 2.39 (d, J=13.20 Hz, 1 H), 2.48-2.66 (m, 2 H), 2.76 (d, J=13.20 Hz, 2 H), 2.91-3.18 (m, 5 H), 3.23-3.53 (m, 5 H), 3.56-3.80 (m, 4 H), 3.90-4.09 (m, 3 H), 6.43 (d, J=7.70 Hz, 1 H), 7.70 (d, J=7.70 Hz, 1 H).

EXAMPLE 24(11)

N-{2-[(2RS,3SR)-3-{[4-(1-azepanyl)-2-pyrimidinyl]
amino}-1-(2-thienylmethyl)-2-piperidinyl]ethyl}-4-
piperidinecarboxamide trihydrochloride (compound
24-11)

TLC: Rf 0.25 (chloroform:methanol:28% aqueous ammonia=80:10:1);

NMR (METHANOL-D₄): δ 1.48-1.67 (m, 4 H), 1.68-2.38 (m, 13 H), 2.53-2.75 (m, J=1 H), 2.95-3.15 (m, 3 H), 3.24-3.61 (m, 7 H), 3.61-3.78 (m, 3 H), 3.85-3.98 (m, 1 H), 4.36-5.17 (m, 3 H), 6.37-6.51 (m, 1 H), 7.04-7.24 (m, 1 H), 7.47 (d, J=6.23 Hz, 1 H), 7.60 (m, 1 H), 7.73 (m, 1 H).

EXAMPLE 24(12)

N-[2-((2RS,3SR)-3-{[4-(1-azepanyl)-2-pyrimidinyl]
amino}-1-isopropyl-2-piperidinyl)ethyl]-4-piperidinecarboxamide trihydrochloride (compound 24-12)

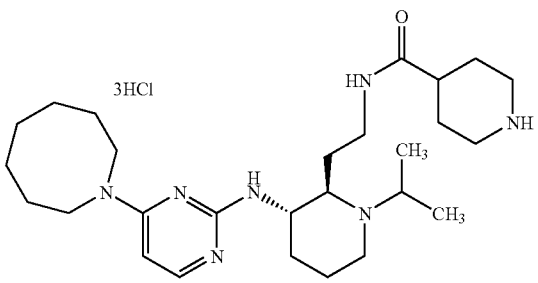 [SMILES: CC(C)N1CCC[C@H](Nc2nccc(N3CCCCCCC3)n2)[C@H]1CCNC(=O)C1CCNCC1 ; "3HCl"]

Description: amorphous powder;

TLC: Rf 0.21 (chloroform:methanol:28% aqueous ammonia=80:10:1);

NMR (METHANOL-D₄): δ 1.34 (d, J=6.60 Hz, 3 H), 1.46-1.69 (m, 7 H), 1.70-1.92 (m, 7 H), 1.92-2.25 (m, 7 H), 2.54 (t, J=10.81 Hz, 1 H), 2.89-3.15 (m, 4 H), 3.35-3.49 (m, 3 H), 3.50-3.78 (m, 4 H), 3.87-4.03 (m, 2 H), 4.10-4.25 (m, 1 H), 4.64-4.81 (m, 1 H), 6.43 (d, J=7.51 Hz, 1 H), 7.71 (d, J=7.51 Hz, 1 H).

EXAMPLE 24(13)

N-(2-{(2RS,3SR)-3-{[4-(1-azepanyl)-2-pyrimidinyl]
amino}-1-[2-(benzyloxy)-2-methylpropyl]-2-
piperidinyl}ethyl)-4-piperidinecarboxamide trihydrochloride (compound 24-13)

TLC: Rf 0.36 (chloroform:methanol:28% aqueous ammonia=80:10:1);

NMR (METHANOL-D₄): δ 1.45-1.72 (m, 10 H), 1.71-2.37 (m, 13 H), 2.46-2.85 (m, 3 H), 3.05 (dd, J=12.46, 9.53 Hz, 2 H), 3.16-3.36 (m, 2 H), 3.43 (dd, J=12.46, 3.67 Hz, 3 H),

EXAMPLE 24(14)

N-(2-{(2RS,3SR)-3-{[4-(1-azepanyl)-2-pyrimidinyl]
amino}-1-[2-hydroxy-1-(hydroxymethyl)ethyl]-2-
piperidinyl}ethyl)-4-piperidinecarboxamide trihydrochloride (compound 24-14)

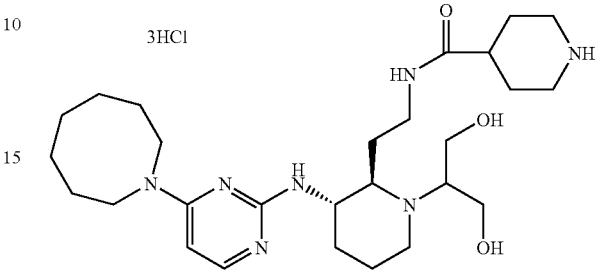

TLC: Rf 0.39 (chloroform:methanol:28% aqueous ammonia=80:20:2);

NMR (METHANOL-D₄): δ 1.52-1.67 (m, 4 H), 1.72-1.91 (m, 7 H), 1.92-2.22 (m, 10 H), 2.55 (t, J=10.25 Hz, 1 H), 3.03 (dd, J=11.62, 8.87 Hz, 2 H), 3.22-3.49 (m, 4 H), 3.52-4.17 (m, 11 H), 4.58-4.79 (m, 1 H), 6.44 (d, J=7.59 Hz, 1 H), 7.71 (d, J=7.59 Hz, 1 H).

EXAMPLE 24(15)

N-{2-[(2RS,3SR)-3-{[4-(1-azepanyl)-2-pyrimidinyl]
amino}-1-(2-hydroxy-2-methylpropyl)-2-piperidinyl]ethyl}-4-piperidinecarboxamide trihydrochloride
(compound 24-15)

TLC: Rf 0.27 (ethyl acetate:methanol:28% aqueous ammonia=90:10:1);

NMR (METHANOL-D₄): δ 1.33-1.47 (m, 6 H), 1.53-1.72 (m, 4 H), 1.73-2.35 (m, 14H), 2.55-2.76 (m, 1 H), 2.95-3.35 (m, 6 H), 3.36-4.10 (m, 10 H), 4.41 (s, 1 H), 6.46 (d, J=7.59 Hz, 1 H), 7.73 (d, J=7.59 Hz, 1 H).

EXAMPLE 24(16)

N-{2-[(2RS,3SR)-3-{[4-(1-azepanyl)-2-pyrimidinyl]
amino}-1-(tetrahydro-2H-pyran-4-yl)-2-piperidinyl]
ethyl}-4-piperidinecarboxamide trihydrochloride
(compound 24-16)

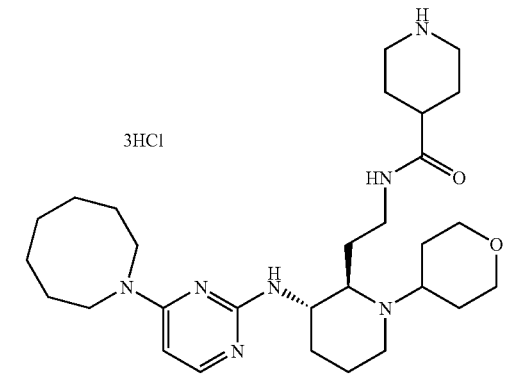 [SMILES: O=C(NCC[C@@H]1[C@@H](Nc2nccc(N3CCCCCCC3)n2)CCCN1C1CCOCC1)C1CCNCC1 ; "3HCl"]

Description: amorphous powder;

TLC: Rf 0.25 (chloroform:methanol:28% aqueous ammonia=80:10:1);

NMR (METHANOL-D$_4$): δ 1.51-1.69 (m, 4 H), 1.69-2.31 (m, 17 H), 2.43-2.66 (m, 1 H), 2.95-3.14 (m, 3 H), 3.27-3.53 (m, 5 H), 3.54-3.79 (m, 6 H), 3.80-4.14 (m, 4 H), 4.14-4.32 (m, 1 H), 4.56-5.00 (m, 1 H), 6.38-6.52 (m, 1 H), 7.65-7.79 (m, 1 H).

EXAMPLE 24(17)

N-[2-((2S*,3S*)-3-{[4-(1-azepanyl)-2-pyrimidinyl]amino}-1-cyclohexyl-2-piperidinyl)ethyl]-4-piperidinecarboxamide trihydrochloride (compound 24-17)

TLC: Rf 0.61 (chloroform:methanol:28% aqueous ammonia=80:20:2);

NMR (METHANOL-D$_4$): δ 1.13-2.39 (m, 31 H), 2.45-2.67 (m, 1 H), 2.96-3.47 (m, 6 H), 3.50-4.20 (m, 6 H), 6.44 (d, J=7.68 Hz, 1 H), 7.66-7.76 (m, 1 H).

EXAMPLE 24(18)

N-[2-((2RS,3SR)-1-ethyl-3-{[4-(1-piperidinyl)-2-pyrimidinyl]amino}-2-piperidinyl)ethyl]-4-piperidinecarboxamide trihydrochloride (compound 24-18)

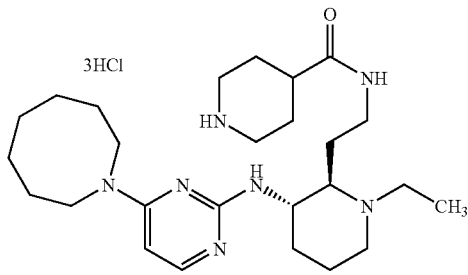 [SMILES: CCN1CCC[C@H](Nc2nccc(N3CCCCCCC3)n2)[C@H]1CCNC(=O)C1CCNCC1 ; "3HCl"]

TLC: Rf 0.31 (dichloromethane:methanol:28% aqueous ammonia=40:10:1);

NMR (METHANOL-D$_4$): δ 1.32-1.48 (m, 3 H), 1.57-2.29 (m, 16 H), 2.46-2.73 (m, 1 H), 2.94-3.14 (m, 2 H), 3.19-3.52 (m, 7 H), 3.52-3.80 (m, 4 H), 3.81-4.13 (m, 2 H), 4.38-4.68 (m, 1 H), 6.45-6.59 (m, 1 H), 7.63-7.77 (m, 1 H).

EXAMPLE 25

{(2RS,3SR)-1-[(benzyloxy)carbonyl]-3-[(tert-butoxycarbonyl)amino]piperidin-2-yl}acetic acid (compound 25)

Benzyl (2RS,3SR)-3-[(tert-butoxycarbonyl)amino]-2-(2-ethoxy-2-oxoethyl)piperidine-1-carboxylate (3.08 g), ethanol (30 mL), tetrahydrofuran (8 mL) and aqueous 2N sodium hydroxide solution (4.4 mL) were stirred at room temperature for 4 hours. The reaction solution was neutralized with aqueous 2N hydrochloric acid solution and then concentrated. The residue was added water and extracted with ethyl acetate. The extract was dried over anhydrous magnesium sulfate, concentrated and obtained the title compound (3.00 g) having the following physical properties.

TLC: Rf 0.44 (chloroform:methanol=9:1);

NMR (CDCl$_3$): δ 1.36-1.44 (m, 9 H), 2.52-2.72 (m, 2 H), 2.79-2.99 (m, 1 H), 3.72-3.87 (m, 1 H), 3.97-4.12 (m, 1 H), 4.68-4.81 (m, 1 H), 4.85-5.01 (m, 1 H), 5.11 (s, 2 H), 7.21-7.45 (m, 5 H).

EXAMPLE 26 benzyl (2RS,3SR)-2-{2-[(3-azidopropyl)amino]-2-oxoethyl}-3-[(tert-butoxycarbonyl)amino]piperidine-1-carboxylate (compound 26)

The compound 25 (784 mg), dimethylformamide (8 mL), propane-1,3-diamine (300 mg), 1-hydroxybenzotriazole (297 mg) and 1,2-dichloroethane (575 mg) were stirred at room temperature for overnight. The reaction solution was added water and extracted with ethyl acetate. The extract was dried over anhydrous magnesium sulfate and then concentrated. The residue was purified by silica gel column chromatography (hexane:ethyl acetate=66:34→0:100) to obtain the title compound (797 mg) having the following physical properties.

TLC: Rf 0.68 (ethyl acetate);

NMR (CDCl$_3$): δ 1.43 (s, 9 H), 1.50-1.65 (m, 2 H), 1.60-1.90 (m, 4 H), 2.40-2.75 (m, 2 H), 2.70-3.00 (m, 1 H), 3.10-3.40 (m, 4 H), 3.66 (m, 1 H), 4.00-4.20 (m, 1 H), 4.70 (m, 1 H), 4.86 (m, 1 H), 5.14 (s, 2 H), 6.60-7.20 (m, 1 H), 7.20-7.45 (m, 5 H).

EXAMPLE 27

N-(3-aminopropyl)-2-((2RS,3SR)-3-{[4-(1-azepanyl)-2-pyrimidinyl]amino}-1-cyclohexyl-2-piperidinyl)acetamide (compound 27)

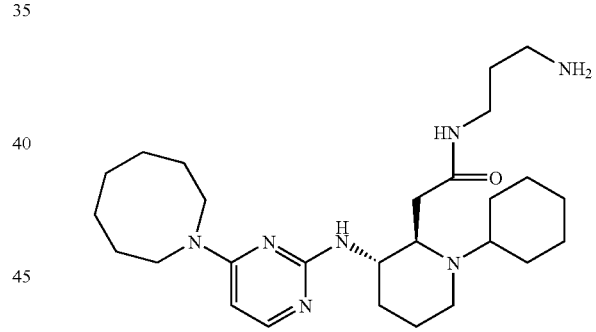

The same procedure as a series of reactions of Example 16→Example 17→Example 18→Example 19→Example 20→Example 21→Example 22 was carried out, except that the compound 26 was used in place of the compound 15 in the process of Example 16, to obtain the title compound (70 mg) having the following physical properties.

Description: amorphous powder;

TLC: Rf 0.41 (chloroform:methanol:28% aqueous ammonia=80:10:1);

NMR (CDCl$_3$): δ 0.97-1.83 (m, 20 H), 1.87-2.16 (m, 7 H), 2.26-2.45 (m, 1 H), 2.49-2.85 (m, 5 H), 2.88-3.01 (m, 1 H), 3.16-3.79 (m, 6 H), 3.98-4.15 (m, 1 H), 4.98-5.29 (m, 1 H), 5.77 (d, J=6.2 Hz, 1 H), 7.73 (d, J=6.2 Hz, 1 H), 8.15-8.48 (m, 1 H).

EXAMPLE 27(1) TO EXAMPLE 27(2)

The same procedure as a series of reactions of Example 26→Example 27 was carried out, except that the corresponding amine was used in place of propane-1,3-diamine and the corresponding carboxylic acid was used in place of the compound 25 in the process of Example 26, to obtain the following compound of the present invention.

EXAMPLE 27(1)

N-(4-aminobutyl)-2-((2RS,3SR)-3-{[4-(1-azepanyl)-2-pyrimidinyl]amino}-1-cyclohexyl-2-piperidinyl)acetamide (compound 27-1)

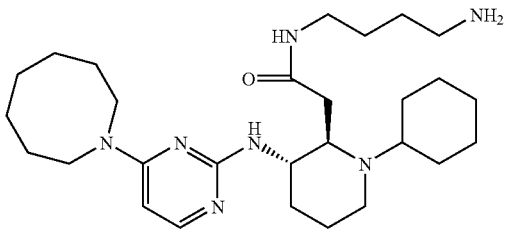 [SMILES: NCCCCNC(=O)C[C@@H]1[C@@H](Nc2nccc(N3CCCCCCC3)n2)CCCN1C1CCCCC1]

TLC: Rf 0.60 (dichloromethane:methanol:28% aqueous ammonia=50:10:1);

NMR (CDCl$_3$): δ1.00-1.80 (m, 26H), 1.98 (m, 1H), 2.33 (m, 1H), 2.48-2.98 (m, 6H), 3.14-3.38 (m, 2H), 3.38-3.70 (m, 4H), 4.06 (m, 1H), 4.88 (m, 1H), 5.76 (d, J=6.3 Hz, 1H), 7.74 (d, J=6.3 Hz, 1H), 8.18 (brs, 1H).

EXAMPLE 27(2)

N-(2-aminoethyl)-2-((2RS,3SR)-3-{[4-(1-azepanyl)-2-pyrimidinyl]amino}-1-cyclohexyl-2-piperidinyl)acetamide (compound 27-2)

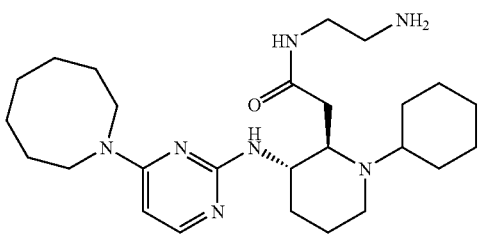 [SMILES: NCCNC(=O)C[C@@H]1[C@@H](Nc2nccc(N3CCCCCCC3)n2)CCCN1C1CCCCC1]

TLC: Rf 0.70 (dichloromethane:methanol:28% aqueous ammonia=50:10:1);

NMR (CDCl$_3$): δ 1.00-1.90 (m, 22H), 2.00 (m, 1 H), 2.30 (m, 1 H), 2.50-2.92 (m, 6 H), 3.20-3.80 (m, 6 H), 4.11 (m, 1 H), 4.85 (m, 1 H), 5.75 (d, J=6.3 Hz, 1 H), 7.72 (d, J=6.3 Hz, 1 H).

EXAMPLE 28

4-(1-azepanyl)-N-[(2S,3S)-1-cyclohexyl-2-(1-piperazinylcarbonyl)-3-pyrrolidinyl]-2-pyrimidinamine (compound 28)

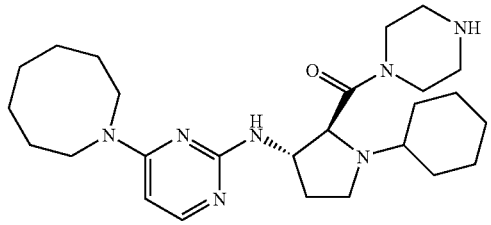 [SMILES: O=C([C@@H]1[C@@H](Nc2nccc(N3CCCCCCC3)n2)CCN1C1CCCCC1)N1CCNCC1]

The same procedure as a series of reactions of Example 26→Example 4→Example 5→Example 15→Example 18→Example 17→Example 19→Example 21→Example 20 was carried out, except that (3S)-1-(tert-butoxycarbonyl)-3-hydroxy-L-proline was used in place of the compound 25 and phenyl piperadine-1-carboxylate was used in place of propane-1,3-diamine in the process of Example 26, to obtain the title compound (97 mg) having the following physical properties.

TLC: Rf 0.55 (ethyl acetate:methanol:28% aqueous ammonia=20:5:1);
NMR (CDCl$_3$): δ 1.50 (m, 19 H), 2.32 (m, 1 H), 2.60 (m, 1 H), 2.80 (m, 4 H), 2.94 (q, J=8.00 Hz, 1 H), 3.18 (dt, J=8.50, 3.50 Hz, 1 H), 3.54 (m, 8 H), 3.76 (d, J=3.00 Hz, 1 H), 4.52 (m, 1 H), 5.11 (d, J=8.50 Hz, 1 H), 5.79 (d, J=6.00 Hz, 1 H), 7.77 (d, J=6.00 Hz, 1 H).

EXAMPLE 28(1) TO EXAMPLE 28(4)

The same procedure as a series of reactions of Example 28 was carried out, except that the corresponding carboxylic acid was used in place of (3S)-1-(tert-butoxycarbonyl)-3-hydroxy-L-proline and the corresponding amine was used in place of phenyl piperadine-1-carboxylate, to obtain the following compound of the present invention.

EXAMPLE 28(1)

(2S,3S)-N-(2-aminoethyl)-3-{[4-(1-azepanyl)-2-pyrimidinyl]amino}-1-cyclohexyl-2-pyrrolidinecarboxamide (compound 28-1)

TLC: Rf 0.38 (ethyl acetate:methanol:28% aqueous ammonia=20:5:1);
NMR (CDCl$_3$): δ 1.56 (m, 19 H), 2.44 (m, 1 H), 2.84 (m, 3 H), 3.12 (ddd, J=9.00, 6.50, 2.00 Hz, 1 H), 3.30 (m, 4 H), 3.55 (m, 4 H), 4.37 (m, 1 H), 4.88 (m, 1 H), 5.80 (d, J=6.00 Hz, 1 H), 7.79 (d, J=6.00 Hz, 1 H), 7.90 (t, J=5.50 Hz, 1 H).

EXAMPLE 28(2)

(2S,3S)-N-(3-aminopropyl)-3-{[4-(1-azepanyl)-2-pyrimidinyl]amino}-1-cyclohexyl-2-pyrrolidinecarboxamide (compound 28-2)

TLC: Rf 0.18 (ethyl acetate:methanol:28% aqueous ammonia=20:5:1);

NMR (CDCl₃): δ 1.56 (m, 21 H), 2.42 (m, 1 H), 2.73 (t, J=6.50 Hz, 2 H), 2.84 (m, 1 H), 3.09 (m, 1 H), 3.33 (m, 4 H), 3.58 (m, 4 H), 4.36 (m, 1 H), 4.86 (d, J=5.50 Hz, 1 H), 5.80 (d, J=6.00 Hz, 1 H), 7.78 (d, J=6.00 Hz, 1 H), 7.81 (m, 1 H).

EXAMPLE 28(3)

(2S,3S)-N-(4-aminobutyl)-3-{[4-(1-azepanyl)-2-pyrimidinyl]amino}-1-cyclohexyl-2-pyrrolidinecarboxamide (compound 28-3)

TLC: Rf 0.16 (ethyl acetate:methanol:28% aqueous ammonia=20:5:1);
NMR (CDCl₃): δ 1.50 (m, 23 H), 2.42 (m, 1 H), 2.72 (t, J=6.50 Hz, 2 H), 2.85 (m, 1 H), 3.10 (m, 1 H), 3.26 (m, 4 H), 3.55 (m, 4 H), 4.35 (m, 1 H), 4.90 (m, 1 H), 5.80 (d, J=6.00 Hz, 1 H), 7.71 (t, J=6.00 Hz, 1 H), 7.78 (d, J=6.00 Hz, 1 H).

EXAMPLE 28(4)

(2S,3S)-N-(5-aminopentyl)-3-{[4-(1-azepanyl)-2-pyrimidinyl]amino}-1-cyclohexyl-2-pyrrolidinecarboxamide (compound 28-4)

TLC: Rf 0.16 (ethyl acetate:methanol:28% aqueous ammonia=20:5:1);
NMR (CDCl₃): δ 1.52 (m, 25 H), 2.42 (m, 1 H), 2.68 (t, J=7.00 Hz, 2 H), 2.84 (m, 1 H), 3.19 (m, 5 H), 3.55 (m, 4 H), 4.35 (m, 1 H), 4.87 (m, 1 H), 5.80 (d, J=6.00 Hz, 1 H), 7.67 (t, J=6.00 Hz, 1 H), 7.78 (d, J=6.00 Hz, 1 H).

EXAMPLE 29

4-azepan-1-yl-N-((2RS,3SR)-2-{2-[(2-{[tert-butyl(dimethyl)silyl]oxy}ethyl)amino]ethyl}-1-cyclohexylpiperidin-3-yl)pyrimidin-2-amine (compound 29)

N-[(2RS,3SR)-2-(2-aminoethyl)-1-cyclohexylpiperidin-3-yl]-4-cycloheptylpyrimidin-2-amine (75 mg), dimethylformamide (1 mL), (2-bromoethoxy)(tert-butyl)dimethylsilane (44 μL) and potassium carbonate (52 mg) were stirred at room temperature for overnight. The reaction solution was added aqueous saturated sodium hydrogen carbonate solution and extracted with ethyl acetate. The extract was dried over anhydrous sodium sulfate and then concentrated. The residue was purified by silica gel column chromatography (ethyl acetate:methanol:aqueous ammonia=70:27:3) to obtain the title compound (89 mg) having the following physical properties.

TLC: Rf 0.60 (dichloromethane:methanol:28% aqueous ammonia=50:10:1);
NMR (CDCl₃): δ 0.06 (s, 6H), 0.89 (s, 9H), 1.02-1.90 (m, 24H), 2.35-2.84 (m, 8H), 3.35-3.70 (m, 4H), 3.71 (t, J=5.4 Hz, 2H), 3.97 (m, 1H), 5.55 (m, 1H), 5.72 (d, J=6.3 Hz, 1H), 7.77 (d, J=6.3 Hz, 1H).

EXAMPLE 30 tert-butyl 4-{[(2-{(2RS,3SR)-3-[(4-azepan-1-ylpyrimidin-2-yl)amino]-1-cyclohexylpiperidin-2-yl}ethyl)(2-{[tert-butyl(dimethyl)silyl]oxy}ethyl)amino]carbonyl}piperidine-1-carboxylate (compound 30)

The compound 29 (89 mg), dimethylformamide (1 mL), 1-(tert-butoxycarbonyl)piperidine-4-carboxylic acid (44 mg), O-(benzotriazol-1-yl)-N,N,N',N'-tetramethyluronium hexafluorophosphate (94 mg) and diisopropylethylamine (42 μL) were stirred at room temperature for overnight. The reaction solution was added aqueous saturated sodium hydrogen carbonate solution and extracted with ethyl acetate. The extract was dried over anhydrous sodium sulfate and then concentrated. The residue was purified by silica gel column chromatography (ethyl acetate:methanol:aqueous ammonia=80:20:1) to obtain the title compound (56 mg) having the following physical properties.

TLC: Rf 0.81 (ethyl acetate:methanol:28% aqueous ammonia=50:10:1);
NMR (CDCl₃): δ 0.04 (s, 6H), 0.87 (s, 9H), 1.00-2.00 (m, 38H), 2.32-2.99 (m, 8H), 3.15-3.75 (m, 8H), 3.82-4.20 (m, 3H), 5.05 (m, 1H), 5.76 (d, J=6.3 Hz, 1H), 7.74 (m, 1H).

EXAMPLE 31

N-[2-((2RS,3SR)-3-{[4-(1-azepanyl)-2-pyrimidinyl]amino}-1-cyclohexyl-2-piperidinyl)ethyl]-N-(2-hydroxyethyl)-4-piperidinecarboxamide (compound 31)

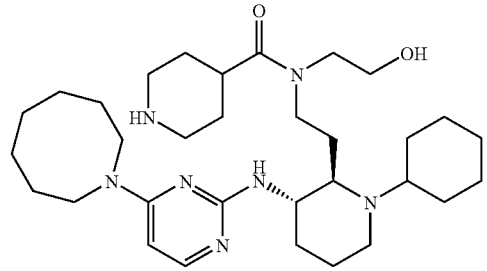 [SMILES: O=C(C1CCNCC1)N(CCO)CC[C@@H]1[C@@H](Nc2nccc(N3CCCCCCC3)n2)CCCN1C1CCCCC1]

The same procedure as a series of reactions of Example 22 was carried out, except that the compound 30 was used in place of the compound 21 in the process of Example 22, to obtain the title compound (35 mg) having the following physical properties.

Description: oil;
TLC: Rf 0.43 (dichloromethane:methanol:28% aqueous ammonia=50:10:1);
NMR (CDCl₃): δ 1.00-2.00 (m, 28H), 2.20-2.90 (m, 10H), 3.05-3.20 (m, 2H), 3.22-3.80 (m, 7H), 3.98 (m, 1H), 5.15 (m, 1H), 5.80 (m, 1H), 7.77 (m, 1H).

EXAMPLE 31(1) TO EXAMPLE 31(5)

The same procedure as a series of reactions of Example 29→Example 30→Example 31 was carried out, except that the corresponding amine was used in place of N-[(2RS,3SR)-2-(2-aminoethyl)-1-cyclohexylpiperidin-3-yl]-4-cycloheptylpyrimidin-2-amine and the corresponding bromide was used in place of (2-bromoethoxy)(tert-butyl)dimethylsilane in the process of Example 29, to obtain the following compound of the present invention.

EXAMPLE 31(1)

N-[2-((2RS,3SR)-3-{[4-(1-azepanyl)-2-pyrimidinyl]amino}-1-cyclohexyl-2-piperidinyl)ethyl]-N-(tetrahydro-2H-pyran-4-yl)-4-piperidinecarboxamide (compound 31-1)

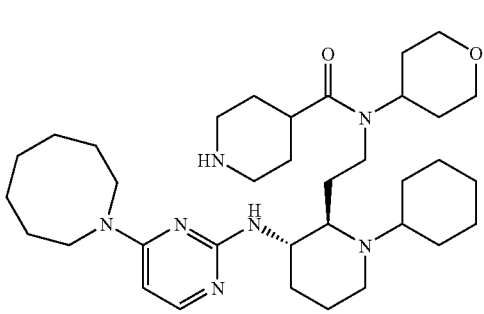 [SMILES: O=C(C1CCNCC1)N(CC[C@@H]1[C@@H](Nc2nccc(N3CCCCCCC3)n2)CCCN1C1CCCCC1)C1CCOCC1]

Description: amorphous powder;
TLC: Rf 0.49 (dichloromethane:methanol:28% aqueous ammonia=50:10:1);
NMR (CDCl$_3$): δ 1.00-2.08 (m, 32H), 2.40-2.80 (m, 6H), 3.02-3.84 (m, 11H), 3.86-4.08 (m, 3H), 4.53 (m, 1H), 5.35 (m, 1H), 5.78 (m, 1H), 7.78 (m, 1H).

EXAMPLE 31(2)

N-[2-((2RS,3SR)-3-{[4-(1-azepanyl)-2-pyrimidinyl]amino}-1-cyclohexyl-2-piperidinyl)ethyl]-N-(2-methoxyethyl)-4-piperidinecarboxamide (compound 31-2)

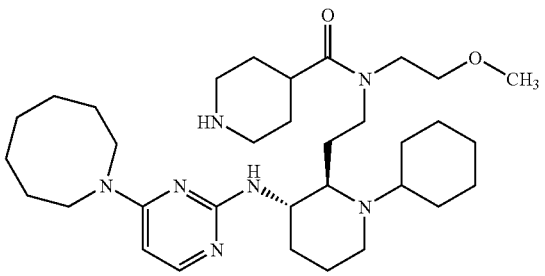 [SMILES: COCCN(CC[C@@H]1[C@@H](Nc2nccc(N3CCCCCCC3)n2)CCCN1C1CCCCC1)C(=O)C1CCNCC1]

Description: oil;
TLC: Rf 0.45 (dichloromethane:methanol:28% aqueous ammonia=50:10:1);
NMR (CDCl$_3$): δ 1.00-2.08 (m, 28H), 2.40-2.80 (m, 10H), 3.05-3.21 (m, 2H), 3.22-3.80 (m, 10H), 3.90-4.05 (m, 1H), 5.79 (m, 1H), 7.78 (m, 1H).

EXAMPLE 31(3)

N-(2-aminoethyl)-N-[2-((2RS,3SR)-3-{[4-(1-azepanyl)-2-pyrimidinyl]amino}-1-cyclohexyl-2-piperidinyl)ethyl]-4-piperidinecarboxamide (compound 31-3)

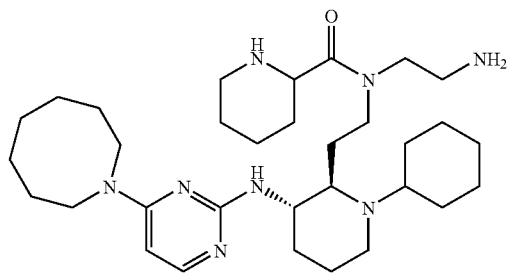 [SMILES: NCCN(CC[C@@H]1[C@@H](Nc2nccc(N3CCCCCCC3)n2)CCCN1C1CCCCC1)C(=O)C1CCCCN1]

Description: amorphous powder;
TLC: Rf 0.46 (dichloromethane:methanol:28% aqueous ammonia=50:10:1);
NMR (CDCl$_3$): δ 1.02-2.00 (m, 29H), 2.34-2.88 (m, 8H), 3.04-3.81 (m, 10H), 3.98 (m, 1H), 5.00 (m, 1H), 5.78 (m, 1H), 7.81 (m, 1H).

Example 31(4)

[[2-((2RS,3SR)-3-{[4-(1-azepanyl)-2-pyrimidinyl]amino}-1-cyclohexyl-2-piperidinyl)ethyl](4-piperidinylcarbonyl)amino]acetic acid (compound 31-4)

TLC: Rf 0.20 (dichloromethane:methanol:28% aqueous ammonia=50:10:1);
NMR (CDCl$_3$): δ 1.00-2.08 (m, 29H), 2.20-3.00 (m, 6H), 3.20-4.40 (m, 11H), 5.50 (m, 1H), 5.90 (m, 1H), 7.65 (m, 1H).

EXAMPLE 31(5)

N-[2-((2RS,3SR)-3-{[4-(1-azepanyl)-2-pyrimidinyl]amino}-1-cyclohexyl-2-piperidinyl)ethyl]-N-(tetrahydro-2H-pyran-4-yl)-2-morpholinecarboxamide (compound 31-5)

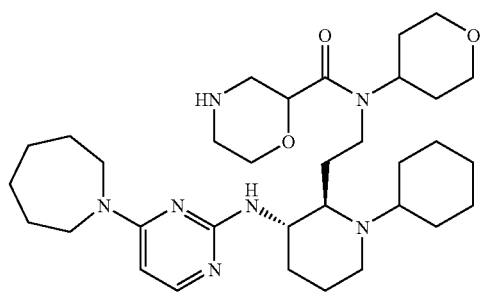

Description: amorphous powder;
TLC: Rf 0.48 (ethyl acetate:methanol:28% aqueous ammonia=50:10:1);

NMR (CDCl$_3$): δ 1.02-2.02 (m, 28H), 2.40-4.20 (m, 22H), 4.40 (m, 1H), 5.40 (m, 1H), 5.78 (m, 1H), 7.79 (m, 1H).

EXAMPLE 32 di-tert-butyl {(E)-[(2-{(2RS,3SR)-3-[(4-azepan-1-ylpyrimidin-2-yl)amino]-1-cyclohexylpiperidin-2-yl}ethyl)amino]methylylidene}biscarbamate (compound 32)

N-[(2RS,3SR)-2-(2-aminoethyl)-1-cyclohexylpiperidin-3-yl]-4-azepan-1-ylpyrimidin-2-amine (72 mg), dichloromethane (2 mL), triethylamine (25 µL) and di-tert-butyl (2Z)-3-(1H-pyrazole-1-yl)penta-2-endioate (56 mg) were stirred at room temperature for overnight. The reaction solution was added water, extracted with methyl-tert-butyl ether and then washed with aqueous 1N sodium hydroxide solution and saturated brine. The extract was dried over anhydrous magnesium sulfate and then concentrated. The residue was purified by silica gel column chromatography (ethyl acetate:methanol:triethylamine=80:10:1) to obtain the title compound (81 mg) having the following physical properties.

TLC: Rf 0.49 (chloroform:methanol=9:1);
NMR (CDCl$_3$): δ 1.00-1.98 (m, 42 H), 2.36-2.62 (m, 2 H), 2.79-2.89 (m, 1 H), 2.93-3.87 (m, 7 H), 3.90-4.04 (m, 1 H), 5.42-5.69 (m, 1 H), 5.74 (d, J=6.2 Hz, 1 H), 7.78 (d, J=6.2 Hz, 1 H), 8.33 (t, J=5.0 Hz, 1 H), 11.45 (s, 1 H).

EXAMPLE 33

N-[2-((2RS,3SR)-3-{[4-(1-azepanyl)-2-pyrimidinyl]amino}-1-cyclohexyl-2-piperidinyl)ethyl]guanidine trihydrochloride (compound 33)

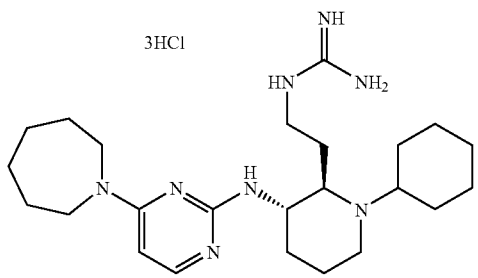

The same procedure as a series of reactions of Example 24 was carried out, except that the compound 32 was used in place of the compound 23 in the process of Example 24, to obtain the title compound (39 mg) having the following physical properties.

TLC: Rf 0.46 (chloroform:methanol:28% aqueous ammonia=80:20:1);
NMR (DMSO-D$_6$): δ 0.92-2.39 (m, 24 H), 2.74-2.97 (m, 1 H), 3.18-3.98 (m, 9 H), 4.64-4.86 (m, 1 H), 6.42 (d, J=7.4 Hz, 1 H), 7.12-7.63 (m, 4 H), 7.84 (d, J=7.4 Hz, 1 H), 7.93 (t, J=5.6 Hz, 1 H), 8.58 (d, J=9.2 Hz, 1 H), 11.19-11.37 (m, 1 H), 12.19-12.36 (m, 1 H).

EXAMPLE 33(1)

The same procedure as a series of reactions of Example 32→Example 33 was carried out, except that the corresponding amine was used in place of N-[(2RS,3SR)-2-(2-aminoethyl)-1-cyclohexylpiperidin-3-yl]-4-azepan-1-ylpyrimidin-2-amine in the process of Example 32, to obtain the following compound of the present invention.

EXAMPLE 33(1)

N-[3-((2RS,3SR)-3-{[4-(1-azepanyl)-2-pyrimidinyl]amino}-1-cyclohexyl-2-pyrrolidinyl)propyl]guanidine trihydrochloride (compound 33-1)

TLC: Rf 0.56 (chloroform:methanol:28% aqueous ammonia=80:20:1);
NMR (DMSO-D$_6$): δ 1.03-2.09 (m, 22 H), 2.13-2.38 (m, 2 H), 3.06-3.21 (m, 2 H), 3.26-3.97 (m, 8 H), 4.44-4.60 (m, 1 H), 6.42 (d, J=7.6 Hz, 1 H), 6.84-7.65 (m, 4 H), 7.85 (d, J=7.6 Hz, 1 H), 8.03 (t, J=5.2 Hz, 1 H), 9.19-9.39 (m, 1 H), 10.74-10.88 (m, 1 H), 11.99-12.19 (m, 1 H).

EXAMPLE 34 tert-butyl 4-[({2-[(2RS,3SR)-3-[(4-azepan-1-ylpyrimidin-2-yl)amino]-1-(1,1-dioxidotetrahydro-2H-thiopyran-4-yl)piperidin-2-yl]ethyl}amino)carbonyl]piperidine-1-carboxylate (compound 34)

To a solution of tert-butyl 4-[({2-[(2RS,3SR)-3-[(4-azepan-1-ylpyrimidin-2-yl)amino]-1-(tetrahydro-2H-thiopyran-4-yl)piperidin-2-yl]ethyl}amino)carbonyl]piperidine-1-carboxylate (73.5 mg) in dichloromethane (1.5 mL), trifluoroacetic acid (17 µL) and m-chloroperbenzoic acid (40 mg) were added and then stirred at room temperature for 3 hours. The reaction solution was added aqueous sodium thiosulfate solution and excessive tert-butylmethyl ether, extracted with aqueous 2N sodium hydroxide solution and saturated brine and obtained a crude product of the title compound (84 mg). The obtained crude product was purified by silica gel column chromatography (ethyl acetate:methanol:28% aqueous ammonia=1000:10:1→80:20:2) to obtain a more polar compound and a less polar compound of the title compound having the following physical properties.

More Polar Compound

TLC: Rf 0.49 (chloroform:methanol:28% aqueous ammonia=80:20:1);
NMR (CDCl$_3$): δ 7.75 (1H, d, J=6.0 Hz), 5.79 (1H, d, J=6.0 Hz), 5.13 (1H, d, J=9.0 Hz), 4.16-3.92 (2H, m), 3.78-3.39 (6H, m), 3.30-3.16 (1H, m), 3.16-3.00 (2H, m), 2.85-2.38 (10H, m), 2.36-2.08 (5H, m), 1.95-1.50 (18H, m), 1.44 (9H, s).

Less Polar Compound

TLC: Rf 0.58 (chloroform:methanol:28% aqueous ammonia=80:20:1);
NMR (CDCl$_3$): δ 7.72 (1H, d, J=6.0 Hz), 5.82 (1H, d, J=6.0 Hz), 4.18-3.94 (3H, m), 3.76-3.38 (6H, m), 3.32-3.15 (2H, m), 3.13-2.88 (2H, m), 2.86-2.42 (9H, m), 2.42-2.26 (1H, m), 2.25-2.01 (4H, m), 1.94-1.49 (18H, m), 1.45 (9H, s).

EXAMPLE 35

N-{2-[(2RS,3SR)-3-{[4-(1-azepanyl)-2-pyrimidinyl]amino}-1-(1-oxidotetrahydro-2H-thiopyran-4-yl)-2-piperidinyl]ethyl}-4-piperidinecarboxamide (compound 35)

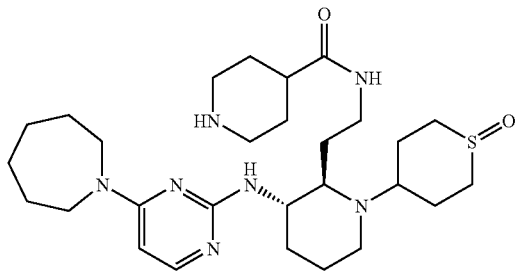

The same procedure as a series of reactions of Example 22 was carried out, except that the more polar compound of the compound 34 was used in place of the compound 21 in the process of Example 22, to obtain the title compound (15 mg) having the following physical properties.

TLC: Rf 0.12 (chloroform:methanol:28% aqueous ammonia=90:10:1);

NMR (METHANOL-$D_4$): δ 1.25-1.97 (m, 20 H), 2.14-2.50 (m, 4 H), 2.50-2.96 (m, 6 H), 2.97-3.22 (m, 5 H), 3.26-3.41 (m, 2 H), 3.43-3.81 (m, 4 H), 3.95 (s, 1 H), 5.90 (d, J=6.22 Hz, 1 H), 7.67 (d, J=6.22 Hz, 1 H).

EXAMPLE 35(1)

The same procedure as a series of reactions of Example 24 was carried out, except that the less polar compound was used in place of the more polar compound of the compound 34 in the process of Example 34, to obtain the title compound (18 mg) having the following physical properties.

EXAMPLE 35(1)

N-{2-[(2RS,3SR)-3-{[4-(1-azepanyl)-2-pyrimidinyl]amino}-1-(1,1-dioxidotetrahydro-2H-thiopyran-4-yl)-2-piperidinyl]ethyl}-4-piperidinecarboxamide trihydrochloride

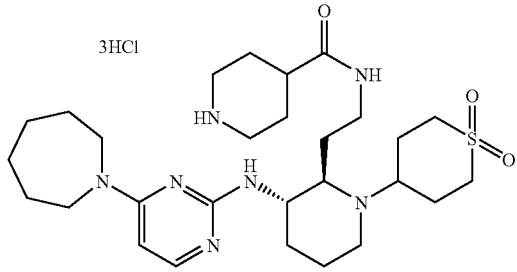

TLC: Rf 0.29 (chloroform:methanol:28% aqueous ammonia=90:10:1);

NMR (METHANOL-$D_4$): δ 1.50-2.63 (m, 22 H), 2.72-2.85 (m, 1 H), 2.96-3.15 (m, 3 H), 3.16-3.33 (m, 3 H), 3.36-3.53 (m, 4 H), 3.54-3.78 (m, 6 H), 3.96 (t, J=6.13 Hz, 2 H), 4.42-4.59 (m, 1 H), 6.44 (d, J=7.50 Hz, 1 H), 7.72 (d, J=7.50 Hz, 1 H).

EXAMPLE 36 tert-butyl 4-{[(2-{(2RS,3SR)-3-[(4-azepan-1-ylpyrimidin-2-yl)amino]-1-cyclohexylpiperidin-2-yl}ethyl)amino]methyl}piperidine-1-carboxylate (compound 36)

The compound 22 (100 mg) was dissolved in 1% acetic acid-dimethylformamide solution, tert-butyl 4-formyl-piperidine-1-carboxylate (62 mg) and sodium triacetoxyborohydride (66 mg) were added into the solution and stirred at room temperature for overnight. The reaction solution was added aqueous 1N sodium hydroxide solution and extracted with dichloromethane. The extract was dried over anhydrous sodium sulfate and then concentrated. The residue was purified by silica gel column chromatography (1% triethylamine:ethyl acetate:methanol=9:1) to obtain a more polar compound (49 mg) and a less polar compound (74 mg) of the title compound having the following physical properties.

More Polar Compound

TLC: Rf 0.40 (chloroform:methanol:28% aqueous ammonia=80:10:1);

NMR (CDCl$_3$): δ 0.96-1.34 (m, 7 H), 1.45 (s, 9 H), 1.49-1.92 (m, 25 H), 2.35-2.51 (m, 3 H), 2.51-2.60 (m, 2 H), 2.60-2.74 (m, 3 H), 2.74-2.83 (m, 1 H), 3.28-3.82 (m, 4 H), 3.89-4.00 (m, 1 H), 4.00-4.16 (m, 1 H), 5.47 (d, J=9.5 Hz, 1 H), 5.73 (d, J=6.2 Hz, 1 H), 7.77 (d, J=5.9 Hz, 1 H).

Less Polar Compound

TLC: Rf 0.42 (chloroform:methanol:28% aqueous ammonia=80:10:1);

NMR (CDCl$_3$): δ 0.80-1.32 (m, 9 H), 1.45 (s, 18 H), 1.47-1.89 (m, 27 H), 1.99-2.24 (m, 4 H), 2.32-2.51 (m, 4 H), 2.50-2.75 (m, 5 H), 3.29-3.67 (m, 4 H), 3.83-4.20 (m, 4 H), 5.27 (d, J=9.5 Hz, 1 H), 5.72 (d, J=5.9 Hz, 1 H), 7.76 (d, J=5.9 Hz, 1 H).

EXAMPLE 37

4-(1-azepanyl)-N-((2RS,3SR)-1-cyclohexyl-2-{2-[(4-piperidinylmethyl)amino]ethyl}-3-piperidinyl)-2-pyrimidinamine (compound 37)

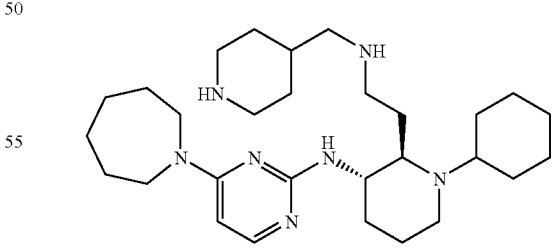

The same procedure as a series of reactions of Example 22 was carried out, except that the compound 36 was used in place of the compound 21 in the process of Example 22, to obtain the title compound (30 mg) having the following physical properties.

TLC: Rf 0.61 (chloroform:methanol:28% aqueous ammonia=40:10:1);

NMR (CDCl$_3$): δ 0.98-1.34 (m, 6 H), 1.36-1.47 (m, 1 H), 1.49-1.94 (m, 24 H), 2.36-2.45 (m, 1 H), 2.47 (d, J=6.6 Hz, 2 H), 2.52-2.60 (m, 3 H), 2.60-2.68 (m, 2 H), 2.75-2.84 (m, 1 H), 2.97-3.17 (m, 2 H), 3.31-3.86 (m, 5 H), 3.91-4.03 (m, 1 H), 5.49 (d, J=9.1 Hz, 1 H), 5.74 (d, J=6.2 Hz, 1 H), 7.80 (d, J=6.2 Hz, 1 H).

EXAMPLE 37(1)

The same procedure as a series of reactions of Example 37 was carried out, except that the less polar compound was used in place of the more polar compound of the compound 36 in the process of Example 37, to obtain the following compound of the present invention.

EXAMPLE 37(1)

4-(1-azepanyl)-N-((2RS,3SR)-2-{2-[bis(4-piperidinylmethyl)amino]ethyl}-1-cyclohexyl-3-piperidinyl)-2-pyrimidinamine (37-1)

TLC: Rf 0.43 (chloroform:methanol:28% aqueous ammonia=40:10:1);
NMR (CDCl$_3$): δ 1.1 (m, 9 H), 1.5 (m, 8 H), 1.7 (m, 14 H), 2.1 (m, 11 H), 2.5 (m, 8 H), 2.9 (m, 1 H), 3.1 (m, 3 H), 3.5 (m, 4 H), 4.0 (m, 1 H), 5.3 (m, 1 H), 5.8 (d, J=6.0 Hz, 1 H), 7.8 (d, J=5.9 Hz, 1 H).

EXAMPLE 38 tert-butyl (2R,3R)-2-(3-{[tert-butyl(diphenyl)silyl]oxy}propyl)-3-hydroxypyrrolidine-1-carboxylate (compound 38)

According to the procedure described in *J.C.S. Perkin. Trans.*, 1, 1421 (2001), the title compound (32.7 g) having the following physical properties was obtained.
TLC: Rf 0.62 (hexane:ethyl acetate=1:1);
NMR (CDCl$_3$): δ 1.05 (s, 9H), 1.44 (s, 9H), 1.52-2.52 (m, 7H), 3.29-3.58 (m, 2H), 3.58-3.83 (m, 3H), 4.31-4.43 (m, 1H), 7.32-7.51 (m, 6H), 7.58-7.75 (m, 4H).

EXAMPLE 39 tert-butyl (2R,3S)-3-[(4-azepan-1-yl-6-chloropyrimidin-2-yl)amino]-2-(3-hydroxypropyl)pyrrolidine-1-carboxylate (compound 39)

The same procedure as a series of reactions of Example 15→Example 18→Example 17→Example 3 was carried out to obtain the title compound (297 mg) having the following physical properties.
TLC: Rf 0.73 (hexane:ethyl acetate=2:1);
NMR (CDCl$_3$): δ 1.46 (s, 9H), 1.49-1.99 (m, 13H), 2.08-2.57 (m, 2H), 3.12-4.04 (m, 9H), 4.05-4.45 (m, 1H), 4.78-5.08 (m, 1H), 5.82 (s, 1H).

EXAMPLE 40 tert-butyl (2R,3S)-3-[(4-azepan-1-yl-6-chloropyrimidin-2-yl)amino]-2-(3-oxopropyl)pyrrolidine-1-carboxylate (compound 40)

To a solution of the compound 39 (174 mg), dimethylsulphoxide (3 mL) and triethylamine (1.5 mL) in dichloromethane (3 mL) with stirring, sulfur trioxide pyridine complex (212 mg) was added into the solution at room temperature. The reaction solution was stirred for 2 hours, added water and extracted with a mixture solution of hexane/ethyl acetate. The extract was washed with water, aqueous 5% potassium bisulfate solution, water and saturated brine, dried over anhydrous magnesium sulfate, concentrated and obtained the title compound (171 mg) having the following physical properties.
TLC: Rf 0.61 (hexane:ethyl acetate=1:1);
NMR (CDCl$_3$): δ 1.45 (s, 9H), 1.48-2.60 (m, 12H), 2.48-2.76 (m, 2H), 3.07-3.99 (m, 7H), 3.99-4.34 (m, 1H), 4.76-5.20 (m, 1H), 5.83 (s, 1H), 9.79 (s, 1H).

EXAMPLE 41

4-(1-azepanyl)-N-{(2R,3S)-1-cyclohexyl-2-[3-(1-piperazinyl)propyl]-3-pyrrolidinyl}-2-pyrimidinamine (compound 41)

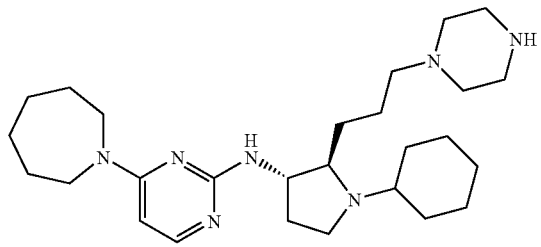

The same procedure as a series of reactions of Example 21→Example 16→Example 21→Example 20 was carried out, except that benzyl piperazine-1-carboxylate was used in place of the compound 20 and the compound 40 was used in place of cyclohexanone in the process of Example 21, to obtain the title compound (1.13 g) having the following physical properties.
TLC: Rf 0.42 (ethyl acetate:methanol:28% aqueous ammonia=20:5:1);
NMR (CDCl$_3$): δ 1.43 (m, 25 H), 2.20 (m, 6 H), 2.81 (m, 7 H), 3.57 (m, 4 H), 4.16 (m, 1 H), 5.06 (m, 1 H), 5.78 (d, J=6.00 Hz, 1 H), 7.76 (d, J=6.00 Hz, 1 H).

EXAMPLE 41(1) TO EXAMPLE 41(2)

The same procedure as a series of reactions of Example 41 was carried out, except that the a corresponding amine was used in place of benzyl piperazine-1-carboxylate and a corresponding aldehyde compound was used in place of the compound 40 in the process of Example 41, to obtain the following compound of the present invention.

EXAMPLE 41(1)

4-(1-azepanyl)-N-((2R,3S)-2-{3-[bis(1H-imidazol-2-ylmethyl)amino]propyl}-1-cyclohexyl-3-pyrrolidinyl)-2-pyrimidinamine (compound 41-1)

TLC: Rf 0.52 (ethyl acetate:methanol:28% aqueous ammonia=20:5:1);
NMR (CDCl$_3$): δ 1.54 (m, 23 H), 2.76 (m, 7 H), 3.53 (d, J=14.00 Hz, 2 H), 3.62 (m, 4 H), 3.70 (d, J=14.00 Hz, 2 H), 4.04 (m, 1 H), 5.85 (d, J=6.50 Hz, 1 H), 6.21 (m, 1 H), 7.05 (s, 4 H), 7.72 (d, J=6.50 Hz, 1 H).

EXAMPLE 41(2)

4-(1-azepanyl)-N-[(2R,3S)-1-cyclohexyl-2-(1-piperazinylmethyl)-3-pyrrolidinyl]-2-pyrimidinamine (compound 41-2)

TLC: Rf 0.69 (ethyl acetate:methanol:28% aqueous ammonia=20:5:1);
NMR (CDCl$_3$): δ 1.49 (m, 19 H), 2.11 (m, 1 H), 2.62 (m, 14 H), 3.55 (m, 4 H), 4.20 (m, 1 H), 4.97 (d, J=7.00 Hz, 1 H), 5.78 (d, J=6.00 Hz, 1 H), 7.80 (d, J=6.00 Hz, 1 H).

EXAMPLE 42

N-({(2R,3S)-3-[(4-azepan-1-ylpyrimidin-2-yl)amino]-1-cyclohexylpyrrolidin-2-yl}methyl)-2-(1,3-dioxo-1,3-dihydro-2H-isoindol-2-yl)ethanesulfonamide (compound 42)

N-[(2R,3S)-2-(aminomethyl)-1-cyclohexylpyrrolidin-3-yl]-4-azepan-1-ylpyrimidine-2-amine (33.2 mg) was dissolved in anhydrous tetrahydrofuran (0.8 mL) and dimethylformamide (0.4 mL) under an argon atmosphere at room temperature, trietylamine (24.8 μL) and 2-(1,3-dioxo-1,3-dihydro-2H-isoindol-2-yl)ethanesulfonyl chloride (48.8 mg) were added into the solution and the solution was stirred at room temperature for overnight. The reaction solution was added aqueous saturated sodium hydrogen carbonate solution and extracted with ethyl acetate. The extract was washed with saturated brine, dried over anhydrous sodium sulfate and then concentrated. The residue was purified by Flash tube (trade mark) to obtain sulfonamide compound (49.0 mg).
TLC: Rf 0.67 (chloroform:methanol=5:1).

EXAMPLE 43

2-amino-N-[((2R,3S)-3-{[4-(1-azepanyl)-2-pyrimidinyl]amino}-1-cyclohexyl-2-pyrrolidinyl)methyl]ethanesulfonamide (compound 43)

To a solution of the compound 42 in methanol (2 mL), hydrazine monohydrate (98%, 19.5 μL) was added and stirred at 40° C. for overnight. The reaction solution was concentrated and purified by thin-layer chromatography to obtain the title compound (21.4 mg) having the following physical properties.
TLC: Rf 0.70 (chloroform:methanol:28% aqueous ammonia=40:10:2);
NMR (METHANOL-D$_4$): δ 1.02-1.40 (m, 6 H), 1.47-1.67 (m, 4 H), 1.68-1.97 (m, 9 H), 1.98-2.17 (m, 1 H), 2.39-2.62 (m, 1 H), 2.75-3.75 (m, 13 H), 3.93-4.15 (m, 1 H), 5.96 (d, J=6.4 Hz, 1 H), 7.72 (d, J=6.4 Hz, 1 H).

EXAMPLE 44

4-azepan-1-yl-N-[(2R,3S)-2-(3-azidopropyl)-1-(1,4-dioxaspiro[4.5]dec-8-yl)pyrrolidin-3-yl]-6-chloropyrimidin-2-amine (compound 44)

The same procedure as a series of reactions of Example 9 was carried out, except that 4-azepan-1-yl-N-[(2R,3S)-2-(3-azidopropyl)pyrrolidin-3-yl]-6-chloropyrimidin-2-amine was used in place of the compound 8 and 1,4-dioxaspiro[4.5]decan-8-one was used in place of cyclohexanone in the process of Example 9, to obtain the title compound (1.25 g) having the following physical properties.
TLC: Rf 0.55 (chloroform:methanol:water=100:20:2);
NMR (CDCl$_3$): δ 1.30-2.24 (m, 20H), 2.39-3.01 (m, 5H), 3.16-4.01 (m, 7H), 3.94 (s, 4H), 4.02-4.25 (m, 1H), 4.89 (d, J=7.5 Hz, 1H), 5.80 (s, 1H).

EXAMPLE 45

4-[(2R,3S)-3-[(4-azepan-1-yl-6-chloropyrimidin-2-yl)amino]-2-(3-azidopropyl)pyrrolidin-1-yl]cyclohexanone (compound 45)

The compound 44 (1.24 g), water (2 mL) and trifluoroacetic acid (18 mL) were stirred at room temperature for 4 hours and then concentrated. The residue was added aqueous saturated sodium hydrogen carbonate solution and extracted with ethyl acetate. The extract was washed with saturated brine, dried over anhydrous magnesium sulfate, concentrated and obtained the title compound (1.13 g) having the following physical properties.
TLC: Rf 0.60 (chloroform:methanol:water=100:20:2);
NMR (CDCl$_3$): δ 1.32-1.95 (m, 16H), 1.95-2.66 (m, 5H), 2.66-3.12 (m, 4H), 3.12-4.02 (m, 7H), 4.02-4.28 (m, 1H), 4.79-5.11 (m, 1H), 5.81 (s, 1H).

EXAMPLE 46 cis-4-[(2R,3S)-3-[(4-azepan-1-yl-6-chloropyrimidin-2-yl)amino]-2-(3-azidopropyl)pyrrolidin-1-yl]cyclohexanol (compound 46)

The compound 45 (1.12 g), tetrahydrofuran (25 mL) and 1.02 mol/L L-Selectride (7.0 mL) were stirred at −78° C. for 1 hour. The reaction solution was added aqueous saturated ammonium chloride solution and extracted with ethyl acetate. The extract was washed with saturated brine, dried over anhydrous magnesium sulfate and concentrated. The obtained residue was purified by silica gel column chromatography (hexane:ethyl acetate:methanol=50:50:0→0:100:0→0:90:10) to obtain the title compound (237 mg) having the following physical properties.
TLC: Rf 0.41 (chloroform:methanol:water=100:20:2);
NMR (CDCl$_3$): δ 1.17-2.00 (m, 21H), 2.00-2.23 (m, 1H), 2.41-2.63 (m, 1H), 2.63-2.99 (m, 3H), 3.15-4.01 (m, 8H), 4.10-4.22 (m, 1H), 4.95 (d, J=8.0 Hz, 1H), 5.80 (s, 1H).

EXAMPLE 47 cis-4-((2R,3S)-2-(3-aminopropyl)-3-{[4-(1-azepanyl)-2-pyrimidinyl]amino}-1-pyrrolidinyl)cyclohexanol (compound 47)

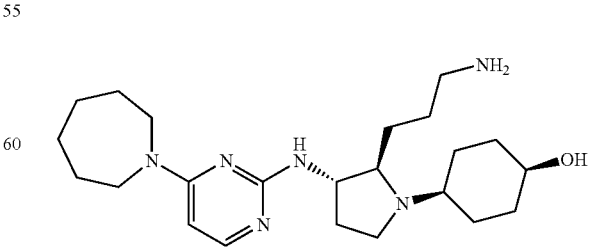

The same procedure as a series of reactions of Example 10 was carried out, except that the compound 46 was used in place of the compound 9 in the process of Example 10, to obtain the title compound (130 mg) having the following physical properties.

Description: amorphous powder;
TLC: Rf 0.09 (ethyl acetate:methanol:28% aqueous ammonia=20:5:1);
NMR (CDCl$_3$): δ 1.61 (m, 22 H), 2.12 (m, 1 H), 2.54 (m, 1 H), 2.75 (m, 4 H), 3.55 (m, 4 H), 3.91 (m, 1 H), 4.17 (m, 1 H), 4.90 (d, J=7.50 Hz, 1 H), 5.77 (d, J=6.00 Hz, 1 H), 7.78 (d, J=6.00 Hz, 1 H).

EXAMPLE 47(1) TO EXAMPLE 47(2)

The same procedure as a series of reactions of Example 44→Example 45→Example 46→Example 47 was carried out, except that the corresponding amine was used in place of 4-azepan-1-yl-N-[(2R,3S)-2-(3-azidopropyl)pyrrolidin-3-yl]-6-chloropyrimidin-2-amine in the process of Example 44, to obtain the following compound of the present invention.

EXAMPLE 47(1)

cis-4-{(2R,3S)-3-{[4-(1-azepanyl)-2-pyrimidinyl]amino}-2-[3-(diethylamino)propyl]-1-pyrrolidinyl}cyclohexanol (compound 47-1)

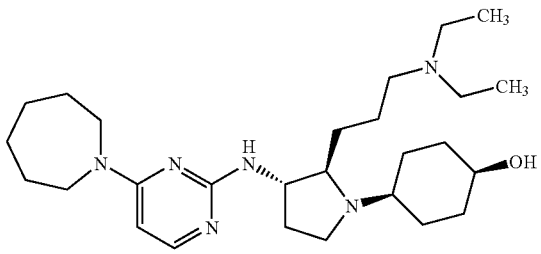

Description: amorphous powder;
TLC: Rf 0.36 (ethyl acetate:methanol:28% aqueous ammonia=80:20:2);
NMR (CDCl$_3$): δ 1.00 (t, J=7.14 Hz, 6 H), 1.23-1.36 (m, 2 H), 1.42-1.90 (m, 20 H), 2.06-2.20 (m, 1 H), 2.34-2.62 (m, 6 H), 2.72 (d, J=8.97 Hz, 1 H), 2.77-2.89 (m, 2 H), 3.21 (s, 1 H), 3.34-3.77 (m, 4 H), 3.84-3.95 (m, 1 H), 4.13-4.24 (m, 1 H), 4.89-5.02 (m, 1 H), 5.78 (d, J=6.13 Hz, 1 H), 7.78 (d, J=6.13 Hz, 1 H).

EXAMPLE 47(2)

cis-4-((2R,3S)-2-[3-(1-azepanyl)propyl]-3-{[4-(1-azepanyl)-2-pyrimidinyl]amino}-1-pyrrolidinyl)cyclohexanol (compound 47-2)

TLC: Rf 0.43 (ethyl acetate:methanol:28% aqueous ammonia=80:20:2);
NMR (CDCl$_3$): δ 1.21-1.94 (m, 31 H), 2.06-2.20 (m, 1 H), 2.41-2.50 (m, 1 H), 2.50-2.66 (m, 4 H), 2.71 (d, J=9.33 Hz, 1 H), 2.76-2.87 (m, 2 H), 3.21 (d, J=0.91 Hz, 1 H), 3.34-3.73 (m, 4 H), 3.83-3.95 (m, 1 H), 4.19 (t, J=7.23 Hz, 1 H), 4.93 (d, J=7.14 Hz, 1 H), 5.77 (d, J=6.04 Hz, 1 H), 7.78 (d, J=6.04 Hz, 1 H).

EXAMPLE 48 tert-butyl (2R,3S)-3-{[tert-butyl(diphenyl)silyl]oxy}-2-(hydroxymethyl)pyrrolidine-1-carboxylate (compound 48)

2.0 M of a solution of (trimethylsilyl)diazomethane in hexane (40 mL) was added dropwise to 1-tert-butyl 2-methyl (2S,3S)-3-{[tert-butyl(diphenyl)silyl]oxy}pyrrolidine-1,2-dicarboxylate (11.6 g) and methanol (50 mL) with stirring. The reaction solution was concentrated and the residue was added dimethylformamide (100 mL), tert-butyldiphenylchlorosilane (13.7 mL) and imidazole (6.37 g) and stirred at room temperature for overnight. The reaction solution was added water and extracted with a mixture solution of hexane/ethyl acetate. The extract was washed with water and saturated brine, dried over anhydrous magnesium sulfate and concentrated. The residue was added tetrahydrofuran (100 mL), methanol (3 mL) and lithium borohydride (2.51 g) at 0° C. and stirred at room temperature for 1 hour. The reaction solution was added water and aqueous 5% potassium sulfate solution and extracted with ethyl acetate. The extract was washed with saturated brine, dried over anhydrous magnesium sulfate and concentrated. The residue was purified by silica gel column chromatography (hexane:ethyl acetate=95:5→75:25) to obtain the title compound (22.7 g) having the following physical properties.

TLC: Rf 0.24 (hexane:ethyl acetate=4:1);
NMR (CDCl$_3$): δ 1.06 (s, 9H), 1.47 (s, 9H), 1.59-1.99 (m, 3H), 3.50-3.72 (m, 1H), 3.72-3.94 (m, 1H), 3.94-4.22 (m, 1H), 7.32-7.49 (m, 6H), 7.58-7.69 (m, 4H).

EXAMPLE 49 tert-butyl (2R,3S)-3-{[tert-butyl(diphenyl)silyl]oxy}-2-[(2-hydroxyethoxy)methyl]pyrrolidine-1-carboxylate (compound 49)

The compound 48 (4.56 g), methyl bromoacetate (2.22 mL) and tetrahydrofuran (25 mL) were stirred at 0° C., 60% sodium hydride suspension (400 mg) was added into the solution. The reaction solution was stirred at room temperature for overnight, added water and extracted with ethyl acetate. The extract was washed with saturated brine, dried over anhydrous magnesium sulfate and concentrated. The residue was purified by silica gel column chromatography (hexane:ethyl acetate=100:0→85:15). The obtained compound (1.46 g) was added tetrahydrofuran (20 mL), methanol (1 mL) and lithium borohydride (117 mg) and stirred at room temperature for 2 hours. The reaction solution was added water and aqueous 5% potassium sulfate solution and extracted with ethyl acetate. The extract was washed with saturated brine, dried over anhydrous magnesium sulfate, concentrated and obtained the title compound (1.40 g) having the following physical properties.

TLC: Rf 0.42 (hexane:ethyl acetate=2:1);
NMR (CDCl$_3$): δ 1.06 (s, 9H), 1.48 (s, 9H), 1.63 (s, 1H), 1.76-1.96 (m, 2H), 2.95-4.01 (m, 9H), 4.22-4.48 (m, 1H), 7.28-7.50 (m, 6H), 7.56-7.71 (m, 4H).

EXAMPLE 50 tert-butyl (2S,3S)-3-amino-2-[(2-{[tert-butyl(diphenyl)silyl]oxy}ethoxy)methyl]pyrrolidine-1-carboxylate (compound 50)

The compound 49 (1.95 g) was added tetrahydrofuran (6 mL) and 1.0 M of a solution of tetrabutylammonium fluoride in tetrahydrofuran (5.9 mL) and stirred at room temperature for overnight. The reaction solution was concentrated and the residue was purified by silica gel column chromatography (hexane:ethyl acetate:methanol=90:10:0→0:100:0→0:90:10). The obtained compound was added dimethylformaminde (10 mL), tert-butyldiphenylsilylchloride (965 mL) and imidazole (450 mg) and stirred at room temperature for overnight. The reaction solution was added water and extracted with a mixture solution of hexane/ethyl acetate. The extract was washed with water and saturated brine, dried over anhydrous magnesium sulfate and concentrated. The residue was purified by silica gel column chromatography (hexane:ethyl acetate=95:5→50:50) to obtained the title compound (1.58 g) having the following physical properties.

TLC: Rf 0.70 (hexane:ethyl acetate=1:1);

NMR (CDCl$_3$): δ 1.05 (s, 9H), 1.45 (s, 9H), 1.73-2.19 (m, 3H), 3.17-3.91 (m, 9H), 4.25-4.45 (m, 1H), 7.30-7.51 (m, 6H), 7.59-7.77 (m, 4H).

EXAMPLE 51

N-{(2S,3S)-2-[(2-aminoethoxy)methyl]-1-cyclohexyl-3-pyrrolidinyl}-4-(1-azepanyl)-2-pyrimidinamine (compound 51)

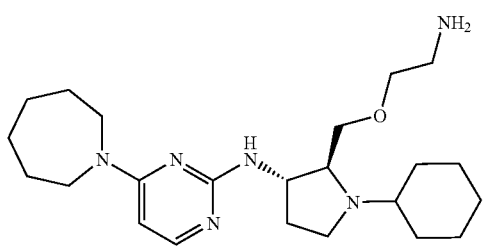

The same procedure as a series of reactions of Example 4→Example 5→Example 15→Example 18→Example 17→Example 3→Example 15→Example 16→Example 21→Example 20 was carried out, except that the compound 50 was used in place of the compound 3 in the process of Example 4, to obtain the title compound having the following physical properties.

TLC: Rf 0.57 (ethyl acetate:methanol:28% aqueous ammonia=20:5:1);

NMR (CDCl$_3$): δ 1.62 (m, 20 H), 2.55 (m, 1 H), 2.75 (m, 1 H), 2.82 (t, J=5.00 Hz, 2 H), 2.93 (m, 2 H), 3.51 (m, 4 H), 3.37 (dd, J=9.50, 6.50 Hz, 1 H), 3.46 (t, J=5.00 Hz, 2 H), 3.50 (m, 1 H), 4.25 (m, 1 H), 5.09 (m, 1 H), 5.77 (d, J=6.00 Hz, 1 H), 7.75 (d, J=6.00 Hz, 1 H).

EXAMPLE 52(1) TO EXAMPLE 52(4)

The same procedure as a series of reactions of Example 11 was carried out, except that the corresponding amine was used in place of the compound 10 in the process of Example 11, to obtain the following compound of the present invention.

EXAMPLE 52(1)

2-((2RS,3SR)-3-{[4-(1-azepanyl)-2-pyrimidinyl]amino}-1-cyclohexyl-2-piperidinyl)-N-[3-(dimethylamino)propyl]acetamide (compound 52-1)

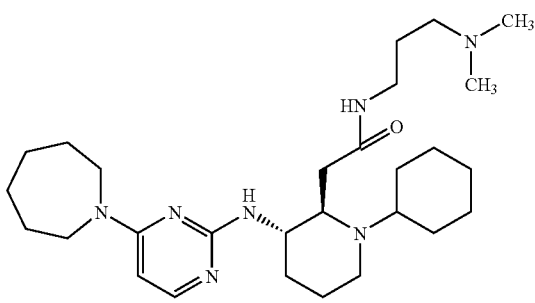

Description: amorphous powder;

TLC: Rf 0.42 (chloroform:methanol:28% aqueous ammonia=80:10:1);

NMR (CDCl$_3$): δ 0.97-1.86 (m, 20 H), 1.87-2.18 (m, 6 H), 2.23 (s, 6 H), 2.30-2.42 (m, 2 H), 2.51-2.59 (m, 1 H), 2.62-2.71 (m, 1 H), 2.72-2.82 (m, 1 H), 2.91-3.06 (m, 1 H), 3.16-3.84 (m, 6 H), 3.99-4.16 (m, 1 H), 5.76 (d, J=6.0 Hz, 1 H), 5.84-6.25 (m, 1 H), 7.63-7.76 (m, J=6.0 Hz, 1 H), 8.21-8.34 (m, 1 H).

EXAMPLE 52(2)

4-(1-azepanyl)-N-{(2RS,3SR)-1-cyclohexyl-2-[2-(dimethylamino)ethyl]-3-piperidinyl}-2-pyrimidinamine (compound 52-2)

TLC: Rf 0.76 (chloroform:methanol:28% aqueous ammonia=80:10:1);

NMR (CDCl$_3$): δ 0.69-1.41 (m, 9 H), 1.41-1.66 (m, 7 H), 1.67-2.00 (m, 9 H), 2.34 (s, 6 H), 2.41-2.93 (m, 5 H), 3.29-3.91 (m, 4 H), 3.93-4.06 (m, 1 H), 5.80 (d, J=6.4 Hz, 1 H), 6.01-6.49 (m, 1 H), 7.72 (d, J=6.4 Hz, 1 H).

EXAMPLE 52(3)

4-(1-azepanyl)-N-{(2R,3S)-1-cyclohexyl-2-[4-(dimethylamino)butyl]-3-pyrrolidinyl}-2-pyrimidinamine (compound 52-3)

TLC: Rf 0.45 (ethyl acetate:methanol:28% aqueous ammonia=20:5:1);

NMR (CDCl$_3$): δ 1.48 (m, 25 H), 2.19 (m, 3 H), 2.19 (s, 6 H), 2.46 (m, 1 H), 2.62 (m, 1 H), 2.73 (dt, J=9.50, 7.00 Hz, 1 H), 2.88 (m, 1 H), 3.55 (m, 4 H), 4.13 (m, 1 H), 4.83 (d, J=7.50 Hz, 1 H), 5.78 (d, J=6.00 Hz, 1 H), 7.79 (d, J=6.00 Hz, 1 H).

EXAMPLE 52(4)

4-(1-azepanyl)-N-{(2S,3S)-1-cyclohexyl-2-[(4-methyl-1-piperazinyl)carbonyl]-3-pyrrolidinyl}-2-pyrimidinamine (compound 52-4)

TLC: Rf 0.26 (chloroform:methanol:water=50:10:1);

NMR (CDCl$_3$): δ 1.46 (m, 19 H), 2.33 (m, 6 H), 2.26 (s, 3 H), 2.60 (m, 1 H), 3.19 (dt, J=9.00, 3.50 Hz, 1 H), 3.57 (m, 8 H), 3.78 (d, J=3.00 Hz, 1 H), 4.55 (m, 1 H), 5.59 (m, 1 H), 5.81 (d, J=6.50 Hz, 1 H), 7.73 (d, J=6.50 Hz, 1 H).

EXAMPLE 53(1) TO EXAMPLE 53(6)

The same procedure as a series of reactions of Example 23 was carried out, except that the corresponding amine was used in place of N-[(2RS,3SR)-2-(2-aminoethyl)-1-cyclohexylpiperidin-3-yl]-4-azepan-1-ylpyrimidin-2-amine and the corresponding carboxylic acid was used in place of 1-(tert-butoxycarbonyl)piperidine-4-carboxylic acid in the process of Example 23, to obtain the following compound of the present invention.

EXAMPLE 53(1)

N-[2-((2RS,3SR)-3-{[4-(1-azepanyl)-2-pyrimidinyl]amino}-1-cyclohexyl-2-piperidinyl)ethyl]-1-isopropyl-4-piperidinecarboxamide (compound 53-1)

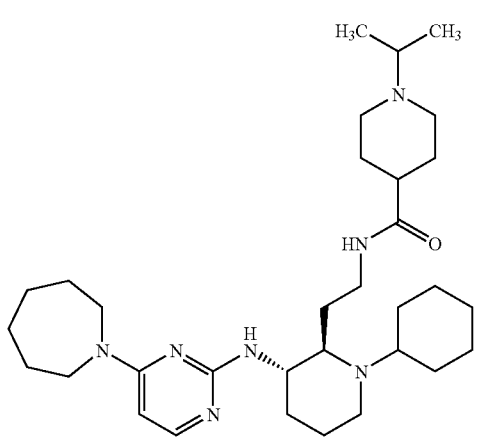

TLC: Rf 0.41 (chloroform:methanol:28% aqueous ammonia=80:10:1);

NMR (CDCl$_3$): δ 0.99-1.07 (m, J=6.6 Hz, 6 H), 1.08-1.20 (m, 3 H), 1.20-1.35 (m, 3 H), 1.39-1.61 (m, 7 H), 1.63-1.91 (m, 15 H), 1.93-2.18 (m, 3 H), 2.41-2.57 (m, 2 H), 2.59-2.84 (m, 3 H), 2.84-2.98 (m, 2 H), 3.16-3.33 (m, 1 H), 3.36-3.88 (m, 5 H), 3.93-4.07 (m, 1 H), 5.21-5.30 (m, 1 H), 5.79 (d, J=6.2 Hz, 1 H), 6.25-6.79 (m, 1 H), 7.80 (d, J=6.2 Hz, 1 H).

EXAMPLE 53(2)

N-[2-((2RS,3SR)-3-{[4-(1-azepanyl)-2-pyrimidinyl]amino}-1-cyclohexyl-2-piperidinyl)ethyl]-1-ethyl-4-piperidinecarboxamide (compound 53-2)

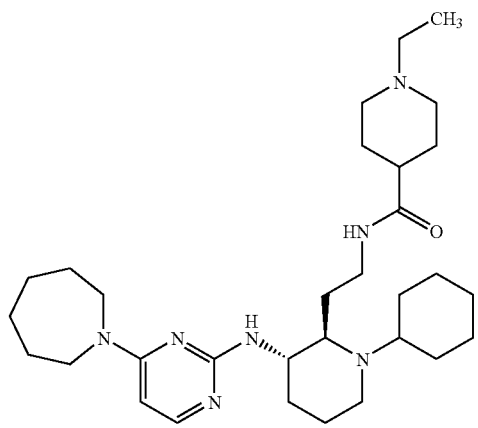

Description: amorphous powder;

TLC: Rf 0.35 (chloroform:methanol:28% aqueous ammonia=80:10:1);

NMR (CDCl$_3$): δ 1.07 (t, J=7.2 Hz, 3 H), 1.10-1.36 (m, 6 H), 1.41-1.63 (m, 6 H), 1.63-1.82 (m, 12 H), 1.83-1.95 (m, 7 H), 1.95-2.09 (m, 1 H), 2.38 (q, J=7.2 Hz, 2 H), 2.42-2.57 (m, 2 H), 2.58-2.70 (m, 1 H), 2.73-2.83 (m, 1 H), 2.90-3.02 (m, 2 H), 3.17-3.34 (m, 1 H), 3.33-3.81 (m, 4 H), 3.93-4.05 (m, 1 H), 5.28 (d, J=7.3 Hz, 1 H), 5.78 (d, J=6.2 Hz, 1 H), 6.28-6.89 (m, 1 H), 7.78 (d, J=6.2 Hz, 1 H).

EXAMPLE 53(3)

N-[2-((2RS,3SR)-3-{[4-(1-azepanyl)-2-pyrimidinyl]amino}-1-cyclohexyl-2-piperidinyl)ethyl]-2-pyridinecarboxamide (compound 53-3)

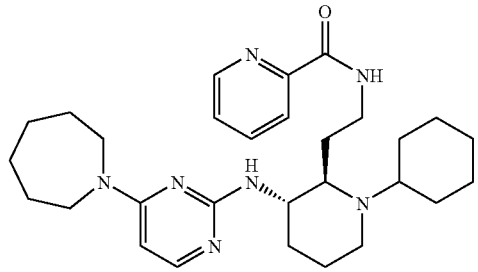

TLC: Rf 0.77 (ethyl acetate:methanol:28% aqueous ammonia=50:10:1);

NMR (CDCl$_3$): δ 1.00-2.08 (m, 24H), 2.42-2.68 (m, 3H), 2.88 (m, 1H), 3.38-3.78 (m, 6H), 4.05 (m, 1H), 5.50 (m, 1H), 5.74 (d, J=6.0 Hz, 1H), 7.39 (dd, J=4.8, 7.8 Hz, 1H), 7.72-7.85 (m, 2H), 8.16 (d, J=7.8 Hz, 1H), 8.22 (m, 1H), 8.50 (d, J=4.8 Hz, 1H).

EXAMPLE 53(4)

N-[2-((2RS,3SR)-3-{[4-(1-azepanyl)-2-pyrimidinyl]amino}-1-cyclohexyl-2-piperidinyl)ethyl]nicotinamide (compound 53-4)

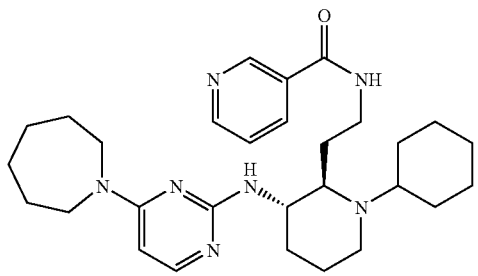

TLC: Rf 0.69 (ethyl acetate:methanol:28% aqueous ammonia=50:10:1);

NMR (CDCl₃): δ 1.00-2.05 (m, 24H), 2.40 (m, 1H), 2.58-2.90 (m, 3H), 3.20-3.80 (m, 6H), 4.09 (m, 1H), 5.07 (m, 1H), 5.74 (d, J=6.3 Hz, 1H), 7.32 (dd, J=4.8, 7.8 Hz, 1H), 7.61 (m, 1H), 8.02-8.14 (m, 2H), 8.66 (dd, J=1.5, 4.8 Hz, 1H), 8.95 (s, 1H).

EXAMPLE 53(5)

N-[2-((2RS,3SR)-3-{[4-(1-azepanyl)-2-pyrimidinyl]amino}-1-cyclohexyl-2-piperidinyl)ethyl]isonicotinamide (compound 53-5)

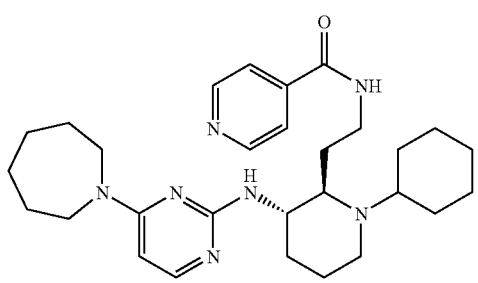

TLC: Rf 0.69 (ethyl acetate:methanol:28% aqueous ammonia=50:10:1);

NMR (CDCl₃): δ 1.00-2.05 (m, 24H), 2.40 (m, 1H), 2.58-2.90 (m, 3H), 3.20-3.80 (m, 6H), 4.07 (m, 1H), 5.05 (m, 1H), 5.74 (d, J=6.3 Hz, 1H), 7.53-7.62 (m, 3H), 8.65 (d, J=4.8 Hz, 1H).

EXAMPLE 53(6)

N-[2-((2RS,3SR)-3-{[4-(1-azepanyl)-2-pyrimidinyl]amino}-1-isopropyl-2-piperidinyl)ethyl]-1-ethyl-4-piperidinecarboxamide (compound 53-6)

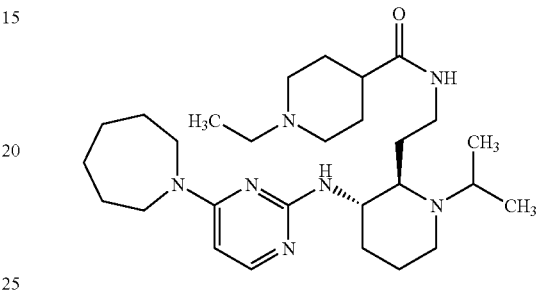

Description: amorphous powder;

TLC: Rf 0.63 (dichloromethane:methanol:28% aqueous ammonia=40:10:1);

NMR (CDCl₃): δ 0.92 (d, J=6.4 Hz, 3 H), 1.02-1.12 (m, 6 H), 1.36-1.62 (m, 6 H), 1.62-1.94 (m, 14 H), 1.94-2.07 (m, 1 H), 2.27-2.45 (m, 3 H), 2.56-2.75 (m, 2 H), 2.90-3.13 (m, 3 H), 3.18-3.34 (m, 1 H), 3.36-3.82 (m, 4 H), 3.89-4.10 (m, 1 H), 5.08 (d, J=9.3 Hz, 1 H), 5.79 (d, J=6.2 Hz, 1 H), 6.26-7.02 (m, 1 H), 7.80 (d, J=6.2 Hz, 1 H).

EXAMPLE 54(1) TO EXAMPLE 54(55)

The same procedure as a series of reactions of Example 23→Example 22 was carried out, except that the corresponding amine was used in place of N-[(2RS,3SR)-2-(2-aminoethyl)-1-cyclohexylpiperidin-3-yl]-4-azepan-1-ylpyrimidin-2-amine and the corresponding carboxylic acid was used in place of 1-(tert-butoxycarbonyl)piperidine-4-carboxylic acid in the process of Example 23, to obtain the following compound of the present invention.

EXAMPLE 54(1)

4-amino-N-[2-((2RS,3SR)-3-{[4-(1-azepanyl)-2-pyrimidinyl]amino}-1-cyclohexyl-2-piperidinyl)ethyl]benzamide (compound 54-1)

MS: 520 (M+H)⁺; HPLC retention time: 3.10 minutes.

EXAMPLE 54(2)

(2S)-N-[2-((2RS,3SR)-3-{[4-(1-azepanyl)-2-pyrimidinyl]amino}-1-cyclohexyl-2-piperidinyl)ethyl]-4-methyl-2-(methylamino)pentanamide (compound 54-2)

MS: 528 (M+H)⁺; HPLC retention time: 3.05 minutes.

EXAMPLE 54(3)

2-(4-aminophenyl)-N-[2-((2RS,3SR)-3-{[4-(1-azepanyl)-2-pyrimidinyl]amino}-1-cyclohexyl-2-piperidinyl)ethyl]acetamide (compound 54-3)

MS: 534 (M+H)+; HPLC retention time: 2.98 minutes.

EXAMPLE 54(4)

N-[2-((2RS,3SR)-3-{[4-(1-azepanyl)-2-pyrimidinyl]amino}-1-cyclohexyl-2-piperidinyl)ethyl]-2-(4-piperidinyl)acetamide (compound 54-4)

MS: 526 (M+H)+; HPLC retention time: 2.96 minutes.

EXAMPLE 54(5)

4-(aminomethyl)-N-[2-((2RS,3SR)-3-{[4-(1-azepanyl)-2-pyrimidinyl]amino}-1-cyclohexyl-2-piperidinyl)ethyl]-2-pyridinecarboxamide (compound 54-5)

MS: 535 (M+H)+; HPLC retention time: 2.98 minutes.

EXAMPLE 54(6)

N-[2-((2RS,3SR)-3-{[4-(1-azepanyl)-2-pyrimidinyl]amino}-1-cyclohexyl-2-piperidinyl)ethyl]-2-indolinecarboxamide (compound 54-6)

MS: 546 (M+H)+; HPLC retention time: 3.29 minutes.

EXAMPLE 54(7)

N-[2-((2RS,3SR)-3-{[4-(1-azepanyl)-2-pyrimidinyl]amino}-1-cyclohexyl-2-piperidinyl)ethyl]-4-(1-piperazinyl)benzamide (compound 54-7)

MS: 589 (M+H)+; HPLC retention time: 3.03 minutes.

EXAMPLE 54(8)

N-[2-((2RS,3SR)-1-cyclohexyl-3-{[4-(1-piperidinyl)-2-pyrimidinyl]amino}-2-piperidinyl)ethyl]-4-piperidinecarboxamide (compound 54-8)

TLC: Rf 0.32 (chloroform:methanol:28% aqueous ammonia=40:10:1);
NMR (METHANOL-D4): δ 0.80-1.01 (m, 1 H), 1.16-1.39 (m, 1 H), 1.38-1.81 (m, 12 H), 1.79-2.21 (m, 12 H), 2.44-2.65 (m, 1 H), 2.92-3.11 (m, 3 H), 3.36-3.50 (m, 3 H), 3.51-3.95 (m, 8 H), 4.51-4.70 (m, 1 H), 6.46 (d, J=7.5 Hz, 1 H), 7.70 (d, J=7.5 Hz, 1 H).

EXAMPLE 54(9)

N-{2-[(2RS,3SR)-3-{[4-(1-azepanyl)-2-pyrimidinyl]amino}-1'-(3-fluorobenzoyl)-1,4'-bipiperidin-2-yl]ethyl}-4-piperidinecarboxamide (compound 54-9)

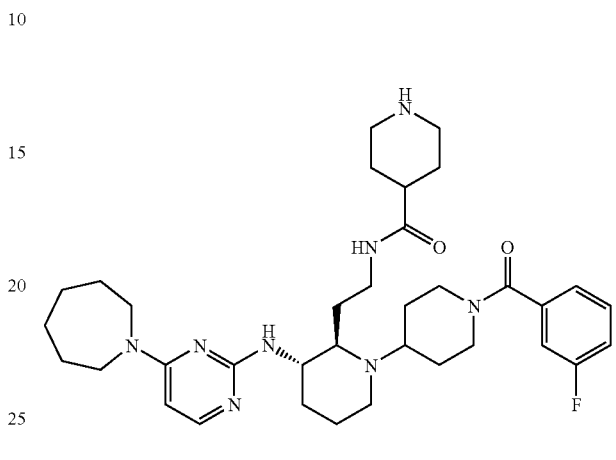

TLC: Rf 0.43 (chloroform:methanol:28% aqueous ammonia=80:20:1);
NMR (CDCl3): δ 1.20-1.96 (m, 27 H), 2.07-2.24 (m, 1 H), 2.48-2.67 (m, 3 H), 2.69-3.33 (m, 6 H), 3.33-3.86 (m, 5 H), 3.95-4.11 (m, 1 H), 4.36-4.76 (m, 1 H), 5.25 (d, J=9.9 Hz, 1 H), 5.82 (d, J=6.2 Hz, 1 H), 7.01-7.21 (m, 3 H), 7.32-7.46 (m, 1 H), 7.80 (d, J=6.2 Hz, 1 H).

EXAMPLE 54(10)

N-{2-[(2RS,3SR)-3-{[4-(1-azepanyl)-2-pyrimidinyl]amino}-1'-(cyclohexylcarbonyl)-1,4'-bipiperidin-2-yl]ethyl}-4-piperidinecarboxamide (compound 54-10)

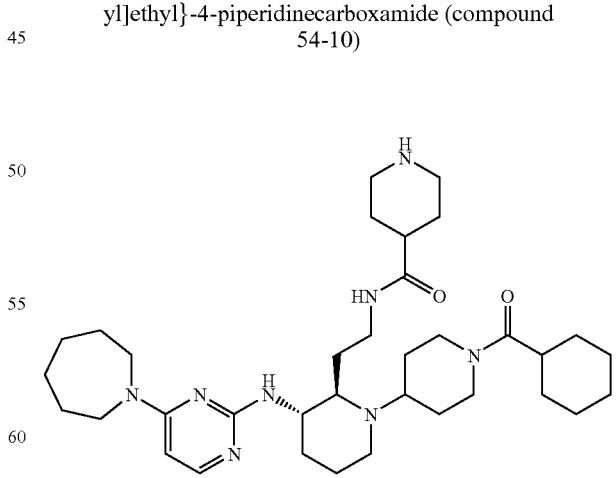

TLC: Rf 0.44 (chloroform:methanol:28% aqueous ammonia=80:20:1);
NMR (CDCl3): δ 1.14-2.06 (m, 34 H), 2.09-2.24 (m, 1 H), 2.34-3.36 (m, 11 H), 3.34-3.77 (m, 6 H), 3.79-3.95 (m, 1 H), 3.96-4.10 (m, 1 H), 4.39-4.63 (m, 1 H), 5.17-5.34 (m, 1 H), 5.81 (d, J=6.0 Hz, 1 H), 7.80 (d, J=6.0 Hz, 1 H).

EXAMPLE 54(11)

N-[2-((2RS,3SR)-3-{[4-(1-azepanyl)-2-pyrimidinyl]amino}-1-cyclohexyl-2-piperidinyl)ethyl]-2-morpholinecarboxamide (compound 54-11)

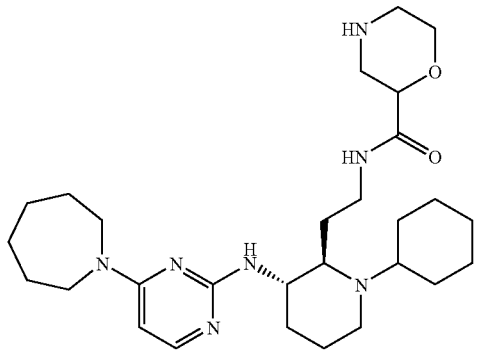 [SMILES: O=C(NCC[C@@H]1[C@@H](Nc2nccc(N3CCCCCC3)n2)CCCN1C1CCCCC1)C1CNCCO1]

Description: amorphous powder;

TLC: Rf 0.68 (ethyl acetate:methanol:28% aqueous ammonia=50:10:1);

NMR (CDCl$_3$): δ 1.00-1.95 (m, 24H), 2.43-2.70 (m, 4H), 2.76-2.86 (m, 3H), 3.15-3.70 (m, 8H), 3.84-3.94 (m, 2H), 3.99 (m, 1H), 5.39 (brs, 1H), 5.76 (d, J=6.0 Hz, 1H), 6.93 (brs, 1H), 7.79 (d, J=6.0 Hz, 1H).

EXAMPLE 54(12)

(3S)-N-[2-((2RS,3SR)-3-{[4-(1-azepanyl)-2-pyrimidinyl]amino}-1-cyclohexyl-2-piperidinyl)ethyl]-3-piperidinecarboxamide (compound 54-12)

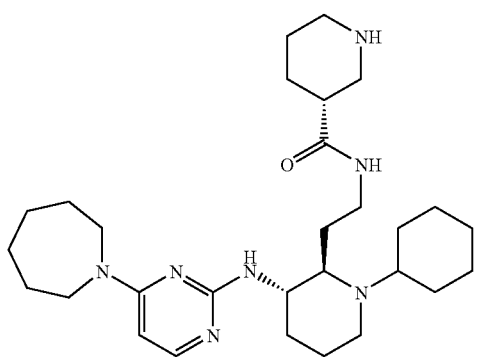 [SMILES: O=C(NCC[C@@H]1[C@@H](Nc2nccc(N3CCCCCC3)n2)CCCN1C1CCCCC1)[C@@H]1CCCNC1]

TLC: Rf 0.46 (ethyl acetate:methanol:28% aqueous ammonia=50:10:1);

NMR (CDCl$_3$): δ 1.00-1.97 (m, 28H), 2.27 (m, 1H), 2.41-2.68 (m, 3H), 2.71-2.86 (m, 2H), 2.94 (t, J=5.4 Hz, 2H), 3.16-3.82 (m, 7H), 4.00 (m, 1H), 5.30 (m, 1H), 5.77 (d, J=6.0 Hz, 1H), 7.68 (brs, 1H), 7.80 (d, J=6.0 Hz, 1H).

EXAMPLE 54(13)

(3R)-N-[2-((2RS,3SR)-3-{[4-(1-azepanyl)-2-pyrimidinyl]amino}-1-cyclohexyl-2-piperidinyl)ethyl]-3-piperidinecarboxamide (compound 54-13)

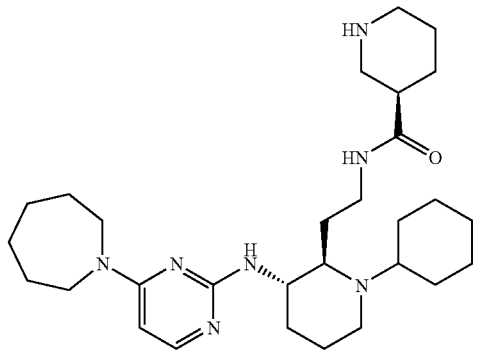 [SMILES: O=C(NCC[C@@H]1[C@@H](Nc2nccc(N3CCCCCC3)n2)CCCN1C1CCCCC1)[C@@H]1CCCNC1]

TLC: Rf 0.46 (ethyl acetate:methanol:28% aqueous ammonia=50:10:1);

NMR (CDCl$_3$): δ 1.00-1.90 (m, 28H), 2.27 (m, 1H), 2.41-2.67 (m, 3H), 2.50-2.86 (m, 2H), 2.94 (t, J=5.4 Hz, 2H), 3.13-3.80 (m, 7H), 4.00 (m, 1H), 5.29 (m, 1H), 5.77 (d, J=6.0 Hz, 1H), 7.68 (brs, 1H), 7.80 (d, J=6.0 Hz, 1H).

EXAMPLE 54(14)

(3R)-N-[2-((2RS,3SR)-3-{[4-(1-azepanyl)-2-pyrimidinyl]amino}-1-cyclohexyl-2-piperidinyl)ethyl]-3-pyrrolidinecarboxamide (compound 54-14)

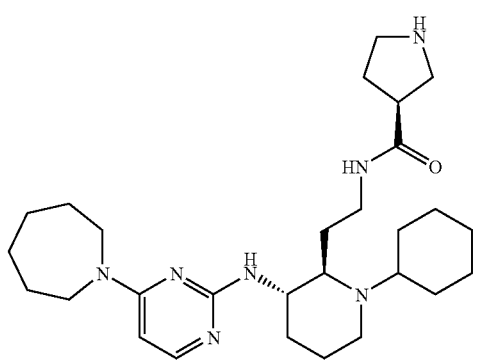 [SMILES: O=C(NCC[C@@H]1[C@@H](Nc2nccc(N3CCCCCC3)n2)CCCN1C1CCCCC1)[C@H]1CCNC1]

TLC: Rf 0.40 (ethyl acetate:methanol:28% aqueous ammonia=50:10:1);

NMR (CDCl₃): δ 1.00-2.20 (m, 26H), 2.38-3.00 (m, 8H), 3.06-3.20 (m, 2H), 3.22-3.80 (m, 5H), 3.99 (m, 1H), 5.79 (d, J=6.3 Hz, 1H), 7.73 (d, J=6.3 Hz, 1H).

EXAMPLE 54(15)

2-amino-N-[2-((2RS,3SR)-3-{[4-(1-azepanyl)-2-pyrimidinyl]amino}-1-cyclohexyl-2-piperidinyl)ethyl]-2-methylpropanamide (compound 54-15)

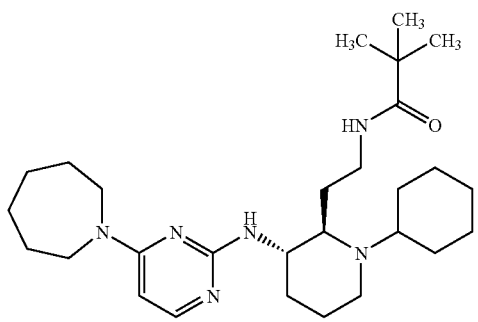 [SMILES: CC(C)(C)C(=O)NCC[C@@H]1[C@@H](Nc2nccc(N3CCCCCC3)n2)CCCN1C1CCCCC1]

Description: amorphous powder;
TLC: Rf 0.72 (ethyl acetate:methanol:28% aqueous ammonia=50:10:1);
NMR (CDCl₃): δ 1.02-1.95 (m, 30H), 2.44 (m, 1H), 2.53-2.61 (m, 2H), 2.83 (m, 1H), 3.18 (m, 1H), 3.32-3.80 (m, 5H), 4.00 (m, 1H), 5.60 (brs, 1H), 5.75 (d, J=6.0 Hz, 1H), 7.70 (brs, 1H), 7.79 (d, J=6.0 Hz, 1H).

EXAMPLE 54(16)

(2S)-N-[2-((2RS,3SR)-3-{[4-(1-azepanyl)-2-pyrimidinyl]amino}-1-cyclohexyl-2-piperidinyl)ethyl]-2-piperidinecarboxamide (compound 54-16)

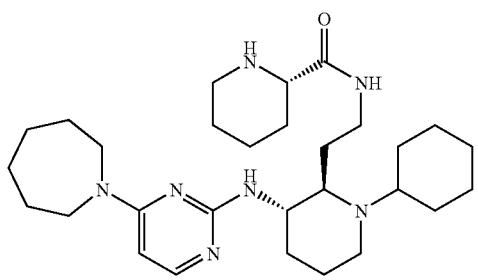 [SMILES: O=C(NCC[C@@H]1[C@@H](Nc2nccc(N3CCCCCC3)n2)CCCN1C1CCCCC1)[C@@H]1CCCCN1]

TLC: Rf 0.29 (chloroform:methanol:28% aqueous ammonia=80:10:1);
NMR (DMSO-D₆): δ 0.95-1.88 (m, 30H), 2.24-2.38 (m, 1H), 2.39-2.52 (m, 1H), 2.54-2.70 (m, 2H), 2.78-3.08 (m, 3H), 3.08-3.37 (m, 3H), 3.35-3.69 (m, 4H), 3.72-3.90 (m, 1H), 5.83 (d, J=5.4 Hz, 1H), 5.88-5.93 (m, 1H), 7.50-7.64 (m, 1H), 7.70 (d, J=5.4 Hz, 1H).

EXAMPLE 54(17)

(2R)-N-[2-((2RS,3SR)-3-{[4-(1-azepanyl)-2-pyrimidinyl]amino}-1-cyclohexyl-2-piperidinyl)ethyl]-2-piperidinecarboxamide (compound 54-17)

TLC: Rf 0.29 (chloroform:methanol:28% aqueous ammonia=80:10:1);

NMR (DMSO-D₆): δ 0.94-1.83 (m, 30 H), 2.23-2.38 (m, 1 H), 2.41-2.53 (m, 1 H), 2.54-2.69 (m, 2 H), 2.82-2.93 (m, 1 H), 2.93-3.09 (m, 2 H), 3.11-3.37 (m, 3 H), 3.39-3.69 (m, 4 H), 3.72-3.87 (m, 1 H), 5.83 (d, J=5.7 Hz, 1 H), 5.87-5.98 (m, 1 H), 7.56-7.67 (m, 1 H), 7.70 (d, J=5.7 Hz, 1 H).

EXAMPLE 54(18)

N-[2-((2RS,3SR)-3-{[4-(1-azepanyl)-2-pyrimidinyl]amino}-1-cyclohexyl-2-piperidinyl)ethyl]-4-hydroxy-4-piperidinecarboxamide (compound 54-18)

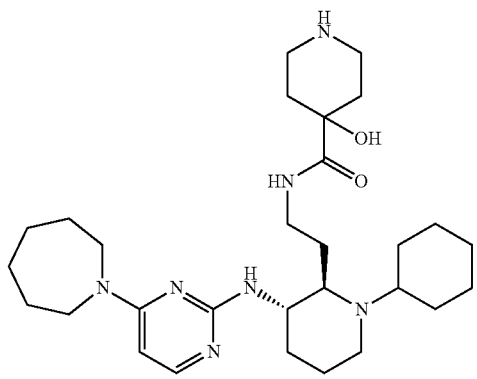 [SMILES: O=C(NCC[C@@H]1[C@@H](Nc2nccc(N3CCCCCC3)n2)CCCN1C1CCCCC1)C1(O)CCNCC1]

Description: amorphous powder;
TLC: Rf 0.29 (chloroform:methanol:28% aqueous ammonia=80:10:1);
NMR (CDCl₃): δ 1.00-2.23 (m, 28 H), 2.27-2.81 (m, 5 H), 2.89-3.09 (m, 4 H), 3.18-3.80 (m, 7 H), 3.86-4.02 (m, 1 H), 4.90-5.37 (m, 1 H), 5.77 (d, J=6.2 Hz, 1 H), 7.20-7.38 (m, 1 H), 7.71 (d, J=6.2 Hz, 1 H).

EXAMPLE 54(19)

5-amino-N-[2-((2RS,3SR)-3-{[4-(1-azepanyl)-2-pyrimidinyl]amino}-1-cyclohexyl-2-piperidinyl)ethyl]pentanamide (compound 54-19)

TLC: Rf 0.37 (chloroform:methanol:28% aqueous ammonia=80:10:1);
NMR (CDCl₃): δ 0.67-2.01 (m, 30 H), 2.04-2.23 (m, 2 H), 2.32-2.60 (m, 2 H), 2.59-2.85 (m, 4 H), 3.07-3.85 (m, 6 H), 3.88-4.07 (m, 1 H), 5.22 (d, J=9.2 Hz, 1 H), 5.79 (d, J=6.0 Hz, 1 H), 6.32-7.57 (m, 1 H), 7.78 (d, J=6.0 Hz, 1 H).

EXAMPLE 54(20)

(2S,4S)-N-[2-((2RS,3SR)-3-{[4-(1-azepanyl)-2-pyrimidinyl]amino}-1-cyclohexyl-2-piperidinyl)ethyl]-4-hydroxy-2-pyrrolidinecarboxamide (compound 54-20)

TLC: Rf 0.36 (ethyl acetate:methanol:28% aqueous ammonia=50:10:1);
NMR (CDCl₃): δ 1.00-2.90 (m, 32H), 3.00 (m, 1H), 3.10-4.00 (m, 7H), 4.35 (m, 1H), 5.50 (m, 1H), 5.74 (d, J=6.3 Hz, 1H), 7.70 (m, 1H), 7.80 (m, 1H).

EXAMPLE 54(21)

(2R,4R)-N-[2-((2RS,3SR)-3-{[4-(1-azepanyl)-2-pyrimidinyl]amino}-1-cyclohexyl-2-piperidinyl)ethyl]-4-hydroxy-2-pyrrolidinecarboxamide (compound 54-21)

TLC: Rf 0.36 (ethyl acetate:methanol:28% aqueous ammonia=50:10:1);
NMR (CDCl$_3$): δ 1.00-2.10 (m, 26H), 2.10-2.85 (m, 6H), 3.01 (dd, J=3.6, 10.2 Hz, 1H), 3.10-3.70 (m, 5H), 3.73 (dt, J=3.0, 10.2 Hz, 1H), 3.89 (m, 1H), 4.35 (m, 1H), 5.55 (m, 1H), 5.74 (d, J=6.3 Hz, 1H), 7.70 (m, 1H), 7.85 (m, 1H).

EXAMPLE 54(22)

(2S,4R)-N-[2-((2RS,3SR)-3-{[4-(1-azepanyl)-2-pyrimidinyl]amino}-1-cyclohexyl-2-piperidinyl)ethyl]-4-hydroxy-2-pyrrolidinecarboxamide (compound 54-22)

TLC: Rf 0.36 (ethyl acetate:methanol:28% aqueous ammonia=50:10:1);
NMR (CDCl$_3$): δ 1.00-2.02 (m, 26H), 2.21 (m, 1H), 2.40-2.62 (m, 3H), 2.74-2.84 (m, 2H), 2.96 (m, 1H), 3.17 (m, 1H), 3.31-3.80 (m, 4H), 3.90-4.02 (m, 2H), 4.39 (m, 1H), 5.58 (m, 1H), 5.74 (d, J=6.0 Hz, 1H), 7.68-7.84 (m, 2H).

EXAMPLE 54(23)

(2R,4S)-N-[2-((2RS,3SR)-3-{[4-(1-azepanyl)-2-pyrimidinyl]amino}-1-cyclohexyl-2-piperidinyl)ethyl]-4-hydroxy-2-pyrrolidinecarboxamide (compound 54-23)

TLC: Rf 0.36 (ethyl acetate:methanol:28% aqueous ammonia=50:10:1);
NMR (CDCl$_3$): δ 1.00-2.10 (m, 26H), 2.22 (m, 1H), 2.39-2.62 (m, 3H), 2.71-2.86 (m, 2H), 2.96 (m, 1H), 3.17 (m, 1H), 3.30-3.80 (m, 4H), 3.89-4.02 (m, 2H), 4.39 (m, 1H), 5.54 (m, 1H), 5.74 (d, J=6.0 Hz, 1H), 7.70-7.83 (m, 2H).

EXAMPLE 54(24)

(2R)-2-amino-N-[2-((2RS,3SR)-3-{[4-(1-azepanyl)-2-pyrimidinyl]amino}-1-cyclohexyl-2-piperidinyl)ethyl]-3-(1H-imidazol-4-yl)propanamide (compound 54-24)

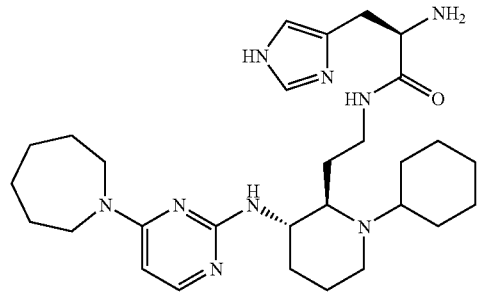 [SMILES: N[C@H](Cc1c[nH]cn1)C(=O)NCC[C@@H]1[C@@H](Nc2nccc(N3CCCCCC3)n2)CCCN1C1CCCCC1]

Description: amorphous powder;
TLC: Rf 0.75 (ethyl acetate:methanol:28% aqueous ammonia=20:5:1);
NMR (DMSO-D$_6$): δ 1.40 (m, 24 H), 2.45 (m, 4 H), 2.81 (m, 1 H), 3.30 (m, 8 H), 3.80 (m, 1 H), 5.82 (m, 1 H), 5.89 (m, 1 H), 6.74 (m, 1 H), 7.47 (m, 1 H), 7.70 (m, 1 H), 7.81 (m, 1 H), 11.76 (m, 1 H).

EXAMPLE 54(25)

(2S)-2-amino-N-[2-((2RS,3SR)-3-{[4-(1-azepanyl)-2-pyrimidinyl]amino}-1-cyclohexyl-2-piperidinyl)ethyl]-3-(1H-imidazol-4-yl)propanamide (compound 54-25)

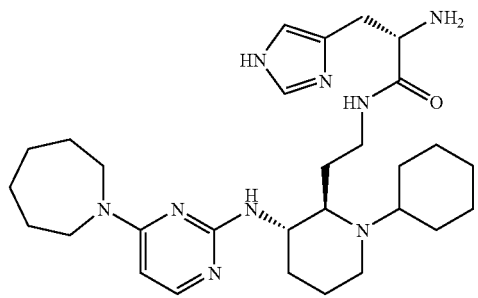 [SMILES: N[C@@H](Cc1c[nH]cn1)C(=O)NCC[C@@H]1[C@@H](Nc2nccc(N3CCCCCC3)n2)CCCN1C1CCCCC1]

TLC: Rf 0.75 (ethyl acetate:methanol:28% aqueous ammonia=20:5:1);
NMR (DMSO-D$_6$): δ 1.39 (m, 24 H), 2.45 (m, 4 H), 2.81 (m, 1 H), 3.30 (m, 8 H), 3.80 (m, 1 H), 5.82 (m, 1 H), 5.89 (m, 1 H), 6.74 (m, 1 H), 7.47 (s, 1 H), 7.70 (m, 1 H), 7.81 (m, 1 H), 11.79 (m, 1 H).

EXAMPLE 54(26)

N-[2-((2RS,3SR)-1-cyclohexyl-3-{[4-(1-pyrrolidinyl)-2-pyrimidinyl]amino}-2-piperidinyl)ethyl]-4-piperidinecarboxamide (compound 54-26)

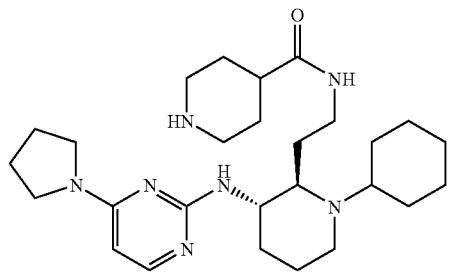 [SMILES: O=C(NCC[C@@H]1[C@@H](Nc2nccc(N3CCCC3)n2)CCCN1C1CCCCC1)C1CCNCC1]

TLC: Rf 0.50 (chloroform:methanol:28% aqueous ammonia=40:10:1);
NMR (CDCl$_3$): δ 0.99-1.38 (m, 6 H), 1.40-2.03 (m, 19 H), 2.06-2.20 (m, 1 H), 2.35-2.82 (m, 6 H), 3.04-3.16 (m, 2 H), 3.17-3.61 (m, 6 H), 3.94-4.14 (m, 1 H), 5.20 (d, J=9.3 Hz, 1 H), 5.67 (d, J=5.9 Hz, 1 H), 6.77 (d, 1 H), 7.78 (d, J=5.9 Hz, 1 H).

EXAMPLE 54(27)

1-amino-N-[2-((2RS,3SR)-3-{[4-(1-azepanyl)-2-pyrimidinyl]amino}-1-cyclohexyl-2-piperidinyl)ethyl]cyclohexanecarboxamide (compound 54-27)

TLC: Rf 0.37 (ethyl acetate:methanol:28% aqueous ammonia=100:10:1);

NMR (CDCl$_3$): δ 1.55 (m, 34 H), 2.42 (m, 1 H), 2.56 (m, 2 H), 2.83 (m, 1 H), 3.16 (m, 1 H), 3.39 (m, 1 H), 3.54 (m, 4 H), 3.99 (m, 1 H), 5.51 (m, 1 H), 5.74 (d, J=6.00 Hz, 1 H), 7.78 (d, J=6.00 Hz, 1 H), 7.90 (m, 1 H).

EXAMPLE 54(28)

N-[2-((2RS,3SR)-1-isopropyl-3-{[4-(1-pyrrolidinyl)-2-pyrimidinyl]amino}-2-piperidinyl)ethyl]-4-piperidinecarboxamide (compound 54-28)

TLC: Rf 0.44 (chloroform:methanol:28% aqueous ammonia=40:10:1);

NMR (CDCl$_3$): δ 0.92 (d, J=6.4 Hz, 3 H), 1.08 (d, J=6.4 Hz, 3 H), 1.33-2.02 (m, 15 H), 2.13 (d, 1 H), 2.25-2.40 (m, 1 H), 2.48-2.73 (m, 4 H), 2.97-3.16 (m, 3 H), 3.20-3.61 (m, 6 H), 3.96-4.11 (m, 1 H), 5.11 (d, J=9.1 Hz, 1 H), 5.67 (d, J=6.0 Hz, 1 H), 6.49-7.00 (m, 1 H), 7.78 (d, J=6.0 Hz, 1 H).

EXAMPLE 54(29)

N-{2-[(2RS,3SR)-3-{[4-(1-azepanyl)-2-pyrimidinyl]amino}-1-(3-hydroxypropyl)-2-piperidinyl]ethyl}-4-piperidinecarboxamide (compound 54-29)

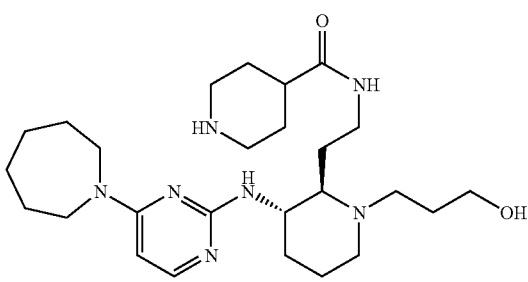 [SMILES: O=C(NCC[C@@H]1[C@@H](Nc2nccc(N3CCCCCC3)n2)CCCN1CCCO)C1CCNCC1]

Description: amorphous powder;

TLC: Rf 0.15 (ethyl acetate:methanol:28% aqueous ammonia=10:10:1);

NMR (CDCl$_3$): δ1.42-1.97 (m, 20 H), 2.11-2.31 (m, 3 H), 2.33-2.77 (m, 7 H), 2.78-2.95 (m, 1 H), 3.02-3.20 (m, 2 H), 3.23-3.88 (m, 8 H), 3.91-4.06 (m, 1 H), 5.11 (d, J=7.87 Hz, 1 H), 5.82 (d, J=6.22 Hz, 1 H), 7.77 (d, J=6.04 Hz, 1 H).

EXAMPLE 54(30)

(2R)-2-amino-N-[2-((2RS,3SR)-3-{[4-(1-azepanyl)-2-pyrimidinyl]amino}-1-cyclohexyl-2-piperidinyl)ethyl]-3-(4-hydroxyphenyl)propanamide (compound 54-30)

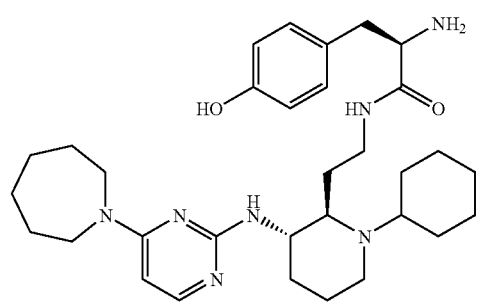 [SMILES: N[C@H](Cc1ccc(O)cc1)C(=O)NCC[C@@H]1[C@@H](Nc2nccc(N3CCCCCC3)n2)CCCN1C1CCCCC1]

Description: amorphous powder;

TLC: Rf 0.70 (ethyl acetate:methanol:28% aqueous ammonia=20:5:1);

NMR (DMSO-D$_6$): δ 1.39 (m, 24 H), 2.29 (m, 1 H), 2.42 (m, 1 H), 2.59 (m, 3 H), 2.73 (m, 1 H), 2.97 (m, 1 H), 3.16 (m, 2 H), 3.50 (m, 4 H), 3.78 (m, 1 H), 5.87 (m, 2 H), 6.61 (d, J=8.50 Hz, 2 H), 6.93 (d, J=8.50 Hz, 2 H), 7.70 (m, 2 H), 9.14 (m, 1 H).

EXAMPLE 54(31)

(2S)-2-amino-N-[2-((2RS,3SR)-3-{[4-(1-azepanyl)-2-pyrimidinyl]amino}-1-cyclohexyl-2-piperidinyl)ethyl]-3-(4-hydroxyphenyl)propanamide (compound 54-31)

TLC: Rf 0.70 (ethyl acetate:methanol:28% aqueous ammonia=20:5:1);

NMR (DMSO-D$_6$): δ 1.40 (m, 24 H), 2.30 (m, 1 H), 2.43 (m, 1 H), 2.59 (m, 3 H), 2.73 (m, 1 H), 2.97 (m, 1 H), 3.16 (m, 2 H), 3.50 (m, 4 H), 3.80 (m, 1 H), 5.86 (m, 2 H), 6.61 (d, J=8.50 Hz, 2 H), 6.92 (d, J=8.50 Hz, 2 H), 7.70 (m, 2 H), 9.13 (m, 1 H).

EXAMPLE 54(32)

(2R)-2-amino-N-[2-((2RS,3SR)-3-{[4-(1-azepanyl)-2-pyrimidinyl]amino}-1-cyclohexyl-2-piperidinyl)ethyl]-4-hydroxybutanamide (compound 54-32)

TLC: Rf 0.56 (ethyl acetate:methanol:28% aqueous ammonia=100:10:1);

NMR (DMSO-D$_6$): δ 1.39 (m, 24 H), 2.29 (m, 1 H), 2.62 (m, 2 H), 3.40 (m, 13 H), 5.82 (m, 1 H), 5.95 (m, 1 H), 7.70 (m, 1 H), 7.91 (m, 1 H).

EXAMPLE 54(33)

(2S)-2-amino-N-[2-((2RS,3SR)-3-{[4-(1-azepanyl)-2-pyrimidinyl]amino}-1-cyclohexyl-2-piperidinyl)ethyl]-4-hydroxybutanamide (compound 54-33)

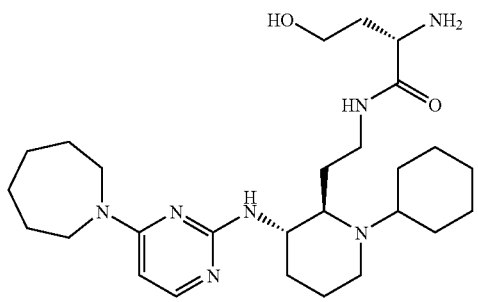 [SMILES: N[C@@H](CCO)C(=O)NCC[C@@H]1[C@@H](Nc2nccc(N3CCCCCC3)n2)CCCN1C1CCCCC1]

Description: amorphous powder;
TLC: Rf 0.56 (ethyl acetate:methanol:28% aqueous ammonia=100:10:1);
NMR (DMSO-D$_6$): δ 1.39 (m, 24 H), 2.30 (m, 1 H), 2.61 (m, 2 H), 3.39 (m, 13 H), 5.82 (m, 1 H), 5.90 (m, 1 H), 7.70 (m, 1 H), 7.77 (m, 1 H).

EXAMPLE 54(34)

(2S,3R)-2-amino-N-[2-((2RS,3RS)-3-{[4-(1-azepanyl)-2-pyrimidinyl]amino}-1-cyclohexyl-2-piperidinyl)ethyl]-3-hydroxybutanamide (compound 54-34)

TLC: Rf 0.53 (ethyl acetate:methanol:28% aqueous ammonia=50:10:1);
NMR (CDCl$_3$): δ 1.00-2.20 (m, 27H), 2.30-2.90 (m, 5H), 3.13 (d, J=3.3 Hz, 1H), 3.21 (m, 1H), 3.35-3.80 (m 4H), 3.90 (m, 1H), 4.30 (m, 1H), 5.43 (m, 1H), 5.76 (d, J=6.3 Hz, 1H), 7.68-7.81 (m, 2H).

EXAMPLE 54(35)

(2R,3S)-2-amino-N-[2-((2RS,3SR)-3-{[4-(1-azepanyl)-2-pyrimidinyl]amino}-1-cyclohexyl-2-piperidinyl)ethyl]-3-hydroxybutanamide (compound 54-35)

TLC: Rf 0.53 (ethyl acetate:methanol:28% aqueous ammonia=50:10:1);
NMR (CDCl$_3$): δ 1.00-2.20 (m, 27H), 2.30-2.90 (m, 5H), 3.13 (d, J=3.3 Hz, 1H), 3.22 (m, 1H), 3.35-3.80 (m 4H), 3.90 (m, 1H), 4.30 (m, 1H), 5.36 (m, 1H), 5.76 (d, J=6.3 Hz, 1H), 7.68-7.81 (m, 2H).

EXAMPLE 54(36)

(2R)-2-amino-N-[2-((2RS,3SR)-3-{[4-(1-azepanyl)-2-pyrimidinyl]amino}-1-cyclohexyl-2-piperidinyl)ethyl]-3-hydroxypropanamide (compound 54-36)

TLC: Rf 0.69 (ethyl acetate:methanol:28% aqueous ammonia=20:5:1);
NMR (DMSO-D$_6$): δ 1.40 (m, 24 H), 2.31 (m, 1 H), 2.60 (m, 2 H), 3.40 (m, 10 H), 4.67 (m, 1 H), 5.82 (m, 1 H), 5.88 (m, 1 H), 7.70 (m, 1 H), 7.78 (m, 1 H).

EXAMPLE 54(37)

(2S)-2-amino-N-[2-((2RS,3SR)-3-{[4-(1-azepanyl)-2-pyrimidinyl]amino}-1-cyclohexyl-2-piperidinyl)ethyl]-3-hydroxypropanamide (compound 54-37)

TLC: Rf 0.69 (ethyl acetate:methanol:28% aqueous ammonia=20:5:1);
NMR (DMSO-D$_6$): δ 1.46 (m, 24 H), 2.30 (m, 1 H), 2.60 (m, 2 H), 3.40 (m, 10 H), 4.67 (m, 1 H), 5.82 (m, 1 H), 5.89 (m, 1 H), 7.70 (m, 1 H), 7.79 (m, 1 H).

EXAMPLE 54(38)

(2S)-2-amino-N-[2-((2RS,3SR)-3-{[4-(1-azepanyl)-2-pyrimidinyl]amino}-1-cyclohexyl-2-piperidinyl)ethyl]-5-hydroxypentanamide (compound 54-38)

TLC: Rf 0.50 (dichloromethane:methanol:28% aqueous ammonia=50:10:1);
NMR (CDCl$_3$): δ 1.00-2.12 (m, 28H), 2.44-3.01 (m, 6H), 3.24-3.80 (m, 6H), 3.86-4.02 (m, 2H), 5.43 (m, 1H), 5.80 (d, J=6.3 Hz, 1H), 7.76 (m, 1H).

EXAMPLE 54(39)

(2R)-2-amino-N-[2-((2RS,3SR)-3-{[4-(1-azepanyl)-2-pyrimidinyl]amino}-1-cyclohexyl-2-piperidinyl)ethyl]-5-hydroxypentanamide (compound 54-39)

TLC: Rf 0.50 (dichloromethane:methanol:28% aqueous ammonia=50:10:1);
NMR (CDCl$_3$): δ 1.00-2.10 (m, 28H), 2.42-3.01 (m, 6H), 3.24-3.80 (m, 6H), 3.82-4.04 (m, 2H), 5.50 (m, 1H), 5.80 (d, J=6.0 Hz, 1H), 7.76 (m, 1H).

EXAMPLE 54(40)

(4S)-4-amino-N-[2-((2RS,3SR)-3-{[4-(1-azepanyl)-2-pyrimidinyl]amino}-1-cyclohexyl-2-piperidinyl)ethyl]-5-hydroxypentanamide (compound 54-40)

TLC: Rf 0.29 (ethyl acetate:methanol:28% aqueous ammonia=50:10:1);
NMR (CDCl$_3$): δ 1.02-2.08 (m, 28H), 2.18-2.88 (m, 6H), 3.24-3.80 (m, 7H), 3.95 (m, 1H), 5.30 (m, 1H), 5.80 (d, J=6.3 Hz, 1H), 7.77 (d, J=6.3 Hz, 1H).

EXAMPLE 54(41)

(4R)-4-amino-N-[2-((2RS,3SR)-3-{[4-(1-azepanyl)-2-pyrimidinyl]amino}-1-cyclohexyl-2-piperidinyl)ethyl]-5-hydroxypentanamide (compound 54-41)

TLC: Rf 0.29 (ethyl acetate:methanol:28% aqueous ammonia=50:10:1);

NMR (CDCl$_3$): δ 1.02-1.99 (m, 24H), 2.08-2.88 (m, 10H), 3.24-3.80 (m, 7H), 3.95 (m, 1H), 5.30 (m, 1H), 5.79 (d, J=6.3 Hz, 1H), 7.77 (d, J=6.3 Hz, 1H).

EXAMPLE 54(42)

(3R)-3-amino-N-[2-((2RS,3SR)-3-{[4-(1-azepanyl)-2-pyrimidinyl]amino}-1-cyclohexyl-2-piperidinyl)ethyl]-4-hydroxybutanamide (compound 54-42)

TLC: Rf 0.52 (ethyl acetate:methanol:28% aqueous ammonia=20:5:1);
NMR (DMSO-D$_6$): δ 1.37 (m, 24 H), 1.93 (dd, J=14.50, 8.00 Hz, 1 H), 2.14 (dd, J=14.50, 5.00 Hz, 1 H), 2.29 (m, 1 H), 2.61 (m, 2 H), 3.35 (m, 11 H), 5.82 (m, 1 H), 5.93 (m, 1 H), 7.70 (m, 1 H), 7.90 (m, 1 H).

EXAMPLE 54(43)

(3S)-3-amino-N-[2-((2RS,3SR)-3-{[4-(1-azepanyl)-2-pyrimidinyl]amino}-1-cyclohexyl-2-piperidinyl)ethyl]-4-hydroxybutanamide (compound 54-43)

TLC: Rf 0.52 (ethyl acetate:methanol:28% aqueous ammonia=20:5:1);
NMR (DMSO-D$_6$): δ 1.39 (m, 24 H), 1.92 (dd, J=14.50, 8.00 Hz, 1 H), 2.13 (dd, J=14.50, 5.00 Hz, 1 H), 2.29 (m, 1 H), 2.60 (m, 2 H), 3.37 (m, 11 H), 5.82 (m, 1 H), 5.93 (m, 1 H), 7.70 (m, 1 H), 7.89 (m, 1 H).

EXAMPLE 54(44)

4-amino-N-[((2R,3S)-3-{[4-(1-azepanyl)-2-pyrimidinyl]amino}-1-cyclohexyl-2-pyrrolidinyl)methyl]benzamide (compound 54-44)

MS: 492 (M+H)$^+$; HPLC retention time: 3.18 minutes.

EXAMPLE 54(45)

(2S)-N-[((2R,3S)-3-{[4-(1-azepanyl)-2-pyrimidinyl]amino}-1-cyclohexyl-2-pyrrolidinyl)methyl]-4-methyl-2-(methylamino)pentanamide (compound 54-45)

MS: 500 (M+H)$^+$; HPLC retention time: 3.06 minutes.

EXAMPLE 54(46)

2-(4-aminophenyl)-N-[((2R,3S)-3-{[4-(1-azepanyl)-2-pyrimidinyl]amino}-1-cyclohexyl-2-pyrrolidinyl)methyl]acetamide (compound 54-46)

MS: 506 (M+H)$^+$; HPLC retention time: 2.99 minutes.

EXAMPLE 54(47)

(3S)-N-[((2R,3S)-3-{[4-(1-azepanyl)-2-pyrimidinyl]amino}-1-cyclohexyl-2-pyrrolidinyl)methyl]-1,2,3,4-tetrahydro-3-isoquinolinecarboxamide (compound 54-47)

MS: 532 (M+H)$^+$; HPLC retention time: 3.11 minutes.

EXAMPLE 54(48)

N-[((2R,3S)-3-{[4-(1-azepanyl)-2-pyrimidinyl]amino}-1-cyclohexyl-2-pyrrolidinyl)methyl]-2-(4-piperidinyl)acetamide (compound 54-48)

MS: 498(M+H)$^+$; HPLC retention time: 2.98 minutes.

EXAMPLE 54(49)

N-[((2R,3S)-3-{[4-(1-azepanyl)-2-pyrimidinyl]amino}-1-cyclohexyl-2-pyrrolidinyl)methyl]-4-(1-piperazinyl)benzamide (compound 54-49)

MS: 561 (M+H)$^+$; HPLC retention time: 3.07 minutes.

EXAMPLE 54(50)

2-amino-N-[((2R,3S)-3-{[4-(1-azepanyl)-2-pyrimidinyl]amino}-1-cyclohexyl-2-pyrrolidinyl)methyl]acetamide (compound 54-50)

TLC: Rf 0.78 (chloroform:methanol:28% aqueous ammonia=40:10:2);
NMR (METHANOL-D$_4$): δ 1.08-1.39 (m, 6 H), 1.50-1.67 (m, 4 H), 1.70-1.85 (m, 7 H), 1.90-1.98 (m, 2 H), 2.02-2.18 (m, 1 H), 2.52-2.66 (m, 1 H), 2.80-2.94 (m, 1 H), 2.95-3.04 (m, 2 H), 3.08-3.20 (m, 1 H), 3.41-3.81 (m, 7 H), 4.01-4.21 (m, 1 H), 5.95 (d, J=6.6 Hz, 1 H), 7.72 (d, J=6.6 Hz, 1 H).

EXAMPLE 54(51)

3-amino-N-[((2R,3S)-3-{[4-(1-azepanyl)-2-pyrimidinyl]amino}-1-cyclohexyl-2-pyrrolidinyl)methyl]propanamide (compound 54-51)

TLC: Rf 0.69 (chloroform:methanol:28% aqueous ammonia=40:10:2);
NMR (METHANOL-D$_4$): δ 1.06-1.44 (m, 6 H), 1.50-2.23 (m, 14 H), 2.34 (t, J=6.7 Hz, 2 H), 2.48-2.67 (m, 1 H), 2.72-3.15 (m, 4 H), 3.25-3.92 (m, 7 H), 4.00-4.20 (m, 1 H), 5.95 (d, J=6.2 Hz, 1 H), 7.74 (d, J=6.2 Hz, 1 H).

EXAMPLE 54(52)

4-amino-N-[((2R,3S)-3-{[4-(1-azepanyl)-2-pyrimidinyl]amino}-1-cyclohexyl-2-pyrrolidinyl)methyl]butanamide (compound 54-52)

TLC: Rf 0.63 (chloroform:methanol:28% aqueous ammonia=40:10:2);
NMR (METHANOL-D$_4$): δ 0.98-1.38 (m, 6 H), 1.40-2.12 (m, 14 H), 2.21 (t, J=7.3 Hz, 2 H), 2.39-2.69 (m, 3 H), 2.75-3.08 (m, 4 H), 3.11-3.84 (m, 7 H), 3.99-4.15 (m, 1 H), 5.95 (d, J=6.2 Hz, 1 H), 7.73 (d, J=6.2 Hz, 1 H).

EXAMPLE 54(53)

(3S)-N-[2-((2R,3S)-3-{[4-(1-azepanyl)-2-pyrimidinyl]amino}-1-cyclohexyl-2-pyrrolidinyl)ethyl]-3-piperidinecarboxamide (compound 54-53)

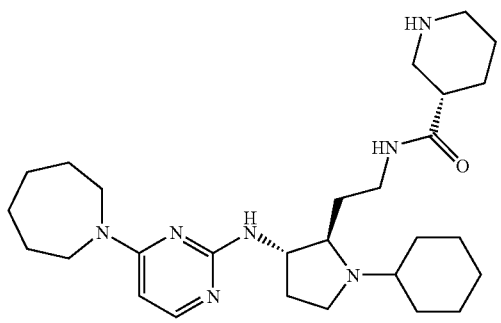 [SMILES: O=C(NCC[C@@H]1[C@@H](Nc2nccc(N3CCCCCC3)n2)CCN1C1CCCCC1)[C@H]1CCCNC1]

TLC: Rf 0.53 (ethyl acetate:methanol:28% aqueous ammonia=20:5:1);
NMR (CDCl$_3$): δ 1.19 (m, 5 H), 1.66 (m, 18 H), 2.13 (m, 1 H), 2.31 (m, 1 H), 2.50 (m, 1 H), 2.85 (m, 10 H), 3.57 (m, 6 H), 4.13 (m, 1 H), 5.83 (d, J=6.50 Hz, 1 H), 7.72 (d, J=6.50 Hz, 1 H), 8.40 (m, 1 H).

EXAMPLE 54(54)

N-[2-((2R,3S)-3-{[4-(1-azepanyl)-2-pyrimidinyl]amino}-1-cyclohexyl-2-pyrrolidinyl)ethyl]-2-morpholinecarboxamide (compound 54-54)

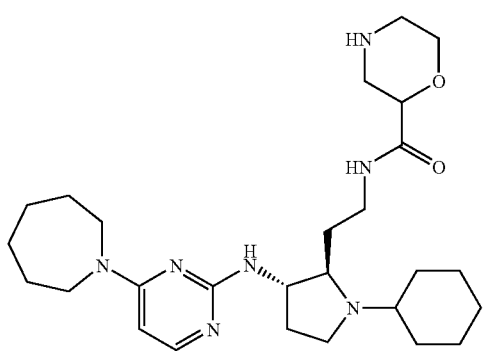 [SMILES: O=C(NCC[C@@H]1[C@@H](Nc2nccc(N3CCCCCC3)n2)CCN1C1CCCCC1)C1CNCCO1]

Description: oil;
TLC: Rf 0.69 (ethyl acetate:methanol:28% aqueous ammonia=20:5:1);
NMR (CDCl$_3$): δ 1.19 (m, 5 H), 1.72 (m, 16 H), 2.10 (m, 1 H), 2.46 (m, 1 H), 2.72 (m, 4 H), 2.94 (m, 2 H), 3.59 (m, 10 H), 4.17 (m, 1 H), 4.91 (m, 1 H), 5.79 (m, 1 H), 7.78 (m, 1 H), 7.99 (m, 1 H).

EXAMPLE 54(55)

2-amino-N-[2-((2R,3S)-3-{[4-(1-azepanyl)-2-pyrimidinyl]amino}-1-cyclohexyl-2-pyrrolidinyl)ethyl]-2-methylpropanamide (compound 54-55)

TLC: Rf 0.80 (ethyl acetate:methanol:28% aqueous ammonia=20:5:1);
NMR (CDCl$_3$): δ 1.19 (m, 5 H), 1.31 (s, 3 H), 1.31 (s, 3 H), 1.71 (m, 16 H), 2.10 (m, 1 H), 2.46 (m, 1 H), 2.76 (ddd, J=9.50, 7.00 Hz, 1 H), 2.84 (m, 1 H), 2.92 (m, 1 H), 3.50 (m, 6 H), 4.15 (m, 1 H), 4.98 (m, 1 H), 5.79 (d, J=6.00 Hz, 1 H), 7.78 (d, J=6.00 Hz, 1 H), 8.15 (m, 1 H).

EXAMPLE 55(1) TO EXAMPLE 55(15)

The same procedure as a series of reactions of Example 21→Example 16→Example 21 was carried out, except that the corresponding amine was used in place of the compound 20 and the corresponding carbonyl compound was used in place of cyclohexanone in the process of Example 21, to obtain the following compound of the present invention.

EXAMPLE 55(1)

4-(1-azepanyl)-N-{(2R,3S)-1-cyclohexyl-2-[3-(dipropylamino)propyl]-3-pyrrolidinyl}-2-pyrimidinamine (compound 55-1)

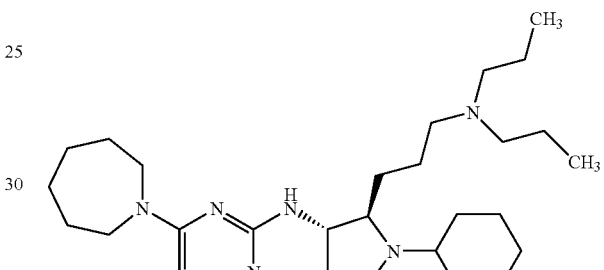

TLC: Rf 0.14 (ethyl acetate:methanol:28% aqueous ammonia=20:5:1);
NMR (CDCl$_3$): δ 0.84 (t, J=7.50 Hz, 6 H), 1.48 (m, 27 H), 2.10 (m, 1 H), 2.40 (m, 7 H), 2.63 (m, 1 H), 2.73 (m, 1 H), 2.86 (m, 1 H), 3.56 (m, 4 H), 4.15 (m, 1 H), 4.81 (d, J=7.50 Hz, 1 H), 5.77 (d, J=6.00 Hz, 1 H), 7.79 (d, J=6.00 Hz, 1 H).

EXAMPLE 55(2)

4-(1-azepanyl)-N-{(2R,3S)-1-cyclohexyl-2-[3-(diethylamino)propyl]-3-pyrrolidinyl}-2-pyrimidinamine (compound 55-2)

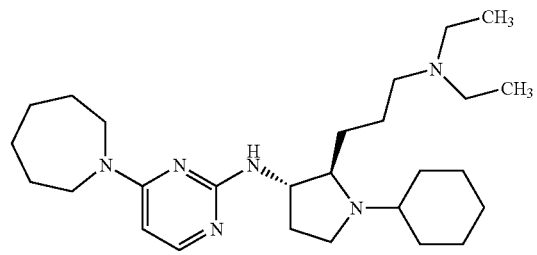 [SMILES: CCN(CC)CCC[C@@H]1[C@@H](Nc2nccc(N3CCCCCC3)n2)CCN1C1CCCCC1]

Description: oil;
TLC: Rf 0.77 (ethyl acetate:methanol:28% aqueous ammonia=20:5:1);
NMR (CDCl$_3$): δ 1.00 (t, J=7.00 Hz, 6 H), 1.45 (m, 19 H), 2.10 (m, 1 H), 2.46 (m, 7 H), 2.50 (q, J=7.00 Hz, 4 H), 2.65 (m, 1 H), 2.74 (dt, J=9.50, 7.00 Hz, 1 H), 2.87 (m, 1 H), 3.56 (m, 4 H), 4.14 (m, 1 H), 4.84 (d, J=8.00 Hz, 1 H), 5.77 (d, J=6.00 Hz, 1 H), 7.78 (d, J=6.00 Hz, 1 H).

EXAMPLE 55(3)

4-(1-azepanyl)-N-{(2R,3S)-1-cyclohexyl-2-[3-(1-pyrrolidinyl)propyl]-3-pyrrolidinyl}-2-pyrimidinamine (compound 55-3)

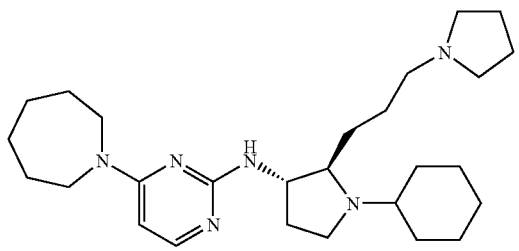 [SMILES: c1cc(N2CCCCCC2)nc(N[C@H]2CCN(C3CCCCC3)[C@@H]2CCCN2CCCC2)n1]

Description: oil;

TLC: Rf 0.71 (ethyl acetate:methanol:28% aqueous ammonia=20:5:1);

NMR (CDCl$_3$): δ 1.45 (m, 27 H), 2.14 (m, 1 H), 2.60 (m, 7 H), 2.78 (m, 2 H), 2.94 (m, 1 H), 3.57 (m, 4 H), 4.15 (m, 1 H), 5.07 (m, 1 H), 5.79 (d, J=6.00 Hz, 1 H), 7.76 (d, J=6.00 Hz, 1 H).

EXAMPLE 55(4)

4-(1-azepanyl)-N-{(2R,3S)-1-cyclohexyl-2-[3-(1-piperidinyl)propyl]-3-pyrrolidinyl}-2-pyrimidinamine (compound 55-4)

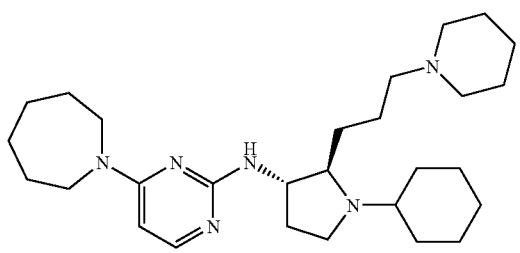 [SMILES: c1cc(N2CCCCCC2)nc(N[C@H]2CCN(C3CCCCC3)[C@@H]2CCCN2CCCCC2)n1]

TLC: Rf 0.79 (ethyl acetate:methanol:28% aqueous ammonia=20:5:1);

NMR (CDCl$_3$): δ 1.46 (m, 29 H), 2.27 (m, 8 H), 2.65 (m, 1 H), 2.73 (dt, J=9.50, 7.00 Hz, 1 H), 2.86 (m, 1 H), 3.56 (m, 4 H), 4.13 (m, 1 H), 4.82 (d, J=7.50 Hz, 1 H), 5.76 (d, J=6.00 Hz, 1 H), 7.78 (d, J=6.00 Hz, 1 H).

EXAMPLE 55(5)

4-(1-azepanyl)-N-{(2R,3S)-1-cyclohexyl-2-[3-(4-morpholinyl)propyl]-3-pyrrolidinyl}-2-pyrimidinamine (compound 55-5)

TLC: Rf 0.79 (ethyl acetate:methanol:28% aqueous ammonia=20:5:1);

NMR (CDCl$_3$): δ 1.44 (m, 23 H), 2.13 (m, 1 H), 2.39 (m, 7 H), 2.64 (m, 1 H), 2.72 (dt, J=9.50, 7.00 Hz, 1 H), 2.86 (m, 1 H), 3.54 (m, 4 H), 3.67 (t, J=4.50 Hz, 4 H), 4.13 (m, 1 H), 4.81 (d, J=7.50 Hz, 1 H), 5.76 (d, J=6.00 Hz, 1 H), 7.77 (d, J=6.00 Hz, 1 H).

EXAMPLE 55(6)

4-(1-azepanyl)-N-{(2R,3S)-1-cyclohexyl-2-[3-(4-methyl-1-piperazinyl)propyl]-3-pyrrolidinyl}-2-pyrimidinamine (compound 55-6)

TLC: Rf 0.49 (ethyl acetate:methanol:28% aqueous ammonia=20:5:1);

NMR (CDCl$_3$): δ 1.46 (m, 23 H), 2.09 (m, 1 H), 2.26 (s, 3 H), 2.43 (m, 11 H), 2.71 (m, 2 H), 2.88 (m, 1 H), 3.55 (m, 4 H), 4.14 (m, 1 H), 4.91 (d, J=7.00 Hz, 1 H), 5.77 (d, J=6.00 Hz, 1 H), 7.77 (d, J=6.00 Hz, 1 H).

EXAMPLE 55(7)

4-(1-azepanyl)-N-{(2R,3S)-1-cyclohexyl-2-[3-(4-cyclohexyl-1-piperazinyl)propyl]-3-pyrrolidinyl}-2-pyrimidinamine (compound 55-7)

TLC: Rf 0.69 (ethyl acetate:methanol:28% aqueous ammonia=20:5:1);

NMR (CDCl$_3$): δ 1.85 (m, 48 H), 2.86 (m, 1 H), 3.54 (m, 4 H), 4.12 (m, 1 H), 4.90 (m, 1 H), 5.77 (d, J=6.00 Hz, 1 H), 7.78 (d, J=6.00 Hz, 1 H).

EXAMPLE 55(8)

N-{(2R,3S)-2-[3-(4-acetyl-1-piperazinyl)propyl]-1-cyclohexyl-3-pyrrolidinyl}-4-(1-azepanyl)-2-pyrimidinamine (compound 55-8)

TLC: Rf 0.42 (ethyl acetate:methanol:28% aqueous ammonia=20:5:1);

NMR (CDCl$_3$): δ 1.59 (m, 23 H), 2.07 (s, 3 H), 2.12 (m, 1 H), 2.36 (m, 7 H), 2.70 (t, 2 H), 2.91 (m, 1 H), 3.50 (m, 4 H), 3.42 (t, J=5.00 Hz, 2 H), 3.58 (t, J=5.00 Hz, 2 H), 4.15 (m, 1 H), 4.91 (m, 1 H), 5.79 (d, J=6.00 Hz, 1 H), 7.78 (d, J=6.00 Hz, 1 H).

EXAMPLE 55(9)

4-(1-azepanyl)-N-{(2R,3S)-2-[3-(4-benzoyl-1-piperazinyl)propyl]-1-cyclohexyl-3-pyrrolidinyl}-2-pyrimidinamine (compound 55-9)

TLC: Rf 0.50 (ethyl acetate:methanol:28% aqueous ammonia=20:5:1);

NMR (CDCl$_3$): δ 1.44 (m, 23 H), 2.10 (m, 1 H), 2.39 (m, 7 H), 2.69 (m, 2 H), 2.89 (m, 1 H), 3.57 (m, 8 H), 4.15 (m, 1 H), 4.83 (m, 1 H), 5.77 (d, J=6.00 Hz, 1 H), 7.39 (m, 5 H), 7.78 (d, J=6.00 Hz, 1 H).

EXAMPLE 55(10)

4-(1-azepanyl)-N-((2R,3S)-1-cyclohexyl-2-{3-[4-(cyclohexylcarbonyl)-1-piperazinyl]propyl}-3-pyrrolidinyl)-2-pyrimidinamine (compound 55-10)

TLC: Rf 0.50 (ethyl acetate:methanol:28% aqueous ammonia=20:5:1);

NMR (CDCl$_3$): δ 1.46 (m, 33 H), 2.10 (m, 1 H), 2.39 (m, 8 H), 2.69 (m, 2 H), 2.88 (m, 1 H), 3.55 (m, 8 H), 4.15 (m, 1 H), 4.85 (m, 1 H), 5.78 (d, J=6.00 Hz, 1 H), 7.78 (d, J=6.00 Hz, 1 H).

EXAMPLE 55(11)

4-(1-azepanyl)-N-{(2R,3S)-2-[3-(1-azepanyl)propyl]-1-cyclohexyl-3-pyrrolidinyl}-2-pyrimidinamine (compound 55-11)

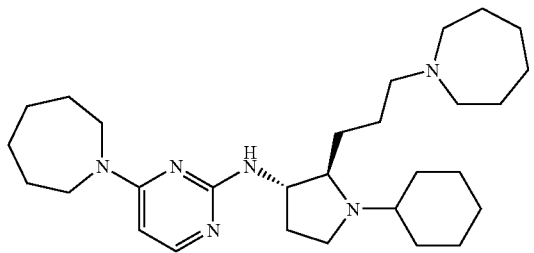 [SMILES: c1cc(N2CCCCCC2)nc(N[C@H]2CCN(C3CCCCC3)[C@@H]2CCCN2CCCCCC2)n1]

TLC: Rf 0.46 (ethyl acetate:methanol:28% aqueous ammonia=20:5:1);
NMR (CDCl$_3$): δ 1.47 (m, 31 H), 2.09 (m, 1 H), 2.52 (m, 8 H), 2.72 (dt, J=9.50, 7.00 Hz, 1 H), 2.86 (m, 1 H), 3.56 (m, 4 H), 4.14 (m, 1 H), 4.79 (d, J=7.50 Hz, 1 H), 5.76 (d, J=6.00 Hz, 1 H), 7.78 (d, J=6.00 Hz, 1 H).

EXAMPLE 55(12)

4-(1-azepanyl)-N-{(2R,3S)-1-cyclohexyl-2-[3-(4,4-difluoro-1-piperidinyl)propyl]-3-pyrrolidinyl}-2-pyrimidinamine (compound 55-12)

TLC: Rf 0.19 (chloroform:methanol:water=50:10:1);
NMR (CDCl$_3$): δ 1.59 (m, 28 H), 2.44 (m, 7 H), 2.64 (m, 1 H), 2.73 (dt, J=9.50, 7.00 Hz, 1 H), 2.87 (m, 1 H), 3.55 (m, 4 H), 4.14 (m, 1 H), 4.82 (d, J=7.50 Hz, 1 H), 5.77 (d, J=6.00 Hz, 1 H), 7.78 (d, J=6.00 Hz, 1 H).

EXAMPLE 55(13)

4-(1-azepanyl)-N-{(2R,3S)-1-cyclohexyl-2-[(4-methyl-1-piperazinyl)methyl]-3-pyrrolidinyl}-2-pyrimidinamine (compound 55-13)

TLC: Rf 0.25 (chloroform:methanol:water=50:10:1);
NMR (CDCl$_3$): δ 1.49 (m, 20 H), 2.54 (m, 14 H), 2.25 (s, 3 H), 3.57 (m, 4 H), 4.20 (m, 1 H), 5.05 (d, J=6.00 Hz, 1 H), 5.79 (d, J=6.00 Hz, 1 H), 7.78 (d, J=6.00 Hz, 1 H).

EXAMPLE 55(14)

4-(1-azepanyl)-N-{(2R,3S)-1-cyclohexyl-2-[(4-cyclohexyl-1-piperazinyl)methyl]-3-pyrrolidinyl}-2-pyrimidinamine (compound 55-141)

TLC: Rf 0.31 (chloroform:methanol:water=50:10:1);
NMR (CDCl$_3$): δ 1.61 (m, 31 H), 2.66 (m, 14 H), 3.57 (m, 4 H), 4.20 (m, 1 H), 4.98 (m, 1 H), 5.78 (m, J=6.04 Hz, 1 H), 7.79 (d, J=6.00 Hz, 1 H).

EXAMPLE 55(15)

4-(1-azepanyl)-N-{(2R,3S)-1-cyclohexyl-2-[(8-cyclohexyl-2,8-diazaspiro[4.5]dec-2-yl)methyl]-3-pyrrolidinyl}-2-pyrimidinamine (compound 55-15)

TLC: Rf 0.18 (chloroform:methanol:water=50:10:1);
NMR (CDCl$_3$): δ 1.47 (m, 35 H), 2.07 (m, 1 H), 2.57 (m, 15 H), 3.56 (m, 4 H), 4.25 (m, 1 H), 4.94 (d, J=7.00 Hz, 1 H), 5.77 (d, J=6.00 Hz, 1 H), 7.79 (d, J=6.00 Hz, 1 H).

EXAMPLE 56

N-[(2R,3S)-2-(4-aminobutyl)-1-cyclohexyl-3-pyrrolidinyl]-4-(1-azepanyl)-2-pyrimidinamine (compound 56)

The same procedure as a series of reactions of Example 10 was carried out, except that the corresponding amine was used in place of the compound 9 in the process of Example 10, to obtain the title compound having the following physical properties.
TLC: Rf 0.13 (ethyl acetate:methanol:28% aqueous ammonia=20:5:1);
NMR (CDCl$_3$): δ 1.47 (m, 25 H), 2.08 (m, 1 H), 2.45 (m, 1 H), 2.69 (m, 4 H), 2.87 (m, 1 H), 3.55 (m, 4 H), 4.14 (m, 1 H), 4.78 (d, J=8.00 Hz, 1 H), 5.77 (d, J=6.00 Hz, 1 H), 7.79 (d, J=6.00 Hz, 1 H).

EXAMPLE 57(1) TO EXAMPLE 57(2)

The same procedure as a series of reactions of Example 24 was carried out, except that the corresponding amine was used in place of the compound 23 in the process of Example 24, to obtain the following compound of the present invention.

EXAMPLE 57(1)

N-[((2R,3S)-3-{[4-(1-azepanyl)-2-pyrimidinyl]amino}-1-cyclohexyl-2-pyrrolidinyl)methyl]-8-azabicyclo[3.2.1]octan-3-amine tetrahydrochloride (compound 57-1)

TLC: Rf 0.63 (chloroform:methanol:28% aqueous ammonia=40:10:1);
NMR (METHANOL-D$_4$): δ 1.18-1.34 (m, 2 H), 1.37-1.77 (m, 9 H), 1.78-2.04 (m, 6 H), 2.04-2.71 (m, 11 H), 3.38-3.93 (m, 9 H), 3.98-4.18 (m, 3 H), 4.22-4.62 (m, 2 H), 4.72-4.83 (m, 1 H), 6.47 (d, J=7.7 Hz, 1 H), 7.73 (d, J=7.7 Hz, 1 H).

EXAMPLE 57(2)

4-(1-azepanyl)-N-((2R,3S)-1-cyclohexyl-2-{[(4-piperidinylmethyl)amino]methyl}-3-pyrrolidinyl)-2-pyrimidinamine tetrahydrochloride (compound 57-2)

TLC: Rf 0.60 (chloroform:methanol:28% aqueous ammonia=40:10:1);
NMR (METHANOL-D$_4$): δ 1.17-1.37 (m, 1 H), 1.37-1.78 (m, 11 H), 1.78-2.01 (m, 6 H), 2.11-2.37 (m, 5 H), 2.39-2.58 (m, 2 H), 2.96-3.09 (m, 2 H), 3.13 (d, J=6.6 Hz, 2 H), 3.38-

3.49 (m, 2 H), 3.50-3.92 (m, 9 H), 4.03-4.18 (m, 1 H), 4.53 (d, 1 H), 4.88 (d, J=6.6 Hz, 1 H), 6.47 (d, J=7.7 Hz, 1 H), 7.72 (d, J=7.7 Hz, 1 H).

EXAMPLE 58

4-(1-azepanyl)-N-{(2R,3S)-1-cyclohexyl-2-[3-(isopropylamino)propyl]-3-pyrrolidinyl}-2-pyrimidinamine (compound 58)

The same procedure as a series of reactions of Example 36 was carried out, except that the corresponding amine was used in place of the compound 22 and the corresponding carbonyl compound was used in place of tert-butyl 4-formyl-piperidine-1-carboxylate in the process of Example 36, to obtain the title compound having the following physical properties.
TLC: Rf 0.63 (ethyl acetate:methanol:28% aqueous ammonia=20:5:1);
NMR (CDCl$_3$): δ 1.57 (m, 24 H), 1.04 (d, J=6.50 Hz, 6 H), 2.73 (m, 7 H), 3.56 (m, 4 H), 4.13 (m, 1 H), 4.91 (d, J=7.50 Hz, 1 H), 5.77 (d, J=6.00 Hz, 1 H), 7.77 (d, J=6.00 Hz, 1 H).

EXAMPLE 59

N-[(2RS,3SR)-2-(2-aminoethyl)-1-(tetrahydro-2H-pyran-4-yl)-3-piperidinyl]-4-(1-azepanyl)-2-pyrimidinamine trihydrochloride (compound 59)

The same procedure as a series of reactions of Example 21→Example 24 was carried out, except that the corresponding amine was used in place of the compound 20 and the corresponding carbonyl compound was used in place of cyclohexanone in the process of Example 21, to obtain the title compound having the following physical properties.
TLC: Rf 0.40 (chloroform:methanol:28% aqueous ammonia=80:10:1);
NMR (METHANOL-D$_4$): δ 1.50-1.71 (m, 4 H), 1.71-1.97 (m, 7 H), 1.98-2.36 (m, 6 H), 2.37-2.54 (m, 1 H), 2.99-3.19 (m, 2 H), 3.33-3.53 (m, 2 H), 3.57-3.87 (m, 7 H), 3.89-4.03 (m, 1 H), 4.01-4.18 (m, 3 H), 6.46 (d, J=7.7 Hz, 1 H), 7.73 (d, J=7.7 Hz, 1 H).

EXAMPLE 60

N-[2-((2RS,3SR)-3-{[4-(1-azepanyl)-2-pyrimidinyl]amino}-2-piperidinyl)ethyl]-4-piperidinecarboxamide trihydrochloride (compound 60)

The same procedure as a series of reactions of Example 23→Example 20→Example 24 was carried out, except that the compound 18 was used in place of N-[(2RS,3SR)-2-(2-aminoethyl)-1-cyclohexylpiperidin-3-yl]-4-azepan-1-ylpyrimidin-2-amine in the process of Example 23, to obtain the title compound having the following physical properties.
TLC: Rf 0.50 (chloroform:methanol:28% aqueous ammonia=80:20:2);
NMR (METHANOL-D$_4$): δ 1.51-1.67 (m, 4 H), 1.69-1.96 (m, 8 H), 1.97-2.25 (m, 5 H), 2.56-2.72 (m, 1 H), 2.89-3.33 (m, 6 H), 3.37-3.54 (m, 3 H), 3.53-3.79 (m, 3 H), 3.92 (t, J=5.87 Hz, 2 H), 4.34 (s, 1 H), 6.42 (d, J=7.50 Hz, 1 H), 7.69 (d, J=7.50 Hz, 1 H).

BIOLOGICAL EXAMPLES

By the biological example shown below, a pharmacological activity of the compound of the present invention can be proved. The entire procedure utilized a standard method together with a cell exhibiting a high expression prepared in accordance with a basic gene engineering technology. In addition, a measuring method of the present invention was modified to improve accuracy and/or sensitivity of the measurement for evaluating the compound of the present invention. The detailed experimental methods are shown below.

Biological Example 1

Study for Inhibition of Binding Human SDF-1 to CEM Cells

As mentioned above, a more direct procedure is a screening a compound that prevents for HIV from binding to CXCR4, which is a receptor on CD4+ cell, on an assay system using HIV. However, using HIV for a large-scale screening is not practical due to its difficult handling. On the other hand, both of T cell-directed (X4) HIV-1 and SDF-1 bind to CXCR4 and therefore CXCR4 binding sites at both of HIV-side and SDF-1-side as well as SDF-1- and HIV-binding sites at the CXCR4 side may presumably have any common characteristics. Thus, to find a compound inhibiting absorption of HIV to a cell that is a different mechanism from those of pre-existing anti-AIDS drugs (reverse transcriptase inhibitors and protease inhibitors), an assay system using an endogenous ligand for CXCR4, SDF-1 instead of HIV may be available.
Specifically, as a system of screening a compound that inhibits the binding between SDF-1 and CXCR4, for example a system of measuring the binding between iodine-labeled SDF-1 and a human T cell strain in which CXCR4 is known to be expressed is operable.
[Experimental Methods]
To human T cell strain CEM cells in a binding buffer (containing HEPES and BSA), the test compound and $^{125}$I-SDF-1 (NEN) were added and the mixture was incubated at 4° C. for 60 minutes. The reacted CEM cells were rapidly filtrated with a GF/B membrane filter plate (Packard) to adsorb. The plate was washed with PBS three times and then dried. Microscint+20 (Packard) was added thereto. An amount of the radioactivity bound to the CEM cells was measured using Top Count (Packard) and inhibition (%) of the test compound was calculated according to the following equation:

Inhibition=(Et−Ea)/(Et−Ec)×100 wherein
Et: amount of radioactivity when the test compound is not added,
Ec: amount of radioactivity when non-radioactive SDF-1 (Pepro Tech) is added in an amount of 1000 times as much as $^{125}$I-SDF-1 as a test compound, and
Ea: amount of radioactivity when the test compound is added.
As the result, the compounds of the present invention exhibited inhibition of 50% or more in a concentration of 10 μM. For example, IC$_{50}$ value for compound 10-2 was 1.6 nM.

Biological Example 2

Safety Estimate

[Experimentanl Methods]
The compound of the present invention was orally administered by gavage with feeding tube into the stomach of SD rat (Crj: CD (SD) IGS system, male, 6 weeks) once a day from 4 days to 14 days. The rat was dissected at the day after end of administration; it was carried out various organ mass measurements, histopathological inspection, hematology inspection and blood biochemistry inspection.

As the result, the compound of the present invention was proved to have an adequate safety.

FORMULATION EXAMPLES

Formulation Example 1

N-[(2R,3S)-2-(2-aminoethyl)-1-cyclohexyl-3-pyrrolidinyl]-4-(1-azepanyl)-2-pyrimidinamine (100 g), calcium carboxymethyl cellulose (disintegrant, 20.0 g), magnesium stearate (lubricants, 10.0 g) and microcrystalline cellulose (870 g) were mixed by a conventional method and then compressed to obtain 10,000 tablets each containing 10 mg of an active ingredient.

Formulation Example 2

N-[(2R,3S)-2-(2-aminoethyl)-1-cyclohexyl-3-pyrrolidinyl]-4-(1-azepanyl)-2-pyrimidinamine (200 g), mannitol (2 kg) and distilled water (50 L) were mixed by a conventional method and filtered with a dust filter, and then each ampoule was filled with 5 mL of the obtained mixture and subjected to heat sterilization in an autoclave to obtain 10,000 ampoules each containing 20 mg of an active ingredient.

Industrial Applicability

The compound of the present invention has CXCR4 antagonistic activity and is therefore useful as a preventive and/or therapeutic agent for CXCR4-mediated diseases. Accordingly, the compound of the present invention can be available as a drug. For example, the compound of the present invention is useful as a preventive and/or therapeutic agent for inflammatory and immune diseases (for example, rheumatoid arthritis, arthritis, pulmonary fibrosis, transplanted organ rejection, etc.), allergic diseases, infections (for example, human immunodeficiency virus infection, acquired immunodeficiency syndrome, etc.), psychoneurotic diseases, cerebral diseases, cardiovascular disease, metabolic diseases, and cancerous diseases (for example, cancer, cancer metastasis, etc.), or an agent for regeneration therapy.

The invention claimed is:
1. A compound represented by formula (I):

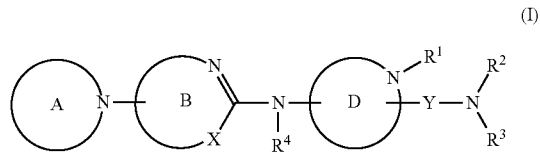

(I)

wherein ring A represents a perhydroazepine ring which may have a substituent(s);
ring B represents a pyrimidine ring which may have a further substituent(s);
ring D represents a 4- to 8-membered nitrogen-containing monocyclic heterocyclic ring which may have a further substituent(s);
X represents a nitrogen atom;
Y represents a C2-5 alkylene group which may have a substituent(s);
$R^1$ represents a hydrogen atom, a C1-8 aliphatic hydrocarbon group which may have a substituent(s), a 3- to 15-membered saturated carbocyclic ring which may have a substituent(s), 3- to 15-membered unsaturated carbocyclic ring which may have a substituent(s) or 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may have a substituent(s);
$R^2$ and $R^3$ each independently represents a hydrogen atom, a C1-8 aliphatic hydrocarbon group which may have a substituent(s), a 3- to 15-membered saturated carbocyclic ring which may have a substituent(s), 3- to 15-membered unsaturated carbocyclic ring which may have a substituent(s) or 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may have a substituent(s), or may be taken together with the nitrogen atom to which they are attached to form a 5- to 8-membered nitrogen-containing monocyclic heterocyclic ring which may have a substituent(s); and
$R^4$ represents a hydrogen atom or a C1-8 aliphatic hydrocarbon group which may have a substituent(s),
wherein the "substituent" in the "perhydroazepine ring which may have a substituent(s)", "pyrimidine ring which may have a further substituent(s)", "4- to 8-membered nitrogen-containing monocyclic heterocyclic ring which may have a further substituent(s)", "C2-5 alkylene group which may have a substituent(s)", "C1-8 aliphatic hydrocarbon group which may have a substituent(s)", "3- to 15-membered saturated carbocyclic ring which may have a substituent(s)", "3- to 15-membered unsaturated carbocyclic ring which may have a substituent(s)", "3- to 15-membered monocyclic or polycyclic heterocyclic ring having, as a hetero atom, 1 to 4 nitrogen atom(s), 1 to 2 oxygen atom(s) and/or 1 to 2 sulfur atom(s)" and "5- to 8-membered nitrogen-containing monocyclic heterocyclic ring which may have a substituent(s)" described above represents 1 to 5 of substituents selected from (1) to (39) described below, if the number of substituents is two or more, each substituent may be same or different;
(1) C1-8 aliphatic hydrocarbon group which may have a substituent(s), (2) 3- to 15-membered saturated carbocyclic ring which may have a substituent(s), or 3- to 15-membered unsaturated carbocyclic ring which may have a substituent(s), (3) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may have a substituent(s), (4) amino group, (5) C1-10 acylamino which may have a substituent(s), (6) secondary or tertiary amine substituted by substituent(s), (7) C1-8 alkylsulfonylamino group which may have a substituent(s), C2-8 alkynylsulfonylamino group which may have a substituent(s) or C2-8 alkenylsulfonylamino group which may have a substituent(s), (8) phenylsulfonylamino group which may have a substituent(s), (9) C1-8 alkylsulfonyl group which may have a substituent(s), C2-8 alkynylsulfonyl group which may have a substituent(s) or C2-8 alkenylsulfonyl group which may have a substituent(s), (10) phenylsulfonyl group which may have a substituent(s), (11) halogen atom, (12) carboxyl group, (13) cyano group, (14) nitro group, (15) oxo group, (16) thioxo group, (17) hydroxy group, (18) C1-8 alkoxy group which may have a substituent(s), C2-8 alkynyloxy group which may have a substituent(s) or C2-8 alkenyloxy group which may have a substituent(s), (19) C3-8 cycloalkoxy group which may have a substituent(s), (20) phenoxy group which may have a substituent(s),

(21) mercapto group, (22) C1-8 alkylthio group which may have a substituent(s), C2-8 alkynylthio group which may have a substituent(s) or C2-8 alkenylthio group which may have a substituent(s), (23) phenylthio group which may have a substituent(s), (24) carbamoyl group, (25) aminocarbonyl group substituted by substituent(s), (26) sulfamoyl group, (27) aminosulfonyl group substituted by substituent(s), (28) C1-8 alkoxycarbonyl group which may have a substituent(s), C2-8 alkynyloxycarbonyl group which may have a substituent(s) or C2-8 alkenyloxycarbonyl group which may have a substituent(s), (29) sulfo group, (30) sulfino group, (31) phosphono group, (32) amidino group, (33) imino group, (34) —B(OH)2 group, (35) C1-8 alkylsulfinyl group which may have a substituent(s), (36) C1-10 acyl group which may have a substituent(s), (37) hydroxyimino group, (38) C1-8 alkyloxyimino group, (39) basic group, wherein the "substituent" represented by (1) to (3), (5), (7) to (10), (18) to (20), (22), (23), (28), (35) and (36) described above represents 1 to 5 of substituents selected from (i) to (xix) described below, if the number of substituents is two or more, each substituent may be same or different;

(i) C1-8 aliphatic hydrocarbon group which may be substituted by amino group, halogen atom, hydroxy group, methoxy group, trifluoromethyl group, trifluoromethoxy group, acetyloxy group or carbamoyl group, (ii) 3- to 15-membered saturated carbocyclic ring which may be substituted by amino group, halogen atom, hydroxy group, methoxy group, trifluoromethyl group, trifluoromethoxy group, acetyloxy group or carbamoyl group, (iii) 3- to 15-membered unsaturated carbocyclic ring which may be substituted by amino group, halogen atom, hydroxy group, methoxy group, trifluoromethyl group, trifluoromethoxy group, acetyloxy group or carbamoyl group, (iv) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may be substituted by amino group, halogen atom, hydroxy group, methoxy group, trifluoromethyl group, trifluoromethoxy group, acetyloxy group or carbamoyl group, (v) amino group, (vi) dimethylamino group, (vii) sulfo group, (viii) halogen atom, (ix) carboxyl group, (x) cyano group, (xi) nitro group, (xii) oxo group, (xiii) thioxo group, (xiv) hydroxy group, (xv) methoxy group, (xvi) acetyl group, (xvii) methoxycarbonyl group, (xviii) trifluoromethyl group, (xix) trifluoromethoxy, wherein the "basic group" represented by (39) described above represents (a) amino group, (b) amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing heterocyclic ring which may have a substituent(s), wherein the "substituent" in the "mono- or di-substituted amino group" represented by (e) described above represents the substituent of (1) to (38) described above, these arbitrary substituent(s) may be substituted on the substitutable position and the number of substituents may be from 1 to 2, if the number of substituents is two, each substituent may be same or different, wherein the "substituent" in the "mono-, di- or tri-substituted amidino group" represented by (f) described above represents the substituent of (1) to (38) described above, these arbitrary substituent(s) may be substituted on the substitutable position and the number of substituents may be from 1 to 3, if the number of substituents is two or more, each substituent may be same or different, wherein the "substituent" in the "mono-, di-, tri- or tetra-substituted guanidino group" represented by (g) described above represents the substituent of (1) to (38) described above, these arbitrary substituent(s) may be substituted on the substitutable position and the number of substituents may be from 1 to 3, if the number of substituents is two or more, each substituent may be same or different, wherein the "substituent" in the "mono-, di- or tri-substituted hydrazino group" represented by (h) described above represents the substituent of (1) to (38) described above, these arbitrary substituent(s) may be substituted on the substitutable position and the number of substituents may be from 1 to 3, if the number of substituents is two or more, each substituent may be same or different, wherein the "nitrogen-containing heterocyclic ring" in the "nitrogen-containing heterocyclic ring which may have a substituent(s)" represented by (i) described above represents pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydroquinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane or 1-thia-4,8-diazaspiro[5.5]undecane ring, wherein the "substituent" in the "nitrogen-containing heterocyclic ring which may have a substituent(s)" represented by (i) described above represents 1 to 8 of substituents selected from (1) to (38) described above, if the number of substituents is two or more, each substituent may be same or different, or a salt thereof, an N-oxide thereof or a solvate thereof, or a prodrug thereof;

wherein the solvate is made with water, an alcoholic solvent, an alkali (earth) metal salt, an ammonium salt, a salt of an organic amino, or an acid addition salt of the compound of formula (I);

wherein the prodrug is one wherein (A) an amino group is acylated, alkylated, or phosphorylated (B) a hydroxyl group is acylated, alkylated, or phosphorylated, or boricated (C) a carboxy group is esterificated, or amidated, and wherein the prodrug may be a hydrate or a non-hydrate.

2. The compound according to claim 1, wherein the compound represented by formula (I) represents a compound represented by formula (I-1):

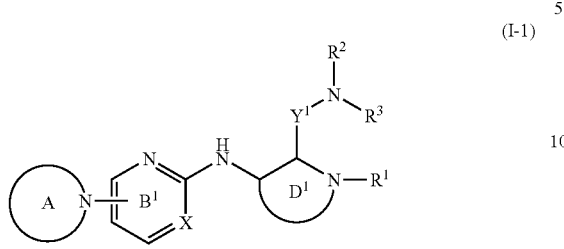

(I-1)

wherein ring $B^1$ represents pyrimidine which may have a further substituent(s);
ring $D^1$ represents a 4- to 8-membered nitrogen-containing saturated monocyclic heterocyclic ring which may have a further substituent(s);
$Y^1$ represents —$(CR^5R^6)_n$—;
$R^5$ and $R^6$ each represents a hydrogen atom, or $R^5$ and $R^6$ taken together represents an oxo group; and
n represents an integer of 2 to 4, and the groups $CR^5R^6$ are the same or different;
wherein the "substituent" in "pyrimidine which may have a further substituent(s)" and "4- to 8-membered nitrogen-containing saturated monocyclic heterocyclic ring which may have a further substituent(s)" represents 1 to 5 of substituents selected from (1) to (39) described below, if the number of substituents is two or more, each substituent may be same or different;
(1) C1-8 aliphatic hydrocarbon group which may have a substituent(s), (2) 3- to 15-membered saturated carbocyclic ring which may have a substituent(s), or 3- to 15-membered unsaturated carbocyclic ring which may have a substituent(s), (3) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may have a substituent(s), (4) amino group, (5) C1-10 acylamino which may have a substituent(s), (6) secondary or tertiary amine substituted by substituent(s), (7) C1-8 alkylsulfonylamino group which may have a substituent(s), C2-8 alkynylsulfonylamino group which may have a substituent(s) or C2-8 alkenylsulfonylamino group which may have a substituent(s), (8) phenylsulfonylamino group which may have a substituent(s), (9) C1-8 alkylsulfonyl group which may have a substituent(s), C2-8 alkynylsulfonyl group which may have a substituent(s) or C2-8 alkenylsulfonyl group which may have a substituent(s), (10) phenylsulfonyl group which may have a substituent(s), (11) halogen atom, (12) carboxyl group, (13) cyano group, (14) nitro group, (15) oxo group, (16) thioxo group, (17) hydroxy group, (18) C1-8 alkoxy group which may have a substituent(s), C2-8 alkynyloxy group which may have a substituent(s) or C2-8 alkenyloxy group which may have a substituent(s), (19) C3-8 cycloalkoxy group which may have a substituent(s), (20) phenoxy group which may have a substituent(s), (21) mercapto group, (22) C1-8 alkylthio group which may have a substituent(s), C2-8 alkynylthio group which may have a substituent(s) or C2-8 alkenylthio group which may have a substituent(s), (23) phenylthio group which may have a substituent(s), (24) carbamoyl group, (25) aminocarbonyl group substituted by substituent(s), (26) sulfamoyl group, (27) aminosulfonyl group substituted by substituent(s), (28) C1-8 alkoxycarbonyl group which may have a substituent(s), C2-8 alkynyloxycarbonyl group which may have a substituent(s) or C2-8 alkenyloxycarbonyl group which may have a substituent(s), (29) sulfo group, (30) sulfino group, (31) phosphono group, (32) amidino group, (33) imino group, (34) —B(OH)2 group, (35) C1-8 alkylsulfinyl group which may have a substituent(s), (36) C1-10 acyl group which may have a substituent(s), (37) hydroxyimino group, (38) C1-8 alkyloxyimino group, (39) basic group,
wherein the "substituent" represented by (1) to (3), (5), (7) to (10), (18) to (20), (22), (23), (28), (35) and (36) described above represents 1 to 5 of substituents selected from (i) to (xix) described below, if the number of substituents is two or more, each substituent may be same or different;
(i) C1-8 aliphatic hydrocarbon group which may be substituted by amino group, halogen atom, hydroxy group, methoxy group, trifluoromethyl group, trifluoromethoxy group, acetyloxy group or carbamoyl group, (ii) 3- to 15-membered saturated carbocyclic ring which may be substituted by amino group, halogen atom, hydroxy group, methoxy group, trifluoromethyl group, trifluoromethoxy group, acetyloxy group or carbamoyl group, (iii) 3- to 15-membered unsaturated carbocyclic ring which may be substituted by amino group, halogen atom, hydroxy group, methoxy group, trifluoromethyl group, trifluoromethoxy group, acetyloxy group or carbamoyl group, (iv) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may be substituted by amino group, halogen atom, hydroxy group, methoxy group, trifluoromethyl group, trifluoromethoxy group, acetyloxy group or carbamoyl group, (v) amino group, (vi) dimethylamino group, (vii) sulfo group, (viii) halogen atom, (ix) carboxyl group, (x) cyano group, (xi) nitro group, (xii) oxo group, (xiii) thioxo group, (xiv) hydroxy group, (xv) methoxy group, (xvi) acetyl group, (xvii) methoxycarbonyl group, (xviii) trifluoromethyl group, (xix) trifluoromethoxy,
wherein the "basic group" represented by (39) described above represents (a) amino group, (b) amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing heterocyclic ring which may have a substituent(s),
wherein the "substituent" in the "mono- or di-substituted amino group" represented by (e) described above represents the substituent of (1) to (38) described above, these arbitrary substituent(s) may be substituted on the substitutable position and the number of substituents may be from 1 to 2, if the number of substituents is two, each substituent may be same or different,
wherein the "substituent" in the "mono-, di- or tri-substituted amidino group" represented by (f) described above represents the substituent of (1) to (38) described above, these arbitrary substituent(s) may be substituted on the substitutable position and the number of substituents may be from 1 to 3, if the number of substituents is two or more, each substituent may be same or different,
wherein the "substituent" in the "mono-, di-, tri- or tetra-substituted guanidino group" represented by (g) described above represents the substituent of (1) to (38)

described above, these arbitrary substituent(s) may be substituted on the substitutable position and the number of substituents may be from 1 to 3, if the number of substituents is two or more, each substituent may be same or different, wherein the "substituent" in the "mono-, di- or tri-substituted hydrazino group" represented by (h) described above represents the substituent of (1) to (38) described above, these arbitrary substituent(s) may be substituted on the substitutable position and the number of substituents may be from 1 to 3, if the number of substituents is two or more, each substituent may be same or different, wherein the "nitrogen-containing heterocyclic ring" in the "nitrogen-containing heterocyclic ring which may have a substituent(s)" represented by (i) described above represents pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydroquinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane or 1-thia-4,8-diazaspiro[5.5]undecane ring, wherein the "substituent" in the "nitrogen-containing heterocyclic ring which may have a substituent(s)" represented by (i) described above represents 1 to 8 of substituents selected from (1) to (38) described above, if the number of substituents is two or more, each substituent may be same or different, and other symbols have the same meanings as described in the claim 1, or a salt thereof, an N-oxide thereof or a solvate thereof, or a prodrug thereof;

wherein the solvate is made with water, an alcoholic solvent, an alkali (earth) metal salt, an ammonium salt, a salt of an organic amino, or an acid addition salt of the compound of formula (I);

wherein the prodrug is one wherein
(A) an amino group is acylated, alkylated, or phosphorylated
(B) a hydroxyl group is acylated, alkylated, or phosphorylated, or boricated
(C) a carboxy group is esterificated, or amidated, and
wherein the prodrug may be a hydrate or a non-hydrate.

3. The compound according to claim 2, wherein $R^2$ represents —(CO)—$R^{2A}$;
$R^{2A}$ represents a 5- to 8-membered nitrogen-containing monocyclic heterocyclic ring, $R^3$ represents a hydrogen atom, a C1-8 aliphatic hydrocarbon group which may have a substituent(s), a 3- to 15-membered saturated carbocyclic ring which may have a substituent(s), 3- to 15-membered unsaturated carbocyclic ring which may have a substituent(s) or 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) cyclic group which may have a substituent(s), wherein the "substituent" in "C1-8 aliphatic hydrocarbon group which may have a substituent(s)", "3- to 15-membered saturated carbocyclic ring which may have a substituent(s)", "3- to 15-membered unsaturated carbocyclic ring which may have a substituent(s)", and "3- to 15-membered monocyclic or polycyclic heterocyclic ring having, as a hetero atom, 1 to 4 nitrogen atom(s), 1 to 2 oxygen atom(s) and/or 1 to 2 sulfur atom(s)" described above represents 1 to 5 of substituents selected from (1) to (39) described below, if the number of substituents is two or more, each substituent may be same or different;

(1) C1-8 aliphatic hydrocarbon group which may have a substituent(s), (2) 3- to 15-membered saturated carbocyclic ring which may have a substituent(s), or 3- to 15-membered unsaturated carbocyclic ring which may have a substituent(s), (3) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may have a substituent(s), (4) amino group, (5) C1-10 acylamino which may have a substituent(s), (6) secondary or tertiary amine substituted by substituent(s), (7) C1-8 alkylsulfonylamino group which may have a substituent(s), C2-8 alkynylsulfonylamino group which may have a substituent(s) or C2-8 alkenylsulfonylamino group which may have a substituent(s), (8) phenylsulfonylamino group which may have a substituent(s), (9) C1-8 alkylsulfonyl group which may have a substituent(s), C2-8 alkynylsulfonyl group which may have a substituent(s) or C2-8 alkenylsulfonyl group which may have a substituent(s), (10) phenylsulfonyl group which may have a substituent(s), (11) halogen atom, (12) carboxyl group, (13) cyano group, (14) nitro group, (15) oxo group, (16) thioxo group, (17) hydroxy group, (18) C1-8 alkoxy group which may have a substituent(s), C2-8 alkynyloxy group which may have a substituent(s) or C2-8 alkenyloxy group which may have a substituent(s), (19) C3-8 cycloalkoxy group which may have a substituent(s), (20) phenoxy group which may have a substituent(s), (21) mercapto group, (22) C1-8 alkylthio group which may have a substituent(s), C2-8 alkynylthio group which may have a substituent(s) or C2-8 alkenylthio group which may have a substituent(s), (23) phenylthio group which may have a substituent(s), (24) carbamoyl group, (25) aminocarbonyl group substituted by substituent(s), (26) sulfamoyl group, (27) aminosulfonyl group substituted by substituent(s), (28) C1-8 alkoxycarbonyl group which may have a substituent(s), C2-8 alkynyloxycarbonyl group which may have a substituent(s) or C2-8 alkenyloxycarbonyl group which may have a substituent(s), (29) sulfo group, (30) sulfino group, (31) phosphono group, (32) amidino group, (33) imino group, (34) —B(OH)2 group, (35) C1-8 alkylsulfinyl group which may have a substituent(s), (36) C1-10 acyl group which may have a substituent(s), (37) hydroxyimino group, (38) C1-8 alkyloxyimino group, (39) basic group, wherein the "substituent" represented by (1) to (3), (5), (7) to (10), (18) to (20), (22), (23), (28), (35) and (36) described above represents 1 to 5 of substituents selected from (i) to (xix) described below, if the number of substituents is two or more, each substituent may be same or different;

(i) C1-8 aliphatic hydrocarbon group which may be substituted by amino group, halogen atom, hydroxy group, methoxy group, trifluoromethyl group, trifluoromethoxy group, acetyloxy group or carbamoyl group, (ii) 3- to 15-membered saturated carbocyclic ring which may be substituted by amino group, halogen atom, hydroxy group, methoxy group, trifluoromethyl group, trifluoromethoxy group, acetyloxy group or carbamoyl group, (iii) 3- to 15-membered unsaturated carbocyclic ring which may be substituted by amino group, halogen atom, hydroxy group, methoxy group, trifluoromethyl group, trifluoromethoxy group, acetyloxy group or carbamoyl group, (iv) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may be substituted by amino group, halogen atom, hydroxy group, methoxy group, trifluoromethyl group, trifluoromethoxy group, acetyloxy group or carbamoyl group, (v) amino group, (vi) dimethylamino group, (vii) sulfo group, (viii) halogen atom, (ix) carboxyl group, (x) cyano group, (xi) nitro group, (xii) oxo group, (xiii) thioxo group, (xiv) hydroxy group, (xv) methoxy group, (xvi) acetyl group, (xvii) methoxycarbonyl group, (xviii) trifluoromethyl group, (xix) trifluoromethoxy, wherein the "basic group" represented by (39) described above represents (a) amino group, (b) amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing heterocyclic ring which may have a substituent(s), wherein the "substituent" in the "mono- or di-substituted amino group" represented by (e) described above represents the substituent of (1) to (38) described above, these arbitrary substituent(s) may be substituted on the substitutable position and the number of substituents may be from 1 to 2, if the number of substituents is two, each substituent may be same or different, wherein the "substituent" in the "mono-, di- or tri-substituted amidino group" represented by (f) described above represents the substituent of (1) to (38) described above, these arbitrary substituent(s) may be substituted on the substitutable position and the number of substituents may be from 1 to 3, if the number of substituents is two or more, each substituent may be same or different, wherein the "substituent" in the "mono-, di-, tri- or tetra-substituted guanidino group" represented by (g) described above represents the substituent of (1) to (38) described above, these arbitrary substituent(s) may be substituted on the substitutable position and the number of substituents may be from 1 to 3, if the number of substituents is two or more, each substituent may be same or different, wherein the "substituent" in the "mono-, di- or tri-substituted hydrazino group" represented by (h) described above represents the substituent of (1) to (38) described above, these arbitrary substituent(s) may be substituted on the substitutable position and the number of substituents may be from 1 to 3, if the number of substituents is two or more, each substituent may be same or different, wherein the "nitrogen-containing heterocyclic ring" in the "nitrogen-containing heterocyclic ring which may have a substituent(s)" represented by (i) described above represents pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydroquinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane or 1-thia-4,8-diazaspiro[5.5]undecane ring, wherein the "substituent" in the "nitrogen-containing heterocyclic ring which may have a substituent(s)" represented by (i) described above represents 1 to 8 of substituents selected from (1) to (38) described above, if the number of substituents is two or more, each substituent may be same or different, or a salt thereof, an N-oxide thereof or a solvate thereof, or a prodrug thereof;

wherein the solvate is made with water, an alcoholic solvent, an alkali (earth) metal salt, an ammonium salt, a salt of an organic amino, or an acid addition salt of the compound of formula (I);

wherein the prodrug is one wherein (A) an amino group is acylated, alkylated, or phosphorylated (B) a hydroxyl group is acylated, alkylated, or phosphorylated, or boricated (C) a carboxy group is esterificated, or amidated, and wherein the prodrug may be a hydrate or a non-hydrate.

4. The compound according to claim 3, wherein the 5- to 8-membered nitrogen-containing monocyclic heterocyclic ring represented by $R^{2A}$ represents pyrrolidine, piperidine or morpholine, or a salt thereof, an N-oxide thereof or a solvate thereof, or a prodrug thereof;

wherein the solvate is made with water, an alcoholic solvent, an alkali (earth) metal salt, an ammonium salt, a salt of an organic amino, or an acid addition salt of the compound of formula (I);

wherein the prodrug is one wherein (A) an amino group is acylated, alkylated, or phosphorylated (B) a hydroxyl group is acylated, alkylated, or phosphorylated, or boricated (C) a carboxy group is esterificated, or amidated, and wherein the prodrug may be a hydrate or a non-hydrate.

5. The compound according to claim 2, wherein the ring which is formed by taking $R^2$ and $R^3$ together with the nitrogen atom to which they are attached represents a 5- to 8-membered nitrogen-containing monocyclic heterocyclic ring which may have a substituent(s), wherein the "substituent" in the "5- to 8-membered nitrogen-containing monocyclic heterocyclic ring which may have a substituent(s)" described above represents 1 to 5 of substituents selected from (1) to (39) described below, if the number of substituents is two or more, each substituent may be same or different;

(1) C1-8 aliphatic hydrocarbon group which may have a substituent(s), (2) 3- to 15-membered saturated carbocyclic ring which may have a substituent(s), or 3- to 15-membered unsaturated carbocyclic ring which may have a substituent(s), (3) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may have a substituent(s), (4) amino group, (5) C1-10 acylamino which may have a substituent(s), (6) secondary or tertiary amine substituted by substituent(s), (7) C1-8 alkylsulfonylamino group which may have a substituent(s), C2-8 alkynylsulfonylamino group which may have a substituent(s) or C2-8 alkenylsulfonylamino group which may have a substituent(s), (8) phenylsulfonylamino group which may have a substituent(s), (9) C1-8 alkylsulfonyl group which may have a substituent(s), C2-8 alkynylsulfonyl group which may have a substituent(s) or C2-8 alkenylsulfonyl group which may have a substituent(s), (10) phenylsulfonyl group which may have a substituent(s), (11) halogen atom, (12) carboxyl group, (13) cyano group, (14) nitro group, (15) oxo group, (16) thioxo group, (17) hydroxy group, (18) C1-8 alkoxy group which may have a substituent(s), C2-8 alkynyloxy group which may have a substituent(s) or C2-8 alkenyloxy group which may have a substituent(s), (19) C3-8 cycloalkoxy group which may have a substituent(s), (20) phenoxy group which may have a substituent(s), (21) mercapto group, (22) C1-8 alkylthio group which may have a substituent(s), C2-8 alkynylthio group which may have a substituent(s) or C2-8 alkenylthio group which may have a substituent(s), (23) phenylthio group which may have a substituent(s), (24) carbamoyl group, (25) aminocarbonyl group substituted by substituent(s), (26) sulfamoyl group, (27) aminosulfonyl group substituted by substituent(s), (28) C1-8 alkoxycarbonyl group which may have a substituent(s), C2-8 alkynyloxycarbonyl group which may have a substituent(s) or C2-8 alkenyloxycarbonyl group which may have a substituent(s), (29) sulfo group, (30) sulfino group, (31) phosphono group, (32) amidino group, (33) imino group, (34) —B(OH)2 group, (35) C1-8 alkylsulfinyl group which may have a substituent(s), (36) C1-10 acyl group which may have a substituent(s), (37) hydroxyimino group, (38) C1-8 alkyloxyimino group, (39) basic group, wherein the "substituent" represented by (1) to (3), (5), (7) to (10), (18) to (20), (22), (23), (28), (35) and (36) described above represents 1 to 5 of substituents selected from (i) to (xix) described below, if the number of substituents is two or more, each substituent may be same or different;

(i) C1-8 aliphatic hydrocarbon group which may be substituted by amino group, halogen atom, hydroxy group, methoxy group, trifluoromethyl group, trifluoromethoxy group, acetyloxy group or carbamoyl group, (ii) 3- to 15-membered saturated carbocyclic ring which may be substituted by amino group, halogen atom, hydroxy group, methoxy group, trifluoromethyl group, trifluoromethoxy group, acetyloxy group or carbamoyl group, (iii) 3- to 15-membered unsaturated carbocyclic ring which may be substituted by amino group, halogen atom, hydroxy group, methoxy group, trifluoromethyl group, trifluoromethoxy group, acetyloxy group or carbamoyl group, (iv) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may be substituted by amino group, halogen atom, hydroxy group, methoxy group, trifluoromethyl group, trifluoromethoxy group, acetyloxy group or carbamoyl group, (v) amino group, (vi) dimethylamino group, (vii) sulfo group, (viii) halogen atom, (ix) carboxyl group, (x) cyano group, (xi) nitro group, (xii) oxo group, (xiii) thioxo group, (xiv) hydroxy group, (xv) methoxy group, (xvi) acetyl group, (xvii) methoxycarbonyl group, (xviii) trifluoromethyl group, (xix) trifluoromethoxy, wherein the "basic group" represented by (39) described above represents (a) amino group, (b) amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing heterocyclic ring which may have a substituent(s), wherein the "substituent" in the "mono- or di-substituted amino group" represented by (e) described above represents the substituent of (1) to (38) described above, these arbitrary substituent(s) may be substituted on the substitutable position and the number of substituents may be from 1 to 2, if the number of substituents is two, each substituent may be same or different, wherein the "substituent" in the "mono-, di- or tri-substituted amidino group" represented by (f) described above represents the substituent of (1) to (38) described above, these arbitrary substituent(s) may be substituted on the substitutable position and the number of substituents may be from 1 to 3, if the number of substituents is two or more, each substituent may be same or different, wherein the "substituent" in the "mono-, di-, tri- or tetra-substituted guanidino group" represented by (g) described above represents the substituent of (1) to (38) described above, these arbitrary substituent(s) may be substituted on the substitutable position and the number of substituents may be from 1 to 3, if the number of substituents is two or more, each substituent may be same or different, wherein the "substituent" in the "mono-, di- or tri-substituted hydrazino group" represented by (h) described above represents the substituent of (1) to (38) described above, these arbitrary substituent(s) may be substituted on the substitutable position and the number of substituents may be from 1 to 3, if the number of substituents is two or more, each substituent may be same or different, wherein the "nitrogen-containing heterocyclic ring" in the "nitrogen-containing heterocyclic ring which may have a substituent(s)" represented by (i) described above represents pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydroquinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro [5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane or 1-thia-4,8-diazaspiro[5.5]undecane ring, wherein the "substituent" in the "nitrogen-containing heterocyclic ring which may have a substituent(s)" represented by (i) described above represents 1 to 8 of substituents selected from (1) to (38) described above, if the number of substituents is two or more, each substituent may be same or different, or a salt thereof, an N-oxide thereof or a solvate thereof, or a prodrug thereof;

wherein the solvate is made with water, an alcoholic solvent, an alkali (earth) metal salt, an ammonium salt, a salt of an organic amino, or an acid addition salt of the compound of formula (I);

wherein the prodrug is one wherein (A) an amino group is acylated, alkylated, or phosphorylated (B) a hydroxyl group is acylated, alkylated, or phosphorylated, or boricated (C) a carboxy group is esterificated, or amidated, and wherein the prodrug may be a hydrate or a non-hydrate.

6. The compound according to claim 2, wherein ring $D^1$ represents pyrrolidine or piperidine, or a salt thereof, an N-oxide thereof or a solvate thereof, or a prodrug thereof;

wherein the solvate is made with water, an alcoholic solvent, an alkali (earth) metal salt, an ammonium salt, a salt of an organic amino, or an acid addition salt of the compound of formula (I);

wherein the prodrug is one wherein (A) an amino group is acylated, alkylated, or phosphorylated (B) a hydroxyl group is acylated, alkylated, or phosphorylated, or boricated (C) a carboxy group is esterificated, or amidated, and wherein the prodrug may be a hydrate or a non-hydrate.

7. The compound according to claim 1, wherein the compound represented by formula (I) represents:

a compound represented by formula (I-2):

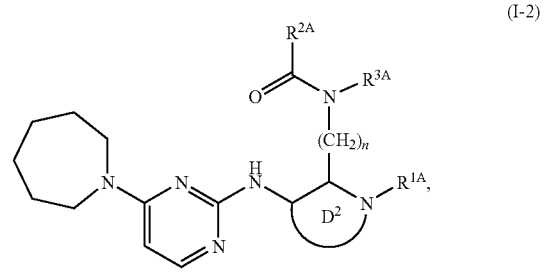

(I-2)

a compound represented by formula (I-3):

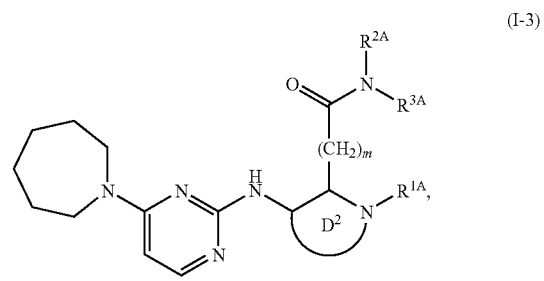

(I-3)

a compound represented by formula (I-4):

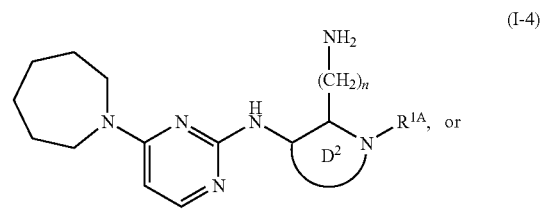

(I-4)

a compound represented by formula (1-5):

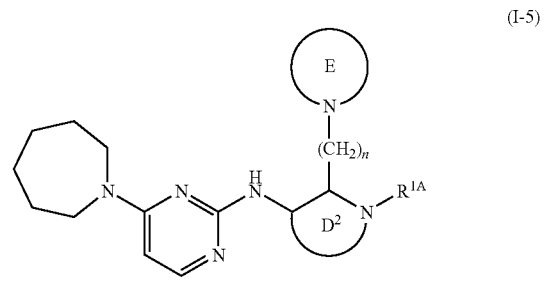

(I-5)

wherein ring $D^2$ represents pyrrolidine or piperidine;
m represents an integer of 1 to 3;
n represents an integer of 2 to 4;
$R^{1A}$ represents a C1-8 aliphatic hydrocarbon group which may be substituted by an amino group, a C1-10 acylamino group, a carboxyl group, an oxo group, a thioxo group, a hydroxy group, a C1-8 alkoxy group, a C3-8 cycloalkoxy group, a carbamoyl group or an aminocarbonyl group, a 3- to 8-membered monocyclic carbocyclic ring which may be substituted by a C1-4 aliphatic hydrocarbon group, amino group, a C1-10 acylamino group, a carboxyl group, an oxo group, a thioxo group, a hydroxy group, a C1-8 alkoxy group, a C3-8 cycloalkoxy group, a carbamoyl group or an aminocarbonyl group or a 3- to 8-membered monocyclic heterocyclic ring having, as a hetero atom, a nitrogen atom(s), an oxygen atom(s) and/or a sulfur atom(s) which may be substituted by a C1-4 aliphatic hydrocarbon group, amino group, a C1-10 acylamino group, a carboxyl group, an oxo group, a thioxo group, a hydroxy group, a C1-8 alkoxy group, a C3-8 cycloalkoxy group, a carbamoyl group or an aminocarbonyl group;

$R^{2,4}$ represents a 5- to 7-membered nitrogen-containing monocyclic heterocyclic ring, a C1-4 aliphatic hydrocarbon group which is substituted by an amino group, an amidino group, a guanidino group, a hydrazino group, a mono- or di-substituted amino group or a nitrogen-containing heterocyclic ring, and also may be substituted by a hydroxy group or a 5- to 7-membered monocyclic carbocyclic ring which is substituted by an amino group, an amidino group, a guanidino group, a hydrazino group, a mono- or di-substituted amino group or a nitrogen-containing heterocyclic ring, and also may be substituted by a hydroxy group, $R^{3,4}$ represents a 5- to 7-membered monocyclic heterocyclic ring or a C1-4 aliphatic hydrocarbon which may be substituted by an amino group, a C1-10 acylamino group, a carboxyl group, an oxo group, a thioxo group, a hydroxy group, a C1-8 alkoxy group, a C3-8 cycloalkoxy group, a carbamoyl group or an amino carbonyl group, ring E represents a 5- to 8-membered nitrogen-containing monocyclic heterocyclic ring which may have a further substituent(s);

wherein the "substituent" in the "5- to 8-membered nitrogen-containing monocyclic heterocyclic ring which may have a further substituent(s)" described above represents 1 to 5 of substituents selected from (1) to (39) described below, if the number of substituents is two or more, each substituent may be same or different;

(1) C1-8 aliphatic hydrocarbon group which may have a substituent(s), (2) 3- to 15-membered saturated carbocyclic ring which may have a substituent(s), or 3- to 15-membered unsaturated carbocyclic ring which may have a substituent(s), (3) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may have a substituent(s), (4) amino group, (5) C1-10 acylamino which may have a substituent(s), (6) secondary or tertiary amine substituted by substituent(s), (7) C1-8 alkylsulfonylamino group which may have a substituent(s), C2-8 alkynylsulfonylamino group which may have a substituent(s) or C2-8 alkenylsulfonylamino group which may have a substituent(s), (8) phenylsulfonylamino group which may have a substituent(s), (9) C1-8 alkylsulfonyl group which may have a substituent(s), C2-8 alkynylsulfonyl group which may have a substituent(s) or C2-8 alkenylsulfonyl group which may have a substituent(s), (10) phenylsulfonyl group which may have a substituent(s), (11) halogen atom, (12) carboxyl group, (13) cyano group, (14) nitro group, (15) oxo group, (16) thioxo group, (17) hydroxy group, (18) C1-8 alkoxy group which may have a substituent(s), C2-8 alkynyloxy group which may have a substituent(s) or C2-8 alkenyloxy group which may have a substituent(s), (19) C3-8 cycloalkoxy group which may have a substituent(s), (20) phenoxy group which may have a substituent(s), (21) mercapto group, (22) C1-8 alkylthio group which may have a substituent(s), C2-8 alkynylthio group which may have a substituent(s) or C2-8 alkenylthio group which may have a substituent(s), (23) phenylthio group which may have a substituent(s), (24) carbamoyl group, (25) aminocarbonyl group substituted by substituent(s), (26) sulfamoyl group, (27) aminosulfonyl group substituted by substituent(s), (28) C1-8 alkoxycarbonyl group which may have a substituent(s), C2-8 alkynyloxycarbonyl group which may have a substituent(s) or C2-8 alkenyloxycarbonyl group which may have a substituent(s), (29) sulfo group, (30) sulfino group, (31) phosphono group, (32) amidino group, (33) imino group, (34) —B(OH)2 group, (35) C1-8 alkylsulfinyl group which may have a substituent(s), (36) C1-10 acyl group which may have a substituent(s), (37) hydroxyimino group, (38) C1-8 alkyloxyimino group, (39) basic group, wherein the "substituent" represented by (1) to (3), (5), (7) to (10), (18) to (20), (22), (23), (28), (35) and (36) described above represents 1 to 5 of substituents selected from (i) to (xix) described below, if the number of substituents is two or more, each substituent may be same or different;

(i) C1-8 aliphatic hydrocarbon group which may be substituted by amino group, halogen atom, hydroxy group, methoxy group, trifluoromethyl group, trifluoromethoxy group, acetyloxy group or carbamoyl group, (ii) 3- to 15-membered saturated carbocyclic ring which may be substituted by amino group, halogen atom, hydroxy group, methoxy group, trifluoromethyl group, trifluoromethoxy group, acetyloxy group or carbamoyl group, (iii) 3- to 15-membered unsaturated carbocyclic ring which may be substituted by amino group, halogen atom, hydroxy group, methoxy group, trifluoromethyl group, trifluoromethoxy group, acetyloxy group or carbamoyl group, (iv) 3- to 15-membered monocyclic or polycyclic heterocyclic ring having, as a hetero atom, 1 to 4 nitrogen atom(s), 1 to 2 oxygen atom(s) and/or 1 to 2 sulfur atom(s) which may be substituted by amino group, halogen atom, hydroxy group, methoxy group, trifluoromethyl group, trifluoromethoxy group, acetyloxy group or carbamoyl group, (v) amino group, (vi) dimethylamino group, (vii) sulfo group, (viii) halogen atom, (ix) carboxyl group, (x) cyano group, (xi) nitro group, (xii) oxo group, (xiii) thioxo group, (xiv) hydroxy group, (xv) methoxy group, (xvi) acetyl group, (xvii) methoxycarbonyl group, (xviii) trifluoromethyl group, (xix) trifluoromethoxy, wherein the "basic group" represented by (39) described above represents (a) amino group, (b) amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing heterocyclic ring which may have a substituent(s), wherein the "substituent" in the "mono- or di-substituted amino group" represented by (e) described above represents the substituent of (1) to (38) described above, these arbitrary substituent(s) may be substituted on the substitutable position and the number of substituents may be from 1 to 2, if the number of substituents is two, each substituent may be same or different, wherein the "substituent" in the "mono-, di- or tri-substituted amidino group" represented by (f) described above represents the substituent of (1) to (38) described above, these arbitrary substituent(s) may be substituted on the substitutable position and the number of substituents may be from 1 to 3, if the number of substituents is two or more, each substituent may be same or different, wherein the "substituent" in the "mono-, di-, tri- or tetra-substituted guanidino group" represented by (g) described above represents the substituent of (1) to (38) described above, these arbitrary substituent(s) may be substituted on the substitutable position and the number of substituents may be from 1 to 3, if the number of substituents is two or more, each substituent may be same or different, wherein the "substituent" in the "mono-, di- or tri-substituted hydrazino group" represented by (h) described above represents the substituent of (1) to (38) described above, these arbitrary substituent(s) may be substituted on the substitutable position and the number of substituents may be from 1 to 3, if the number of substituents is two or more, each substituent may be same or different, wherein the "nitrogen-containing heterocyclic ring" in the "nitrogen-containing heterocyclic ring which may have a substituent(s)" represented by (i) described above represents pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydroquinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[4.5]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane or 1-thia-4,8-diazaspiro[5.5]undecane ring, wherein the "substituent" in the "nitrogen-containing heterocyclic ring which may have a substituent(s)" represented by (i) described above represents 1 to 8 of substituents selected from (1) to (38) described above, if the number of substituents is two or more, each substituent may be same or different, or a salt thereof, an N-oxide thereof or a solvate thereof, or a prodrug thereof;

wherein the solvate is made with water, an alcoholic solvent, an alkali (earth) metal salt, an ammonium salt, a salt of an organic amino, or an acid addition salt of the compound of formula (I);

wherein the prodrug is one wherein (A) an amino group is acylated, alkylated, or phosphorylated (B) a hydroxyl group is acylated, alkylated, or phosphorylated, or boricated (C) a carboxy group is esterificated, or amidated, and wherein the prodrug may be a hydrate or a non-hydrate.

8. The compound according to claim 7, wherein the 3- to 8-membered saturated monocyclic carbocyclic ring may be substituted by a C1-4 aliphatic hydrocarbon group or a hydroxy group, and the 3- to 8-membered saturated monocyclic heterocyclic ring may be substituted by a C1-4 aliphatic hydrocarbon group or a hydroxy group.

9. The compound according to claim 1, wherein the compound represented by formula (I) represents N-[(2R,3S)-2-(2-aminoethyl)-1-cyclohexyl-3-pyrrolidinyl]-4-(1-azepanyl)-2-pyrimidinamine;

N-[(2R,3S)-2-(3-aminopropyl)-1-cyclohexyl-3-pyrrolidinyl]-4-(1-azepanyl)-2-pyrimidinamine;

N-[(2R,3S)-2-(5-aminopentyl)-1-cyclohexyl-3-pyrrolidinyl]-4-(1-azepanyl)-2-pyrimidinamine;

4-(1-azepanyl)-N-{(2R,3S)-1-cyclohexyl-2-[2-(dimethylamino)ethyl]-3-pyrrolidinyl}-2-pyrimidinamine;

4-(1-azepanyl)-N-{(2R,3S)-1-cyclohexyl-2-[3-(dimethylamino)propyl]-3-pyrrolidinyl}-2-pyrimidinamine;

4-(1-azepanyl)-N-{(2R,3S)-1-cyclohexyl-2-[5-(dimethylamino)pentyl]-3-pyrrolidinyl}-2-pyrimidinamine;

4-(1-azepanyl)-N-{(2R,3S)-1-cyclohexyl-2-[3-(dipropylamino)propyl]-3-pyrrolidinyl}-2-pyrimidinamine;

cis-4-((2R,3S)-2-(3-aminopropyl)-3-{[4-(1-azepanyl)-2-pyrimidinyl]amino}-1-pyrrolidinyl)cyclohexanol;

4-(1-azepanyl)-N-{(2R,3S)-1-cyclohexyl-2-[3-(diethylamino)propyl]-3-pyrrolidinyl}-2-pyrimidinamine;

4-(1-azepanyl)-N-{(2R,3S)-1-cyclohexyl-2-[3-(1-pyrrolidinyl)propyl]-3-pyrrolidinyl}-2-pyrimidinamine;

4-(1-azepanyl)-N-{(2R,3S)-1-cyclohexyl-2-[3-(1-piperidinyl)propyl]-3-pyrrolidinyl}-2-pyrimidinamine;

4-(1-azepanyl)-N-{(2R,3S)-2-[3-(1-azepanyl)propyl]-1-cyclohexyl-3-pyrrolidinyl}-2-pyrimidinamine;

N-{(2R,3S)-2-(3-aminopropyl)-1-[1-(cyclohexylcarbonyl)-4-piperidinyl]-3-pyrrolidinyl}-4-(1-azepanyl)-2-pyrimidinamine;

N-{(2R,3S)-2-(3-aminopropyl)-1-[1-(cyclopentylcarbonyl)-4-piperidinyl]-3-pyrrolidinyl}-4-(1-azepanyl)-2-pyrimidinamine;

N-{(2R,3S)-2-(3-aminopropyl)-1-[1-(3-fluorobenzoyl)-4-piperidinyl]-3-pyrrolidinyl}-4-(1-azepanyl)-2-pyrimidinamine;

cis-4-{(2R,3S)-3-{[4-(1-azepanyl)-2-pyrimidinyl]amino}-2-[3-(diethylamino)propyl]-1-pyrrolidinyl}cyclohexanol;

(3S)-N-[2-((2R,3S)-3-{[4-(1-azepanyl)-2-pyrimidinyl]amino}-1-cyclohexyl-2-piperidinyl)ethyl]-3-piperidinecarboxamide;

N-[2-((2R,3S)-3-{[4-(1-azepanyl)-2-pyrimidinyl]amino}-1-cyclohexyl-2-pyrrolidinyl)ethyl]-2-morpholinecarboxamide; or a salt thereof, an N-oxide thereof or a solvate thereof, or a prodrug thereof;

wherein the solvate is made with water, an alcoholic solvent, an alkali (earth) metal salt, an ammonium salt, a salt of an organic amino, or an acid addition salt of the compound of formula (I);

wherein the prodrug is one wherein (A) an amino group is acylated, alkylated, or phosphorylated (B) a hydroxyl group is acylated, alkylated, or phosphorylated, or boricated (C) a carboxy group is esterificated, or amidated, and wherein the prodrug may be a hydrate or a non-hydrate.

10. A pharmaceutical composition comprising the compound represented by formula (I) described in claim 1, a salt thereof, an N-oxide thereof or a solvate thereof, or a prodrug thereof;
  wherein the solvate is made with water, an alcoholic solvent, an alkali (earth) metal salt, an ammonium salt, a salt of an organic amino, or an acid addition salt of the compound of formula (I);
  wherein the prodrug is one wherein
  (A) an amino group is acylated, alkylated, or phosphorylated
  (B) a hydroxyl group is acylated, alkylated, or phosphorylated, or boricated
  (C) a carboxy group is esterificated, or amidated, and
  wherein the prodrug may be a hydrate or a non-hydrate.

* * * * *